United States Patent
Bacac et al.

(10) Patent No.: US 10,781,258 B2
(45) Date of Patent: Sep. 22, 2020

(54) BISPECIFIC T CELL ACTIVATING ANTIGEN BINDING MOLECULES

(71) Applicant: Roche Glycart AG, Schlieren (CH)

(72) Inventors: Marina Bacac, Zurich (CH); Thomas Hofer, Zurich (CH); Ralf Hosse, Cham (CH); Christiane Neumann, Niederweningen (CH); Christian Klein, Bonstetten (CH); Ekkehard Moessner, Kreuzlingen (CH); Pablo Umana, Wollerau (CH); Tina Weinzierl, Schlieren (CH)

(73) Assignee: Roche Glycart AG, Schlieren (CH)

( * ) Notice: Subject to any disclaimer, the term of this patent is extended or adjusted under 35 U.S.C. 154(b) by 0 days.

(21) Appl. No.: 16/134,494

(22) Filed: Sep. 18, 2018

(65) Prior Publication Data

US 2019/0002565 A1    Jan. 3, 2019

Related U.S. Application Data

(62) Division of application No. 14/188,486, filed on Feb. 24, 2014, now Pat. No. 10,155,815.

(30) Foreign Application Priority Data

Feb. 26, 2013   (EP) .................... 13156686

(51) Int. Cl.
*C07K 16/28* (2006.01)
*C07K 16/30* (2006.01)
*A61K 39/00* (2006.01)

(52) U.S. Cl.
CPC ...... *C07K 16/2809* (2013.01); *C07K 16/3007* (2013.01); *C07K 16/3053* (2013.01); *A61K 2039/505* (2013.01); *C07K 2317/31* (2013.01); *C07K 2317/33* (2013.01); *C07K 2317/526* (2013.01); *C07K 2317/53* (2013.01); *C07K 2317/55* (2013.01); *C07K 2317/64* (2013.01); *C07K 2317/66* (2013.01); *C07K 2317/71* (2013.01); *C07K 2317/73* (2013.01); *C07K 2317/92* (2013.01); *C07K 2317/94* (2013.01); *C07K 2319/00* (2013.01)

(58) Field of Classification Search
CPC ............ C07K 16/2809; C07K 16/3007; C07K 16/3053; C07K 16/2896; C07K 2317/31; C07K 2317/33; C07K 2317/35; C07K 2317/51; C07K 2317/55; C07K 2317/565; C07K 2317/64; C07K 2317/66; C07K 2317/71; C07K 2317/73; C07K 2317/92; C07K 2317/94; C07K 2319/00; A61K 2039/505; A61P 43/00; A61P 37/04; A61P 35/00
See application file for complete search history.

(56) References Cited

U.S. PATENT DOCUMENTS

| | | |
|---|---|---|
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,737,086 B2 | 5/2004 | Gutierrez et al. |
| 6,809,185 B1 | 10/2004 | Schoonjans et al. |
| 7,235,641 B2 | 6/2007 | Kufer et al. |
| 7,332,581 B2 | 2/2008 | Presta |
| 7,695,936 B2 | 4/2010 | Carter et al. |
| 8,227,577 B2 | 7/2012 | Klein et al. |
| 8,236,308 B2 | 8/2012 | Kischel et al. |
| 8,242,247 B2 | 8/2012 | Klein et al. |
| 8,642,742 B2 | 2/2014 | Hofer et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,846,042 B2 | 9/2014 | Zhou |
| 8,969,526 B2 | 3/2015 | Baehner et al. |
| 9,068,008 B2 | 6/2015 | Mossner et al. |
| 9,206,260 B2 | 12/2015 | Hofer et al. |
| 9,266,938 B2 | 2/2016 | Ast et al. |
| 9,266,967 B2 | 2/2016 | Klein et al. |

(Continued)

FOREIGN PATENT DOCUMENTS

| | | |
|---|---|---|
| EP | 0404097 B1 | 9/1996 |
| EP | 1870459 A1 | 12/2007 |

(Continued)

OTHER PUBLICATIONS

Bacac et al., Clinical Cancer Research 1-12 (Year: 2016).*
Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).

(Continued)

*Primary Examiner* — Phuong Huynh
(74) *Attorney, Agent, or Firm* — Clark & Elbing LLP; Karen L. Elbing

(57) ABSTRACT

The present invention generally relates to novel bispecific antigen binding molecules for T cell activation and redirection to specific target cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

39 Claims, 38 Drawing Sheets
Specification includes a Sequence Listing.

(56) References Cited

U.S. PATENT DOCUMENTS

| | | |
|---|---|---|
| 9,382,323 B2 | 7/2016 | Brinkmann et al. |
| 9,447,159 B2 | 9/2016 | Ast et al. |
| 9,526,797 B2 | 12/2016 | Gerdes et al. |
| 10,155,815 B2 | 12/2018 | Bacac et al. |
| 2002/0004587 A1 | 1/2002 | Miller et al. |
| 2005/0244333 A1 | 11/2005 | Yazaki et al. |
| 2006/0115475 A1 | 6/2006 | Carton et al. |
| 2007/0071675 A1 | 3/2007 | Wu et al. |
| 2007/0111281 A1 | 5/2007 | Sondermann et al. |
| 2007/0219133 A1 | 9/2007 | Lazar et al. |
| 2008/0241152 A1 | 10/2008 | Alitalo et al. |
| 2009/0162359 A1 | 6/2009 | Klein et al. |
| 2009/0162360 A1 | 6/2009 | Klein et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0316645 A1 | 12/2010 | Imhof-Jung et al. |
| 2011/0293613 A1 | 12/2011 | Brinkmann et al. |
| 2012/0149876 A1 | 6/2012 | Von Kreudenstein et al. |
| 2012/0225071 A1 | 9/2012 | Klein et al. |
| 2012/0251531 A1 | 10/2012 | Baehner et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0166661 A1 | 6/2015 | Chen et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0175397 A1 | 6/2016 | Umana et al. |
| 2016/0200833 A1 | 7/2016 | Amann et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |

FOREIGN PATENT DOCUMENTS

| | | |
|---|---|---|
| EP | 1870459 A4 | 9/2010 |
| EP | 2261258 A1 | 12/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2012-528092 A | 11/2012 |
| JP | 2014-534806 A | 12/2014 |
| TW | 201321413 A | 6/2013 |
| TW | 201326212 A | 7/2013 |
| WO | WO-91/03493 A1 | 3/1991 |
| WO | WO-93/01161 A1 | 1/1993 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-2005/044859 A2 | 5/2005 |
| WO | WO-2006/082515 A2 | 8/2006 |
| WO | WO-2007/024715 A2 | 3/2007 |
| WO | WO-2007/042261 A2 | 4/2007 |
| WO | WO-2007/071426 A1 | 6/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2008/052187 A2 | 5/2008 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/023787 A1 | 3/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/058768 A1 | 5/2012 |
| WO | WO-2012/058768 A8 | 6/2012 |
| WO | WO-2012/073985 A1 | 6/2012 |
| WO | WO-2012/107417 A1 | 8/2012 |
| WO | WO-2012/117002 A1 | 9/2012 |
| WO | WO-2012/130831 A1 | 10/2012 |
| WO | WO-2012/146628 A1 | 11/2012 |
| WO | WO-2012/158818 A2 | 11/2012 |
| WO | WO-2012/162067 A2 | 11/2012 |
| WO | WO-2013/012414 A1 | 1/2013 |
| WO | WO-2013/026831 A1 | 2/2013 |
| WO | WO-2013/026832 A1 | 2/2013 |
| WO | WO-2013/026833 A1 | 2/2013 |
| WO | WO-2013/026837 A1 | 2/2013 |
| WO | WO-2013/096291 A2 | 6/2013 |
| WO | WO-2013/157953 A1 | 10/2013 |
| WO | WO-2013/157954 A1 | 10/2013 |
| WO | WO-2014/022540 A1 | 2/2014 |
| WO | WO-2014/028560 A2 | 2/2014 |
| WO | WO-2014/047231 A1 | 3/2014 |
| WO | WO-2014/056783 A1 | 4/2014 |
| WO | WO-2014/028560 A3 | 5/2014 |
| WO | WO-2014/081955 A1 | 5/2014 |
| WO | WO-2014/122143 A1 | 8/2014 |
| WO | WO-2014/122144 A1 | 8/2014 |
| WO | WO-2014/122251 A2 | 8/2014 |
| WO | WO-2014/141152 A2 | 9/2014 |
| WO | WO-2014/153002 A1 | 9/2014 |
| WO | WO-2014/122251 A3 | 10/2014 |
| WO | WO-2014/167022 A1 | 10/2014 |
| WO | WO-2014/141152 A3 | 12/2014 |

(56) References Cited

FOREIGN PATENT DOCUMENTS

| WO | WO-2014/191113 A1 | 12/2014 |
|---|---|---|
| WO | WO-2014/191113 A8 | 2/2015 |
| WO | WO-2015/150447 A1 | 10/2015 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/179003 A1 | 11/2016 |
| WO | WO-2017/021450 A1 | 2/2017 |

OTHER PUBLICATIONS

Carter, "Bispecific human IgG by design," J Immunol Methods. 248(1-2):7-15 (2001).
Chan et al., "Variable region domain exchange in human IgGs promotes antibody complex formation with accompanying structural changes and altered effector functions," Mol Immunol. 41(5):527-38 (2004).
Conaghan et al., "Targeted killing of colorectal cancer cell lines by a humanised IgG1 monoclonal antibody that binds to membrane-bound carcinoembryonic antigen," Br J Cancer. 98(7):1217-25 (2008).
Edelman et al., "The covalent structure of an entire gammaG immunoglobulin molecule," Proc Natl Acad Sci U S A. 63(1):78-85 (1969).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
MacLean et al., "Anti-CD3:anti-IL-2 receptor-bispecific mAb-mediated immunomodulation. Low systemic toxicity, differential effect on lymphoid tissue, and inhibition of cell-mediated hypersensitivity," J Immunol. 155(7):3674-82 (1995).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).

Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Peng et al., "The CEA/CD3-bispecific antibody MEDI-565 (MT111) binds a nonlinear epitope in the full-length but not a short splice variant of CEA," PLoS One. 7(5):e36412 (2012) (14 pages).
Pessano et al., "The T3/T cell receptor complex: antigenic distinction between the two 20-kd T3 (T3-delta and T3-epsilon) subunits," Embo J. 4(2):337-44 (1985).
Plückthun, Antibodies from *Escherichia coli. The Pharmacology of Monoclonal Antibodies*. Rosenberg & Moore, 269-315 (1994).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Stancovski et al., "Mechanistic aspects of the opposing effects of monoclonal antibodies to the ERBB2 receptor on tumor growth," Proc Natl Acad Sci U S A. 88(19):8691-5 (1991).
Stewart et al., "Humanisation and characterisation of PR1A3, a monoclonal antibody specific for cell-bound carcinoembryonic antigen," Cancer Immunol Immunother. 47(6):299-306 (1999).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Wolf et al., "BiTEs: bispecific antibody constructs with unique anti-tumor activity," Drug Discov Today. 10(18):1237-44 (2005).
Wu et al., "Humanization of a murine monoclonal antibody by simultaneous optimization of framework and CDR residues," J Mol Biol. 294(1):151-62 (1999).
Zhu et al., "Identification of heavy chain residues in a humanized anti-CD3 antibody important for efficient antigen binding and T cell activation," J Immunol. 155(4):1903-10 (1995).
International Preliminary Report on Patentability for International Patent Application No. PCT/EP2014/053490, dated Sep. 1, 2015 (11 pages).
International Search Report and Written Opinion for International Patent Application No. PCT/EP2014/053489, dated Jun. 5, 2014 (14 pages).
International Search Report and Written Opinion for International Patent Application No. PCT/EP2014/053490, dated Jun. 10, 2014 (16 pages).
Almagro et al., "Humanization of antibodies," Front Biosci. 13:1619-33 (2008).
Regula et al., "Variable heavy-variable light domain and Fab-arm CrossMabs with charged residue exchanges to enforce correct light chain assembly," Protein Eng Des Sel. 31(7-8):1-11 (2018).
Office Action for U.S. Appl. No. 16/134,391, dated Nov. 15, 2019 (31 pages).

* cited by examiner

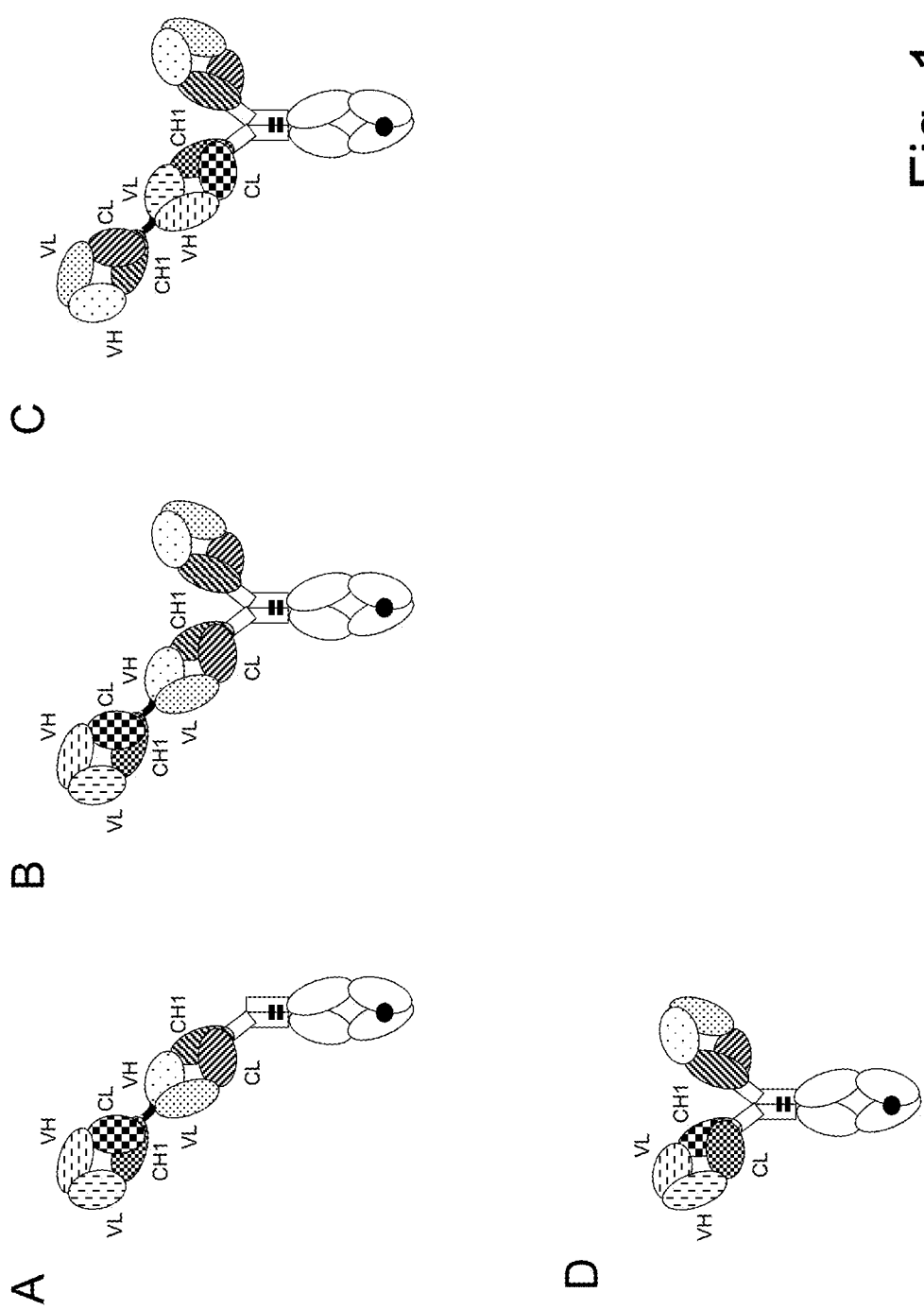

```
parental HC      1 QVQLQESGPGLVKPSQTLSLTCTVSGGSITSGYYWNWIRQHPGKGLEWIGYITYDGSNNYNPSLKSRVTISRDTSKNQFSLKLSSVTAADTAVYYCADFDYWGQGTLVTVSS
D6 (SEQ ID NO 34) 1 ................................................................F.K.................................................
A7 (SEQ ID NO 36) 1 ................................D...............................F.R.................................................
B7 (SEQ ID NO 39) 1 ................................................................F.I.................................................
B8 (SEQ ID NO 41) 1 ................................................................F.R.................................................
C1 (SEQ ID NO 13) 1 ................................................................F...................................................

parental LC      1 DIQMTQSPSSLSASVGDRVTITCRASQGIRNYLNWYQQKPGKAPKLLIYYTSSLHSGVPSRFSGSGSGTDFTLTISSLQPEDFATYYCQQYSKLPWTFGQGTKVEIK
G3 (SEQ ID NO 17) 1 ..........................................................Y.......................A......................
E10 (SEQ ID NO 43) 1 ............................Y..G..................................................H......................
E10-G3 (SEQ ID NO 46) 1 ............................Y..G..........................Y.......................H..A...................
C5 (SEQ ID NO 47) 1 ............................R..E.................................G................E......................
C5-G3 (SEQ ID NO 51) 1 ............................R..E.................................G................A......................
```

Fig. 2

■ MCSP TCB   ▧ untargeted TCB

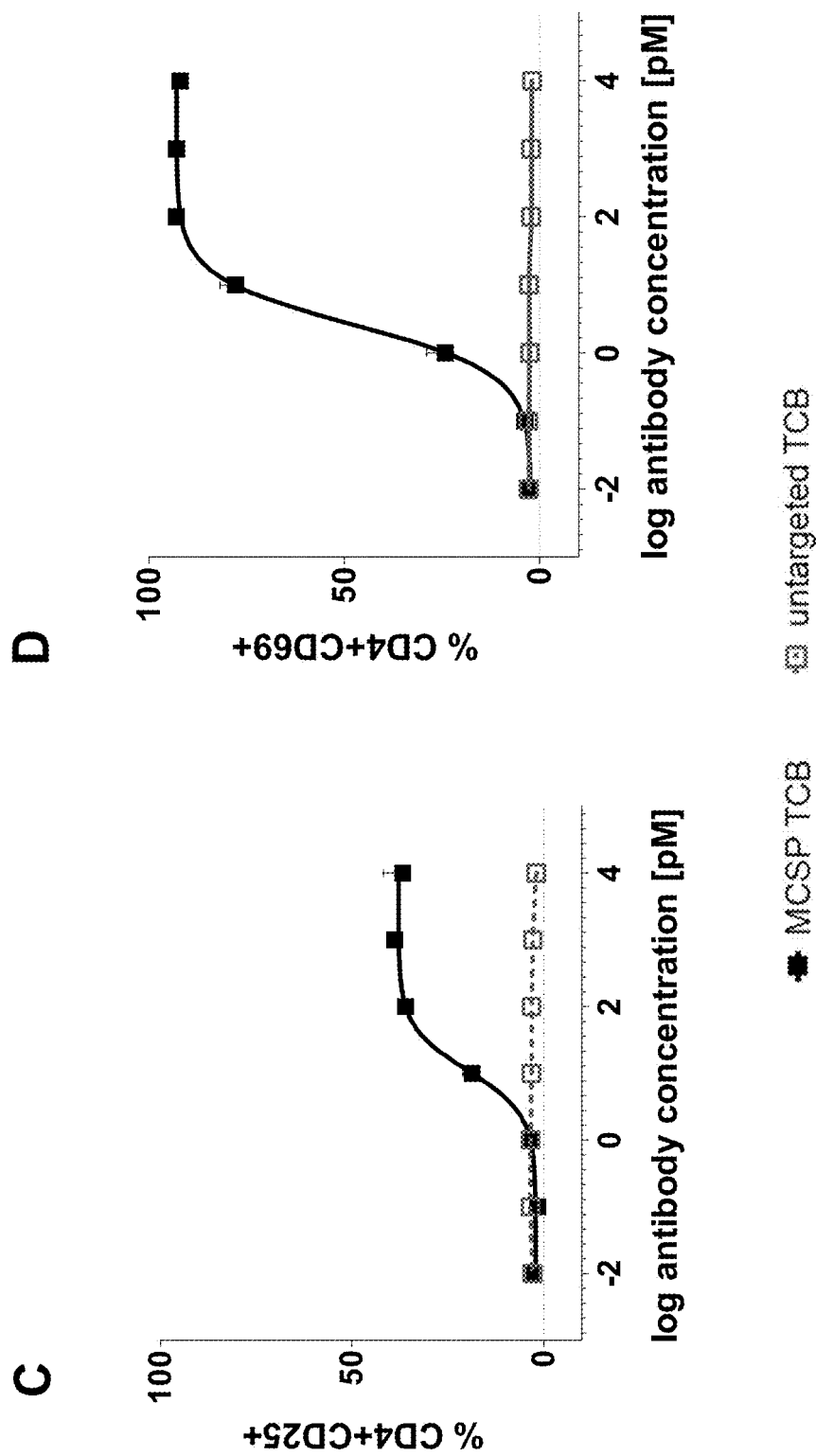

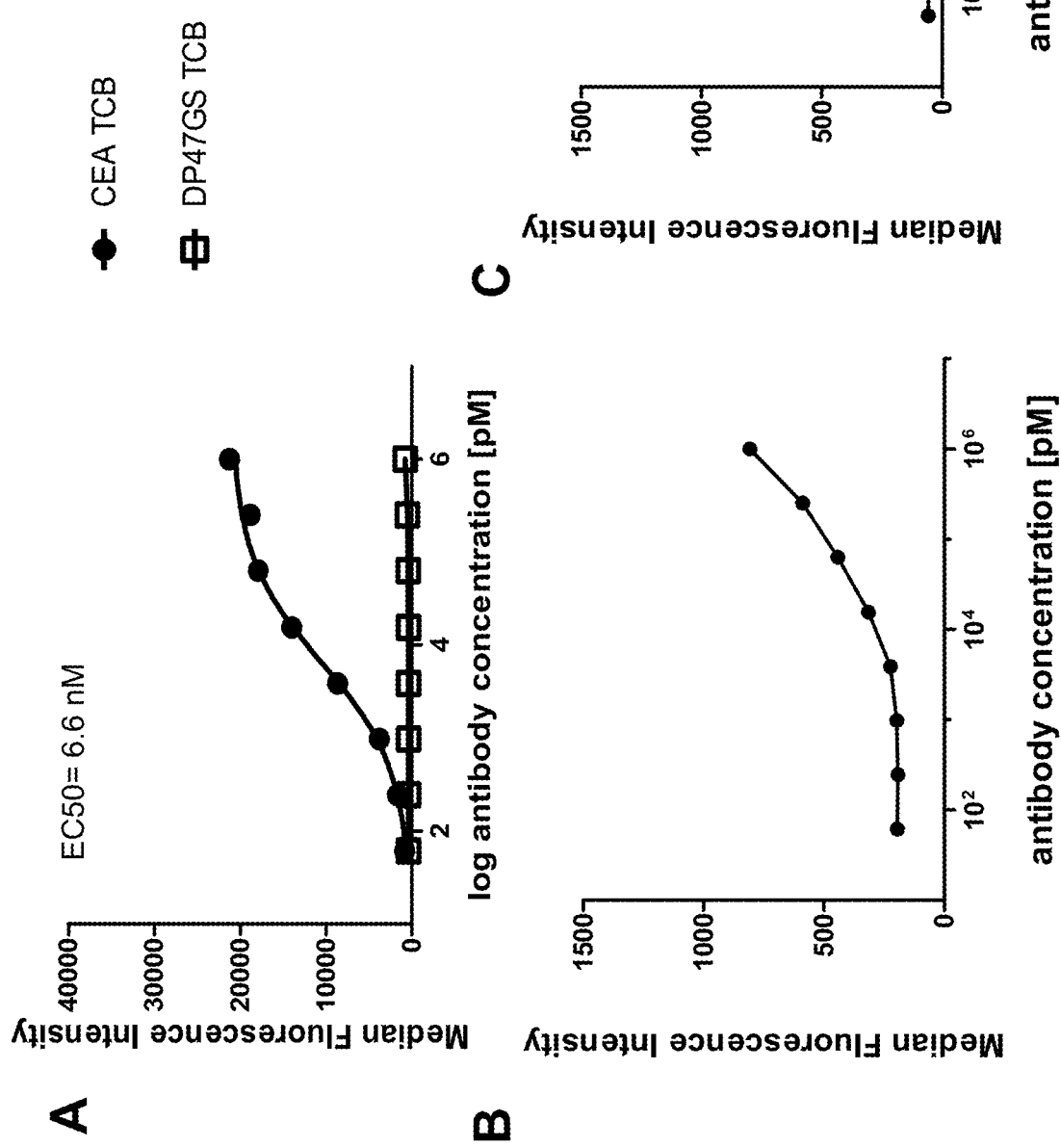

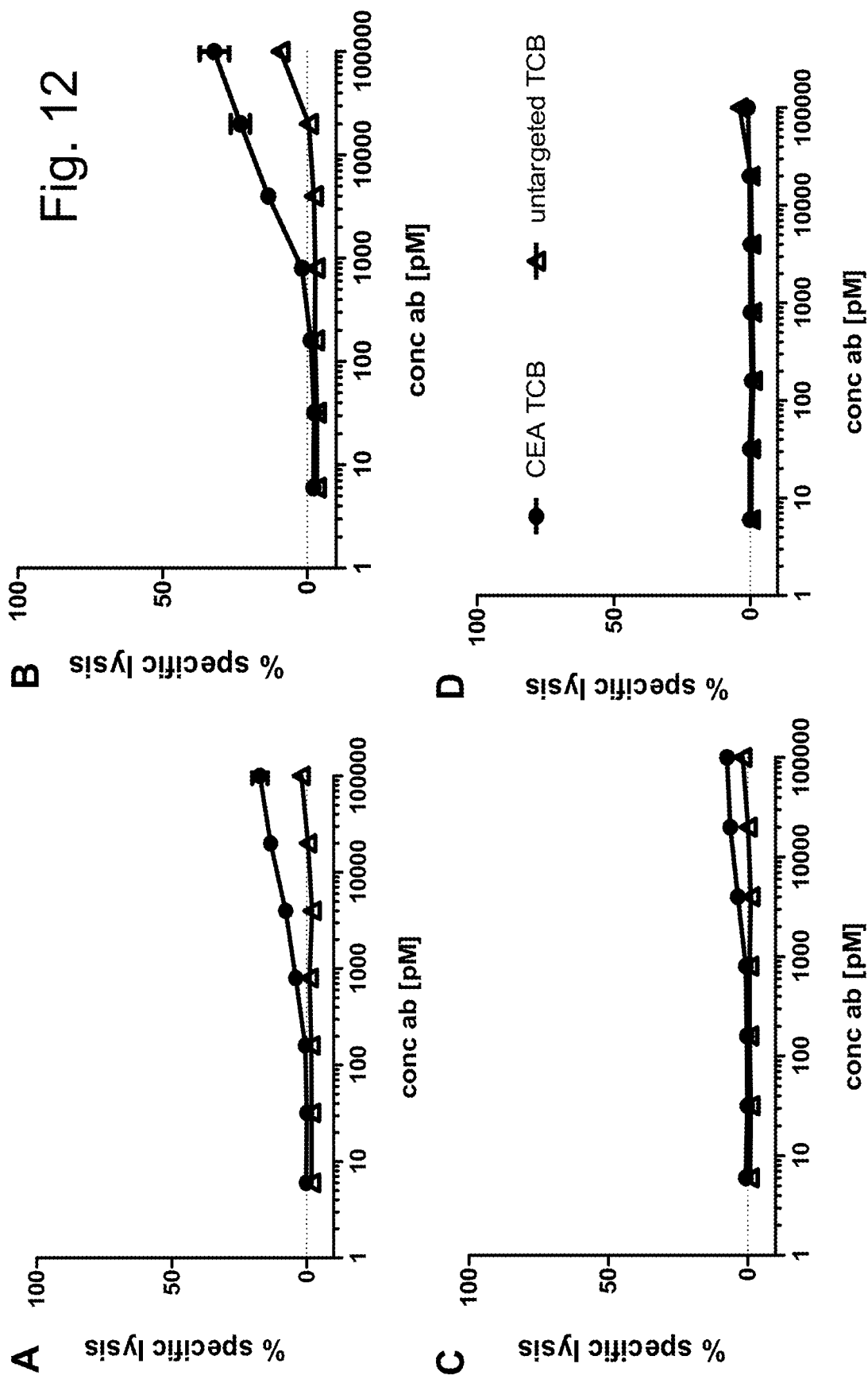

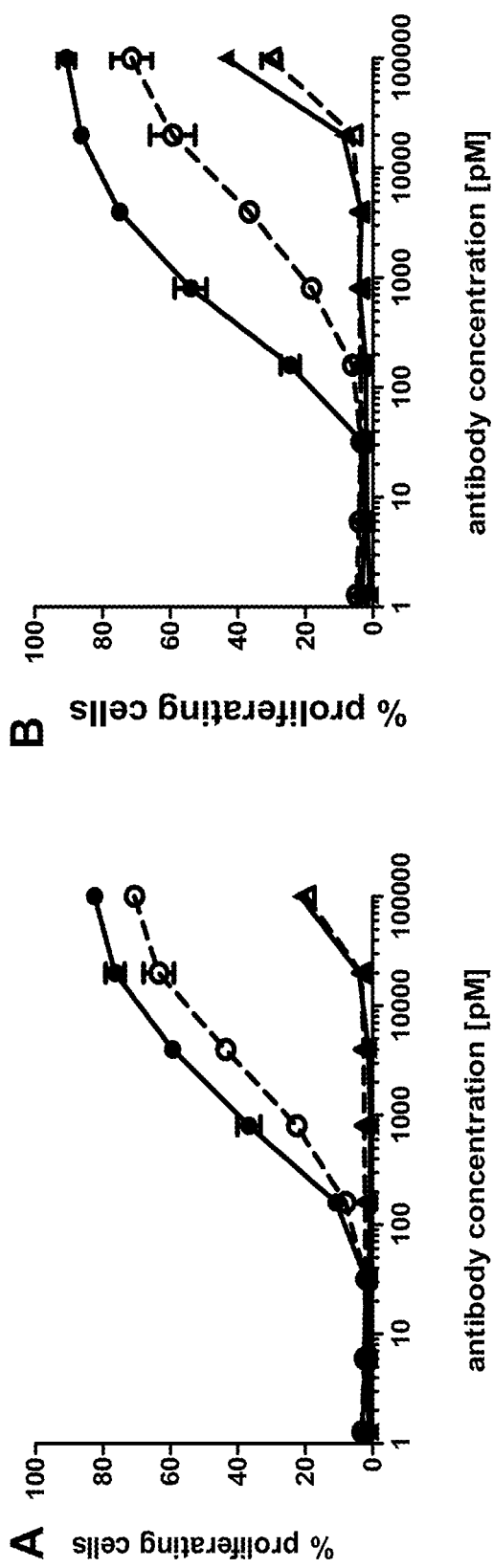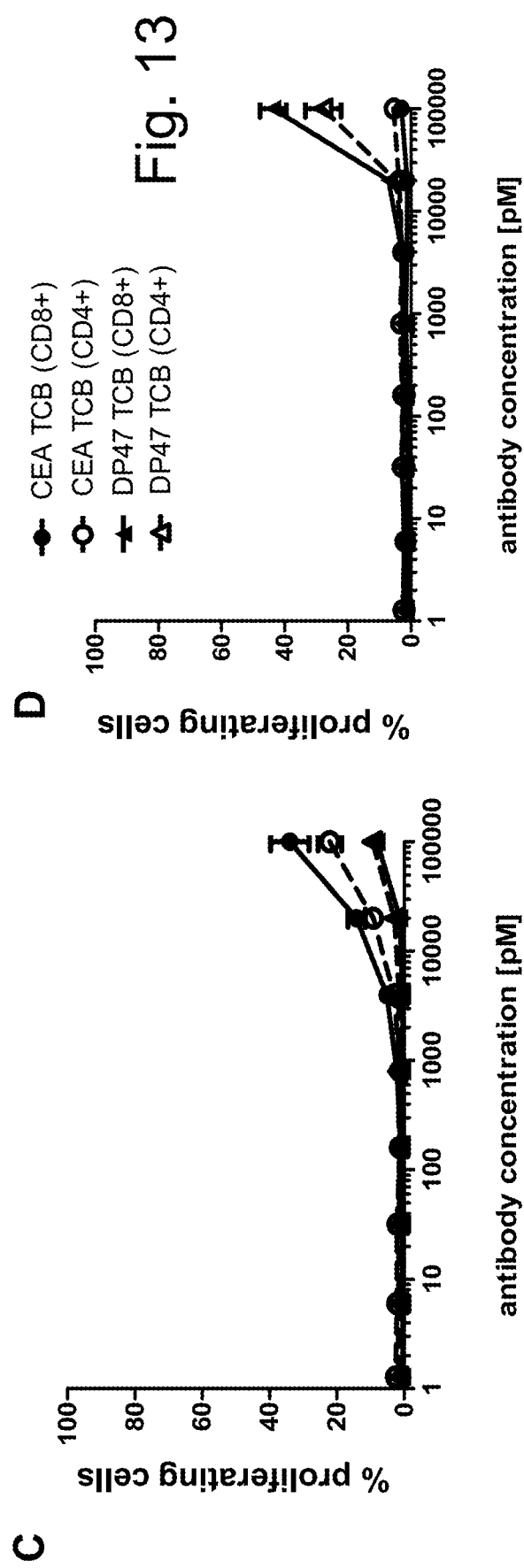
Fig. 13

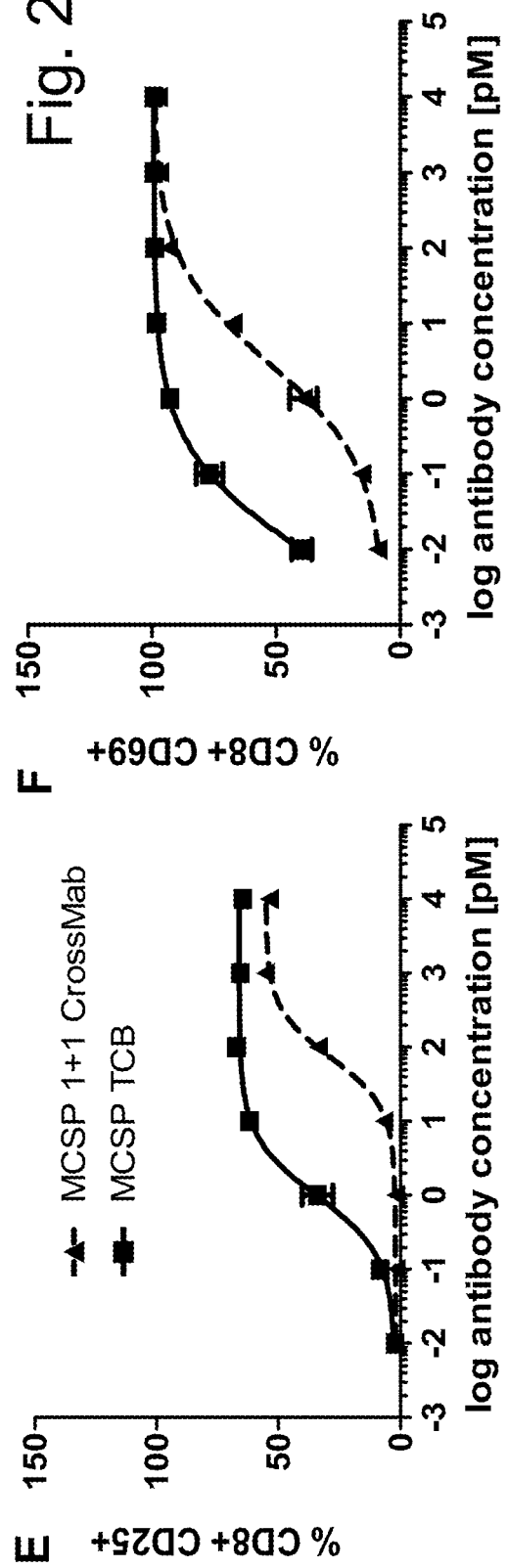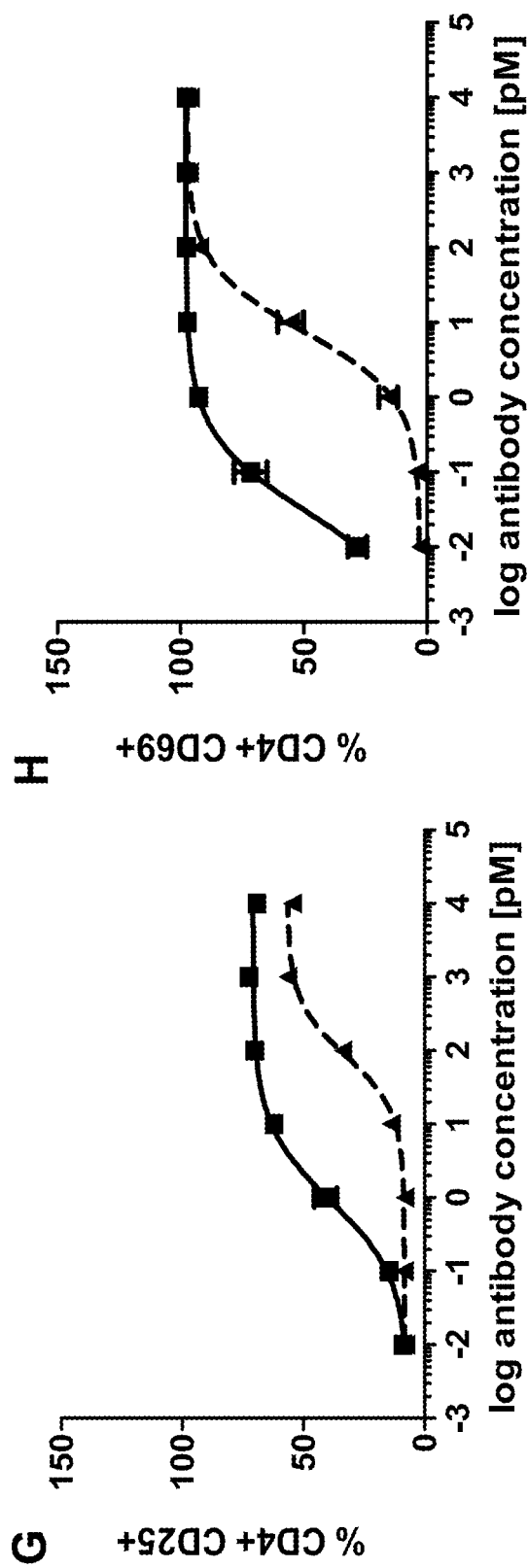
Fig. 24

BISPECIFIC T CELL ACTIVATING ANTIGEN BINDING MOLECULES

CROSS REFERENCE TO RELATED APPLICATIONS

This application is a divisional application of U.S. application Ser. No. 14/188,486, filed on Feb. 24, 2014, now U.S. Pat. No. 10,155,815, which claims benefit from European Patent Application No. 13156686.1, filed on Feb. 26, 2013.

FIELD OF THE INVENTION

The present invention generally relates to bispecific antigen binding molecules for activating T cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bäuerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). A more recent development are the so-called DART (dual affinity retargeting) molecules, which are based on the diabody format but feature a C-terminal disulfide bridge for additional stabilization (Moore et al., Blood 117, 4542-51 (2011)). The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The variety of formats that are being developed shows the great potential attributed to T cell re-direction and activation in immunotherapy. The task of generating bispecific antibodies suitable therefor is, however, by no means trivial, but involves a number of challenges that have to be met related to efficacy, toxicity, applicability and produceability of the antibodies.

Small constructs such as, for example, BiTE molecules—while being able to efficiently crosslink effector and target cells—have a very short serum half life requiring them to be administered to patients by continuous infusion. IgG-like formats on the other hand—while having the great benefit of a long half life—suffer from toxicity associated with the native effector functions inherent to IgG molecules. Their immunogenic potential constitutes another unfavorable feature of IgG-like bispecific antibodies, especially non-human formats, for successful therapeutic development. Finally, a major challenge in the general development of bispecific antibodies has been the production of bispecific antibody constructs at a clinically sufficient quantity and purity, due to the mispairing of antibody heavy and light chains of different specificities upon co-expression, which decreases the yield of the correctly assembled construct and results in a number of non-functional side products from which the desired bispecific antibody may be difficult to separate.

Given the difficulties and disadvantages associated with currently available bispecific antibodies for T cell mediated immunotherapy, there remains a need for novel, improved formats of such molecules. The present invention provides bispecific antigen binding molecules designed for T cell activation and re-direction that combine good efficacy and produceability with low toxicity and favorable pharmacokinetic properties.

SUMMARY OF THE INVENTION

In a first aspect the present invention provides a T cell activating bispecific antigen binding molecule comprising
(i) a first antigen binding moiety which is a Fab molecule capable of specific binding to CD3, comprising at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10;
(ii) a second antigen binding moiety which is a Fab molecule capable of specific binding to a target cell antigen.

In one embodiment the first antigen binding moiety which is a Fab molecule capable of specific binding to CD3 comprises a heavy chain variable region comprising an amino acid sequence that is at least about 95%, 96%, 97%, 98%, 99% or 100% identical to an amino acid sequence selected from the group of: SEQ ID NO: 3, SEQ ID NO: 32 and SEQ ID NO: 33 and a variable light chain comprising an amino acid sequence that is at least about 95%, 96%, 97%, 98%, 99% or 100% identical to an amino acid sequence selected from the group of: SEQ ID NO: 7 and SEQ ID NO: 31.

In one embodiment the first antigen binding moiety which is a Fab molecule capable of specific binding to CD3 comprises a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7.

In a specific embodiment the second antigen binding moiety is capable of specific binding to Carcinoembryonic Antigen (CEA, CEACAM5) and comprises at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In another specific embodiment, the second antigen binding moiety is capable of specific binding to CEA and comprises a heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In another specific embodiment, the second antigen binding moiety is capable of specific binding to MCSP (CSPG4) and comprises at least one heavy chain complementarity determining region (CDR) selected from the group consisting of SEQ ID NO: 14, SEQ ID NO: 15, SEQ ID NO: 16, SEQ ID NO: 35, SEQ ID NO: 37, SEQ ID NO: 38 and SEQ ID NO: 40 and at least one light chain CDR selected from the group of SEQ ID NO: 18, SEQ ID NO: 19, SEQ ID NO: 20, SEQ ID NO: 44, SEQ ID NO: 45, SEQ ID NO: 48, SEQ ID NO: 49 and SEQ ID NO: 50.

In another specific embodiment, the second antigen binding moiety is capable of specific binding to Melanoma-associated Chondroitin Sulfate Proteoglycan (MCSP, CSPG4) and comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 18, SEQ ID NO: 19 and SEQ ID NO: 20.

In another specific embodiment, the second antigen binding moiety is capable of specific binding to MCSP and comprises a heavy chain variable region comprising an amino acid sequence that is at least about 95%, 96%, 97%, 98%, 99% or 100% identical to an amino acid sequence selected from the group of SEQ ID NO: 13, SEQ ID NO: 34, SEQ ID NO: 36, SEQ ID NO: 39 and SEQ ID NO: 41 and a light chain variable region comprising an amino acid sequence that is at least about 95%, 96%, 97%, 98%, 99% or 100% identical to an amino acid sequence selected from the group of SEQ ID NO: 17, SEQ ID NO: 43, SEQ ID NO: 46, SEQ ID NO: 47 and SEQ ID NO: 51.

In another specific embodiment, the second antigen binding moiety is capable of specific binding to MCSP and comprises a heavy chain variable region comprising an amino acid sequence that is at least about 95%, 96%, 97%, 98%, 99% or 100% identical to the amino acid sequence of SEQ ID NO: 13 and a light chain variable region comprising an amino acid sequence that is at least about 95%, 96%, 97%, 98%, 99% or 100% identical to the amino acid sequence of SEQ ID NO: 17.

In a particular embodiment, the first antigen binding moiety is a crossover Fab molecule wherein either the variable or the constant regions of the Fab light chain and the Fab heavy chain are exchanged. In an even more particular embodiment, the first antigen binding moiety is a crossover Fab molecule wherein the constant regions of the Fab light chain and the Fab heavy chain are exchanged.

In one embodiment, the second antigen binding moiety is a conventional Fab molecule.

In a further particular embodiment, not more than one antigen binding moiety capable of specific binding to CD3 is present in the T cell activating bispecific antigen binding molecule (i.e. the T cell activating bispecific antigen binding molecule provides monovalent binding to CD3).

In a further embodiment said T cell activating bispecific antigen binding molecule further comprises a third antigen binding moiety which is a Fab molecule capable of specific binding to a target cell antigen. In one embodiment said third antigen binding molecule is a conventional Fab molecule. In one embodiment said third antigen binding molecule is identical to the second antigen binding moiety.

In a particular embodiment said T cell activating bispecific antigen binding molecule further comprises a third antigen binding moiety which is a Fab molecule capable of specific binding to CEA, and comprises at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In a particular embodiment said T cell activating bispecific antigen binding molecule further comprises a third antigen binding moiety which is a Fab molecule capable of specific binding to CEA, and comprises a heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In one embodiment said T cell activating bispecific antigen binding molecule further comprises a third antigen binding moiety which is a Fab molecule capable of specific binding to MCSP, and comprises at least one heavy chain complementarity determining region (CDR) selected from the group consisting of SEQ ID NO: 14, SEQ ID NO: 15, SEQ ID NO: 16, SEQ ID NO: 35, SEQ ID NO: 37, SEQ ID NO: 38 and SEQ ID NO: 40 and at least one light chain CDR selected from the group of SEQ ID NO: 18, SEQ ID NO: 19, SEQ ID NO: 20, SEQ ID NO: 44, SEQ ID NO: 45, SEQ ID NO: 48, SEQ ID NO: 49 and SEQ ID NO: 50.

In a particular embodiment said T cell activating bispecific antigen binding molecule further comprises a third antigen binding moiety which is a Fab molecule capable of specific binding to MCSP, and comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 18, SEQ ID NO: 19 and SEQ ID NO: 20.

In one embodiment said T cell activating bispecific antigen binding molecule further comprises a third antigen binding moiety which is a Fab molecule capable of specific binding to MCSP, and comprises a heavy chain variable region comprising an amino acid sequence that is at least about 95%, 96%, 97%, 98%, 99% or 100% identical to an amino acid sequence selected from the group of SEQ ID NO: 13, SEQ ID NO: 34, SEQ ID NO: 36, SEQ ID NO: 39 and SEQ ID NO: 41 and a light chain variable region comprising an amino acid sequence that is at least about 95%, 96%, 97%, 98%, 99% or 100% identical to the amino acid sequence selected from the group of SEQ ID NO: 17, SEQ ID NO: 43, SEQ ID NO: 46, SEQ ID NO: 47 and SEQ ID NO: 51.

In a particular embodiment said T cell activating bispecific antigen binding molecule further comprises a third antigen binding moiety which is a Fab molecule capable of specific binding to MCSP, and comprises a heavy chain variable region comprising an amino acid sequence that is at least about 95%, 96%, 97%, 98%, 99% or 100% identical to the amino acid sequence of SEQ ID NO: 13 and a light chain variable region comprising an amino acid sequence that is at least about 95%, 96%, 97%, 98%, 99% or 100% identical to the amino acid sequence of SEQ ID NO: 17.

In some embodiments, the first and the second antigen binding moiety of the T cell activating bispecific antigen binding molecule are fused to each other, optionally via a peptide linker. In one such embodiment, the second antigen binding moiety is fused at the C-terminus of the Fab heavy chain to the N-terminus of the Fab heavy chain of the first antigen binding moiety. In another such embodiment, the first antigen binding moiety is fused at the C-terminus of the Fab heavy chain to the N-terminus of the Fab heavy chain of the second antigen binding moiety. In embodiments wherein either (i) the second antigen binding moiety is fused at the C-terminus of the Fab heavy chain to the N-terminus of the Fab heavy chain of the first antigen binding moiety or (ii) the first antigen binding moiety is fused at the C-terminus of the Fab heavy chain to the N-terminus of the Fab heavy chain of the second antigen binding moiety, additionally the Fab light chain of the first antigen binding moiety and the Fab light chain of the second antigen binding moiety may be fused to each other, optionally via a peptide linker.

In one embodiment said T cell activating bispecific antigen binding molecule further comprises (iii) an Fc domain composed of a first and a second subunit capable of stable association.

In one embodiment, the second antigen binding moiety of the T cell activating bispecific antigen binding molecule is fused at the C-terminus of the Fab heavy chain to the N-terminus of the first or the second subunit of the Fc domain. In another embodiment, the first antigen binding moiety is fused at the C-terminus of the Fab heavy chain to the N-terminus of the first or second subunit of the Fc domain. In one embodiment, the first and the second antigen binding moiety of the T cell activating bispecific antigen binding molecule are each fused at the C-terminus of the Fab heavy chain to the N-terminus of one of the subunits of the Fc domain.

In one embodiment, the third antigen binding moiety is fused at the C-terminus of the Fab heavy chain to the N-terminus of the first or second subunit of the Fc domain. In a particular embodiment, the second and the third antigen binding moiety of the T cell activating antigen binding molecule are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second antigen binding moiety. In another particular embodiment, the first and the third antigen binding moiety of the T cell activating antigen binding molecule are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. The components of the T cell activating bispecific antigen binding molecule may be fused directly or through suitable peptide linkers. In one embodiment the first and the third antigen binding moiety and the Fc domain are part of an immunoglobulin molecule.

In a particular embodiment the immunoglobulin molecule is an IgG class immunoglobulin. In an even more particular embodiment the immunoglobulin is an $IgG_1$ subclass immunoglobulin. In another embodiment, the immunoglobulin is an $IgG_4$ subclass immunoglobulin.

In a particular embodiment, the Fc domain is an IgG Fc domain. In a specific embodiment, the Fc domain is an $IgG_1$ Fc domain. In another specific embodiment, the Fc domain is an $IgG_4$ Fc domain.

In an even more specific embodiment, the Fc domain is an $IgG_4$ Fc domain comprising the amino acid substitution S228P (Kabat numbering). In particular embodiments the Fc domain is a human Fc domain.

In particular embodiments the Fc domain comprises a modification promoting the association of the first and the second Fc domain subunit. In a specific such embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

In a particular embodiment the Fc domain exhibits reduced binding affinity to an Fc receptor and/or reduced effector function, as compared to a native $IgG_1$ Fc domain. In certain embodiments the Fc domain is engineered to have reduced binding affinity to an Fc receptor and/or reduced effector function, as compared to a non-engineered Fc domain. In one embodiment, the Fc domain comprises one or more amino acid substitution that reduces binding to an Fc receptor and/or effector function. In one embodiment, the one or more amino acid substitution in the Fc domain that reduces binding to an Fc receptor and/or effector function is at one or more position selected from the group of L234, L235, and P329 (Kabat numbering). In particular embodiments, each subunit of the Fc domain comprises three amino acid substitutions that reduce binding to an Fc receptor and/or effector function wherein said amino acid substitutions are L234A, L235A and P329G. In one such embodiment, the Fc domain is an $IgG_1$ Fc domain, particularly a human $IgG_1$ Fc domain. In other embodiments, each subunit of the Fc domain comprises two amino acid substitutions that reduce binding to an Fc receptor and/or effector function wherein said amino acid substitutions are L235E and P329G. In one such embodiment, the Fc domain is an $IgG_4$ Fc domain, particularly a human $IgG_4$ Fc domain. In one embodiment, the Fc domain of the T cell activating bispecific antigen binding molecule is an $IgG_4$ Fc domain and comprises the amino acid substitutions L235E and S228P (SPLE).

In one embodiment the Fc receptor is an Fcγ receptor. In one embodiment the Fc receptor is a human Fc receptor. In one embodiment, the Fc receptor is an activating Fc receptor. In a specific embodiment, the Fc receptor is human FcγRIIa, FcγRI, and/or FcγRIIIa. In one embodiment, the effector function is antibody-dependent cell-mediated cytotoxicity (ADCC).

According to another aspect of the invention there is provided an isolated polynucleotide encoding a T cell activating bispecific antigen binding molecule of the invention or a fragment thereof. The invention also encompasses polypeptides encoded by the polynucleotides of the invention. The invention further provides an expression vector comprising the isolated polynucleotide of the invention, and a host cell comprising the isolated polynucleotide or the expression vector of the invention. In some embodiments the host cell is a eukaryotic cell, particularly a mammalian cell.

In another aspect is provided a method of producing the T cell activating bispecific antigen binding molecule of the invention, comprising the steps of a) culturing the host cell of the invention under conditions suitable for the expression of the T cell activating bispecific antigen binding molecule and b) recovering the T cell activating bispecific antigen binding molecule. The invention also encompasses a T cell activating bispecific antigen binding molecule produced by the method of the invention.

The invention further provides a pharmaceutical composition comprising the T cell activating bispecific antigen binding molecule of the invention and a pharmaceutically acceptable carrier.

Also encompassed by the invention are methods of using the T cell activating bispecific antigen binding molecule and pharmaceutical composition of the invention. In one aspect the invention provides a T cell activating bispecific antigen binding molecule or a pharmaceutical composition of the invention for use as a medicament. In one aspect is provided a T cell activating bispecific antigen binding molecule or a pharmaceutical composition according to the invention for use in the treatment of a disease in an individual in need thereof. In a specific embodiment the disease is cancer.

Also provided is the use of a T cell activating bispecific antigen binding molecule of the invention for the manufacture of a medicament for the treatment of a disease in an individual in need thereof; as well as a method of treating a disease in an individual, comprising administering to said individual a therapeutically effective amount of a composition comprising the T cell activating bispecific antigen binding molecule according to the invention in a pharmaceutically acceptable form. In a specific embodiment the disease is cancer. In any of the above embodiments the individual preferably is a mammal, particularly a human.

The invention also provides a method for inducing lysis of a target cell, particularly a tumor cell, comprising contacting a target cell with a T cell activating bispecific antigen binding molecule of the invention in the presence of a T cell, particularly a cytotoxic T cell.

BRIEF DESCRIPTION OF THE DRAWINGS

FIG. 2. Alignment of affinity matured anti-MCSP clones compared to the non-matured parental clone (M4-3 ML2).

FIG. 11. Binding of CEA TCB (SEQ ID NOs: 22, 56, 57 and 58) to CEA-expressing A549 lung adenocarcinoma cells (A) and CD3-expressing immortalized human and cynomolgus T lymphocyte lines (Jurkat (B) and HSC-F (C), respectively).

"Untargeted TCB": bispecific antibody engaging CD3 but no second antigen (SEQ ID NOs: 59, 60, 61 and 62).

Figure 15:
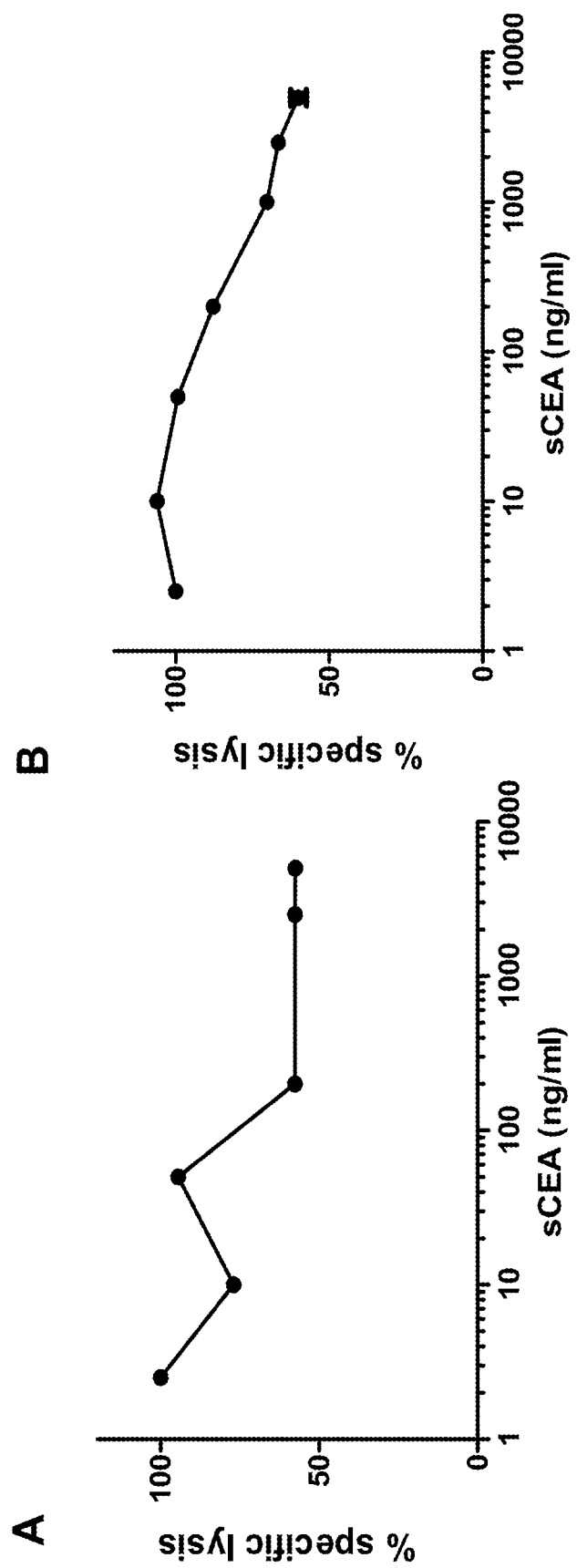

FIG. 15. T cell-mediated killing of CEA-expressing LS180 tumor target cells induced by CEA TCB (SEQ ID NOs: 22, 56, 57 and 58) in presence of increasing concentrations of shed CEA (sCEA), detected 24 h (A) or 48 h (B) after incubation with the CEA TCB and sCEA.

Figure 16:
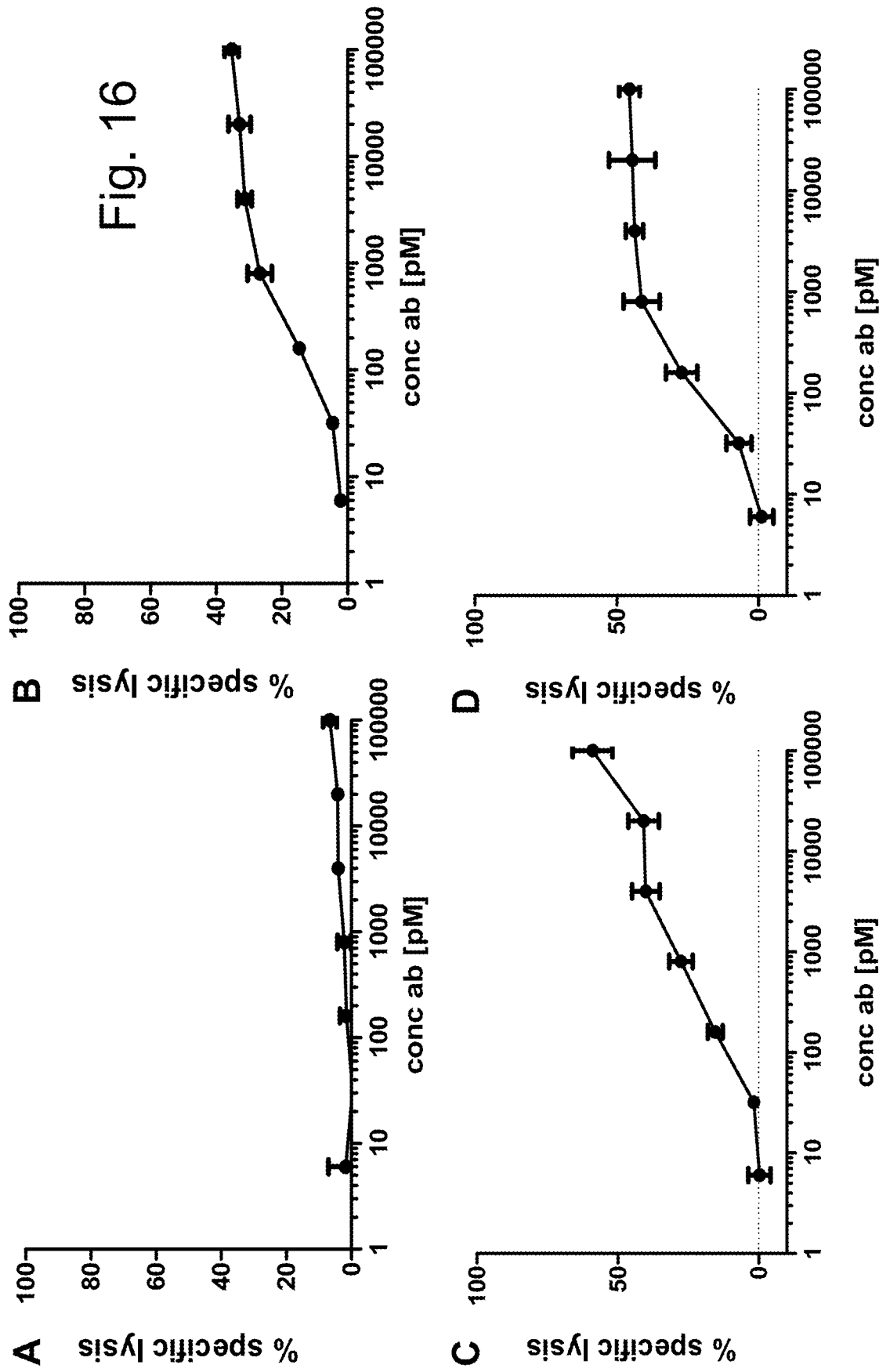

FIG. 16. T cell-mediated killing of A549 (lung adenocarcinoma) cells overexpressing human CEA (A549-hCEA), assessed 21 h (A, B) and 40 h (C, D) after incubation with CEA TCB (SEQ ID NOs: 22, 56, 57 and 58) and human PBMCs (A, C) or cynomolgus PBMCs (B, D) as effector cells.

Figure 17:
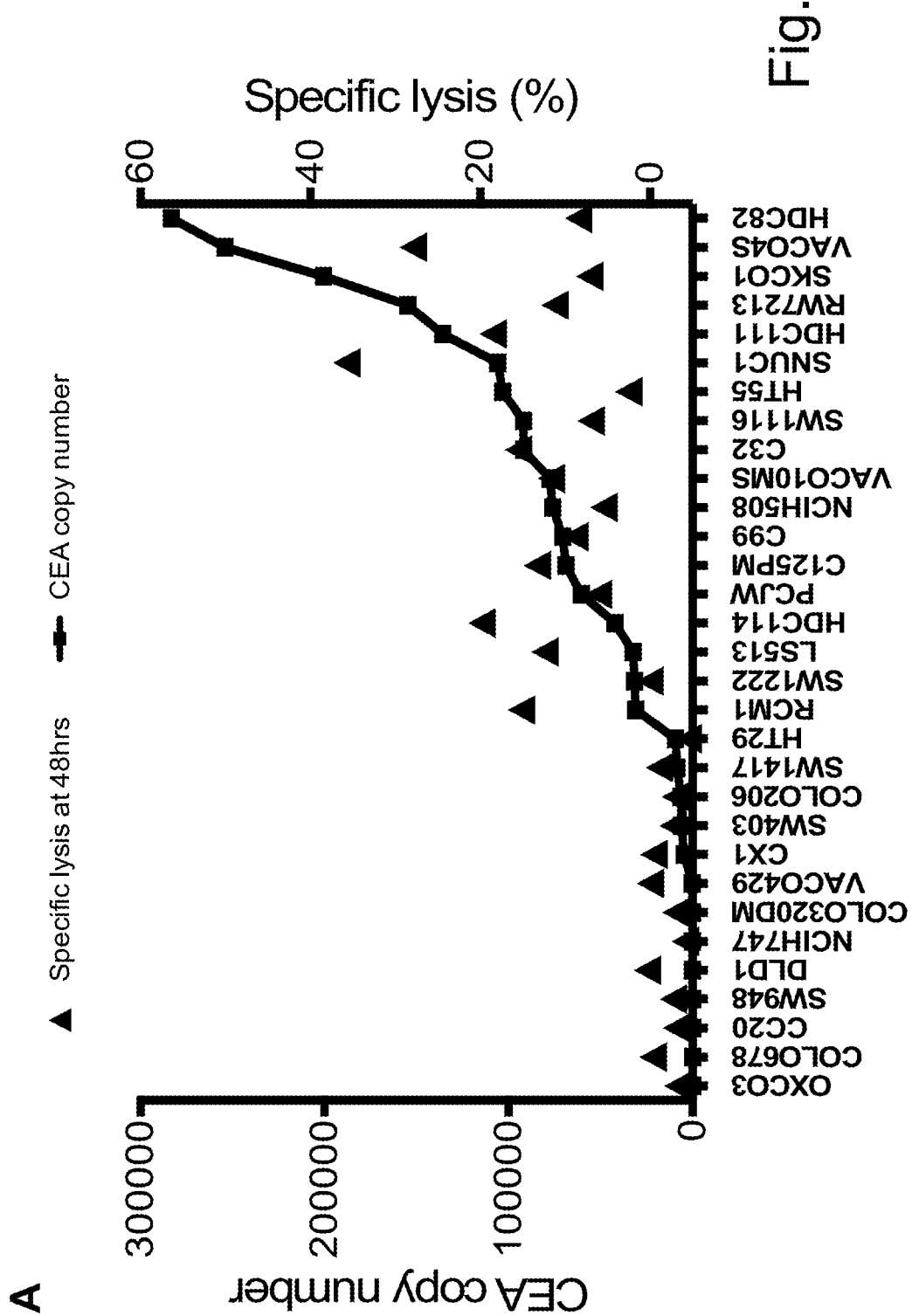
Figure 17:
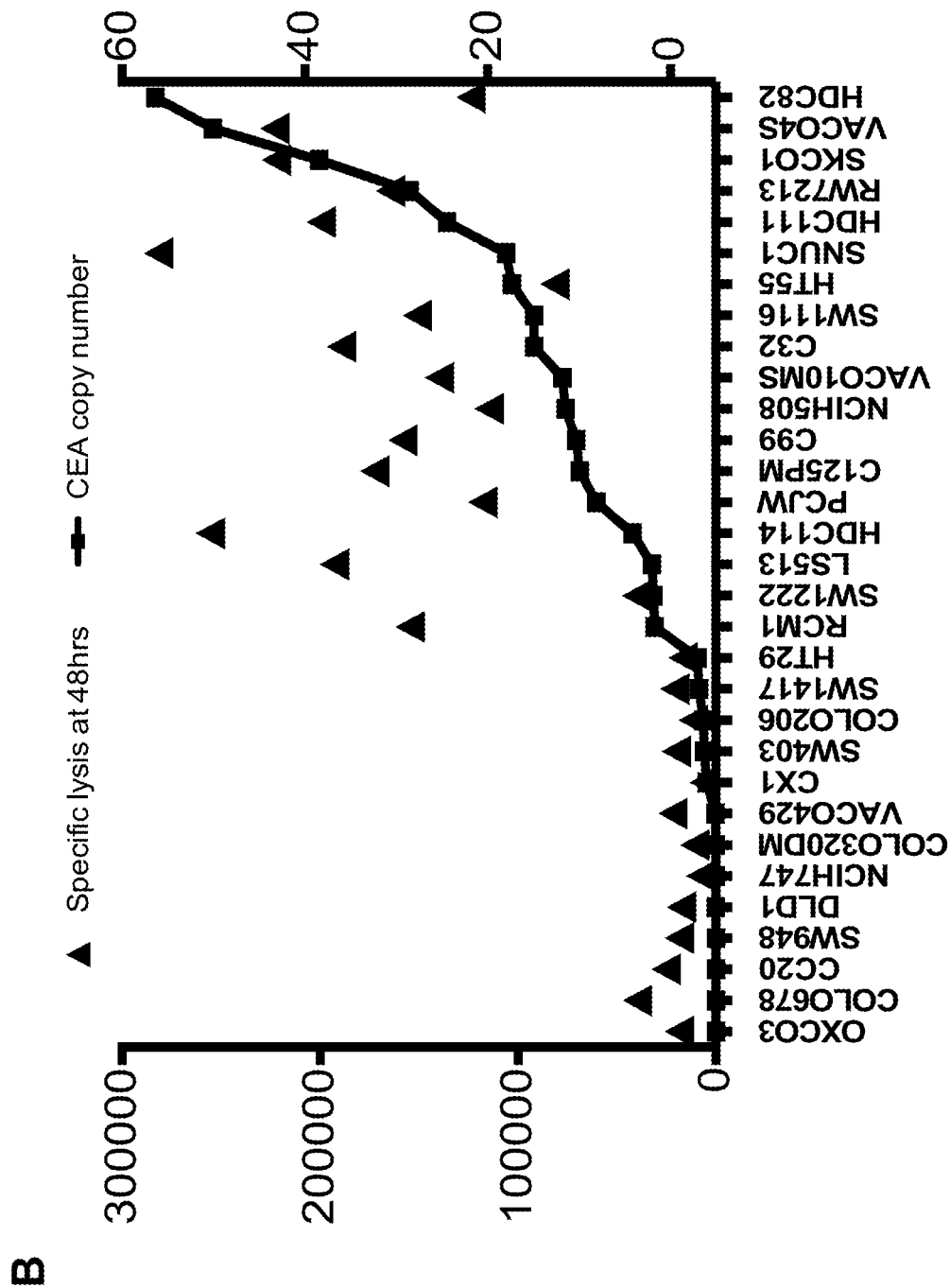
Figure 17:
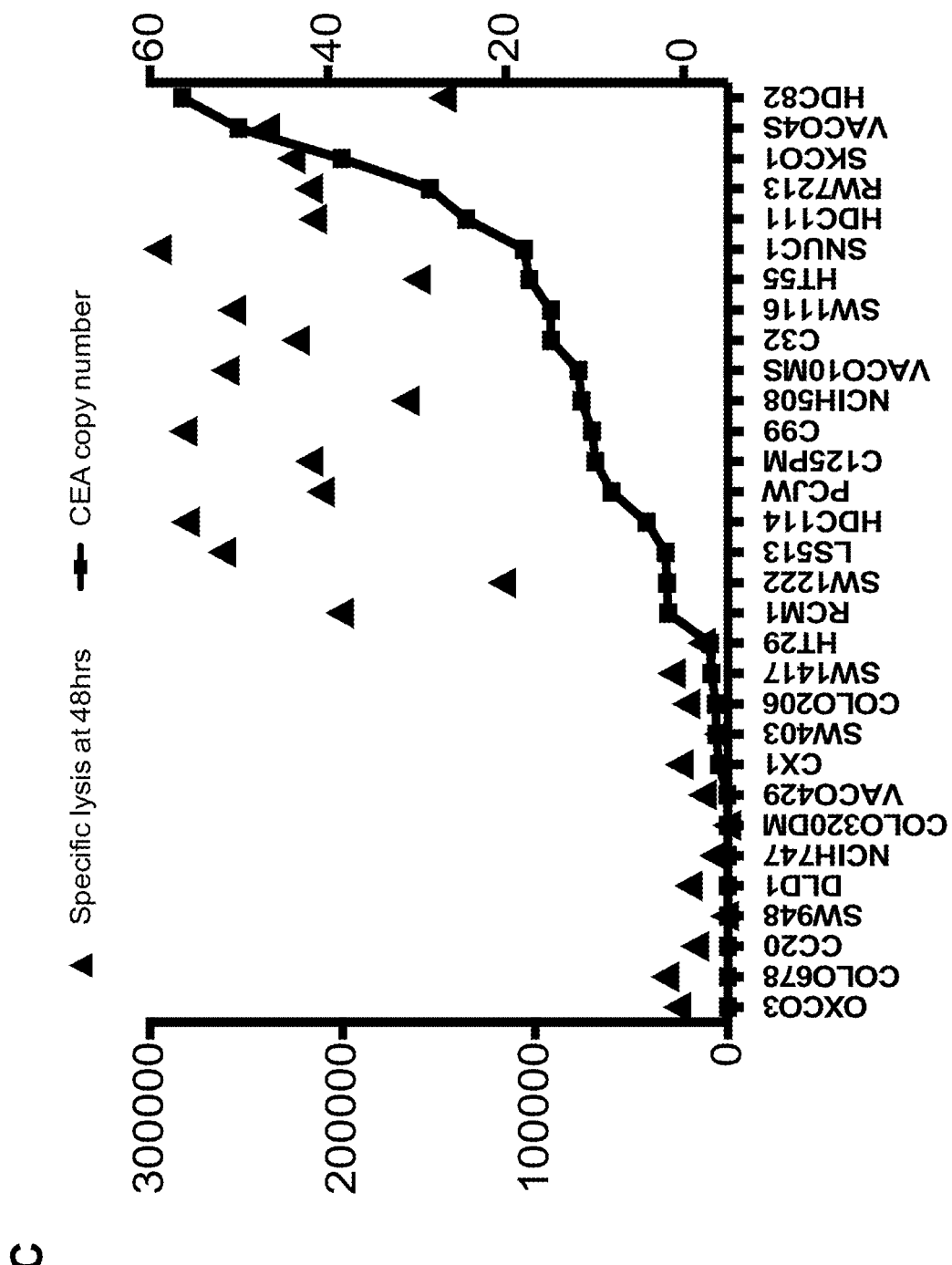
Figure 17:
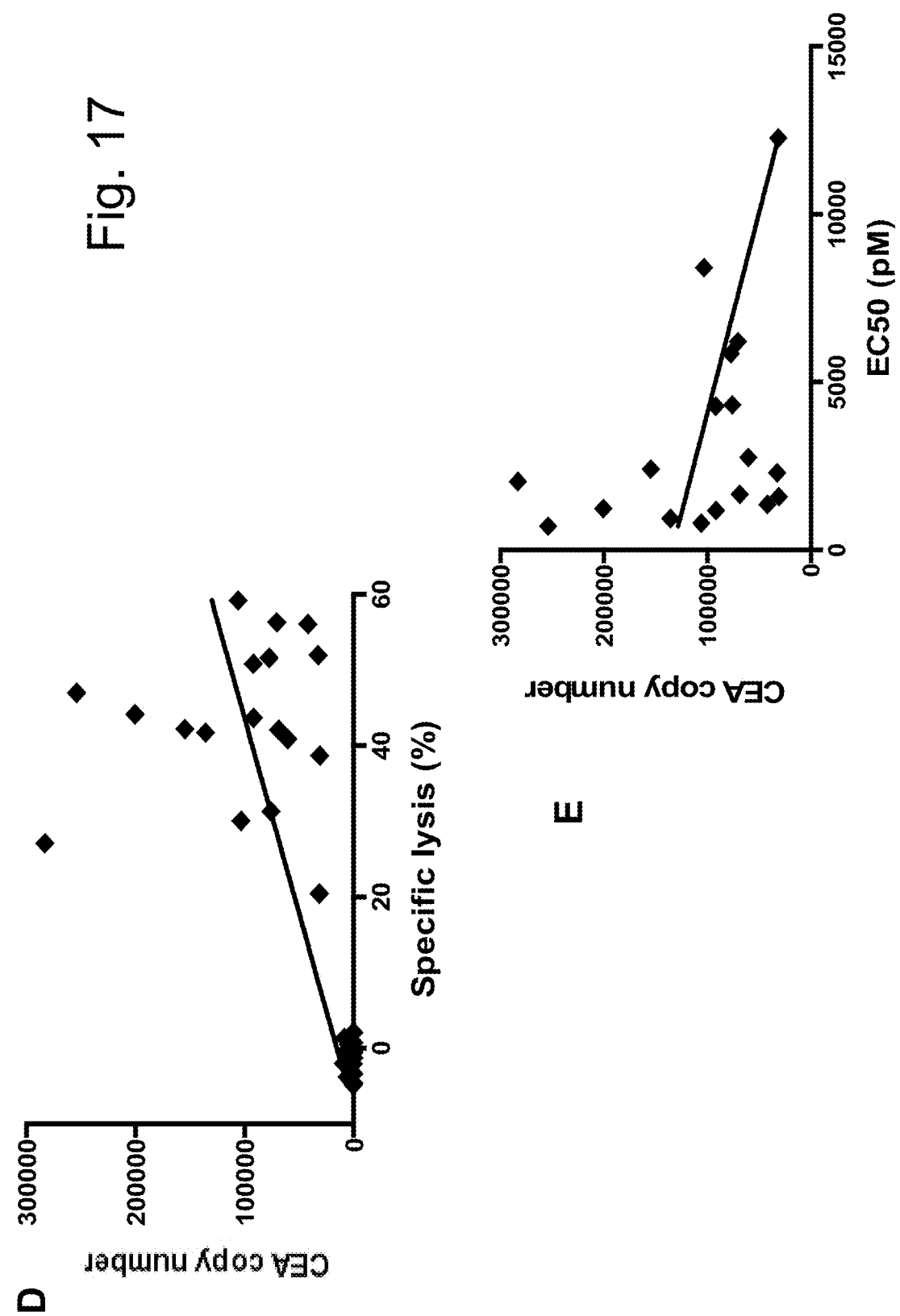

FIG. 17. T cell-mediated killing of CEA-expressing human colorectal cancer cell lines induced by CEA TCB (SEQ ID NOs: 22, 56, 57 and 58) at 0.8 nM (A), 4 nM (B) and 20 nM (C). (D) correlation between CEA expression and % specific lysis at 20 nM of CEA TCB, (E) correlation between CEA expression and $EC_{50}$ of CEA TCB.

Figure 18:
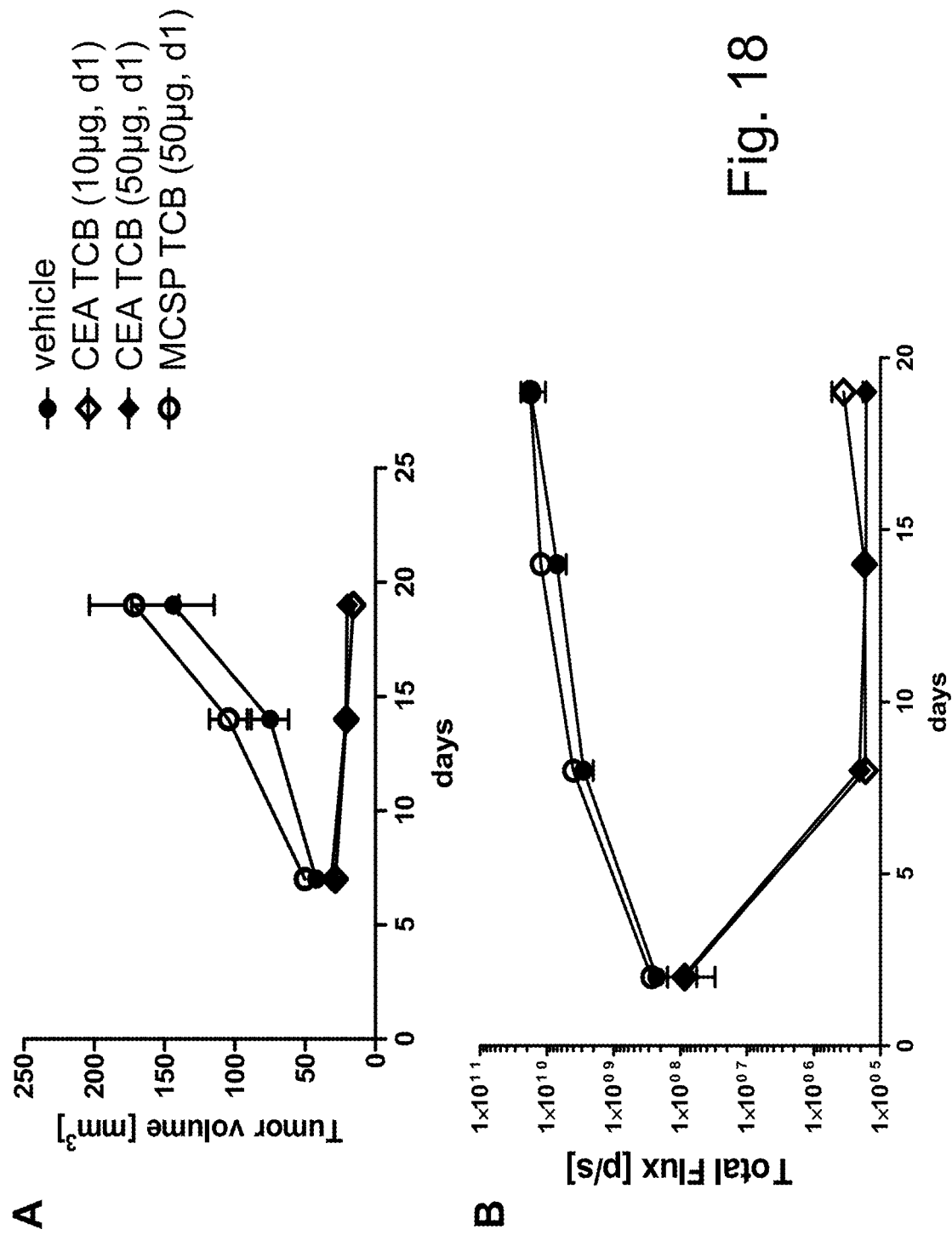
Figure 18:
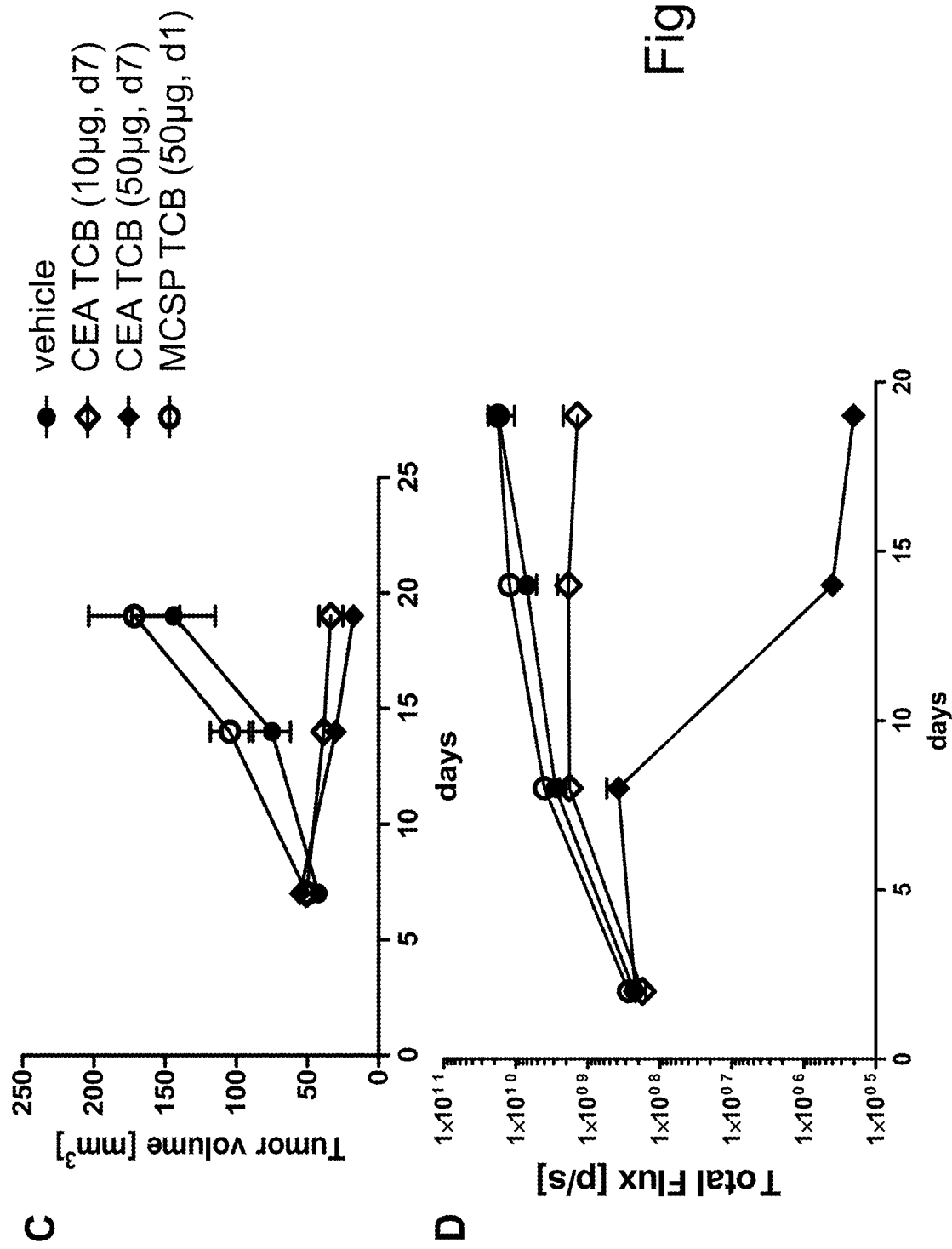

FIG. 18. In vivo anti-tumor efficacy of CEA TCB (SEQ ID NOs: 22, 56, 57 and 58) in a LS174T-fluc2 human colon carcinoma co-grafted with human PBMC (E:T ratio 5:1). Results show average and SEM from 12 mice of tumor volume measured by caliper (A and C) and by bioluminescence (Total Flux, B and D) in the different study groups. (A, B) early treatment starting at day 1, (C, D) delayed treatment starting at day 7. The MCSP TCB (SEQ ID NOs: 12, 53, 54 and 55) was used as negative control.

Figure 19:
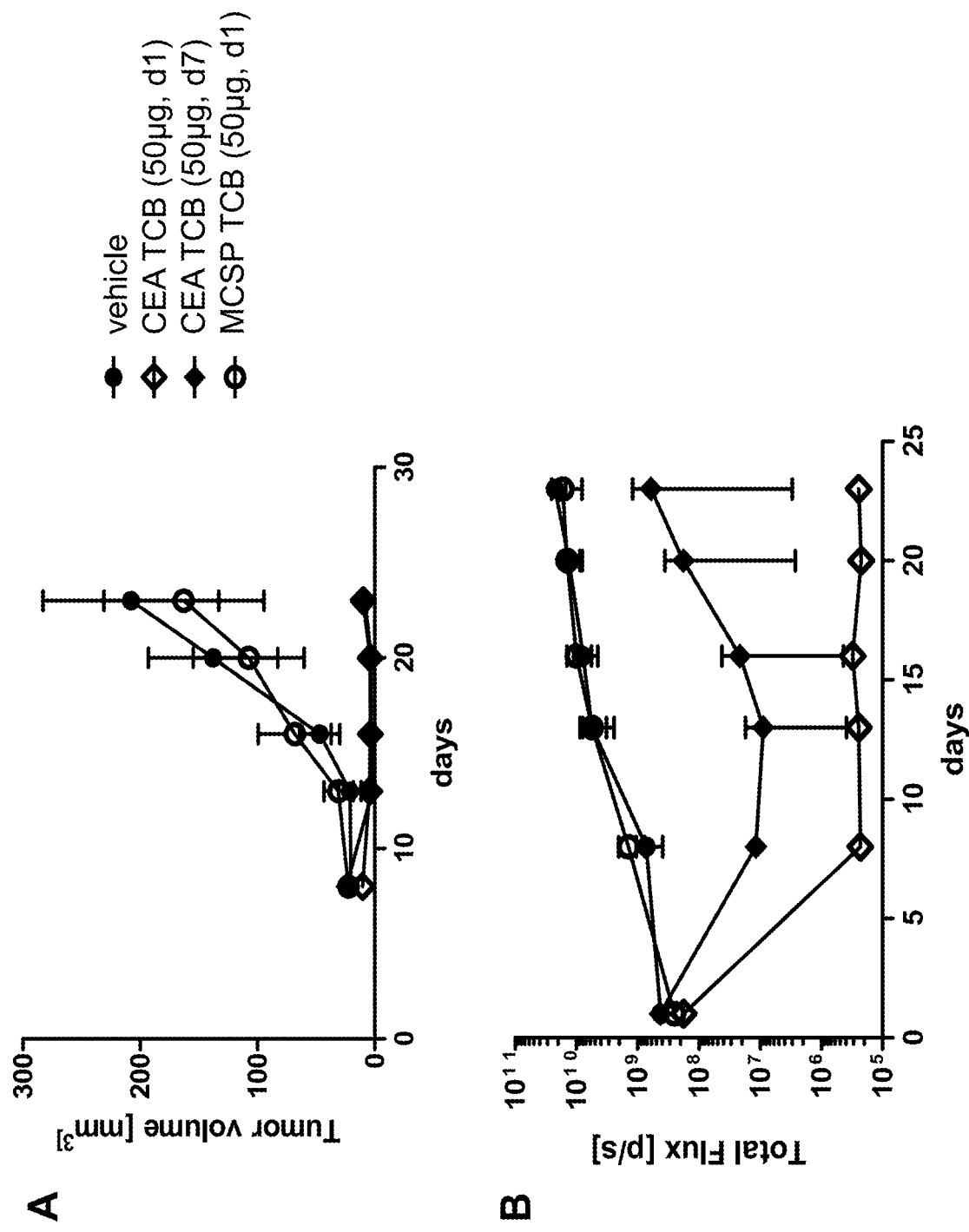

FIG. 19. In vivo anti-tumor efficacy of CEA TCB (SEQ ID NOs: 22, 56, 57 and 58) in a LS174T-fluc2 human colon carcinoma co-grafted with human PBMC (E:T ratio 1:1). Results show average and SEM from 10 mice of tumor volume measured by caliper (A) and by bioluminescence (Total Flux, B) in the different study groups. The MCSP TCB (SEQ ID NOs: 12, 53, 54 and 55) was used as negative control.

Figure 20:
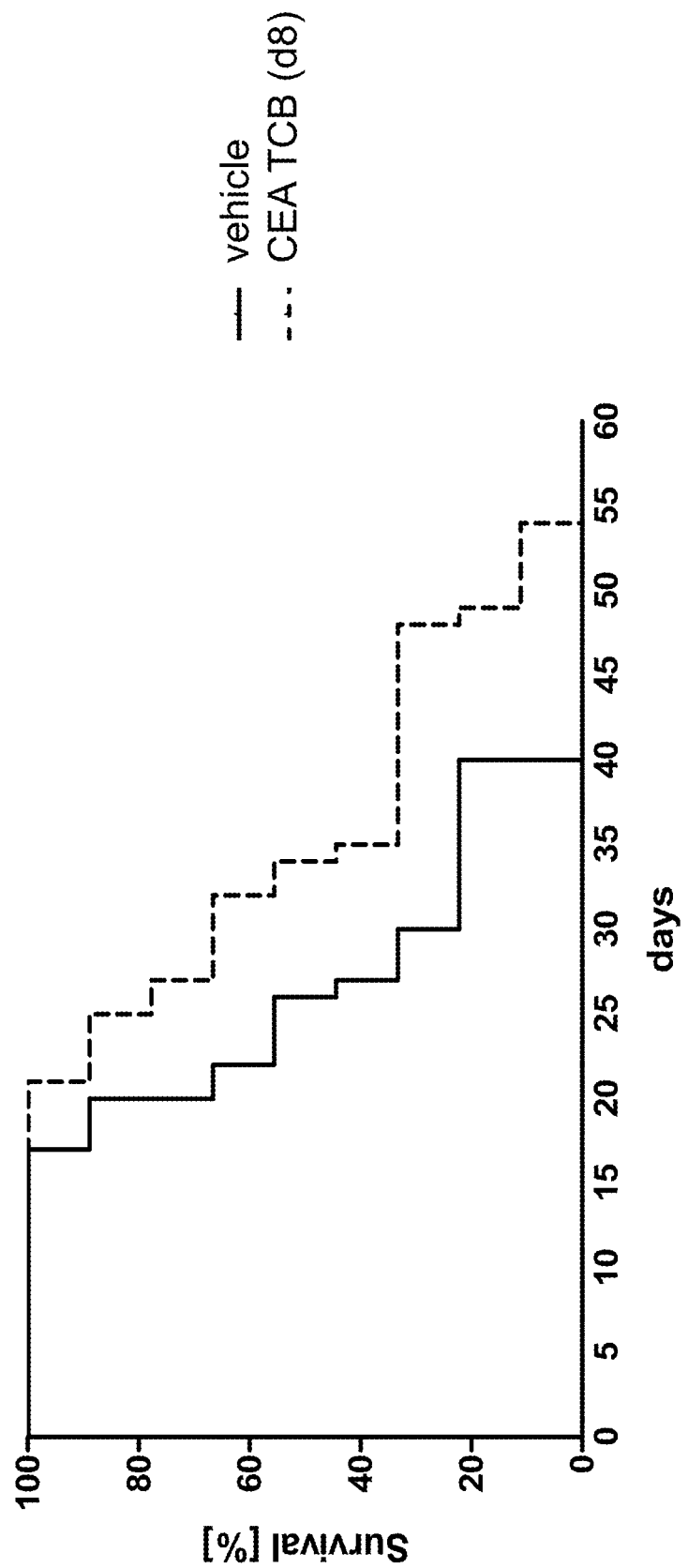

FIG. 20. In vivo efficacy of murinized CEA TCB in a Panco2-huCEA orthotopic tumor model in immunocompetent huCD3ε/huCEA transgenic mice.

Figure 21:
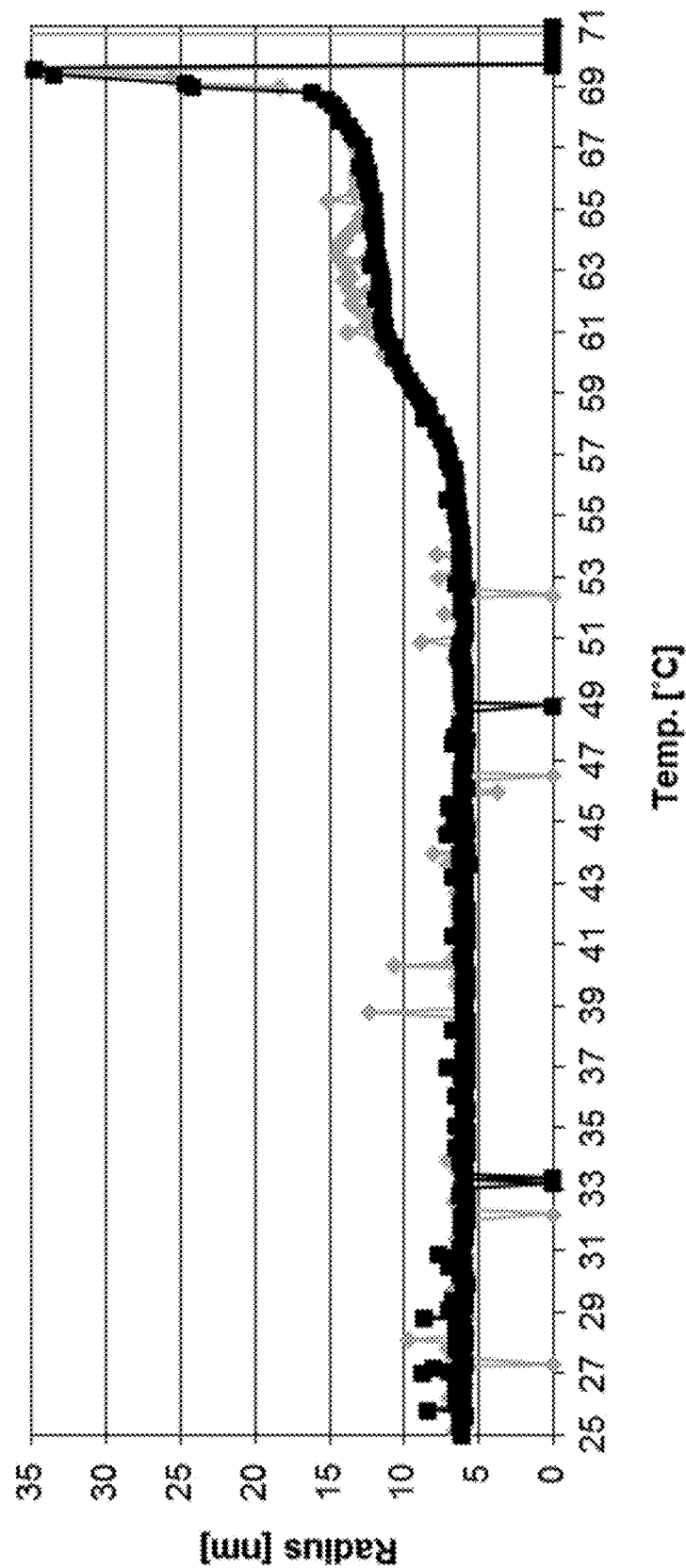

FIG. 21. Thermal stability of CEA TCB. Dynamic Light Scattering measured in a temperature ramp from 25-75° C. at 0.05° C./min. Duplicate is shown in grey.

Figure 22:
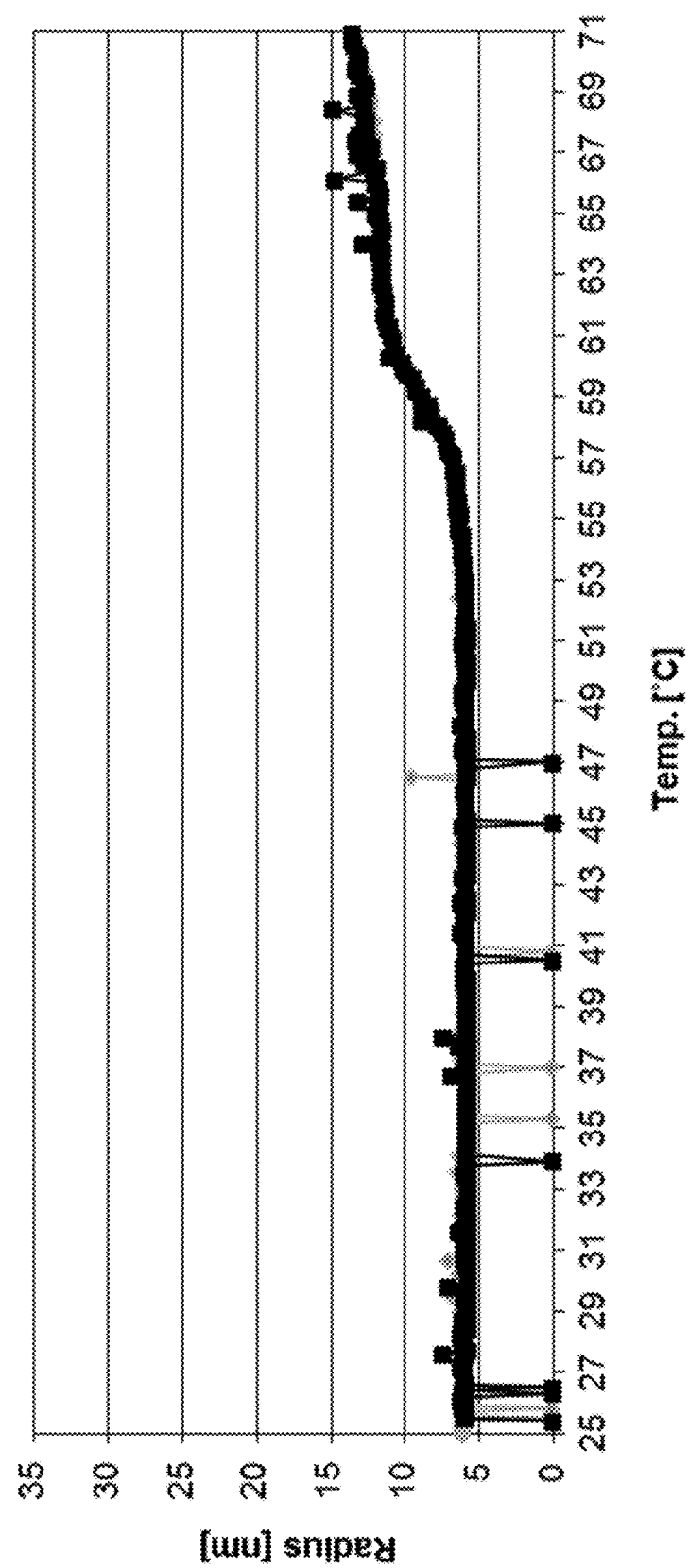

FIG. 22. Thermal stability of MCSP TCB. Dynamic Light Scattering measured in a temperature ramp from 25-75° C. at 0.05° C./min. Duplicate is shown as grey line.

Figure 23:
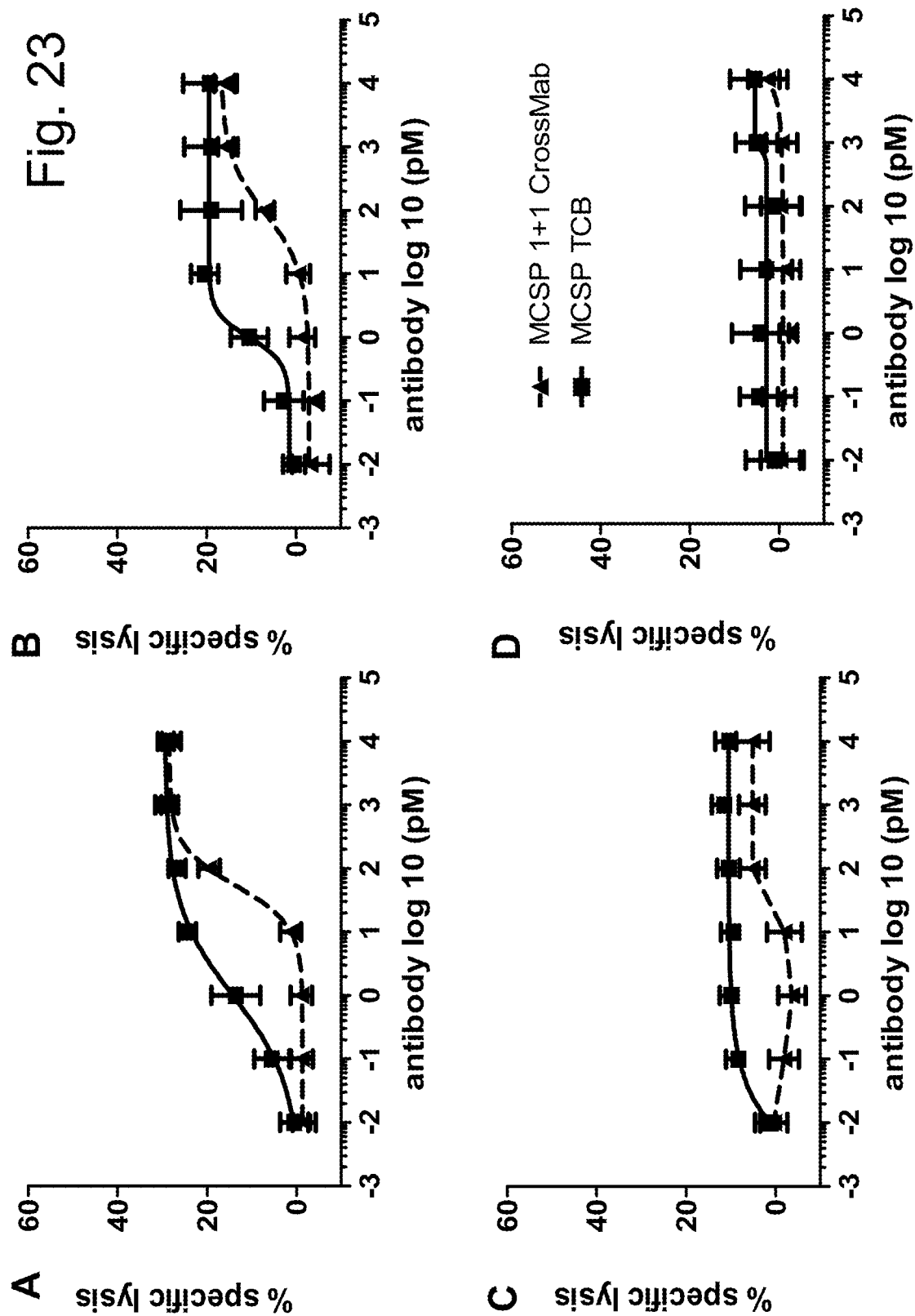
Figure 23:
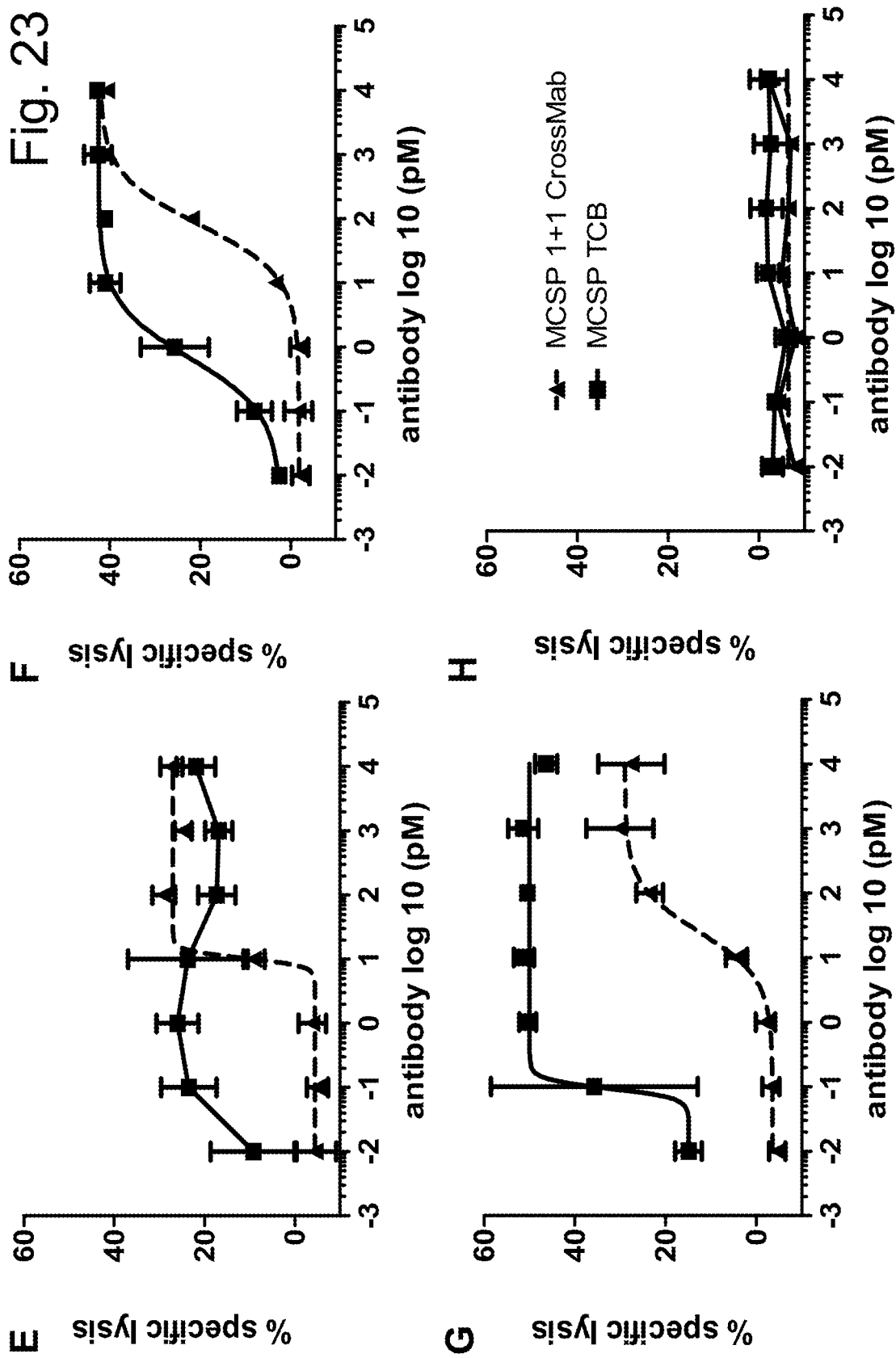

FIG. 23. T cell-mediated killing induced by MCSP TCB (SEQ ID NOs: 12, 53, 54 and 55) and MCSP 1+1 CrossMab TCB antibodies of (A) A375 (high MCSP), (B) MV-3 (medium MCSP) and (C) HCT-116 (low MCSP) tumor target cells. (D) LS180 (MCSP negative tumor cell line) was used as negative control. Tumor cell killing was assessed 24 h (A-D) and 48 h (E-H) post incubation of target cells with the antibodies and effector cells (human PBMCs).

Figure 24:
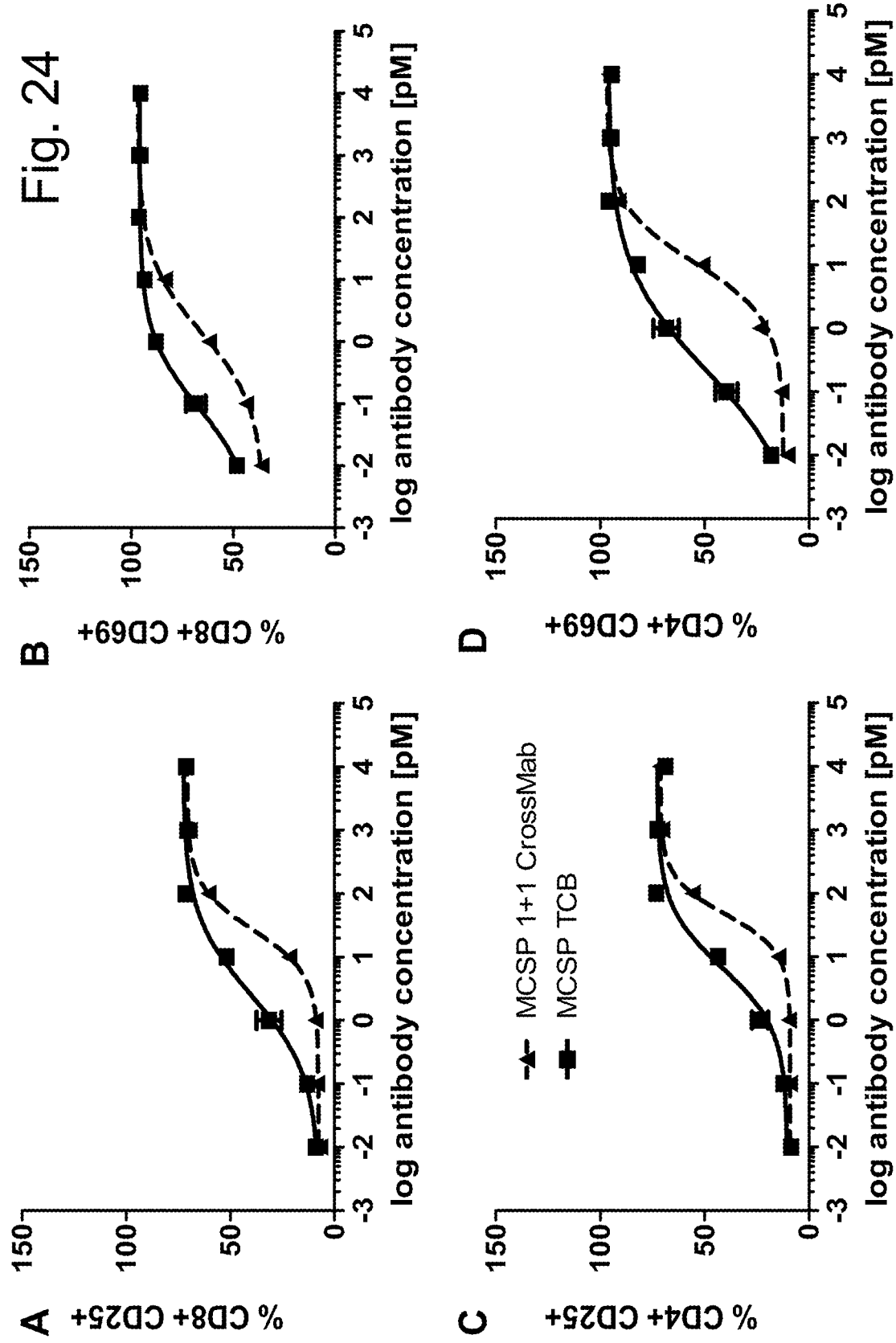

FIG. 24. CD25 and CD69 upregulation on $CD8^+$ and $CD4^+$ T cells after T-cell killing of MCSP-expressing tumor cells (A375, A-D and MV-3, E-H) mediated by the MCSP TCB (SEQ ID NOs: 12, 53, 54 and 55) and MCSP 1+1 CrossMab TCB antibodies.

Figure 25:
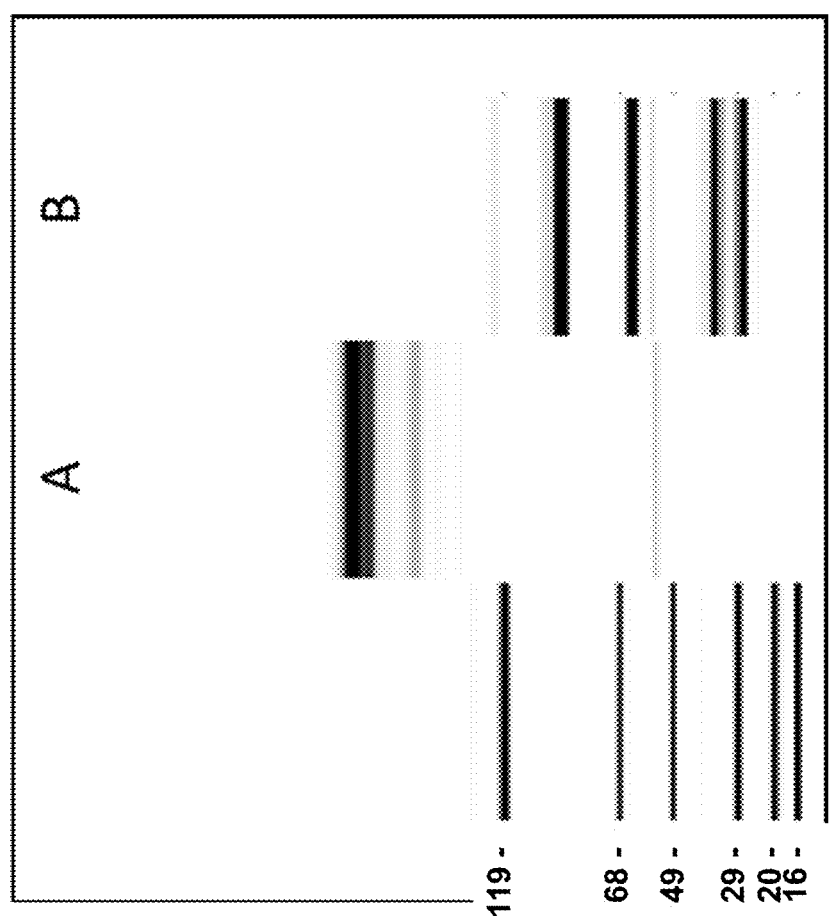

FIG. 25. CE-SDS analyses of DP47 GS TCB (2+1 Crossfab-IgG P329G LALA inverted="Untargeted TCB" SEQ ID NOs: 59, 60, 61 and 62) containing DP47 GS as non binding antibody and humanized CH2527 as anti CD3 antibody. Electropherogram shown as SDS-PAGE of DP47 GS TCB: A) non reduced, B) reduced.

DETAILED DESCRIPTION OF THE INVENTION

Definitions

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. MCSP, CEA, CD3)

can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. Exemplary human proteins useful as antigens include, but are not limited to: Melanoma-associated Chondroitin Sulfate Proteoglycan (MCSP), also known as Chondroitin Sulfate Proteoglycan 4 (CSPG4, UniProt no. Q6UVK1 (version 70), NCBI RefSeq no. NP_001888.2); Carcinoembroynic antigen (CEA), also known as Carcinoembryonic antigen-related cell adhesion molecule 5 (CEACAM5, UniProt no. P06731 (version 119), NCBI RefSeq no. NP_004354.2); and CD3, particularly the epsilon subunit of CD3 (see UniProt no. P07766 (version 130), NCBI RefSeq no. NP_000724.1, SEQ ID NO: 103 for the human sequence; or UniProt no. Q95LI5 (version 49), NCBI GenBank no. BAB71849.1, SEQ ID NO: 104 for the cynomolgus [*Macaca fascicularis*] sequence). In certain embodiments the T cell activating bispecific antigen binding molecule of the invention binds to an epitope of CD3 or a target cell antigen that is conserved among the CD3 or target antigen from different species. In certain embodiments the T cell activating bispecific antigen binding molecule of the invention binds to CD3 and CEACAM5, but does not bind to CEACAM1 or CEACAM6. By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma.

As used herein, the terms "first" and "second" with respect to antigen binding moieties etc., are used for convenience of distinguishing when there is more than one of each type of moiety. Use of these terms is not intended to confer a specific order or orientation of the T cell activating bispecific antigen binding molecule unless explicitly so stated.

A "Fab molecule" refers to a protein consisting of the VH and CH1 domain of the heavy chain (the "Fab heavy chain") and the VL and CL domain of the light chain (the "Fab light chain") of an immunoglobulin.

By "fused" is meant that the components (e.g. a Fab molecule and an Fc domain subunit) are linked by peptide bonds, either directly or via one or more peptide linkers.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

By a "crossover" Fab molecule (also termed "Crossfab") is meant a Fab molecule wherein either the variable regions or the constant regions of the Fab heavy and light chain are exchanged, i.e. the crossover Fab molecule comprises a peptide chain composed of the light chain variable region and the heavy chain constant region, and a peptide chain composed of the heavy chain variable region and the light chain constant region. For clarity, in a crossover Fab molecule wherein the variable regions of the Fab light chain and the Fab heavy chain are exchanged, the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged, the peptide chain comprising the heavy chain variable region is referred to herein as the "heavy chain" of the crossover Fab molecule.

In contrast thereto, by a "conventional" Fab molecule is meant a Fab molecule in its natural format, i.e. comprising a heavy chain composed of the heavy chain variable and constant regions (VH-CH1), and a light chain composed of the light chain variable and constant regions (VL-CL).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator. By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, T cell activating bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

In a first aspect the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10;

(ii) a second antigen binding moiety which is a Fab molecule capable of specific binding to a target cell antigen.

In one embodiment the first antigen binding moiety comprises a heavy chain variable region comprising an amino acid sequence that is at least about 95%, 96%, 97%, 98%, 99% or 100% identical to an amino acid sequence selected from the group of: SEQ ID NO: 3, SEQ ID NO: 32 and SEQ ID NO: 33 and a light chain variable region comprising an amino acid sequence that is at least about 95%, 96%, 97%, 98%, 99% or 100% identical to an amino acid sequence selected from the group of: SEQ ID NO: 7 and SEQ ID NO: 31.

In one embodiment the first antigen binding moiety comprises a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7.

In a specific embodiment the second antigen binding moiety is capable of specific binding to CEA and comprises at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In another specific embodiment, the second antigen binding moiety is capable of specific binding to CEA and comprises a heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In another specific embodiment, the second antigen binding moiety is capable of specific binding to MCSP and comprises at least one heavy chain complementarity determining region (CDR) selected from the group consisting of SEQ ID NO: 14, SEQ ID NO: 15, SEQ ID NO: 16, SEQ ID NO: 35, SEQ ID NO: 37, SEQ ID NO: 38 and SEQ ID NO: 40 and at least one light chain CDR selected from the group of SEQ ID NO: 18, SEQ ID NO: 19, SEQ ID NO: 20, SEQ ID NO: 44, SEQ ID NO: 45, SEQ ID NO: 48, SEQ ID NO: 49 and SEQ ID NO: 50.

In another specific embodiment, the second antigen binding moiety is capable of specific binding to MCSP and comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 18, SEQ ID NO: 19 and SEQ ID NO: 20.

In another specific embodiment, the second antigen binding moiety is capable of specific binding to MCSP and comprises a heavy chain variable region comprising an amino acid sequence that is at least about 95%, 96%, 97%, 98%, 99% or 100% identical to an amino acid sequence selected from the group of SEQ ID NO: 13, SEQ ID NO: 34, SEQ ID NO: 36, SEQ ID NO: 39 and SEQ ID NO: 41 and a light chain variable region comprising an amino acid sequence that is at least about 95%, 96%, 97%, 98%, 99% or 100% identical to an amino acid sequence selected from the group of SEQ ID NO: 17, SEQ ID NO: 43, SEQ ID NO: 46, SEQ ID NO: 47 and SEQ ID NO: 51.

In another specific embodiment, the second antigen binding moiety is capable of specific binding to MCSP and comprises a heavy chain variable region comprising an amino acid sequence that is at least about 95%, 96%, 97%, 98%, 99% or 100% identical to the amino acid sequence of SEQ ID NO: 13 and a light chain variable region comprising an amino acid sequence that is at least about 95%, 96%, 97%, 98%, 99% or 100% identical to the amino acid sequence of SEQ ID NO: 17.

In one embodiment the present invention provides a T cell activating bispecific antigen binding molecule comprising (i) a first antigen binding moiety which is a Fab molecule capable of specific binding to CD3, comprising at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10;

(ii) a second antigen binding moiety which is a Fab molecule capable of specific binding to CEA comprising at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In one embodiment the present invention provides a T cell activating bispecific antigen binding molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7, (ii) a second antigen binding moiety which is a Fab molecule capable of specific binding to CEA comprising heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In one embodiment the present invention provides a T cell activating bispecific antigen binding molecule comprising (i) a first antigen binding moiety which is a Fab molecule capable of specific binding to CD3, comprising at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10;

(ii) a second antigen binding moiety which is a Fab molecule capable of specific binding to MCSP comprising at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 18, SEQ ID NO: 19 and SEQ ID NO: 20.

In one embodiment the present invention provides a T cell activating bispecific antigen binding molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7.

(ii) a second antigen binding moiety which is a Fab molecule capable of specific binding to MCSP comprising a heavy chain variable region comprising an amino acid sequence that is at least about 95%, 96%, 97%, 98%, 99% or 100% identical to the amino acid sequence of SEQ ID NO: 13 and a light chain variable region comprising an amino acid sequence that is at least about 95%, 96%, 97%, 98%, 99% or 100% identical to the amino acid sequence of SEQ ID NO: 17.

In a particular embodiment, the first antigen binding moiety is a crossover Fab molecule wherein either the variable or the constant regions of the Fab light chain and the Fab heavy chain are exchanged.

In one embodiment, the second antigen binding moiety is a conventional Fab molecule.

In a particular embodiment, the first antigen binding moiety is a crossover Fab molecule wherein the constant regions of the Fab light chain and the Fab heavy chain are exchanged, and the second antigen binding moiety is a conventional Fab molecule. In a further particular embodiment, the first and the second antigen binding moiety are fused to each other, optionally through a peptide linker.

In particular embodiments, the T cell activating bispecific antigen binding molecule further comprises an Fc domain composed of a first and a second subunit capable of stable association.

In a further particular embodiment, not more than one antigen binding moiety capable of specific binding to CD3 is present in the T cell activating bispecific antigen binding molecule (i.e. the T cell activating bispecific antigen binding molecule provides monovalent binding to CD3).

T Cell Activating Bispecific Antigen Binding Molecule Formats

Figure 1:
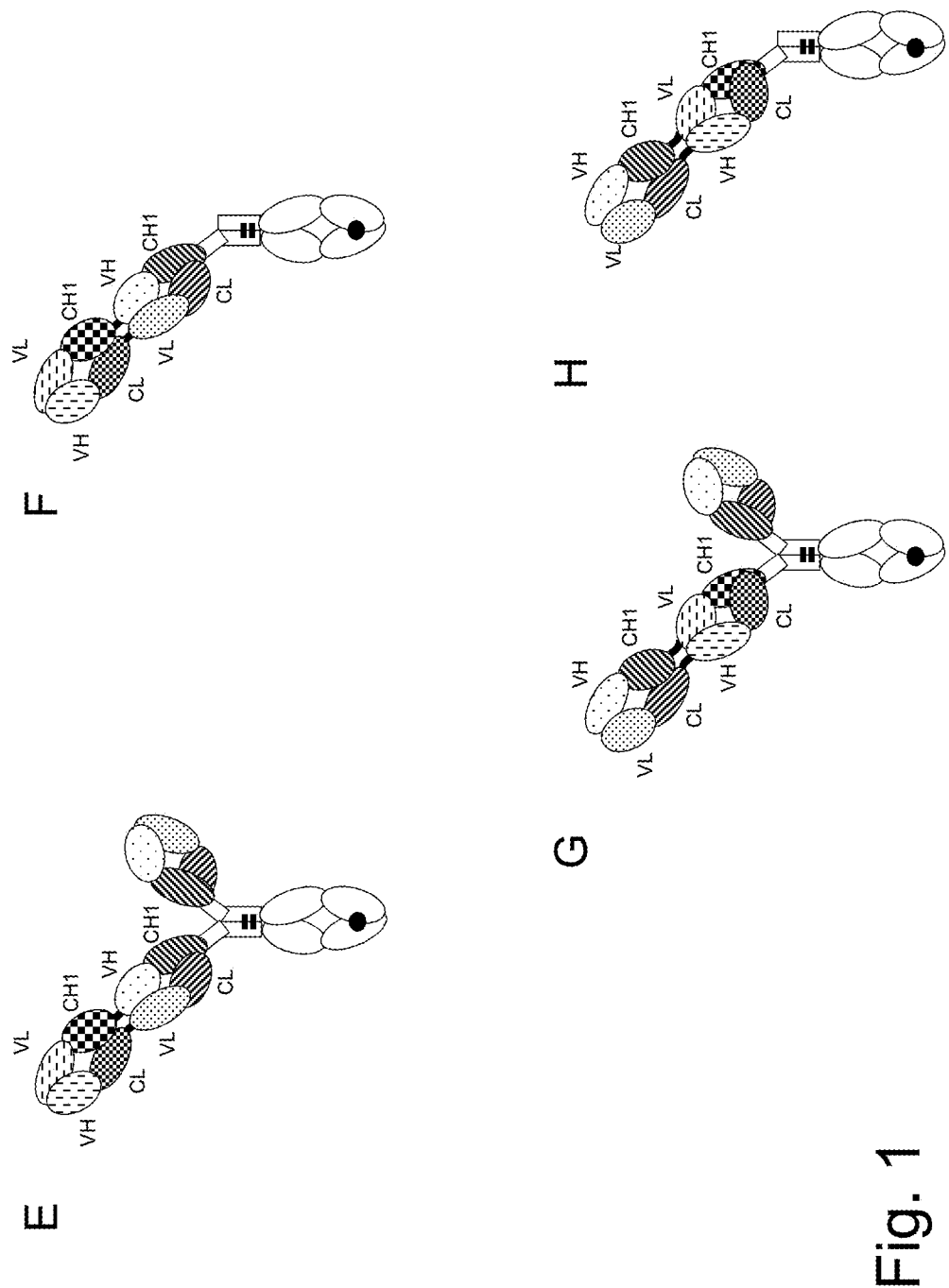
FIG. 1. Exemplary configurations of the T cell activating bispecific antigen binding molecules (TCBs) of the invention. (A) Illustration of the "1+1 IgG Crossfab" molecule. (B) Illustration of the "2+1 IgG Crossfab" molecule. (C) Illustration of the "2+1 IgG Crossfab" molecule with alternative order of Crossfab and Fab components ("inverted"). (D) Illustration of the "1+1 CrossMab" molecule. (E) Illustration of the "2+1 IgG Crossfab, linked light chain" molecule. (F) Illustration of the "1+1 IgG Crossfab, linked light chain" molecule. (G) Illustration of the "2+1 IgG Crossfab, inverted, linked light chain" molecule. (H) Illustration of the "1+1 IgG Crossfab, inverted, linked light chain" molecule. Black dot: optional modification in the Fc domain promoting heterodimerization.
Figure 3:
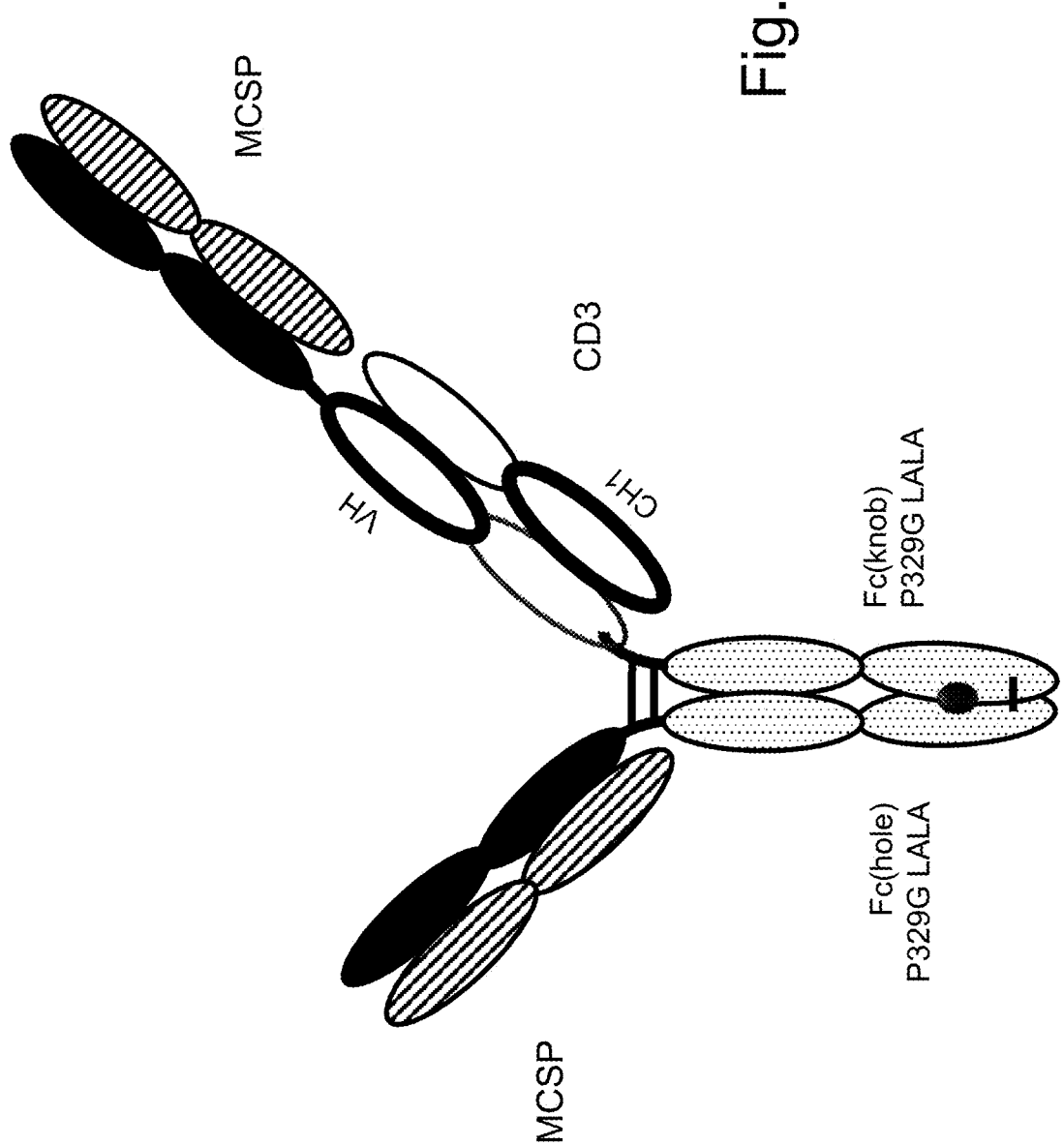
FIG. 3. Schematic drawing of the MCSP TCB (2+1 Crossfab-IgG P329G LALA inverted) molecule.
Figure 5:
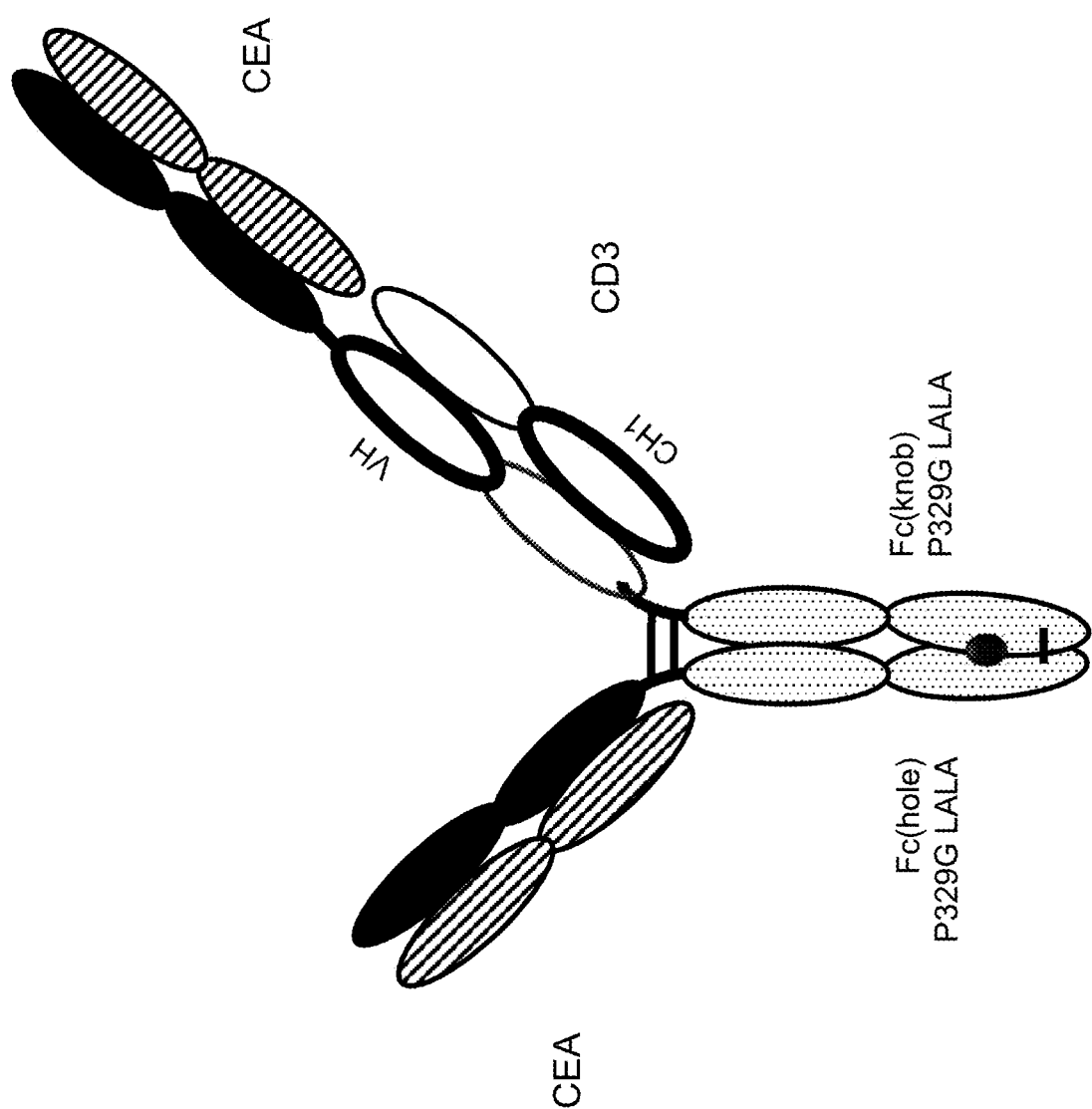
FIG. 5. Schematic drawing of CEA TCB (2+1 Crossfab-IgG P329G LALA inverted) molecule.

The components of the T cell activating bispecific antigen binding molecule can be fused to each other in a variety of configurations. Exemplary configurations are depicted in FIGS. 1, 3 and 5.

In particular embodiments, the T cell activating bispecific antigen binding molecule comprises an Fc domain composed of a first and a second subunit capable of stable association. In some embodiments, the second antigen binding moiety is fused at the C-terminus of the Fab heavy chain to the N-terminus of the first or the second subunit of the Fc domain.

In one such embodiment, the first antigen binding moiety is fused at the C-terminus of the Fab heavy chain to the N-terminus of the Fab heavy chain of the second antigen binding moiety. In a specific such embodiment, the T cell activating bispecific antigen binding molecule essentially consists of a first and a second antigen binding moiety, an Fc domain composed of a first and a second subunit, and optionally one or more peptide linkers, wherein the first antigen binding moiety is fused at the C-terminus of the Fab heavy chain to the N-terminus of the Fab heavy chain of the second antigen binding moiety, and the second antigen binding moiety is fused at the C-terminus of the Fab heavy chain to the N-terminus of the first or the second subunit of the Fc domain. Optionally, the Fab light chain of the first antigen binding moiety and the Fab light chain of the second antigen binding moiety may additionally be fused to each other.

In another such embodiment, the first antigen binding moiety is fused at the C-terminus of the Fab heavy chain to the N-terminus of the first or second subunit of the Fc domain. In a specific such embodiment, the T cell activating bispecific antigen binding molecule essentially consists of a first and a second antigen binding moiety, an Fc domain composed of a first and a second subunit, and optionally one or more peptide linkers, wherein the first and the second antigen binding moiety are each fused at the C-terminus of the Fab heavy chain to the N-terminus of one of the subunits of the Fc domain.

In other embodiments, the first antigen binding moiety is fused at the C-terminus of the Fab heavy chain to the N-terminus of the first or second subunit of the Fc domain.

In a particular such embodiment, the second antigen binding moiety is fused at the C-terminus of the Fab heavy chain to the N-terminus of the Fab heavy chain of the first antigen binding moiety. In a specific such embodiment, the T cell activating bispecific antigen binding molecule essentially consists of a first and a second antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first or the second subunit of the Fc domain. Optionally, the Fab light chain of the first antigen binding moiety and the Fab light chain of the second antigen binding moiety may additionally be fused to each other.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally a number between 1 and 10, typically between 2 and 4. A particularly suitable peptide linker for fusing the Fab light chains of the first and the second antigen binding moiety to each other is $(G4S)_2$. An exemplary peptide linker suitable for connecting the Fab heavy chains of the first and the second antigen binding moiety is EPKSC(D)-$(G_4S)_2$ (SEQ ID NOs 105 and 106). Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

A T cell activating bispecific antigen binding molecule with a single antigen binding moiety capable of specific binding to a target cell antigen (for example as shown in FIG. 1A, 1D, 1F or 1H) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a T cell activating bispecific antigen binding molecule comprising two or more antigen binding moieties specific for a target cell antigen (see examples in shown in FIG. 1B, 1C, 1E or 1G), for example to optimize targeting to the target site or to allow crosslinking of target cell antigens.

Accordingly, in certain embodiments, the T cell activating bispecific antigen binding molecule of the invention further comprises a third antigen binding moiety which is a Fab molecule capable of specific binding to a target cell antigen. In one embodiment, the third antigen binding moiety is a conventional Fab molecule. In one embodiment, the third antigen binding moiety is capable of specific binding to the same target cell antigen as the second antigen binding moiety. In a particular embodiment, the first antigen binding moiety is capable of specific binding to CD3, and the second and third antigen binding moieties are capable of specific binding to a target cell antigen. In a particular embodiment, the second and the third antigen binding moiety are identical (i.e. they comprise the same amino acid sequences).

In a particular embodiment, the first antigen binding moiety is capable of specific binding to CD3, and the second and third antigen binding moieties are capable of specific binding to CEA, wherein the second and third antigen binding moieties comprise at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In a particular embodiment, the first antigen binding moiety is capable of specific binding to CD3, and comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10; and the second and third antigen binding moieties are capable of specific binding to CEA, wherein the second and third antigen binding moieties comprise at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In a particular embodiment, the first antigen binding moiety is capable of specific binding to CD3, and comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10; and the second and third antigen binding moieties are capable of specific binding to CEA, wherein the second and third antigen binding moieties comprise at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In a particular embodiment, the first antigen binding moiety is capable of specific binding to CD3, and comprises a heavy chain variable region comprising an amino acid sequence that is at least about 95%, 96%, 97%, 98%, 99% or 100% identical to an amino acid sequence selected from the group of: SEQ ID NO: 3, SEQ ID NO: 32 and SEQ ID NO: 33 and a light chain variable region comprising an amino acid sequence that is at least about 95%, 96%, 97%, 98%, 99% or 100% identical to an amino acid sequence selected from the group of: SEQ ID NO: 7 and SEQ ID NO: 31, and the second and third antigen binding moieties are capable of specific binding to CEA, wherein the second and third antigen binding moieties comprise a heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In a particular embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 3, and a light chain variable region comprising an amino acid sequence that is at least about 95%, 96%, 97%, 98%, 99% or 100% identical to the amino acid sequence of SEQ ID NO: 7, and the second and third antigen binding moieties are capable of specific binding to CEA, wherein the second and third antigen binding moieties comprise a heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In one embodiment, the first antigen binding moiety is capable of specific binding to CD3, and the second and third antigen binding moieties are capable of specific binding to MCSP, wherein the second and third antigen binding moieties comprise at least one heavy chain complementarity determining region (CDR) selected from the group consisting of SEQ ID NO: 14, SEQ ID NO: 15, SEQ ID NO: 16, SEQ ID NO: 35, SEQ ID NO: 37, SEQ ID NO: 38 and SEQ ID NO: 40 and at least one light chain CDR selected from the group of SEQ ID NO: 18, SEQ ID NO: 19, SEQ ID NO: 20, SEQ ID NO: 44, SEQ ID NO: 45, SEQ ID NO: 48, SEQ ID NO: 49 and SEQ ID NO: 50.

In a particular embodiment, the first antigen binding moiety is capable of specific binding to CD3, and comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10; and the second and third antigen binding moieties are capable of specific binding to MCSP, wherein the second and third antigen binding moieties comprise at least one heavy chain complementarity determining region (CDR) selected from the group consisting of SEQ ID NO: 14, SEQ ID NO: 15, SEQ ID NO: 16, SEQ ID NO: 35, SEQ ID NO: 37, SEQ ID NO: 38 and SEQ ID NO: 40 and at least one light chain CDR selected from the group of SEQ ID NO: 18, SEQ ID NO: 19, SEQ ID NO: 20, SEQ ID NO: 44, SEQ ID NO: 45, SEQ ID NO: 48, SEQ ID NO: 49 and SEQ ID NO: 50.

In one embodiment, the first antigen binding moiety is capable of specific binding to CD3, and comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10; and the second and third antigen binding moieties are capable of specific binding to MCSP, wherein the second and third antigen binding moieties comprise at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 18, SEQ ID NO: 19 and SEQ ID NO: 20.

In one embodiment, the first antigen binding moiety is capable of specific binding to CD3, and comprises a heavy chain variable region comprising an amino acid sequence that is at least about 95%, 96%, 97%, 98%, 99% or 100% identical to an amino acid sequence selected from the group of: SEQ ID NO: 3, SEQ ID NO: 32 and SEQ ID NO: 33 and a light chain variable region comprising an amino acid sequence that is at least about 95%, 96%, 97%, 98%, 99% or 100% identical to an amino acid sequence selected from the group of: SEQ ID NO: 7 and SEQ ID NO: 31, and the second and third antigen binding moieties are capable of specific binding to MCSP, wherein the second and third antigen binding moieties comprise a heavy chain variable region comprising an amino acid sequence that is at least about 95%, 96%, 97%, 98%, 99% or 100% identical to an amino acid sequence selected from the group of SEQ ID NO: 13, SEQ ID NO: 34, SEQ ID NO: 36, SEQ ID NO: 39 and SEQ ID NO: 41 and a light chain variable region comprising an amino acid sequence that is at least about 95%, 96%, 97%, 98%, 99% or 100% identical to an amino acid sequence selected from the group of SEQ ID NO: 17, SEQ ID NO: 43, SEQ ID NO: 46, SEQ ID NO: 47 and SEQ ID NO: 51.

In one embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7, and the second and third antigen binding moieties are capable of specific binding to MCSP, wherein the second and third antigen binding moieties comprise a heavy chain variable region comprising an amino acid sequence that is at least about 95%, 96%, 97%, 98%, 99% or 100% identical to the amino acid sequence of SEQ ID NO: 13 and a light chain variable region comprising an amino acid sequence that is at least about 95%, 96%, 97%, 98%, 99% or 100% identical to the amino acid sequence of SEQ ID NO: 17. In one embodiment, the third antigen binding moiety is fused at the C-terminus of the Fab heavy chain to the N-terminus of the first or second subunit of the Fc domain. In a more specific embodiment, the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second antigen binding moiety. Optionally, the Fab light chain of the first antigen binding moiety and the Fab light chain of the second antigen binding moiety may additionally be fused to each other.

The second and the third antigen binding moiety may be fused to the Fc domain directly or through a peptide linker. In a particular embodiment the second and the third antigen binding moiety are each fused to the Fc domain through an immunoglobulin hinge region. In a specific embodiment, the immunoglobulin hinge region is a human IgG$_1$ hinge region. In one embodiment the second and the third antigen binding moiety and the Fc domain are part of an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin. In one embodiment, the T cell activating bispecific antigen binding molecule essentially consists of an immunoglobulin molecule capable of specific binding to a target cell antigen, and an antigen binding moiety capable of specific binding to CD3 wherein the antigen binding moiety is a Fab molecule, particularly a crossover Fab molecule, fused to the N-terminus of one of the immunoglobulin heavy chains, optionally via a peptide linker.

In a particular embodiment, the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. In a specific such embodiment, the T cell activating bispecific antigen binding molecule essentially consists of a first, a second and a third antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain. Optionally, the Fab light chain of the first antigen binding moiety and the Fab light chain of the second antigen binding moiety may additionally be fused to each other.

In one embodiment the present invention provides a T cell activating bispecific antigen binding molecule comprising (i) a first antigen binding moiety which is a Fab molecule capable of specific binding to CD3, comprising the heavy chain complementarity determining region (CDR) 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to CEA comprising the heavy chain CDR 1 of SEQ ID NO: 24, the heavy chain CDR 2 of SEQ ID NO: 25, the heavy chain CDR 3 of SEQ ID NO: 26, the light chain CDR 1 of SEQ ID NO: 28, the light chain CDR 2 of SEQ ID NO: 29 and the light chain CDR3 of SEQ ID NO: 30.

In one embodiment the present invention provides a T cell activating bispecific antigen binding molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to CEA comprising heavy chain variable region comprising an amino acid sequence that is at least about 95%, 96%, 97%, 98%, 99% or 100% identical to the amino acid sequence of SEQ ID NO: 23 and a light chain variable region comprising an amino acid sequence that is at least about 95%, 96%, 97%, 98%, 99% or 100% identical to the amino acid sequence of SEQ ID NO: 27.

In one embodiment the present invention provides a T cell activating bispecific antigen binding molecule comprising (i) a first antigen binding moiety which is a Fab molecule capable of specific binding to CD3, comprising the heavy chain complementarity determining region (CDR) 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to MCSP comprising the heavy chain CDR 1 of SEQ ID NO: 14, the heavy chain CDR 2 of SEQ ID NO: 15, the heavy chain CDR 3 of SEQ ID NO: 16, the light chain CDR 1 of SEQ ID NO: 18, the light chain CDR 2 of SEQ ID NO: 19 and the light chain CDR3 of SEQ ID NO: 20.

In one embodiment the present invention provides a T cell activating bispecific antigen binding molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to MCSP comprising a heavy chain variable region comprising an amino acid sequence that is at least about 95%, 96%, 97%, 98%, 99% or 100% identical to the amino acid sequence of SEQ ID NO: 13 and a light chain variable region comprising an amino acid sequence that is at least about 95%, 96%, 97%, 98%, 99% or 100% identical to the amino acid sequence of SEQ ID NO: 17.

The T cell activating bispecific antigen binding molecule according to any of the four above embodiments may further comprise (iii) an Fc domain composed of a first and a second subunit capable of stable association, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In some of the T cell activating bispecific antigen binding molecule of the invention, the Fab light chain of the first antigen binding moiety and the Fab light chain of the second antigen binding moiety are fused to each other, optionally via a linker peptide. Depending on the configuration of the first and the second antigen binding moiety, the Fab light chain of the first antigen binding moiety may be fused at its C-terminus to the N-terminus of the Fab light chain of the second antigen binding moiety, or the Fab light chain of the second antigen binding moiety may be fused at its C-terminus to the N-terminus of the Fab light chain of the first antigen binding moiety. Fusion of the Fab light chains of the first and the second antigen binding moiety further reduces mispairing of unmatched Fab heavy and light chains, and also reduces the number of plasmids needed for expression of some of the T cell activating bispecific antigen binding molecules of the invention.

In certain embodiments the T cell activating bispecific antigen binding molecule comprises a polypeptide wherein the Fab light chain variable region of the first antigen binding moiety shares a carboxy-terminal peptide bond with the Fab heavy chain constant region of the first antigen binding moiety (i.e. a the first antigen binding moiety comprises a crossover Fab heavy chain, wherein the heavy chain variable region is replaced by a light chain variable region), which in turn shares a carboxy-terminal peptide bond with an Fc domain subunit ($VL_{(1)}$-$CH1_{(1)}$-CH2-CH3 (—CH4)), and a polypeptide wherein a the Fab heavy chain of the second antigen binding moiety shares a carboxy-terminal peptide bond with an Fc domain subunit ($VH_{(2)}$-$CH1_{(2)}$-CH2-CH3(—CH4)). In some embodiments the T cell activating bispecific antigen binding molecule further comprises a polypeptide wherein the Fab heavy chain variable region of the first antigen binding moiety shares a carboxy-terminal peptide bond with the Fab light chain constant region of the first antigen binding moiety ($VH_{(1)}$-$CL_{(1)}$) and the Fab light chain polypeptide of the second antigen binding moiety ($VL_{(2)}$-$CL_{(2)}$). In certain embodiments the polypeptides are covalently linked, e.g., by a disulfide bond.

In alternative embodiments the T cell activating bispecific antigen binding molecule comprises a polypeptide wherein the Fab heavy chain variable region of the first antigen binding moiety shares a carboxy-terminal peptide bond with the Fab light chain constant region of the first antigen binding moiety (i.e. the first antigen binding moiety comprises a crossover Fab heavy chain, wherein the heavy chain constant region is replaced by a light chain constant region), which in turn shares a carboxy-terminal peptide bond with an Fc domain subunit ($VH_{(1)}$-$CL_{(1)}$-CH2-CH3(—CH4)), and a polypeptide wherein the Fab heavy chain of the second antigen binding moiety shares a carboxy-terminal peptide bond with an Fc domain subunit ($VH_{(2)}$-$CH1_{(2)}$-CH2-CH3 (—CH4)). In some embodiments the T cell activating bispecific antigen binding molecule further comprises a polypeptide wherein the Fab light chain variable region of the first antigen binding moiety shares a carboxy-terminal peptide bond with the Fab heavy chain constant region of the first antigen binding moiety ($VL_{(1)}$-$CH1_{(1)}$) and the Fab light chain polypeptide of the second antigen binding moiety ($VL_{(2)}$-$CL_{(2)}$). In certain embodiments the polypeptides are covalently linked, e.g., by a disulfide bond.

In some embodiments, the T cell activating bispecific antigen binding molecule comprises a polypeptide wherein the Fab light chain variable region of the first antigen binding moiety shares a carboxy-terminal peptide bond with the Fab heavy chain constant region of the first antigen binding moiety (i.e. the first antigen binding moiety comprises a crossover Fab heavy chain, wherein the heavy chain variable region is replaced by a light chain variable region), which in turn shares a carboxy-terminal peptide bond with the Fab heavy chain of the second antigen binding moiety, which in turn shares a carboxy-terminal peptide bond with an Fc domain subunit ($VL_{(1)}$-$CH1_{(1)}$-$VH_{(2)}$-$CH1_{(2)}$-CH2-CH3(—CH4)). In other embodiments, the T cell activating bispecific antigen binding molecule comprises a polypeptide wherein the Fab heavy chain variable region of the first antigen binding moiety shares a carboxy-terminal peptide bond with the Fab light chain constant region of the first antigen binding moiety (i.e. the first antigen binding moiety comprises a crossover Fab heavy chain, wherein the heavy chain constant region is replaced by a light chain constant region), which in turn shares a carboxy-terminal peptide bond with the Fab heavy chain of the second antigen binding moiety, which in turn shares a carboxy-terminal peptide bond with an Fc domain subunit ($VH_{(1)}$-$CL_{(1)}$-$VH_{(2)}$-$CH1_{(2)}$-CH2-CH3(—CH4)). In still other embodiments, the T cell activating bispecific antigen binding molecule comprises a polypeptide wherein the Fab heavy chain of the second antigen binding moiety shares a carboxy-terminal peptide bond with the Fab light chain variable region of the first antigen binding moiety which in turn shares a carboxy-terminal peptide bond with the Fab heavy chain constant region of the first antigen binding moiety (i.e. the first antigen binding moiety comprises a crossover Fab heavy chain, wherein the heavy chain variable region is replaced by a light chain variable region), which in turn shares a carboxy-terminal peptide bond with an Fc domain subunit ($VH_{(2)}$-$CH1_{(2)}$-$VL_{(1)}$-$CH1_{(1)}$-CH2-CH3(—CH4)). In other embodiments, the T cell activating bispecific antigen binding molecule comprises a polypeptide wherein the Fab heavy chain of the second antigen binding moiety shares a carboxy-terminal peptide bond with the Fab heavy chain variable region of the first antigen binding moiety which in turn shares a carboxy-terminal peptide bond with the Fab light chain constant region of the first antigen binding moiety (i.e. the first antigen binding moiety comprises a crossover Fab heavy chain, wherein the heavy chain constant region is replaced by a light chain constant region), which in turn shares a carboxy-terminal peptide bond with an Fc domain subunit ($VH_{(2)}$-$CH1_{(2)}$-$VH_{(1)}$-$CL_{(1)}$-CH2-CH3(—CH4)).

In some of these embodiments the T cell activating bispecific antigen binding molecule further comprises a crossover Fab light chain polypeptide of the first antigen binding moiety, wherein the Fab heavy chain variable region of the first antigen binding moiety shares a carboxy-terminal peptide bond with the Fab light chain constant region of the first antigen binding moiety ($VH_{(1)}$-$CL_{(1)}$), and the Fab light chain polypeptide of the second antigen binding moiety ($VL_{(2)}$-$CL_{(2)}$). In others of these embodiments the T cell activating bispecific antigen binding molecule further comprises a crossover Fab light chain polypeptide, wherein the Fab light chain variable region of the first antigen binding moiety shares a carboxy-terminal peptide bond with the Fab heavy chain constant region of the first antigen binding moiety ($VL_{(1)}$-$CH1_{(1)}$), and the Fab light chain polypeptide of the second antigen binding moiety ($VL_{(2)}$-$CL_{(2)}$). In still others of these embodiments the T cell activating bispecific antigen binding molecule further comprises a polypeptide wherein the Fab light chain variable region of the first antigen binding moiety shares a carboxy-terminal peptide bond with the Fab heavy chain constant region of the first antigen binding moiety which in turn shares a carboxy-terminal peptide bond with the Fab light chain polypeptide of the second antigen binding moiety ($VL_{(1)}$-$CH1_{(1)}$-$VL_{(2)}$-$CL_{(2)}$), a polypeptide wherein the Fab heavy chain variable region of the first antigen binding moiety shares a carboxy-terminal peptide bond with the Fab light chain constant region of the first antigen binding moiety which in turn shares a carboxy-terminal peptide bond with the Fab light chain polypeptide of the second antigen binding moiety ($VH_{(1)}$-$CL_{(1)}$-$VL_{(2)}$-$CL_{(2)}$), a polypeptide wherein the Fab light chain polypeptide of the second antigen binding moiety shares a carboxy-terminal peptide bond with the Fab light chain variable region of the first antigen binding moiety which in turn shares a carboxy-terminal peptide bond with the Fab heavy chain constant region of the first antigen binding moiety ($VL_{(2)}$-CL(2)-$VL_{(1)}$-$CH1_{(1)}$), or a polypeptide wherein the Fab light chain polypeptide of the second antigen binding moiety shares a carboxy-terminal peptide bond with the Fab heavy chain variable region of the first antigen binding moiety which in turn shares a carboxy-terminal peptide bond with the Fab light chain constant region of the first antigen binding moiety ($VL_{(2)}$-$CL_{(2)}$-$VH_{(1)}$-$CL_{(1)}$).

The T cell activating bispecific antigen binding molecule according to these embodiments may further comprise (i) an Fc domain subunit polypeptide (CH2-CH3(—CH4)), or (ii) a polypeptide wherein the Fab heavy chain of a third antigen binding moiety shares a carboxy-terminal peptide bond with an Fc domain subunit ($VH_{(3)}$-$CH1_{(3)}$-CH2-CH3(—CH4)) and the Fab light chain polypeptide of a third antigen binding moiety ($VL_{(3)}$-$CL_{(3)}$). In certain embodiments the polypeptides are covalently linked, e.g., by a disulfide bond.

According to any of the above embodiments, components of the T cell activating bispecific antigen binding molecule (e.g. antigen binding moiety, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally a number between 1 and 10, typically between 2 and 4.

Fc Domain

The Fc domain of the T cell activating bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the T cell activating bispecific antigen binding molecule of the invention comprises not more than one Fc domain.

In one embodiment according the invention the Fc domain of the T cell activating bispecific antigen binding molecule is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment the Fc domain is human. An exemplary sequence of a human $IgG_1$ Fc region is given in SEQ ID NO: 107.

Fc Domain Modifications Promoting Heterodimerization

T cell activating bispecific antigen binding molecules according to the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of T cell activating bispecific antigen binding molecules in recombinant production, it will thus be advantageous to introduce in the Fc domain of the T cell activating bispecific antigen binding molecule a modification promoting the association of the desired polypeptides.

Accordingly, in particular embodiments the Fc domain of the T cell activating bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Accordingly, in a particular embodiment, in the CH3 domain of the first subunit of the Fc domain of the T cell activating bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In a particular embodiment the antigen binding moiety capable of binding to CD3 is fused (optionally via the antigen binding moiety capable of binding to a target cell antigen) to the first subunit of the Fc domain (comprising the "knob" modification). Without wishing to be bound by theory, fusion of the antigen binding moiety capable of binding to CD3 to the knob-containing subunit of the Fc domain will (further) minimize the generation of antigen binding molecules comprising two antigen binding moieties capable of binding to CD3 (steric clash of two knob-containing polypeptides).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Fc Domain Modifications Reducing Fc Receptor Binding and/or Effector Function

The Fc domain confers to the T cell activating bispecific antigen binding molecule favorable pharmacokinetic properties, including a long serum half-life which contributes to good accumulation in the target tissue and a favorable tissue-blood distribution ratio. At the same time it may, however, lead to undesirable targeting of the T cell activating bispecific antigen binding molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the T cell activating bispecific antigen binding molecule due to the potential destruction of T cells e.g. by NK cells.

Accordingly, in particular embodiments the Fc domain of the T cell activating bispecific antigen binding molecules according to the invention exhibits reduced binding affinity to an Fc receptor and/or reduced effector function, as compared to a native $IgG_1$ Fc domain. In one such embodiment the Fc domain (or the T cell activating bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a T cell activating bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain (or a T cell activating bispecific antigen binding molecule comprising a native $IgG_1$ Fc domain). In one embodiment, the Fc domain (or the T cell activating bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain exhibits substantially similar binding affinity to neonatal Fc receptor (FcRn), as compared to a native $IgG_1$ Fc domain. Substantially similar binding to FcRn is achieved when the Fc domain (or the T cell activating bispecific antigen binding molecule comprising said Fc domain) exhibits greater than about 70%, particularly greater than about 80%, more particularly greater than about 90% of the binding affinity of a native $IgG_1$ Fc domain (or the T cell activating bispecific antigen binding molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the T cell activating bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the T cell activating bispecific antigen binding molecule comprising an engineered Fc domain exhibits less than 20%, particularly less than 10%, more particularly less than 5% of the binding affinity to an Fc receptor as compared to a T cell activating bispecific antigen binding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the T cell activating bispecific antigen binding molecule comprising said Fc domain) exhibits greater than about 70% of the binding affinity of a non-engineered form of the Fc domain (or the T cell activating bispecific antigen binding molecule comprising said non-engineered form of the Fc domain) to FcRn. The Fc domain, or T cell activating bispecific antigen binding molecules of the invention comprising said Fc domain, may exhibit greater than about 80% and even greater than about 90% of such affinity. In certain embodiments the Fc domain of the T cell activating bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a T cell activating bispecific antigen binding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A. In one such embodiment, the Fc domain is an $IgG_1$ Fc domain, particularly a human $IgG_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions. $IgG_4$ antibodies exhibit reduced binding affinity to Fc receptors and reduced effector functions as compared to $IgG_1$ antibodies. Hence, in some embodiments the Fc domain of the T cell activating bispecific antigen binding molecules of the invention is an $IgG_4$ Fc domain, particularly a human $IgG_4$ Fc domain. In one embodiment the $IgG_4$ Fc domain comprises amino acid substitutions at position S228, specifically the amino acid substitution S228P. To further reduce its binding affinity to an Fc receptor and/or its effector function, in one embodiment the $IgG_4$ Fc domain comprises an amino acid substitution at position L235, specifically the amino acid substitution L235E. In another embodiment, the $IgG_4$ Fc domain comprises an amino acid substitution at position P329, specifically the amino acid substitution P329G. In a particular embodiment, the $IgG_4$ Fc domain comprises amino acid substitutions at positions S228, L235 and P329, specifically amino acid substitutions S228P, L235E and P329G. Such IgG$_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or a T cell activating bispecific antigen binding molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the T cell activating bispecific antigen binding molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Antigen Binding Moieties

The antigen binding molecule of the invention is bispecific, i.e. it comprises at least two antigen binding moieties capable of specific binding to two distinct antigenic determinants. According to the invention, the antigen binding moieties are Fab molecules (i.e. antigen binding domains composed of a heavy and a light chain, each comprising a variable and a constant region). In one embodiment said Fab molecules are human. In another embodiment said Fab molecules are humanized. In yet another embodiment said Fab molecules comprise human heavy and light chain constant regions.

At least one of the antigen binding moieties is a crossover Fab molecule. Such modification prevent mispairing of heavy and light chains from different Fab molecules, thereby improving the yield and purity of the T cell activating bispecific antigen binding molecule of the invention in recombinant production. In a particular crossover Fab molecule useful for the T cell activating bispecific antigen binding molecule of the invention, the constant regions of the Fab light chain and the Fab heavy chain are exchanged. In another crossover Fab molecule useful for the T cell activating bispecific antigen binding molecule of the invention, the variable regions of the Fab light chain and the Fab heavy chain are exchanged.

In a particular embodiment according to the invention, the T cell activating bispecific antigen binding molecule is capable of simultaneous binding to a target cell antigen, particularly a tumor cell antigen, and CD3. In one embodiment, the T cell activating bispecific antigen binding molecule is capable of crosslinking a T cell and a target cell by simultaneous binding to a target cell antigen and CD3. In an even more particular embodiment, such simultaneous binding results in lysis of the target cell, particularly a tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antigen binding molecule to CD3 without simultaneous binding to the target cell antigen does not result in T cell activation.

In one embodiment, the T cell activating bispecific antigen binding molecule is capable of re-directing cytotoxic activity of a T cell to a target cell. In a particular embodiment, said re-direction is independent of MHC-mediated peptide antigen presentation by the target cell and and/or specificity of the T cell.

Particularly, a T cell according to any of the embodiments of the invention is a cytotoxic T cell. In some embodiments the T cell is a CD4$^+$ or a CD8$^+$ T cell, particularly a CD8$^+$ T cell.

CD3 Binding Moiety

The T cell activating bispecific antigen binding molecule of the invention comprises at least one antigen binding moiety capable of binding to CD3 (also referred to herein as an "CD3 antigen binding moiety" or "first antigen binding moiety"). In a particular embodiment, the T cell activating bispecific antigen binding molecule comprises not more than one antigen binding moiety capable of specific binding to CD3. In one embodiment the T cell activating bispecific antigen binding molecule provides monovalent binding to CD3. The CD3 antigen binding is a crossover Fab molecule, i.e. a Fab molecule wherein either the variable or the constant regions of the Fab heavy and light chains are exchanged. In embodiments where there is more than one antigen binding moiety capable of specific binding to a target cell antigen comprised in the T cell activating bispecific antigen binding molecule, the antigen binding moiety capable of specific binding to CD3 preferably is a crossover Fab molecule and the antigen binding moieties capable of specific binding to a target cell antigen are conventional Fab molecules.

In a particular embodiment CD3 is human CD3 (SEQ ID NO: 103) or cynomolgus CD3 (SEQ ID NO: 104), most particularly human CD3. In a particular embodiment the CD3 antigen binding moiety is cross-reactive for (i.e. specifically binds to) human and cynomolgus CD3. In some embodiments, the first antigen binding moiety is capable of specific binding to the epsilon subunit of CD3.

The CD3 antigen binding moiety comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10.

In one embodiment the CD3 antigen binding moiety comprises the heavy chain CDR1 of SEQ ID NO: 4, the heavy chain CDR2 of SEQ ID NO: 5, the heavy chain CDR3 of SEQ ID NO: 6, the light chain CDR1 of SEQ ID NO: 8, the light chain CDR2 of SEQ ID NO: 9, and the light chain CDR3 of SEQ ID NO: 10.

In one embodiment the CD3 antigen binding moiety comprises a heavy chain variable region sequence that is at least about 95%, 96%, 97%, 98%, 99% or 100% identical to an amino acid sequence selected from the group of: SEQ ID NO: 3, SEQ ID NO: 32 and SEQ ID NO: 33, and a light chain variable region sequence that is at least about 95%, 96%, 97%, 98%, 99% or 100% identical to an amino acid sequence selected from the group of: SEQ ID NO: 7 and SEQ ID NO: 31.

In one embodiment the CD3 antigen binding moiety comprises a heavy chain variable region comprising an amino acid sequence selected from the group of: SEQ ID NO: 3, SEQ ID NO: 32 and SEQ ID NO: 33 and a light chain variable region comprising an amino acid sequence selected from the group of: SEQ ID NO: 7 and SEQ ID NO: 31.

In one embodiment the CD3 antigen binding moiety comprises a heavy chain variable region sequence that is at least about 95%, 96%, 97%, 98%, 99% or 100% identical to SEQ ID NO: 3 and a light chain variable region sequence that is at least about 95%, 96%, 97%, 98%, 99% or 100% identical to SEQ ID NO: 7.

In one embodiment the CD3 antigen binding moiety comprises a heavy chain variable region comprising the amino acid sequence of SEQ ID NO: 3 and a light chain variable region comprising the amino acid sequence of SEQ ID NO: 7.

In one embodiment the CD3 antigen binding moiety comprises the heavy chain variable region sequence of SEQ ID NO: 3 and the light chain variable region sequence of SEQ ID NO: 7.

Target Cell Antigen Binding Moiety

The T cell activating bispecific antigen binding molecule of the invention comprises at least one antigen binding moiety capable of binding to a target cell antigen (also referred to herein as an "target cell antigen binding moiety" or "second" or "third" antigen binding moiety). In certain embodiments, the T cell activating bispecific antigen binding molecule comprises two antigen binding moieties capable of binding to a target cell antigen. In a particular such embodiment, each of these antigen binding moieties specifically binds to the same antigenic determinant. In an even more particular embodiment, all of these antigen binding moieties are identical. In one embodiment, the T cell activating bispecific antigen binding molecule comprises an immunoglobulin molecule capable of specific binding to a target cell antigen. In one embodiment the T cell activating bispecific antigen binding molecule comprises not more than two antigen binding moieties capable of binding to a target cell antigen.

The target cell antigen binding moiety is generally a Fab molecule, particularly a conventional Fab molecule that binds to a specific antigenic determinant and is able to direct the T cell activating bispecific antigen binding molecule to a target site, for example to a specific type of tumor cell that bears the antigenic determinant.

In certain embodiments the target cell antigen binding moiety specifically binds to a cell surface antigen. In a particular embodiment the target cell antigen binding moiety specifically binds to a membrane-proximal region of a cell surface antigen. In a specific such embodiment the cell surface antigen is Carcinoembryonic Antigen (CEA) and the membrane-proximal region is the B3 domain of CEA (residues 208-286 of SEQ ID NO: 119). In another specific such embodiment the cell surface antigen is Melanoma-associated Chondroitin Sulfate Proteoglycan (MCSP) and the membrane-proximal region is the D3 domain of MSCP (SEQ ID NO: 118).

In certain embodiments the target cell antigen binding moiety is directed to an antigen associated with a pathological condition, such as an antigen presented on a tumor cell or on a virus-infected cell. Suitable antigens are cell surface antigens, for example, but not limited to, cell surface receptors. In particular embodiments the antigen is a human antigen. In a specific embodiment the target cell antigen is selected from Melanoma-associated Chondroitin Sulfate Proteoglycan (MCSP, CSPG4) and Carcinoembryonic Antigen (CEA, CEACAM5).

In some embodiments the T cell activating bispecific antigen binding molecule comprises at least one antigen binding moiety that is specific for Melanoma-associated Chondroitin Sulfate Proteoglycan (MCSP). In one embodiment, the antigen binding moiety that is specific for MCSP comprises at least one heavy chain complementarity determining region (CDR) selected from the group consisting of SEQ ID NO: 14, SEQ ID NO: 15, SEQ ID NO: 16, SEQ ID NO: 35, SEQ ID NO: 37, SEQ ID NO: 38 and SEQ ID NO: 40 and at least one light chain CDR selected from the group of SEQ ID NO: 18, SEQ ID NO: 19, SEQ ID NO: 20, SEQ ID NO: 44, SEQ ID NO: 45, SEQ ID NO: 48, SEQ ID NO: 49 and SEQ ID NO: 50.

In one embodiment, the antigen binding moiety that is specific for MCSP comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 18, SEQ ID NO: 19 and SEQ ID NO: 20.

In one embodiment, the antigen binding moiety that is specific for MCSP comprises the heavy chain CDR1 of SEQ ID NO: 14, the heavy chain CDR2 of SEQ ID NO: 15, the heavy chain CDR3 of SEQ ID NO: 16, the light chain CDR1 of SEQ ID NO: 18, the light chain CDR2 of SEQ ID NO: 19, and the light chain CDR3 of SEQ ID NO: 20.

In a further embodiment, the antigen binding moiety that is specific for MCSP comprises a heavy chain variable region sequence that is at least about 95%, 96%, 97%, 98%, 99% or 100% identical to an amino acid sequence selected from the group of SEQ ID NO: 13, SEQ ID NO: 34, SEQ ID NO: 36, SEQ ID NO: 39 and SEQ ID NO: 41 and a light chain variable region sequence that is at least about 95%, 96%, 97%, 98%, 99% or 100% identical to an amino acid sequence selected from the group of SEQ ID NO: 17, SEQ ID NO: 43, SEQ ID NO: 46, SEQ ID NO: 47 and SEQ ID NO: 51.

In a further embodiment, the antigen binding moiety that is specific for MCSP comprises a heavy chain variable region comprising an amino acid sequence selected from the group of SEQ ID NO: 13, SEQ ID NO: 34, SEQ ID NO: 36, SEQ ID NO: 39 and SEQ ID NO: 41 and a light chain variable region comprising an amino acid sequence selected from the group of SEQ ID NO: 17, SEQ ID NO: 43, SEQ ID NO: 46, SEQ ID NO: 47 and SEQ ID NO: 51.

In a further embodiment, the antigen binding moiety that is specific for MCSP comprises a heavy chain variable region sequence that is at least about 95%, 96%, 97%, 98%, 99% or 100% identical to SEQ ID NO:13 and a light chain variable region sequence that is at least about 95%, 96%, 97%, 98%, 99% or 100% identical to SEQ ID NO: 17 or variants thereof that retain functionality.

In one embodiment, the antigen binding moiety that is specific for MCSP comprises a heavy chain variable region comprising an amino acid sequence of SEQ ID NO: 13 and a light chain variable region comprising an amino acid sequence of SEQ ID NO: 17.

In one embodiment, the antigen binding moiety that is specific for MCSP comprises the heavy chain variable region sequence of SEQ ID NO: 13 and the light chain variable region sequence of SEQ ID NO: 17.

In one embodiment the T cell activating bispecific antigen binding molecule comprises a polypeptide sequence that is at least about 95%, 96%, 97%, 98%, 99% or 100% identical to SEQ ID NO: 12, a polypeptide sequence that is at least about 95%, 96%, 97%, 98%, 99% or 100% identical to SEQ ID NO: 53, a polypeptide sequence that is at least about 95%, 96%, 97%, 98%, 99% or 100% identical to SEQ ID NO: 54, and a polypeptide sequence that is at least about 95%, 96%, 97%, 98%, 99% or 100% identical to SEQ ID NO: 55.

In particular embodiments the T cell activating bispecific antigen binding molecule comprises at least one antigen binding moiety that is specific for Carcinoembryonic Antigen (CEA). In one embodiment, the antigen binding moiety that is specific for CEA comprises at least one heavy chain complementarity determining region (CDR) selected from the group consisting of SEQ ID NO: 24, SEQ ID NO: 25 and SEQ ID NO: 26 and at least one light chain CDR selected from the group of SEQ ID NO: 28, SEQ ID NO: 29 and SEQ ID NO: 30.

In one embodiment, the antigen binding moiety that is specific for CEA comprises the heavy chain CDR1 of SEQ ID NO: 24, the heavy chain CDR2 of SEQ ID NO: 25, the heavy chain CDR3 of SEQ ID NO: 26, the light chain CDR1 of SEQ ID NO: 28, the light chain CDR2 of SEQ ID NO: 29, and the light chain CDR3 of SEQ ID NO: 30.

In a further embodiment, the antigen binding moiety that is specific for CEA comprises a heavy chain variable region sequence that is at least about 95%, 96%, 97%, 98%, 99% or 100% identical to SEQ ID NO: 23 and a light chain variable region sequence that is at least about 95%, 96%, 97%, 98%, 99% or 100% identical to SEQ ID NO: 27, or variants thereof that retain functionality.

In one embodiment, the antigen binding moiety that is specific for CEA comprises a heavy chain variable region comprising an amino acid sequence of SEQ ID NO: 23 and a light chain variable region comprising an amino acid sequence of SEQ ID NO: 27.

In one embodiment, the antigen binding moiety that is specific for CEA comprises the heavy chain variable region sequence of SEQ ID NO: 23 and the light chain variable region sequence of SEQ ID NO: 27.

In one embodiment the T cell activating bispecific antigen binding molecule comprises a polypeptide sequence that is at least about 95%, 96%, 97%, 98%, 99% or 100% identical to SEQ ID NO: 22, a polypeptide sequence that is at least about 95%, 96%, 97%, 98%, 99% or 100% identical to SEQ ID NO: 56, a polypeptide sequence that is at least about 95%, 96%, 97%, 98%, 99% or 100% identical to SEQ ID NO: 57, and a polypeptide sequence that is at least about 95%, 96%, 97%, 98%, 99% or 100% identical to SEQ ID NO: 58.

Polynucleotides

The invention further provides isolated polynucleotides encoding a T cell activating bispecific antigen binding molecule as described herein or a fragment thereof. In some embodiments, said fragment is an antigen binding fragment.

Polynucleotides of the invention include those that are at least about 80%, 85%, 90%, 95%, 96%, 97%, 98%, 99%, or 100% identical to the sequences set forth in SEQ ID NOs 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 and 98 including functional fragments or variants thereof.

The polynucleotides encoding T cell activating bispecific antigen binding molecules of the invention may be expressed as a single polynucleotide that encodes the entire T cell activating bispecific antigen binding molecule or as multiple (e.g., two or more) polynucleotides that are co-expressed. Polypeptides encoded by polynucleotides that are co-expressed may associate through, e.g., disulfide bonds or other means to form a functional T cell activating bispecific antigen binding molecule. For example, the light chain portion of an antigen binding moiety may be encoded by a separate polynucleotide from the portion of the T cell activating bispecific antigen binding molecule comprising the heavy chain portion of the antigen binding moiety, an Fc domain subunit and optionally (part of) another antigen binding moiety. When co-expressed, the heavy chain polypeptides will associate with the light chain polypeptides to form the antigen binding moiety. In another example, the portion of the T cell activating bispecific antigen binding molecule comprising one of the two Fc domain subunits and optionally (part of) one or more antigen binding moieties could be encoded by a separate polynucleotide from the portion of the T cell activating bispecific antigen binding molecule comprising the other of the two Fc domain subunits and optionally (part of) an antigen binding moiety. When co-expressed, the Fc domain subunits will associate to form the Fc domain.

In some embodiments, the isolated polynucleotide encodes the entire T cell activating bispecific antigen binding molecule according to the invention as described herein. In other embodiments, the isolated polynucleotide encodes a polypeptides comprised in the T cell activating bispecific antigen binding molecule according to the invention as described herein.

In another embodiment, the present invention is directed to an isolated polynucleotide encoding a T cell activating bispecific antigen binding molecule of the invention or a fragment thereof, wherein the polynucleotide comprises a sequence that encodes a variable region sequence as shown in SEQ ID NOs 3, 7, 13, 17, 23, 27, 31, 32, 33, 34, 36, 39, 41, 43, 46, 47 or 51 In another embodiment, the present invention is directed to an isolated polynucleotide encoding a T cell activating bispecific antigen binding molecule or fragment thereof, wherein the polynucleotide comprises a sequence that encodes a polypeptide sequence as shown in SEQ ID NOs 22, 56, 57, 58, 12, 53, 54 and 55 In another embodiment, the invention is further directed to an isolated polynucleotide encoding a T cell activating bispecific antigen binding molecule of the invention or a fragment thereof, wherein the polynucleotide comprises a sequence that is at least about 80%, 85%, 90%, 95%, 96%, 97%, 98%, or 99% identical to the nucleotide sequence shown in SEQ ID NOs 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98. In another embodiment, the invention is directed to an isolated polynucleotide encoding a T cell activating bispecific antigen binding molecule of the invention or a fragment thereof, wherein the polynucleotide comprises the nucleic acid sequence shown in SEQ ID NOs 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98. In another embodiment, the invention is directed to an isolated polynucleotide encoding a T cell activating bispecific antigen binding molecule of the invention or a fragment thereof, wherein the polynucleotide comprises a sequence that encodes a variable region sequence that is at least about 80%, 85%, 90%, 95%, 96%, 97%, 98%, or 99% identical to the amino acid sequence in SEQ ID NOs 3, 7, 13, 17, 23, 27, 31, 32, 33, 34, 36, 39, 41, 43, 46, 47 or 51. In another embodiment, the invention is directed to an isolated polynucleotide encoding a T cell activating bispecific antigen binding molecule or a fragment thereof, wherein the polynucleotide comprises a sequence that encodes a polypeptide sequence that is at least 80%, 85%, 90%, 95%, 96%, 97%, 98%, or 99% identical to the amino acid sequence in SEQ ID NOs 22, 56, 57, 58, 12, 53, 54 or 55. The invention encompasses an isolated polynucleotide encoding a T cell activating bispecific antigen binding molecule of the invention or a fragment thereof, wherein the polynucleotide comprises a sequence that encodes the variable region sequence of SEQ ID NOs SEQ ID NOs 3, 7, 13, 17, 23, 27, 31, 32, 33, 34, 36, 39, 41, 43, 46, 47 or 51 with conservative amino acid substitutions. The invention also encompasses an isolated polynucleotide encoding a T cell activating bispecific antigen binding molecule of the invention or a fragment thereof, wherein the polynucleotide comprises a sequence that encodes the polypeptide sequence of SEQ ID NOs 22, 56, 57, 58, 12, 53, 54 or 55 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

T cell activating bispecific antigen binding molecules of the invention may be obtained, for example, by solid-state peptide synthesis (e.g. Merrifield solid phase synthesis) or recombinant production. For recombinant production one or more polynucleotide encoding the T cell activating bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a T cell activating bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the T cell activating bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the T cell activating bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the T cell activating bispecific antigen binding molecule is desired, DNA encoding a signal sequence may be placed upstream of the nucleic acid encoding a T cell activating bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. Exemplary amino acid and polynucleotide sequences of secretory signal peptides are given in SEQ ID NOs 108-116.

DNA encoding a short protein sequence that could be used to facilitate later purification (e.g. a histidine tag) or assist in labeling the T cell activating bispecific antigen binding molecule may be included within or at the ends of the T cell activating bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a T cell activating bispecific antigen binding molecule of the invention. As used herein, the term "host cell" refers to any kind of cellular system which can be engineered to generate the T cell activating bispecific antigen binding molecules of the invention or fragments thereof. Host cells suitable for replicating and for supporting expression of T cell activating bispecific antigen binding molecules are well known in the art. Such cells may be transfected or transduced as appropriate with the particular expression vector and large quantities of vector containing cells can be grown for seeding large scale fermenters to obtain sufficient quantities of the T cell activating bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a T cell activating bispecific antigen binding molecule according to the invention is provided, wherein the method comprises culturing a host cell comprising a polynucleotide encoding the T cell activating bispecific antigen binding molecule, as provided herein, under conditions suitable for expression of the T cell activating bispecific antigen binding molecule, and recovering the T cell activating bispecific antigen binding molecule from the host cell (or host cell culture medium).

The components of the T cell activating bispecific antigen binding molecule are genetically fused to each other. T cell activating bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of T cell activating bispecific antigen binding molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the T cell activating bispecific antigen binding molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the T cell activating bispecific antigen binding molecules of the invention. Non-limiting antibodies, antibody fragments, antigen binding domains or variable regions useful in the present invention can be of murine, primate, or human origin. If the T cell activating bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CD3) is incubated in a solution comprising a first labeled antibody that binds to the antigen (e.g. V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

T cell activating bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the T cell activating bispecific antigen binding molecule binds. For example, for affinity chromatography purification of T cell activating bispecific antigen binding molecules of the invention, a matrix with protein A or protein G may be used. Sequential Protein A or G affinity chromatography and size exclusion chromatography can be used to isolate a T cell activating bispecific antigen binding molecule essentially as described in the Examples. The purity of the T cell activating bispecific antigen binding molecule can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIG. 4). Three bands were resolved at approximately Mr 25,000, Mr 50,000 and Mr 75,000, corresponding to the predicted molecular weights of the T cell activating bispecific antigen binding molecule light chain, heavy chain and heavy chain/light chain fusion protein.

Assays

T cell activating bispecific antigen binding molecules provided herein may be identified, screened for, or characterized for their physical/chemical properties and/or biological activities by various assays known in the art.

Affinity Assays

The affinity of the T cell activating bispecific antigen binding molecule for an Fc receptor or a target antigen can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of T cell activating bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below. According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody. The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the T cell activating bispecific antigen binding molecules of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the T cell activating bispecific antigen binding molecules provided herein, e.g., for use in any of the below therapeutic methods. In one embodiment, a pharmaceutical composition comprises any of the T cell activating bispecific antigen binding molecules provided herein and a pharmaceutically acceptable carrier. In another embodiment, a pharmaceutical composition comprises any of the T cell activating bispecific antigen binding molecules provided herein and at least one additional therapeutic agent, e.g., as described below.

Further provided is a method of producing a T cell activating bispecific antigen binding molecule of the invention in a form suitable for administration in vivo, the method comprising (a) obtaining a T cell activating bispecific antigen binding molecule according to the invention, and (b) formulating the T cell activating bispecific antigen binding molecule with at least one pharmaceutically acceptable carrier, whereby a preparation of T cell activating bispecific antigen binding molecule is formulated for administration in vivo.

Pharmaceutical compositions of the present invention comprise a therapeutically effective amount of one or more T cell activating bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one T cell activating bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. T cell activating bispecific antigen binding molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the T cell activating bispecific antigen binding molecules of the invention.

Parenteral compositions include those designed for administration by injection, e.g. subcutaneous, intradermal, intralesional, intravenous, intraarterial intramuscular, intrathecal or intraperitoneal injection. For injection, the T cell activating bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the T cell activating bispecific antigen binding molecules may be in powder form for constitution with a suitable vehicle, e.g., sterile pyrogen-free water, before use. Sterile injectable solutions are prepared by incorporating the T cell activating bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the T cell activating bispecific antigen binding molecules may also be formulated as a depot preparation. Such long acting formulations may be administered by implantation (for example subcutaneously or intramuscularly) or by intramuscular injection. Thus, for example, the T cell activating bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the T cell activating bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The T cell activating bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

Pharmaceutical salts tend to be more soluble in aqueous and other protic solvents than are the corresponding free base forms.

Therapeutic Methods and Compositions

Any of the T cell activating bispecific antigen binding molecules provided herein may be used in therapeutic methods. T cell activating bispecific antigen binding molecules of the invention can be used as immunotherapeutic agents, for example in the treatment of cancers.

For use in therapeutic methods, T cell activating bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, T cell activating bispecific antigen binding molecules of the invention for use as a medicament are provided. In further aspects, T cell activating bispecific antigen binding molecules of the invention for use in treating a disease are provided. In certain embodiments, T cell activating bispecific antigen binding molecules of the invention for use in a method of treatment are provided. In one embodiment, the invention provides a T cell activating bispecific antigen binding molecule as described herein for use in the treatment of a disease in an individual in need thereof. In certain embodiments, the invention provides a T cell activating bispecific antigen binding molecule for use in a method of treating an individual having a disease comprising administering to the individual a therapeutically effective amount of the T cell activating bispecific antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a T cell activating bispecific antigen binding molecule as described herein for use in inducing lysis of a target cell, particularly a tumor cell. In certain embodiments, the invention provides a T cell activating bispecific antigen binding molecule for use in a method of inducing lysis of a target cell, particularly a tumor cell, in an individual comprising administering to the individual an effective amount of the T cell activating bispecific antigen binding molecule to induce lysis of a target cell. An "individual" according to any of the above embodiments is a mammal, preferably a human.

In a further aspect, the invention provides for the use of a T cell activating bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a T cell activating bispecific antigen binding molecule of the invention. In one embodiment a composition is administered to said individual, comprising the T cell activating bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a T cell activating bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a T cell activating bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a T cell activating bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the T cell activating bispecific antigen binding molecule may not provide a cure but may only provide partial benefit. In some embodiments, a physiological change having some benefit is also considered therapeutically beneficial. Thus, in some embodiments, an amount of T cell activating bispecific antigen binding molecule that provides a physiological change is considered an "effective amount" or a "therapeutically effective amount". The subject, patient, or individual in need of treatment is typically a mammal, more specifically a human.

In some embodiments, an effective amount of a T cell activating bispecific antigen binding molecule of the invention is administered to a cell. In other embodiments, a therapeutically effective amount of a T cell activating bispecific antigen binding molecule of the invention is administered to an individual for the treatment of disease.

For the prevention or treatment of disease, the appropriate dosage of a T cell activating bispecific antigen binding molecule of the invention (when used alone or in combination with one or more other additional therapeutic agents) will depend on the type of disease to be treated, the route of administration, the body weight of the patient, the type of T cell activating bispecific antigen binding molecule, the severity and course of the disease, whether the T cell activating bispecific antigen binding molecule is administered for preventive or therapeutic purposes, previous or concurrent therapeutic interventions, the patient's clinical history and response to the T cell activating bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The T cell activating bispecific antigen binding molecule is suitably administered to the patient at one time or over a series of treatments. Depending on the type and severity of the disease, about 1 µg/kg to 15 mg/kg (e.g. 0.1 mg/kg-10 mg/kg) of T cell activating bispecific antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the T cell activating bispecific antigen binding molecule). An initial higher loading dose, followed by one or more lower doses may be administered. However, other dosage regimens may be useful. The progress of this therapy is easily monitored by conventional techniques and assays.

The T cell activating bispecific antigen binding molecules of the invention will generally be used in an amount effective to achieve the intended purpose. For use to treat or prevent a disease condition, the T cell activating bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the T cell activating bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC. In cases of local administration or selective uptake, the effective local concentration of the T cell activating bispecific antigen binding molecules may not be related to plasma concentration. One having skill in the art will be able to optimize therapeutically effective local dosages without undue experimentation.

A therapeutically effective dose of the T cell activating bispecific antigen binding molecules described herein will generally provide therapeutic benefit without causing substantial toxicity. Toxicity and therapeutic efficacy of a T cell activating bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. T cell activating bispecific antigen binding molecules that exhibit large therapeutic indices are preferred. In one embodiment, the T cell activating bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety). The attending physician for patients treated with T cell activating bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The T cell activating bispecific antigen binding molecules of the invention may be administered in combination with one or more other agents in therapy. For instance, a T cell activating bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disrupter, an anti-metabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of T cell activating bispecific antigen binding molecule used, the type of disorder or treatment, and other factors discussed above. The T cell activating bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the T cell activating bispecific antigen binding molecule of the invention can occur prior to, simultaneously, and/or following, administration of the additional therapeutic agent and/or adjuvant. T cell activating bispecific antigen binding molecules of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating bispecific antigen binding molecule of the invention. The label or package insert indicates that the composition is used for treating the condition of choice. Moreover, the article of manufacture may comprise (a) a first container with a composition contained therein, wherein the composition comprises a T cell activating bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

General Methods

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, 5$^{th}$ ed., NIH Publication No. 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells. Exemplary leader peptides and polynucleotide sequences encoding them are depicted SEQ ID NOs 108-116.

Isolation of Primary Human Pan T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (Vi-Cell) and stored in RPMI1640 medium, containing 10% FCS and 1% L-alanyl-L-glutamine (Biochrom, K0302) at 37° C., 5% $CO_2$ in the incubator until assay start. T cell enrichment from PBMCs was performed using the Pan T Cell Isolation Kit II (Miltenyi Biotec #130-091-156), according to the manufacturer's instructions. Briefly, the cell pellets were diluted in 40 µl cold buffer per 10 million cells (PBS with 0.5% BSA, 2 mM EDTA, sterile filtered) and incubated with 10 µl Biotin-Antibody Cocktail per 10 million cells for 10 min at 4° C. 30 µl cold buffer and 20 µl Anti-Biotin magnetic beads per 10 million cells were added, and the mixture incubated for another 15 min at 4° C. Cells were washed by adding 10-20× the current volume of buffer and a subsequent centrifugation step at 300×g for 10 min. Up to 100 million cells were resuspended in 500 µl buffer. Magnetic separation of unlabeled human pan T cells was performed using LS columns (Miltenyi Biotec #130-042-401) according to the manufacturer's instructions. The resulting T cell population was counted automatically (Vi-Cell) and stored in AIM-V medium at 37° C., 5% $CO_2$ in the incubator until assay start (not longer than 24 h).

Isolation of Primary Human Naive T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. T-cell enrichment from PBMCs was performed using the Naive $CD8^+$ T cell isolation Kit from Miltenyi Biotec (#130-093-244), according to the manufacturer's instructions, but skipping the last isolation step of $CD8^+$ T cells (also see description for the isolation of primary human pan T cells).

Isolation of Murine Pan T Cells from Splenocytes

Spleens were isolated from C57BL/6 mice, transferred into a GentleMACS C-tube (Miltenyi Biotech #130-093-237) containing MACS buffer (PBS+0.5% BSA+2 mM EDTA) and dissociated with the GentleMACS Dissociator to obtain single-cell suspensions according to the manufacturer's instructions. The cell suspension was passed through a pre-separation filter to remove remaining undissociated tissue particles. After centrifugation at 400×g for 4 min at 4° C., ACK Lysis Buffer was added to lyse red blood cells (incubation for 5 min at room temperature). The remaining cells were washed with MACS buffer twice, counted and used for the isolation of murine pan T cells. The negative (magnetic) selection was performed using the Pan T Cell Isolation Kit from Miltenyi Biotec (#130-090-861), following the manufacturer's instructions. The resulting T cell population was automatically counted (ViCell) and immediately used for further assays.

Isolation of Primary Cynomolgus PBMCs from Heparinized Blood

Peripheral blood mononuclear cells (PBMCs) were prepared by density centrifugation from fresh blood from healthy cynomolgus donors, as follows: Heparinized blood was diluted 1:3 with sterile PBS, and Lymphoprep medium (Axon Lab #1114545) was diluted to 90% with sterile PBS. Two volumes of the diluted blood were layered over one volume of the diluted density gradient and the PBMC fraction was separated by centrifugation for 30 min at 520×g, without brake, at room temperature. The PBMC band was transferred into a fresh 50 ml Falcon tube and washed with sterile PBS by centrifugation for 10 min at 400×g at 4° C. One low-speed centrifugation was performed to remove the platelets (15 min at 150×g, 4° C.), and the resulting PBMC population was automatically counted (ViCell) and immediately used for further assays.

Target Cells

For the assessment of MCSP-targeting bispecific antigen binding molecules, the following tumor cell lines were used: the human melanoma cell line WM266-4 (ATCC #CRL-1676), derived from a metastatic site of a malignant melanoma and expressing high levels of human MCSP; the human melanoma cell line MV-3 (a kind gift from The Radboud University Nijmegen Medical Centre), expressing medium levels of human MCSP; the human malignant melanoma (primary tumour) cell line A375 (ECACC #88113005) expressing high levels of MCSP; the human colon carcinoma cell line HCT-116 (ATCC #CCL-247) that does not express MCSP; and the human Caucasian colon adenocarcinoma cell line LS180 (ECACC #87021202) that does not express MCSP.

For the assessment of CEA-targeting bispecific antigen binding molecules, the following tumor cell lines were used: the human gastric cancer cell line MKN45 (DSMZ #ACC 409), expressing very high levels of human CEA; the human pancreas adenocarcinoma cell line HPAF-II (kind gift of Roche Nutley), expressing high levels of human CEA; the human primary pancreatic adenocarcinoma cell line BxPC-3 (ECACC #93120816) expressing medium levels of human CEA; the human female Caucasian colon adenocarcinoma cell line LS-174T (ECACC #87060401), expressing medium levels of human CEA; the human pancreas adenocarcinoma cell line ASPC-1 (ECACC #96020930) expressing low levels of human CEA; the human epitheloid pancreatic carcinoma cell line Panc-1 (ATCC #CRL-1469), expressing (very) low levels of human CEA; the human colon carcinoma cell line HCT-116 (ATCC #CCL-247) that does not express CEA; a human adenocarcinomic alveolar basal epithelial cell line A549-huCEA that was stably transfected in-house to express human CEA; and a murine colon carcinoma cell line MC38-huCEA, that was engineered in-house to stably express human CEA.

In addition, a human T cell leukaemia cell line, Jurkat (ATCC #TIB-152), was used to assess binding of different bispecific constructs to human CD3 on cells.

Example 1

Affinity Maturation of Anti-MCSP Antibody M4-3/ML2

Affinity maturation was performed via the oligonucleotide-directed mutagenesis procedure. For this the heavy chain variant M4-3, and the light chain variant ML2 were cloned into a phagemid vector, similar to those described by Hoogenboom, (Hoogenboom et al., Nucleic Acids Res. 1991, 19, 4133-4137). Residues to be randomized were identified by first generating a 3D model of that antibody via classical homology modeling and then identifying the solvent accessible residues of the complementary determining regions (CDRs) of heavy and light chain. Oligonucleotides with randomization based on trinucleotide synthesis as shown in Table 1 were purchased from Ella Biotech (Munich, Germany). Three independent sublibraries were generated via classical PCR, and comprised randomization in CDR-H1 together with CDR-H2, or CDR-L1 together with CDR-L2. CDR-L3 was randomized in a separate approach. The DNA fragments of those libraries were cloned into the phagemid via restriction digest and ligation, and subsequently electroporated into TG1 bacteria.

Library Selection

The antibody variants thus generated were displayed in a monovalent fashion from filamentous phage particles as fusions to the gene III product of M13 packaged within each particle. The phage-displayed variants were then screened for their biological activities (here: binding affinity) and candidates that have one or more improved activities were used for further development. Methods for making phage display libraries can be found in Lee et al., J. Mol. Biol. (2004) 340, 1073-1093. Selections with all affinity maturation libraries were carried out in solution according to the following procedure: 1. binding of ~1012 phagemid particles of each affinity maturation libraries to 100 nM biotinylated hu-MCSP(D3 domain)-avi-his (SEQ ID NO: 118) for 0.5 h in a total volume of 1 ml, 2. capture of biotinylated hu-MCSP(D3 domain)-avi-his and specifically bound phage particles by addition of $5.4 \times 10^7$ streptavidin-coated magnetic beads for 10 min, 3. washing of beads using 5-10×1 ml PBS/Tween-20 and 5-10×1 ml PBS, 4. elution of phage particles by addition of 1 ml 100 mM TEA (triethylamine) for 10 min and neutralization by adding 500 µl 1M Tris/HCl pH 7.4 and 5. re-infection of exponentially growing E. coli TG1 bacteria, infection with helper phage VCSM13 and subsequent PEG/NaCl precipitation of phagemid particles to be used in subsequent selection rounds. Selections were carried out over 3-5 rounds using either constant or decreasing (from $10^{-7}$ M to $2 \times 10^{-9}$ M) antigen concentrations. In round 2, capture of antigen-phage complexes was performed using neutravidin plates instead of streptavidin beads. Specific binders were identified by ELISA as follows: 100 µl of 10 nM biotinylated hu-MCSP(D3 domain)-avi-his per well were coated on neutravidin plates. Fab-containing bacterial supernatants were added and binding Fabs were detected via their Flag-tags by using an anti-Flag/HRP secondary antibody. ELISA-positive clones were bacterially expressed as soluble Fab fragments in 96-well format and supernatants were subjected to a kinetic screening experiment by SPR-analysis using ProteOn XPR36 (BioRad). Clones expressing Fabs with the highest affinity constants were identified and the corresponding phagemids were sequenced.

TABLE 1

(excluded were always Cys and Met. Lys was excluded on top in those cases where the oligonucleotide was a reverse primer)

| Position | Randomization |
|---|---|
| Heavy chain | |
| CDR1 | |
| Ser31 | S (40%), rest (60%, 4% each) |
| Gly32 | G (40%), rest (60%, 4% each). |
| Tyr33 | Y (40%), rest (60%, 4% each) |
| Tyr34 | Y (40%), rest (60%, 4% each) |
| CDR2 | |
| Tyr50 | Y 40%, (F, W, L, A, I, 30%, 6% each), rest (30%, 2.5% each) |
| Thr52 | T (60%), rest (40%, 2.5% each) |
| Tyr53 | Y (40%), rest (60%, 3.8% each) |
| Asp54 | D (40%), rest (60%, 3.8% each) |
| Ser56 | S (40%), rest (60%, 3.8% each) |
| Light chain | |
| CDR1 | |
| Gln27 | Q (40%), (E, D, N, S, T, R, 40%, 6.7% each), rest (total 20%, 2.2% each) |
| Gly28 | G (40%), (N, T, S, Q, Y, D, E, 40%, 5.7% each), rest (20%, 2.5% each) |
| Asn31 | N (40%), (S, T, G, Q, Y, D, E, R, 50%, 6.3% each), rest (10%, 1.4% each) |
| Tyr32 | Y (40%), (W, S, R, 30%, 10% each), rest (30%, 2.3% each) |
| CDR2 | |
| Tyr50 | Y (70%), (E, R, K, A, Q, T, S, D, G, W, F, 30%, 2.7% each) |
| Thr51 | T (50%), (S, A, G, N, Q, V, 30%, 5% each), rest (20%, 2% each) |
| Ser52 | S (50%), rest (50%, 3.1% each) |
| Ser53 | S (40%), (N, T, Q, Y, D, E, I, 40%, 5.7% each), rest (20%, 2.2% each) |
| CDR3 | |
| Tyr91 | Y (50%), rest (50%, 3.1% each) |
| Ser92 | S (50%), (N, Q, T, A, G 25%, 5% each), rest (25%, 2.3% each) |
| Lys93 | K (50%), S (5%), T (5%), N (5%), rest (35%, 2.7% each) |
| Leu94 | L (50%), (Y, F, S, I, A, V, 30%, 5% each), rest (20%, 2% each) |
| Pro95 | P (50%), (S, A, 20%, 10% each), rest (30%, 2.1% each) |
| Trp96 | W 50%, (Y, R, L, 15%, 5% each), rest (35%, 2.5% each) |

FIG. 2 shows an alignment of affinity matured anti-MCSP clones compared to the non-matured parental clone (M4-3 ML2). Heavy chain randomization was performed only in the CDR1 and 2. Light chain randomization was performed in CDR1 and 2, and independently in CDR3.

During selection, a few mutations in the frameworks occurred like F71Y in clone G3 or Y87H in clone E10.

Production and Purification of Human IgG$_1$

The variable region of heavy and light chain DNA sequences of the affinity matured variants were subcloned in frame with either the constant heavy chain or the constant light chain pre-inserted into the respective recipient mammalian expression vector. The antibody expression was driven by an MPSV promoter and carries a synthetic polyA signal sequence at the 3' end of the CDS. In addition each vector contained an EBV OriP sequence.

The molecule was produced by co-transfecting HEK293-EBNA cells with the mammalian expression vectors using polyethylenimine (PEI). The cells were transfected with the corresponding expression vectors in a 1:1 ratio. For transfection HEK293 EBNA cells were cultivated in suspension serum-free in CD CHO culture medium. For the production in 500 ml shake flask, 400 million HEK293 EBNA cells were seeded 24 hours before transfection. For transfection cells were centrifuged for 5 min at 210×g, supernatant was replaced by pre-warmed 20 ml CD CHO medium. Expression vectors were mixed in 20 ml CD CHO medium to a final amount of 200 μg DNA. After addition of 540 μl PEI solution, the mixture was vortexed for 15 s and subsequently incubated for 10 min at room temperature. Afterwards cells were mixed with the DNA/PEI solution, transferred to a 500 ml shake flask and incubated for 3 hours at 37° C. in an incubator with a 5% CO$_2$ atmosphere. After incubation time 160 ml F17 medium was added and cells were cultivated for 24 hours. One day after transfection 1 mM valproic acid and 7% Feed 1 (Lonza) was added. After 7 days cultivation supernatant was collected for purification by centrifugation for 15 min at 210×g, the solution was sterile filtered (0.22 μm filter) and sodium azide in a final concentration of 0.01% w/v was added, and kept at 4° C.

The secreted protein was purified from cell culture supernatants by affinity chromatography using Protein A. Supernatant was loaded on a HiTrap Protein A HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volumes 20 mM sodium phosphate, 20 mM sodium citrate, 0.5 M sodium chloride, pH 7.5. Target protein was eluted during a gradient over 20 column volumes from 20 mM sodium citrate, 0.5 M sodium chloride, pH 7.5 to 20 mM sodium citrate, 0.5 M sodium chloride, pH 2.5. Protein solution was neutralized by adding 1/10 of 0.5 M sodium phosphate, pH 8. Target protein was concentrated and filtrated prior loading on a HiLoad Superdex 200 column (GE Healthcare) equilibrated with 20 mM histidine, 140 mM sodium chloride solution of pH 6.0.

The protein concentration of purified protein samples was determined by measuring the optical density (OD) at 280 nm, using the molar extinction coefficient calculated on the basis of the amino acid sequence. Purity and molecular weight of molecules were analyzed by CE-SDS analyses in the presence and absence of a reducing agent. The Caliper LabChip GXII system (Caliper Life Sciences) was used according to the manufacturer's instruction. 2 µg sample was used for analyses. The aggregate content of antibody samples was analyzed using a TSKgel G3000 SW XL analytical size-exclusion column (Tosoh) in 25 mM $K_2HPO_4$, 125 mM NaCl, 200 mM L-arginine monohydrochloride, 0.02% (w/v) $NaN_3$, pH 6.7 running buffer at 25° C.

TABLE 2

Production and purification of affinity matured anti-MCSP IgGs

| Construct | Yield [mg/l] | HMW [%] | LMW [%] | Monomer [%] |
|---|---|---|---|---|
| M4-3(C1) ML2(G3) | 43.9 | 0 | 0 | 100 |
| M4-3(C1) ML2(E10) | 59.5 | 0 | 0 | 100 |
| M4-3(C1) ML2(C5) | 68.9 | 0 | 0.8 | 99.2 |

Affinity Determination
ProteOn Analysis $K_D$ was measured by surface plasmon resonance using a ProteOn XPR36 machine (BioRad) at 25° C. with anti-human F(ab')2 fragment specific capture antibody (Jackson ImmunoResearch #109-005-006) immobilized by amine coupling on CM5 chips and subsequent capture of Fabs from bacterial supernatant or from purified Fab preparations. Briefly, carboxymethylated dextran biosensor chips (CM5, GE Healthcare) were activated with N-ethyl-N'-(3-dimethylaminopropyl)-carbodiimide hydrochloride (EDC) and N-hydroxysuccinimide (NHS) according to the supplier's instructions. Anti-human F(ab')2 fragment specific capture antibody was diluted with 10 mM sodium acetate, pH 5.0 at 50 µg/ml before injection at a flow rate of 10 µl/minute to achieve approximately up to 10.000 response units (RU) of coupled capture antibody. Following the injection of the capture antibody, 1 M ethanolamine is injected to block unreacted groups. For kinetics measurements, Fabs from bacterial supernatant or purified Fabs were injected at a flow rate of 10 µl/minute for 300 s and a dissociation of 300 s for capture baseline stabilization. Capture levels were in the range of 100-500 RU. In a subsequent step, human MCSP (D3 domain)-avi-his analyte was injected either as a single concentration or as a concentration series (depending of clone affinity in a range between 100 nM and 250 pM) diluted into HBS-EP+ (GE Healthcare, 10 mM HEPES, 150 mM NaCl, 3 mM EDTA, 0.05% Surfactant P20, pH 7.4) at 25° C. at a flow rate of 50 µl/min. The surface of the sensorchip was regenerated by injection of glycine pH 1.5 for 30 s at 90 µl/min followed by injection of NaOH for 20 s at the same flow rate. Association rates ($k_{on}$) and dissociation rates ($k_{off}$) were calculated using a simple one-to-one Langmuir binding model (ProteOn XPR36 Evaluation Software or Scrubber software (BioLogic)) by simultaneously fitting the association and dissociation sensorgrams. The equilibrium dissociation constant ($K_D$) was calculated as the ratio $k_{off}/k_{on}$. This data was used to determine the comparative binding affinity of the affinity matured variants with the parental antibody. Table 3a shows the data generated from these assays.

G3, E10, C5 for the light chain, and D6, A7, B7, B8, C1 for the heavy chain were chosen for conversion into human $IgG_1$ format. Since CDR1 and 2 of the light chain were randomized independent from CDR3, the obtained CDRs were combined during IgG conversion.

In the IgG format affinities were measured again to the human MCSP antigen (SEQ ID NO: 118), in addition also to the cynomolgus homologue (SEQ ID NO: 117).

The method used was exactly as described for the Fab fragments, just using purified IgG from mammalian production.

TABLE 3a

MCSP affinity matured clones: Proteon data.

| Variant | Human MCSP Fab $K_D$ | Human MCSP IgG $K_D$ | Cyno MCSP IgG $K_D$ | Human MCSP IgG $K_D$ Comparative binding affinity - Fold increase over parent | Cyno MCSP IgG $K_D$ |
|---|---|---|---|---|---|
| Parental M4-3/ML2 | $5 * 10^{-9}$ | $2 * 10^{-9}$ | $2 * 10^{-9}$ | | |
| M4-3/ML2(G3) | $4 * 10^{-10}$ | $3 * 10^{-10}$ | $6 * 10^{-10}$ | 6.7 | 3.3 |
| M4-3/ML2(E10) | $7 * 10^{-10}$ | $1 * 10^{-9}$ | $2 * 10^{-9}$ | 2.0 | 1.0 |
| M4-3/ML2(E10/G3) | | $4 * 10^{-10}$ | $9 * 10^{-10}$ | 5.0 | 2.2 |
| M4-3/ML2(C5) | $7 * 10^{-10}$ | $4 * 10^{-10}$ | $1 * 10^{-9}$ | 5.0 | 2.0 |
| M4-3/ML2(C5/G3) | | $7 * 10^{-10}$ | $1 * 10^{-9}$ | 2.9 | 2.0 |
| M4-3(D6)/ML2 | $2 * 10^{-9}$ | $4 * 10^{-10}$ | $1 * 10^{-9}$ | 5.0 | 2.0 |
| M4-3(A7)/ML2 | $2 * 10^{-11}$ | $8 * 10^{-10}$ | $1 * 10^{-9}$ | 2.5 | 2.0 |
| M4-3(B7)/ML2 | | $5 * 10^{-10}$ | $7 * 10^{-10}$ | 4.0 | 2.9 |
| M4-3(B8)/ML2 | $3 * 10^{-10}$ | $9 * 10^{-10}$ | $1 * 10^{-9}$ | 2.2 | 2.0 |
| M4-3(C1)/ML2 | $6 * 10^{-10}$ | $9 * 10^{-10}$ | $8 * 10^{-10}$ | 2.2 | 2.5 |
| M4-3(C1)/ML2(G3) | | $7 * 10^{-11}$ | $2 * 10^{-10}$ | 28.6 | 10.0 |
| M4-3(C1)/ML2(E10) | | $5 * 10^{-10}$ | $6 * 10^{-10}$ | 4.0 | 3.3 |
| M4-3(A7)/ML2(G3) | | $7 * 10^{-11}$ | $2 * 10^{-10}$ | 28.6 | 10.0 |
| M4-3(A7)/ML2(E10) | | $3 * 10^{-10}$ | $7 * 10^{-10}$ | 6.7 | 2.9 |
| M4-3(C1)/ML2(C5) | | $2 * 10^{-10}$ | $3 * 10^{-10}$ | 10.0 | 6.7 |
| M4-3(A7)/ML2(C5) | | $7 * 10^{-11}$ | $2 * 10^{-10}$ | 28.6 | 10.0 |

Affinity Determination by Surface Plasmon Resonance (SPR) Using Biacore T200

Surface plasmon resonance (SPR) experiments to determine the affinity and the avidity of the affinity matured IgGs were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

For analyzing the avidity of the interaction of different anti-MCSP IgGs to human and cynomolgus MCSP D3 direct coupling of around 9,500 resonance units (RU) of the anti-Penta His antibody (Qiagen) was performed on a CM5 chip at pH 5.0 using the standard amine coupling kit (Biacore, Freiburg/Germany). Antigens were captured for 60 s at 30 nM with 10 μl/min respectively. IgGs were passed at a concentration of 0.0064-100 nM with a flowrate of 30 μl/min through the flow cells over 280 s. The dissociation was monitored for 180 s. Bulk refractive index differences were corrected for by subtracting the response obtained on reference flow cell. Here, the IgGs were flown over a surface with immobilized anti-Penta His antibody but on which HBS-EP has been injected rather than human MCSP D3 or cynomolgus MCSP D3.

For affinity measurements IgGs were captured on a CM5 sensorchip surface with immobilized anti human Fc. Capture IgG was coupled to the sensorchip surface by direct immobilization of around 9,500 resonance units (RU) at pH 5.0 using the standard amine coupling kit (Biacore, Freiburg/Germany). IgGs are captured for 25 s at 10 nM with 30 μl/min. Human and cynomolgus MCSP D3 were passed at a concentration of 2-500 nM with a flowrate of 30 μl/min through the flow cells over 120 s. The dissociation was monitored for 60 s. Association and dissociation for concentration 166 and 500 nM was monitored for 1200 and 600 s, respectively. Bulk refractive index differences were corrected for by subtracting the response obtained on reference flow cell. Here, the antigens were flown over a surface with immobilized anti-human Fc antibody but on which HBS-EP has been injected rather than anti-MCSP IgGs.

Kinetic constants were derived using the Biacore T200 Evaluation Software (vAA, Biacore AB, Uppsala/Sweden), to fit rate equations for 1:1 Langmuir binding by numerical integration.

Higher affinity to human and cynomolgus MCSP D3 were confirmed by surface plasmon resonance measurements using Biacore T200. In addition, avidity measurements showed an up to 3-fold increase in bivalent binding (Table 3b).

TABLE 3b

Affinity and avidity of anti MCSP IgGs to human MCSP-D3 and cynomolgus MCSP-D3.

| $K_D$ in nM | Human MCSP D3 | | Cynomolgus MCSP D3 | |
| --- | --- | --- | --- | --- |
| T = 25° C. | Affinity | Avidity | Affinity | Avidity |
| M4-3(C1) ML2(G3) | 1.8 | 0.0045 | 1.4 | 0.0038 |
| M4-3(C1) ML2(E10) | 4.6 | 0.0063 | 3.8 | 0.0044 |
| M4-3(C1) ML2(C5) | 1.8 | 0.0046 | 1.3 | 0.0044 |
| M4-3 ML2 (parental) | 8.6 | 0.0090 | 11.4 | 0.0123 |

Example 2

Preparation of MCSP TCB (2+1 Crossfab-IgG P329G LALA Inverted) Containing M4-3(C1) ML2(G3) as Anti MCSP Antibody and Humanized CH2527 as Anti CD3 Antibody The variable region of heavy and light chain DNA sequences were subcloned in frame with either the constant heavy chain or the constant light chain pre-inserted into the respective recipient mammalian expression vector. The antibody expression was driven by an MPSV promoter and carries a synthetic polyA signal sequence at the 3' end of the CDS. In addition each vector contains an EBV OriP sequence.

The molecule was produced by co-transfecting HEK293-EBNA cells with the mammalian expression vectors using polyethylenimine (PEI). The cells were transfected with the corresponding expression vectors in a 1:2:1:1 ratio ("vector heavy chain Fc(hole)": "vector light chain": "vector light chain Crossfab": "vector heavy chain Fc(knob)-FabCrossfab").

For transfection HEK293 EBNA cells were cultivated in suspension serum-free in CD CHO culture medium. For the production in 500 ml shake flask 400 million HEK293 EBNA cells were seeded 24 hours before transfection. For transfection cells were centrifuged for 5 min at 210×g, supernatant was replaced by pre-warmed 20 ml CD CHO medium. Expression vectors were mixed in 20 ml CD CHO medium to a final amount of 200 μg DNA. After addition of 540 μl PEI solution the mixture was vortexed for 15 s and subsequently incubated for 10 min at room temperature. Afterwards cells were mixed with the DNA/PEI solution, transferred to a 500 ml shake flask and incubated for 3 hours at 37° C. in an incubator with a 5% $CO_2$ atmosphere. After incubation time 160 ml F17 medium was added and cell were cultivated for 24 hours. One day after transfection 1 mM valproic acid and 7% Feed 1 (Lonza) was added. After 7 days cultivation supernatant was collected for purification by centrifugation for 15 min at 210×g, the solution was sterile filtered (0.22 μm filter) and sodium azide in a final concentration of 0.01% w/v was added, and kept at 4° C.

The secreted protein was purified from cell culture supernatants by affinity chromatography using Protein A. Supernatant was loaded on a HiTrap Protein A HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volumes 20 mM sodium phosphate, 20 mM sodium citrate, 0.5 M sodium chloride, pH 7.5. Target protein was eluted during a gradient over 20 column volumes from 20 mM sodium citrate, 0.5 M sodium chloride, pH 7.5 to 20 mM sodium citrate, 0.5 M sodium chloride, pH 2.5. Protein solution was neutralized by adding 1/10 of 0.5 M sodium phosphate, pH 8. Target protein was concentrated and filtrated prior loading on a HiLoad Superdex 200 column (GE Healthcare) equilibrated with 20 mM histidine, 140 mM sodium chloride solution of pH 6.0.

The protein concentration of purified protein samples was determined by measuring the optical density (OD) at 280 nm, using the molar extinction coefficient calculated on the basis of the amino acid sequence.

Purity and molecular weight of molecules were analyzed by CE-SDS analyses in the presence and absence of a reducing agent. The Caliper LabChip GXII system (Caliper lifescience) was used according to the manufacturer's instruction. 2 μg sample was used for analyses.

The aggregate content of antibody samples was analyzed using a TSKgel G3000 SW XL analytical size-exclusion column (Tosoh) in 25 mM $K_2HPO_4$, 125 mM NaCl, 200 mM L-arginine monohydrochloride, 0.02% (w/v) $NaN_3$, pH 6.7 running buffer at 25° C.

TABLE 4a

Summary production and purification of MCSP TCB.

| Construct | Titer [mg/l] | Yield [mg/l] | Aggregate after 1st purification step [%] | HMW [%] | LMW [%] | Monomer [%] |
|---|---|---|---|---|---|---|
| MCSP TCB | 157 | 0.32 | 32 | 3.3 | 0 | 96.7 |

FIG. 3 shows a schematic drawing of the MCSP TCB (2+1 Crossfab-IgG P329G LALA inverted) molecule.

Figure 4:
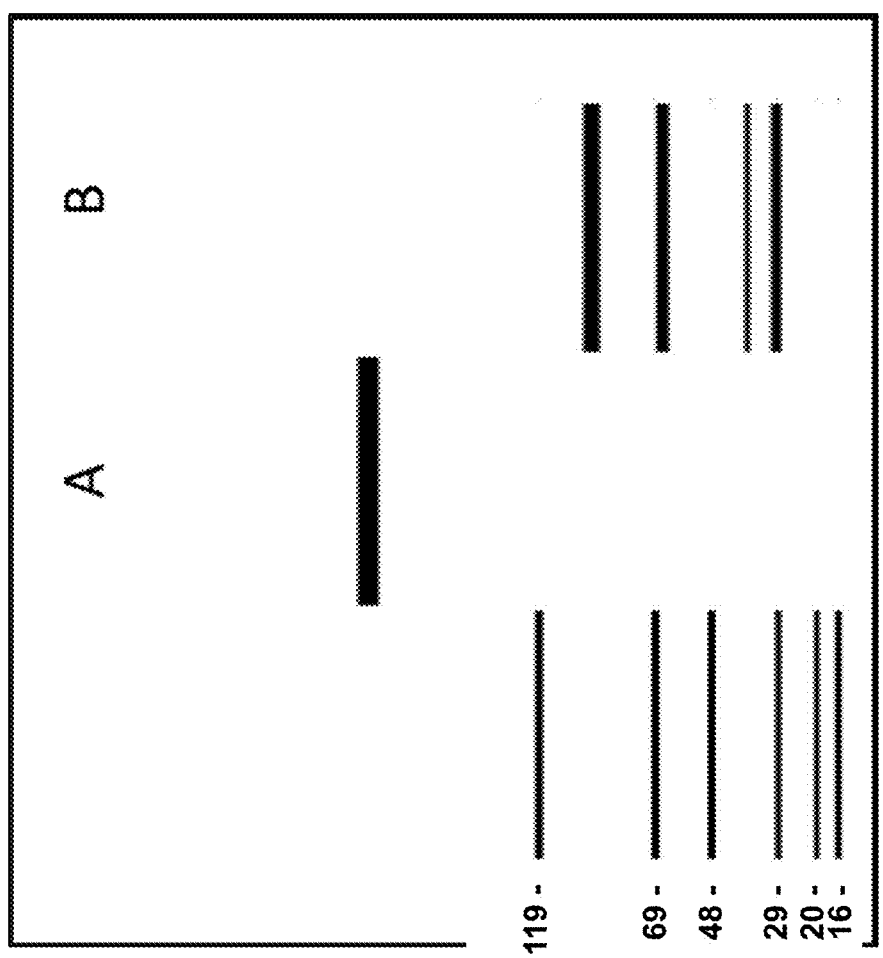
FIG. 4. CE-SDS analyses of MCSP TCB (2+1 Crossfab-IgG P329G LALA inverted, SEQ ID NOs: 12, 53, 54 and 55). Electropherogram shown as SDS-Page of MCSP TCB: A) non reduced, B) reduced.

FIG. 4 and Table 4b show CE-SDS analyses of a MCSP TCB (2+1 Crossfab-IgG P329G LALA inverted) molecule (SEQ ID NOs: 12, 53, 54 and 55).

TABLE 4b

CE-SDS analyses of MCSP TCB.

| | Peak | kDa | Corresponding Chain |
|---|---|---|---|
| MCSP TCB non reduced (A) | 1 | 206.47 | |
| MCSP TCB reduced (B) | 1 | 29.15 | Light chain ML2 (C1) |
| | 2 | 37.39 | Light chain huCH2527 |
| | 3 | 66.07 | Fc (hole) |
| | 4 | 94.52 | Fc (knob) |

Example 3

Preparation of CEA TCB (2+1 Crossfab-IgG P329G LALA Inverted) Containing CH1A1A 98/99 2F1 as Anti CEA Antibody and Humanized CH2527 as Anti CD3 Antibody The variable region of heavy and light chain DNA sequences were subcloned in frame with either the constant heavy chain or the constant light chain pre-inserted into the respective recipient mammalian expression vector. The antibody expression was driven by an MPSV promoter and carries a synthetic polyA signal sequence at the 3' end of the CDS. In addition each vector contains an EBV OriP sequence.

The molecule was produced by co-transfecting HEK293 EBNA cells with the mammalian expression vectors using polyethylenimine (PEI). The cells were transfected with the corresponding expression vectors in a 1:2:1:1 ratio ("vector heavy chain Fc(hole)": "vector light chain": "vector light chain Crossfab": "vector heavy chain Fc(knob)-FabCrossfab").

For transfection HEK293 EBNA cells were cultivated in suspension serum-free in CD CHO culture medium. For the production in 500 ml shake flask 400 million HEK293 EBNA cells were seeded 24 hours before transfection. For transfection cells were centrifuged for 5 min at 210×g, supernatant was replaced by pre-warmed 20 ml CD CHO medium. Expression vectors were mixed in 20 ml CD CHO medium to a final amount of 200 µg DNA. After addition of 540 µl PEI solution the mixture was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO$_2$ atmosphere. After incubation time 160 ml F17 medium was added and cell were cultivated for 24 hours. One day after transfection 1 mM valproic acid and 7% Feed 1 (Lonza) was added. After 7 days cultivation supernatant was collected for purification by centrifugation for 15 min at 210×g, the solution was sterile filtered (0.22 µm filter) and sodium azide in a final concentration of 0.01% w/v was added, and kept at 4° C.

The secreted protein was purified from cell culture supernatants by affinity chromatography using Protein A. Supernatant was loaded on a HiTrap Protein A HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volumes 20 mM sodium phosphate, 20 mM sodium citrate, 0.5 M sodium chloride, pH 7.5. Target protein was eluted during a gradient over 20 column volumes from 20 mM sodium citrate, 0.5 M sodium chloride, pH 7.5 to 20 mM sodium citrate, 0.5 M sodium chloride, pH 2.5. Protein solution was neutralized by adding 1/10 of 0.5 M sodium phosphate, pH 8. Target protein was concentrated and filtrated prior loading on a HiLoad Superdex 200 column (GE Healthcare) equilibrated with 20 mM histidine, 140 mM sodium chloride solution of pH 6.0.

The protein concentration of purified protein samples was determined by measuring the optical density (OD) at 280 nm, using the molar extinction coefficient calculated on the basis of the amino acid sequence.

Purity and molecular weight of molecules were analyzed by CE-SDS analyses in the presence and absence of a reducing agent. The Caliper LabChip GXII system (Caliper lifescience) was used according to the manufacturer's instructions. 2 µg sample was used for analyses.

The aggregate content of antibody samples was analyzed using a TSKgel G3000 SW XL analytical size-exclusion column (Tosoh) in 25 mM K$_2$HPO$_4$, 125 mM NaCl, 200 mM L-arginine monohydrocloride, 0.02% (w/v) NaN$_3$, pH 6.7 running buffer at 25° C.

TABLE 5

Summary production and purification of CEA TCB.

| Construct | Titer [mg/l] | Yield [mg/l] | Aggregate after 1st purification step [%] | HMW [%] | LMW [%] | Monomer [%] |
|---|---|---|---|---|---|---|
| CEA TCB | 66 | 0.31 | 21.5 | 8.1 | 4.4 | 87.5 |

FIG. 5 shows a schematic drawing of CEA TCB (2+1 Crossfab-IgG P329G LALA inverted) molecule.

Figure 6:
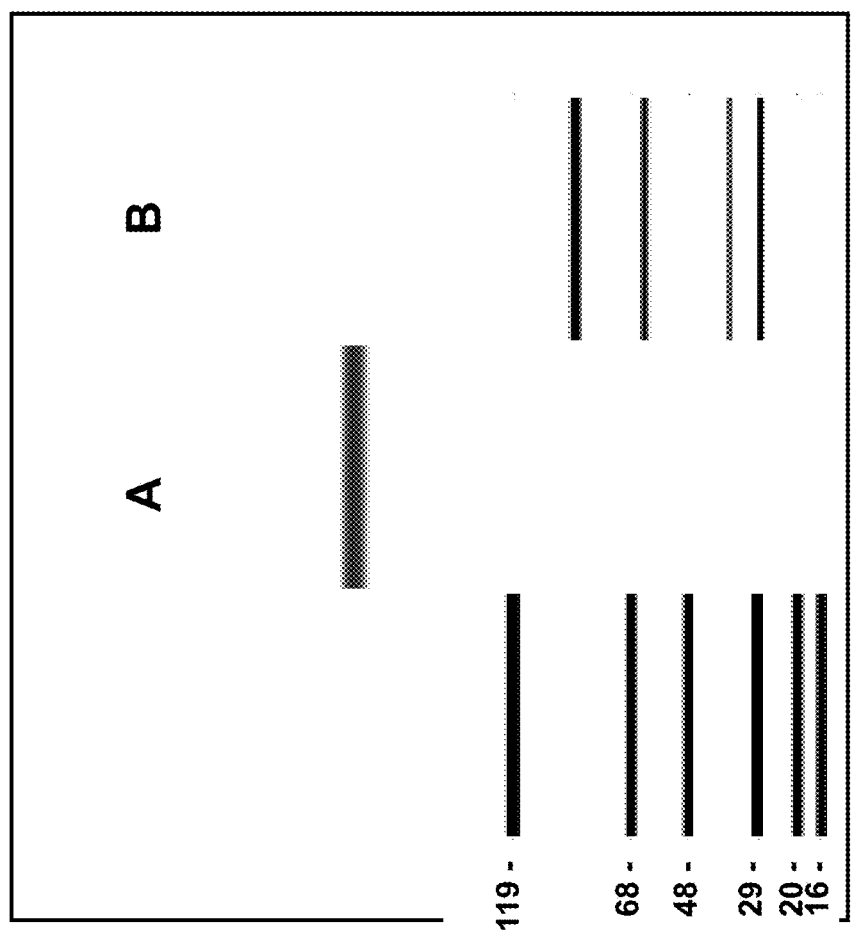
FIG. 6. CE-SDS analyses of CEA TCB (2+1 Crossfab-IgG P329G LALA inverted, SEQ ID NOs: 22, 56, 57 and 58) molecule. Electropherogram shown as SDS-Page of CEA TCB: A) non reduced, B) reduced.

FIG. 6 and Table 6 show CE-SDS analyses of a CEA TCB (2+1 Crossfab-IgG P329G LALA inverted) molecule (SEQ ID NOs: 22, 56, 57 and 58).

TABLE 6

CE-SDS analyses of CEA TCB.

| | Peak | kDa | Corresponding Chain |
|---|---|---|---|
| CEA TCB non reduced (A) | 1 | 205.67 | Correct molecule |
| CEA TCB reduced (B) | 1 | 28.23 | Light chain CH1A1A 98/99 × 2F1 |
| | 2 | 36.31 | Light chain CH2527 |
| | 3 | 63.48 | Fc (hole) |
| | 4 | 90.9 | Fc (knob) |

In an alternative purification method, the CEA TCB was captured from harvested and clarified fermentation supernatant by Protein A affinity chromatography (MabSelect SuRe). The Protein A eluate was then submitted to cation exchange chromatography (Poros 50 HS) and subsequently fractionated and analyzed by means of SE-HPLC and capillary electrophoresis. The product containing fractions were pooled and subjected to hydrophobic interaction chromatography (Butyl-Sepharose 4FF) at room temperature in a bind-elute mode. The eluate therefrom was then fractionated and analyzed by means of SE-HPLC and capillary electrophoresis. The product containing fractions were pooled and subsequently anion exchange chromatography (Q-Sepharose FF) in flow-through mode was performed. The material obtained using this purification method had a monomer content of >98%.

Example 4

Binding of MCSP TCB to MCSP- and CD3-Expressing Cells

Figure 7:
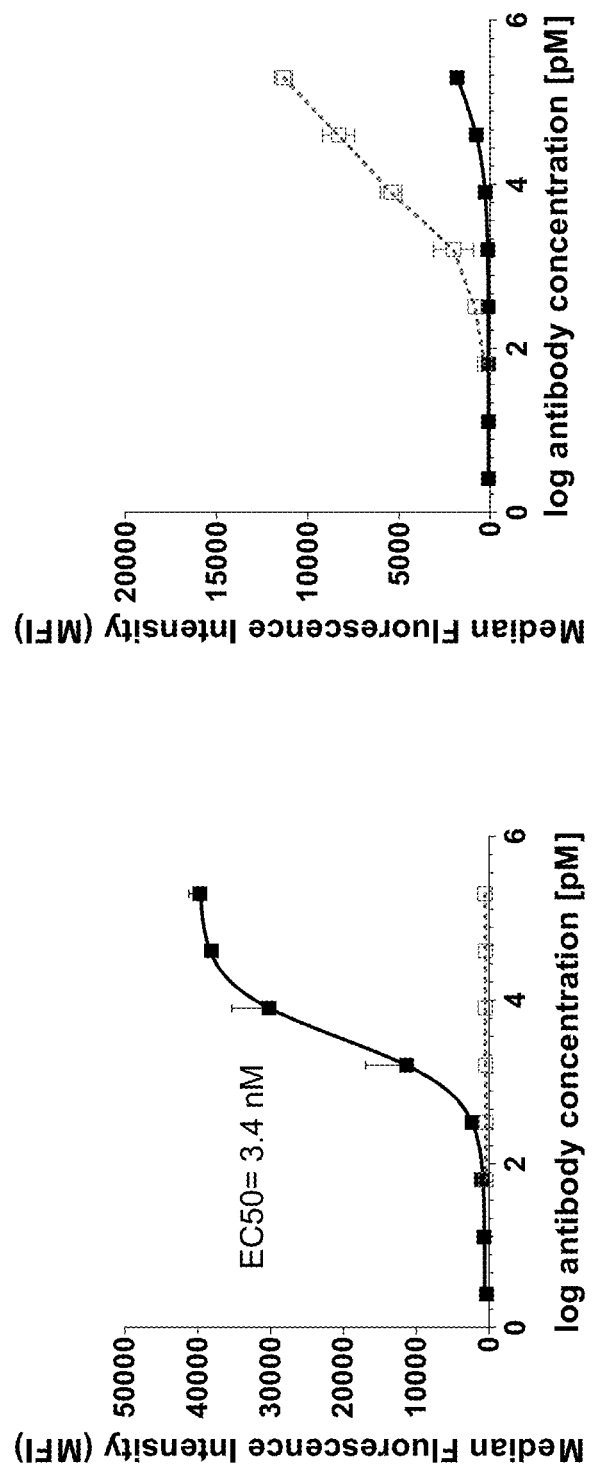
FIG. 7. Binding of MCSP TCB (SEQ ID NOs: 12, 53, 54 and 55) to A375 cells (MCSP$^+$) (A) and Jurkat (CD3$^+$ cells) (B). "Untargeted TCB": bispecific antibody engaging CD3 but no second antigen (SEQ ID NOs: 59, 60, 61 and 62).

The binding of MCSP TCB was tested on a MCSP-expressing human malignant melanoma cell line (A375) and a CD3-expressing immortalized T lymphocyte line (Jurkat). Briefly, cells were harvested, counted, checked for viability and resuspended at $2 \times 10^6$ cells/ml in FACS buffer (100 µl PBS 0.1% BSA). 100 µl cell suspension (containing $0.2 \times 10^6$ cells) were incubated in round-bottom 96-well plate for 30 min at 4° C. with increasing concentrations of the MCSP TCB (2.6 pM-200 nM), washed twice with cold PBS 0.1% BSA, re-incubated for further 30 min at 4° C. with the PE-conjugated AffiniPure F(ab')2 Fragment goat anti-human IgG Fcγ Fragment Specific secondary antibody (Jackson Immuno Research Lab PE #109-116-170), washed twice with cold PBS 0.1% BSA and immediately analyzed by FACS using a FACS CantoII (Software FACS Diva) by gating live, DAPI-negative, cells. Binding curves were obtained using GraphPadPrism5 (FIG. 7A, binding to A375 cells, $EC_{50}$=3381 pM; FIG. 7B, binding to Jurkat cells).

Example 5

T-Cell Killing Induced by MCSP TCB Antibody

Figure 8:
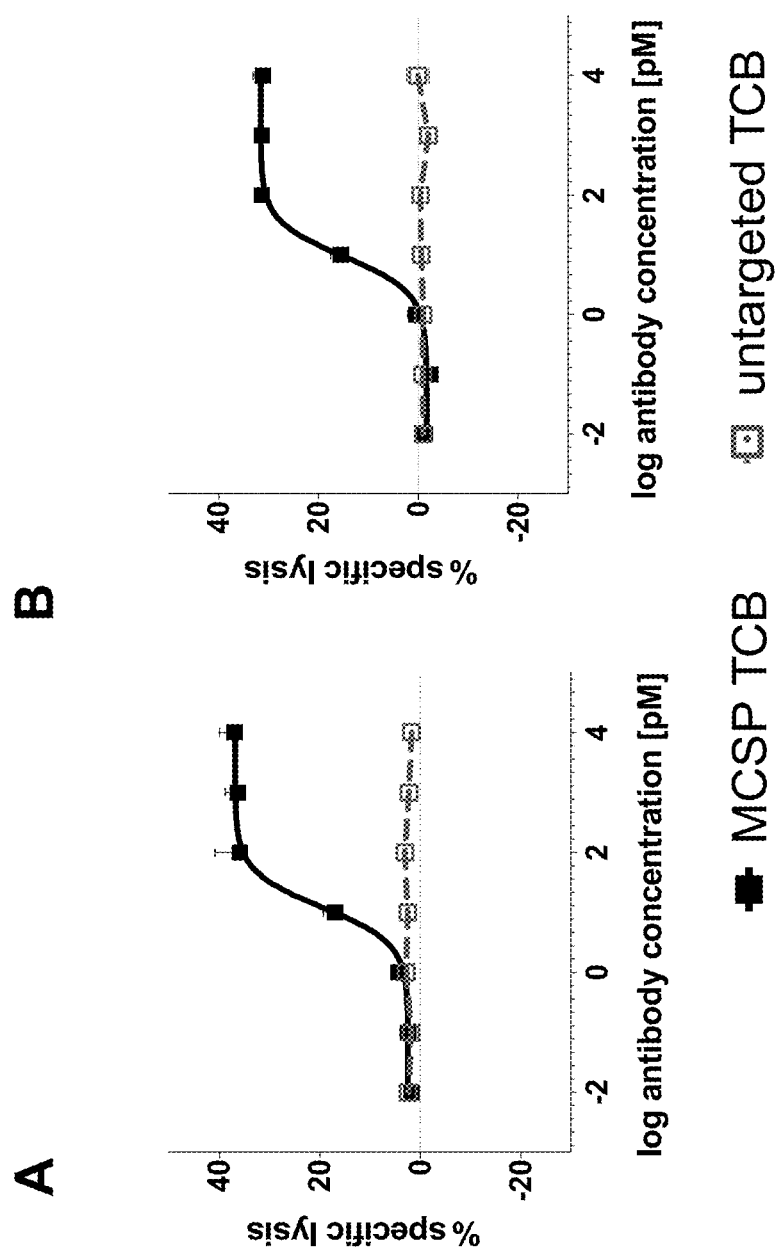
FIG. 8. T-cell killing induced by MCSP TCB antibody (SEQ ID NOs: 12, 53, 54 and 55) of A375 (high MCSP) (A), MV-3 (medium MCSP) (B), HCT-116 (low MCSP) (C) and LS180 (MCSP negative) (D) target cells (E:T=10:1, effectors human PBMCs, incubation time 24 h). "Untargeted TCB": bispecific antibody engaging CD3 but no second antigen (SEQ ID NOs: 59, 60, 61 and 62).
Figure 8:
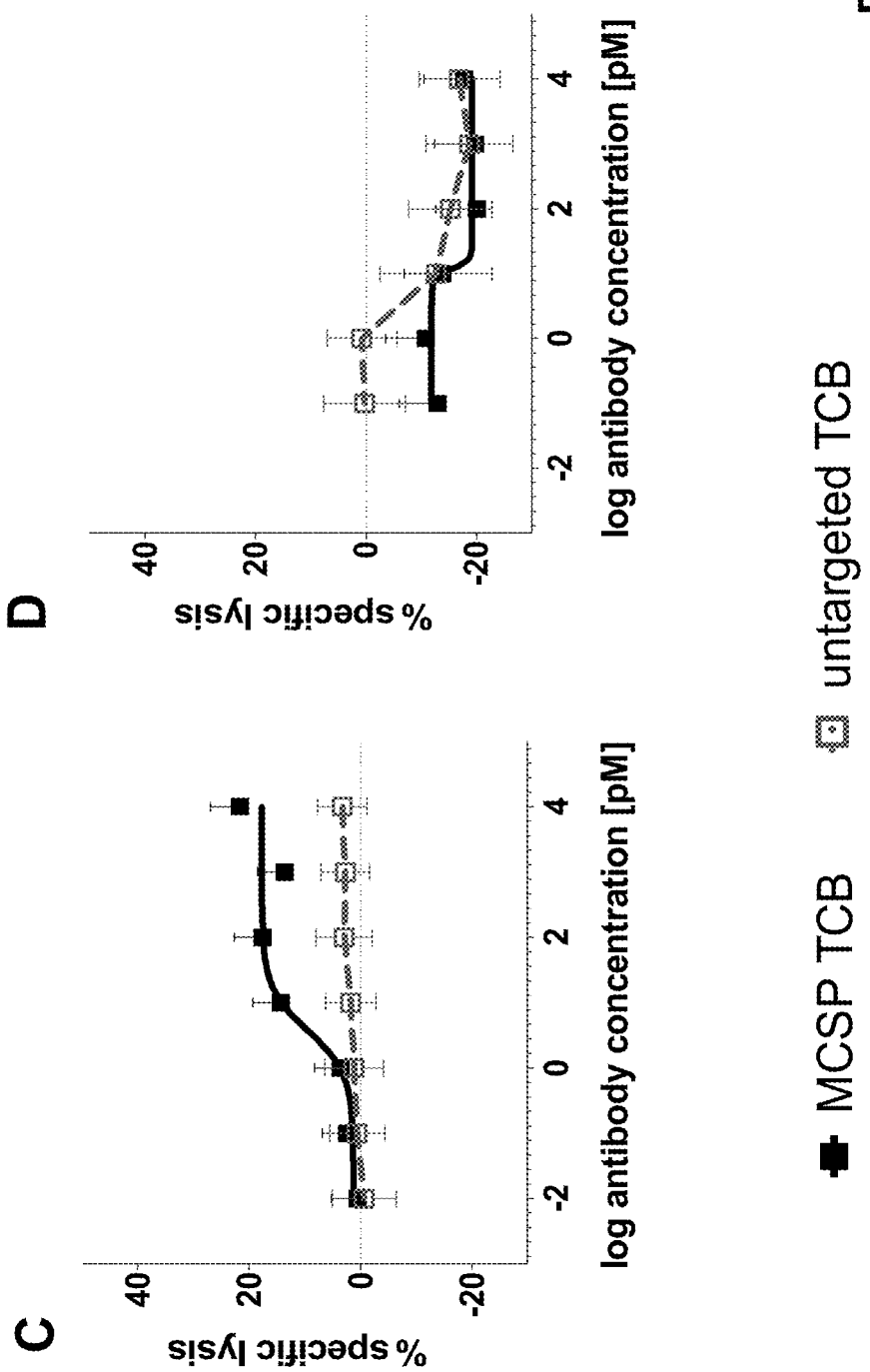

T-cell killing mediated by MCSP TCB antibody was assessed using a panel of tumor cell lines expressing different levels of MCSP (A375=MCSP high, MV-3=MSCP medium, HCT-116=MCSP low, LS180=MCSP negative). Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% $CO_2$ in cell incubator until further use (no longer than 24 h). For the killing assay, the antibody was added at the indicated concentrations (range of 1 pM-10 nM in triplicates). PBMCs were added to target cells at final effector to target (E:T) ratio of 10:1. Target cell killing was assessed after 24 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct. The results show that MCSP TCB induced a strong and target-specific killing of MCSP-positive target cell lines with no killing of MCSP-negative cell lines (FIG. 8, A-D). The $EC_{50}$ values related to the killing assays, calculated using GraphPadPrism5 are given in Table 7.

TABLE 7

$EC_{50}$ values (pM) for T-cell mediated killing of MCSP-expressing tumor cells induced by MCSP TCB antibody.

| Cell line | MCSP receptor copy number | $EC_{50}$ [pM] |
| --- | --- | --- |
| A375 | 387 058 | 12.3 |
| MV-3 | 260 000 | 9.4 |
| HCT-116 | 36770 | 3.7 |
| LS180 | Negative | n.d. |

Example 6

CD25 and CD69 Upregulation on $CD8^+$ and $CD4^+$ Effector Cells after T Cell Killing of MCSP-Expressing Tumor Cells Induced by MCSP TCB Antibody Activation of $CD8^+$ and $CD4^+$ T cells after T-cell killing of MCSP-expressing MV-3 tumor cells mediated by the MCSP TCB antibody was assessed by FACS analysis using antibodies recognizing the T cell activation markers CD25 (late activation marker) and CD69 (early activation marker). The antibody and the killing assay conditions were essentially as described above (Example 5), using the same antibody concentration range (1 pM-10 nM in triplicates), E:T ratio 10:1 and an incubation time 24 h.

Figure 9:
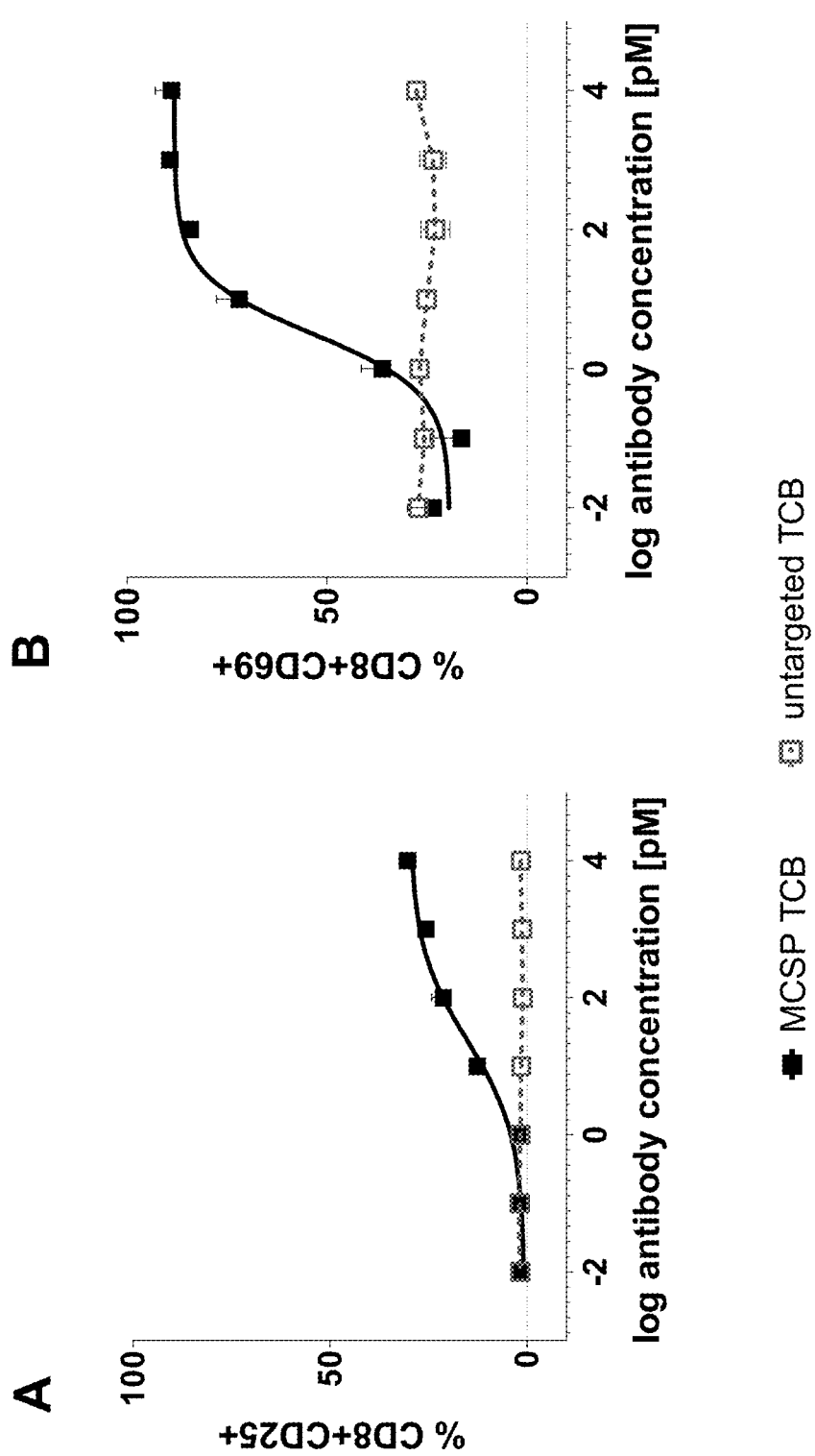
FIG. 9. Upregulation of CD25 and CD69 on human CD8$^+$ (A, B) and CD4$^+$ (C, D) T cells after T cell-mediated killing of MV3 melanoma cells (E:T=10:1, 24 h incubation) induced by MCSP TCB antibody (SEQ ID NOs: 12, 53, 54 and 55). "Untargeted TCB": bispecific antibody engaging CD3 but no second antigen (SEQ ID NOs: 59, 60, 61 and 62).

After the incubation, PBMCs were transferred to a round-bottom 96-well plate, centrifuged at 350×g for 5 min and washed twice with PBS containing 0.1% BSA. Surface staining for CD8 (FITC anti-human CD8, BD #555634), CD4 (PECy7 anti-human CD4, BD #557852), CD69 (PE anti-human CD69, Biolegend #310906) and CD25 (APC anti-human CD25, BD #555434) was performed according to the suppliers' indications. Cells were washed twice with 150 µl/well PBS containing 0.1% BSA and fixed for 15 min at 4° C. using 100 µl/well fixation buffer (BD #554655). After centrifugation, the samples were resuspended in 200 µl/well PBS 0.1% BSA containing DAPI to exclude dead cells for the FACS measurement. Samples were analyzed at BD FACS Fortessa. The results show that MCSP TCB induced a strong and target-specific upregulation of activation markers (CD25, CD69) on $CD8^+$ T cells (FIGS. 9 A, B) and $CD4^+$ T cells (FIGS. 9 C, D) after killing.

Example 7

Cytokine Secretion by Human Effector Cells after T Cell-Killing of MCSP-Expressing Tumor Cells Induced by MCSP TCB Antibody Cytokine secretion by human PBMCs after T-cell killing of MCSP-expressing MV-3 tumor cells induced by the MCSP TCB antibody was assessed by FACS analysis of cell supernatants after the killing assay.

The same antibody was used and the killing assay was performed essentially as described above (Example 5 and 6), using an E:T ratio of 10:1 and an incubation time of 24 h.

At the end of the incubation time, the plate was centrifuged for 5 min at 350×g, the supernatant transferred in a new 96-well plate and stored at −20° C. until subsequent analysis. Granzyme B, TNFα, IFN-γ, IL-2, IL-4 and IL-10 secreted into in cell supernatants were detected using the BD CBA Human Soluble Protein Flex Set, according to manufacturer's instructions on a FACS CantoII. The following kits were used: BD CBA human Granzyme B BD CBA human Granzyme B Flex Set #BD 560304; BD CBA human TNF Flex Set #BD 558273; BD CBA human IFN-γ Flex Set #BD 558269; BD CBA human IL-2 Flex Set #BD 558270; BD CBA human IL-4 Flex Set #BD 558272; BD CBA human IL-10 Flex Set #BD 558274.

Figure 10:
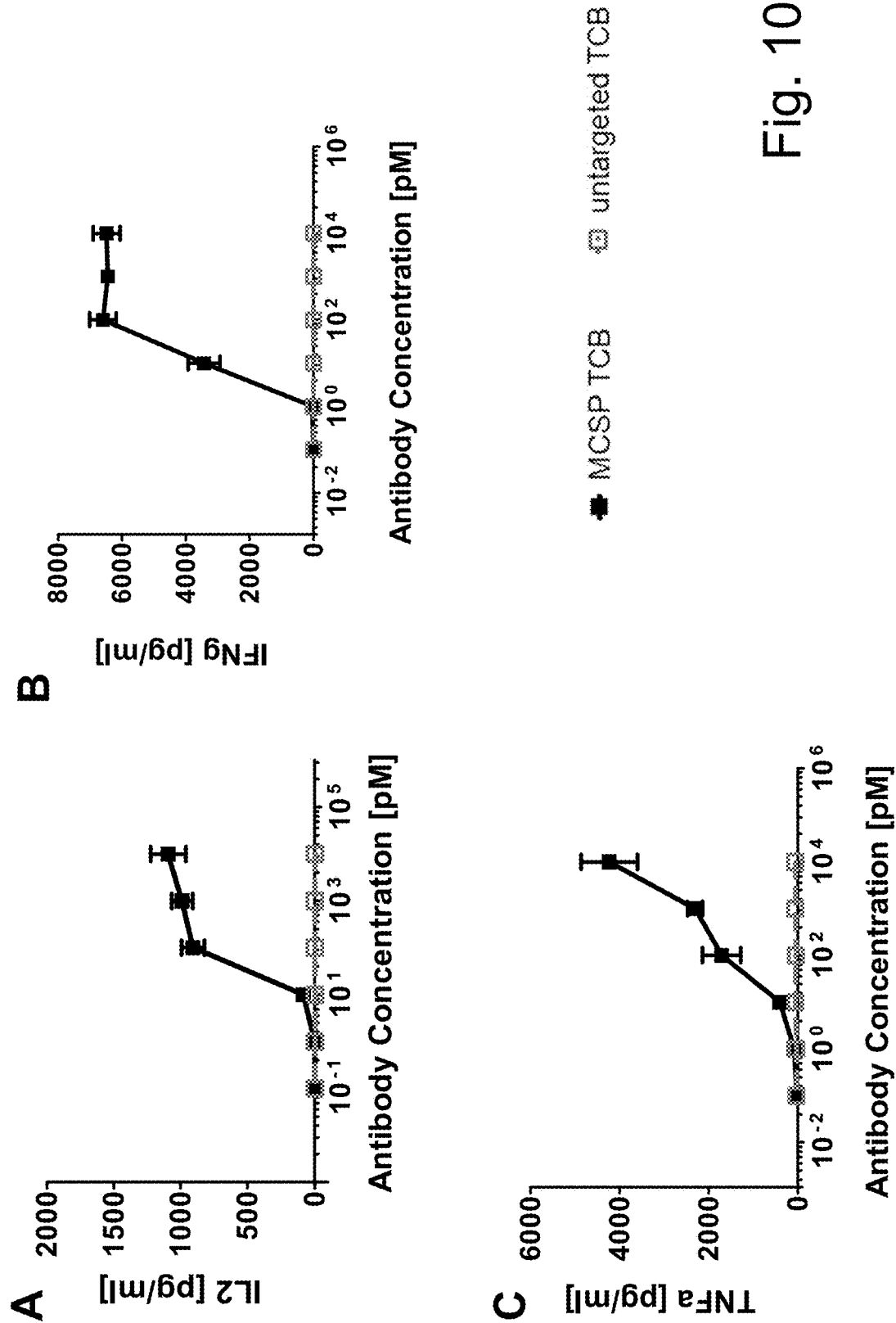
FIG. 10. Secretion of IL-2 (A), IFN-γ (B), TNFα (C), IL-4 (D), IL-10 (E) and Granzyme B (F) by human PBMCs after T cell mediated killing of MV3 melanoma cells (E:T=10:1, 24 h incubation) induced by MCSP TCB antibody (SEQ ID NOs: 12, 53, 54 and 55). "Untargeted TCB": bispecific antibody engaging CD3 but no second antigen (SEQ ID NOs: 59, 60, 61 and 62).
Figure 10:
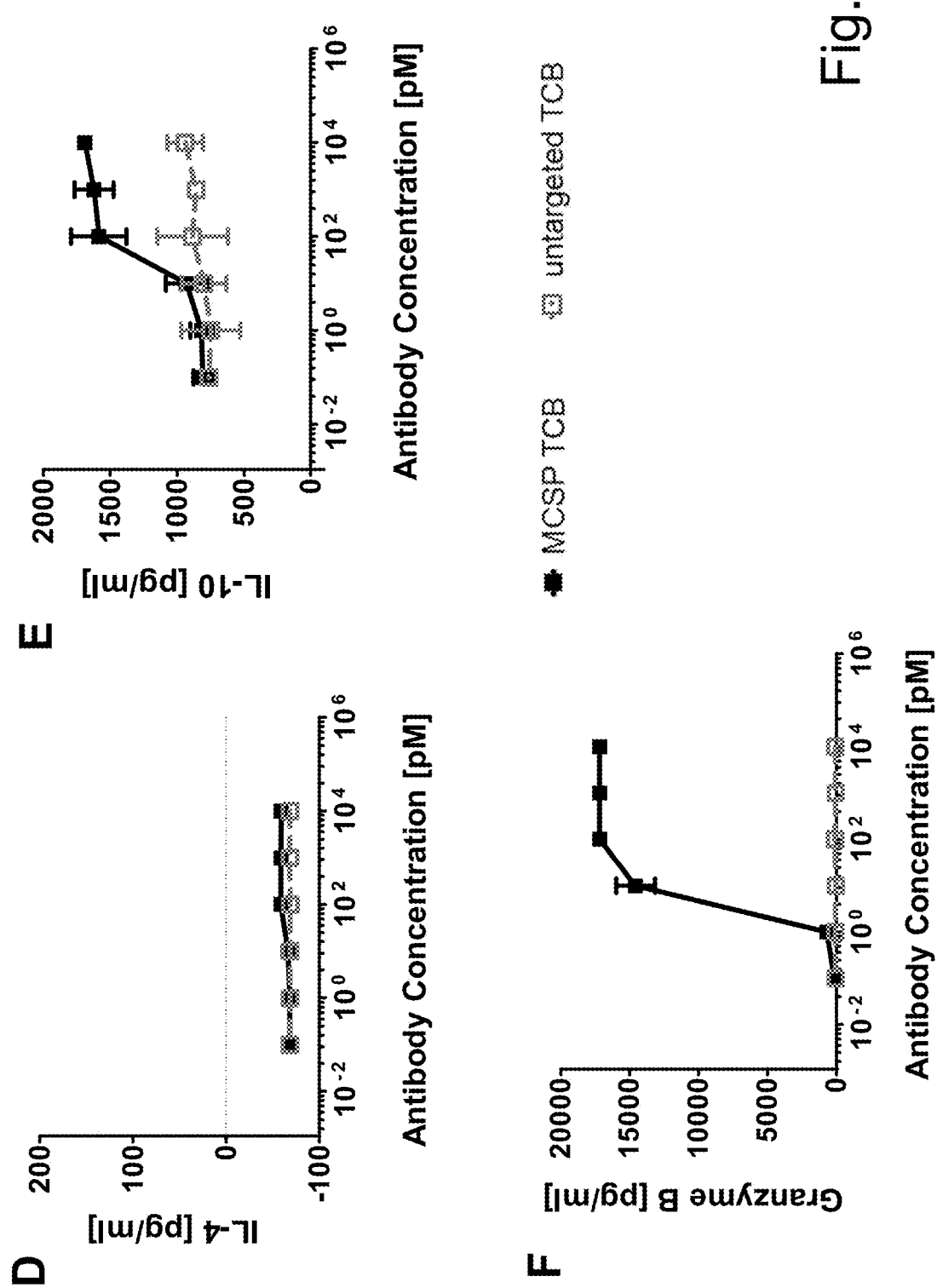

The results show that MCSP TCB induced secretion of IL-2, IFN-γ, TNFα, Granzyme B and IL-10 (but no IL-4) upon killing (FIG. 10, A-F).

Taken together, these examples show that the MCSP CD3 bispecific antibody
- Showed a good binding to MCSP-positive A375 cells
- Induced a strong and target-specific killing of MCSP-positive target cell lines, and no killing of MCSP-negative cell lines
- Induced a strong and target-specific upregulation of activation markers (CD25, CD69) on CD8+ and CD4+ T cells after killing
- Induced secretion of IL-2, IFN-γ, TNFα, Granzyme B and IL-10 (no IL-4) upon killing.

Example 8

Binding of CEA TCB to CEA- and CD3-Expressing Cells

The binding of CEA TCB was tested on transfected CEA-expressing lung adenocarcinoma cells (A549-huCEA) and CD3-expressing immortalized human and cynomolgus T lymphocyte lines (Jurkat and HSC-F, respectively). An untargeted TCB (SEQ ID NOs: 59, 60, 61 and 62; see example 24) was used as control. Briefly, cells were harvested, counted, checked for viability and resuspended at $2 \times 10^6$ cells/ml in FACS buffer (100 μl PBS 0.1% BSA). 100 μl cell suspension (containing $0.2 \times 10^6$ cells) were incubated in round-bottom 96-well plate for 30 min at 4° C. with increasing concentrations of the CEA TCB (61 pM-1000 nM), washed twice with cold PBS 0.1% BSA, re-incubated for further 30 min at 4° C. with the FITC-conjugated AffiniPure F(ab')2 Fragment goat anti-human IgG F(ab')2 Fragment Specific secondary antibody (Jackson Immuno Research Lab FITC #109-096-097), washed twice with cold PBS 0.1% BSA and immediately analyzed by FACS using a FACS CantoII or Fortessa (Software FACS Diva) by gating live, PI-negative, cells. Binding curves were obtained using GraphPadPrism5 (FIG. 11A, binding to A549 cells ($EC_{50}$ 6.6 nM); FIG. 11B, binding to Jurkat cells; FIG. 11C, binding to HSC-F cells).

Example 9

Figure 12:
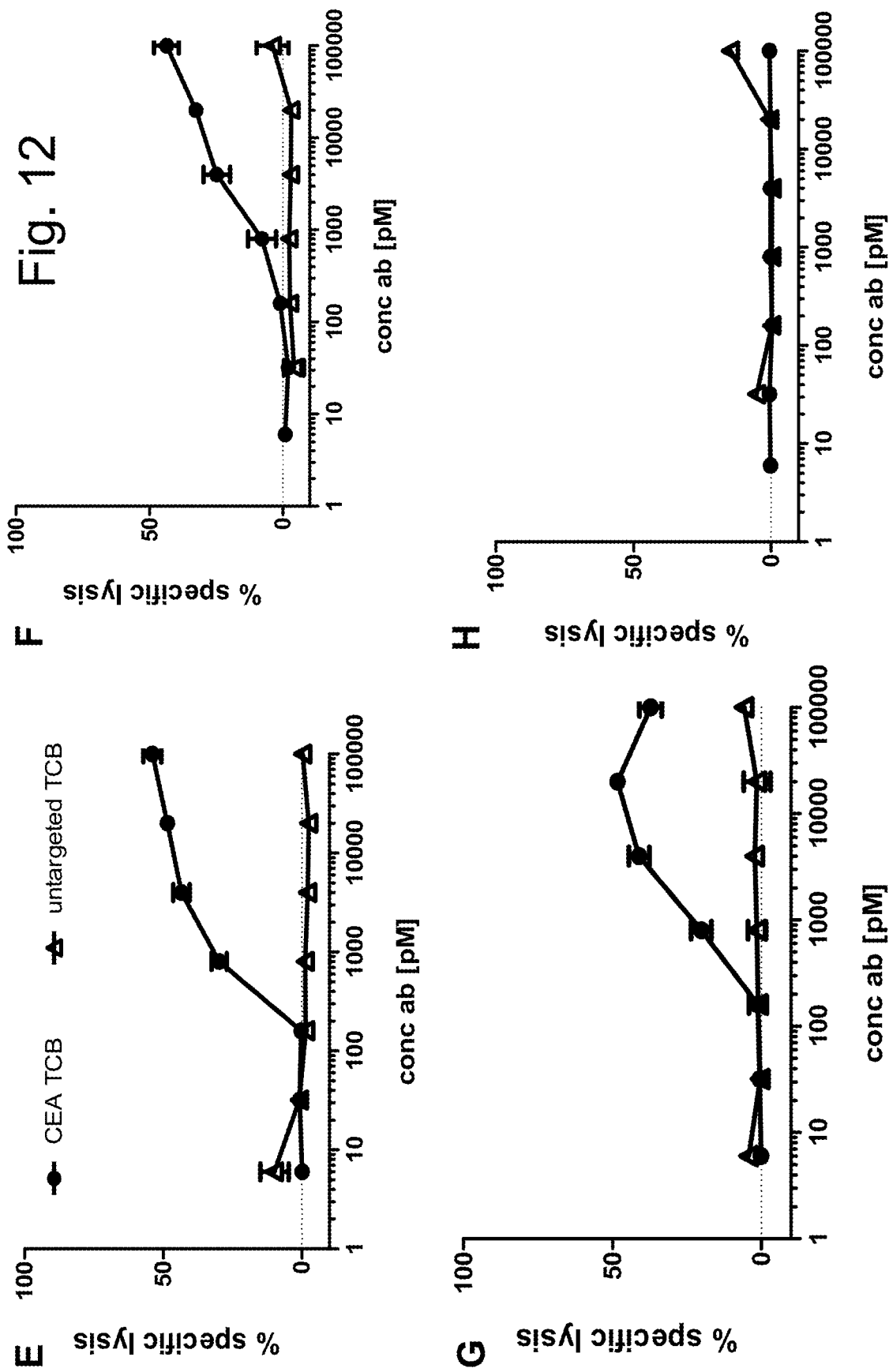
FIG. 12. T-cell killing induced by CEA TCB (SEQ ID NOs: 22, 56, 57 and 58) of HPAFII (high CEA) (A, E), BxPC-3 (medium CEA) (B, F), ASPC-1 (low CEA) (C, G) and HCT-116 cells (CEA negative) (D, H). E:T=10:1, effectors human PBMCs, incubation time 24 h (A-D) or 48 h (E-H). "Untargeted TCB": bispecific antibody engaging CD3 but no second antigen (SEQ ID NOs: 59, 60, 61 and 62).

T Cell-Mediated Killing of CEA-Expressing Tumor Target Cells Induced by CEA TCB Antibody T cell-mediated killing of target cells induced by CEA TCB antibody was assessed on HPAFII (high CEA), BxPC-3 (medium CEA) and ASPC-1 (low CEA) human tumor cells. HCT-116 (CEA negative tumor cell line) and the untargeted TCB were used as negative controls. Human PBMCs were used as effectors and killing detected 24 h and 48 h after incubation with the bispecific antibody. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and kept in RPMI1640 medium containing 10% FCS and 1% L-alanyl-L-glutamine (Biochrom, K0302) in cell incubator (37° C., 5% $CO_2$) until further use (no longer than 24 h). For the killing assay, the antibodies were added at indicated concentrations (range of 6 pM-100 nM in triplicates). PBMCs were added to target cells at the final E:T ratio of 10:1. Target cell killing was assessed after 24 h and 48 h of incubation by quantification of LDH (lactate dehydrogenase) released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific antibody. The results show that CEA TCB induced a strong and target-specific killing of CEA-positive target cells (FIG. 12, A-H). The $EC_{50}$ values related to the killing assays, calculated using GraphPadPrism5 are given in Table 8.

TABLE 8

CEA receptor copy number and $EC_{50}$ values (pM) for T-cell mediated killing of CEA-expressing tumor cells induced by CEA TCB antibody.

| Cell line | CEA receptor copy number | EC50 [pM] 48 h |
|---|---|---|
| HPAFII | 120 000-205 000 | 667 |
| BxPC-3 | 41 000 | 3785 |
| ASPC1 | 3500-8000 | 846 |

Example 10

Figure 13:
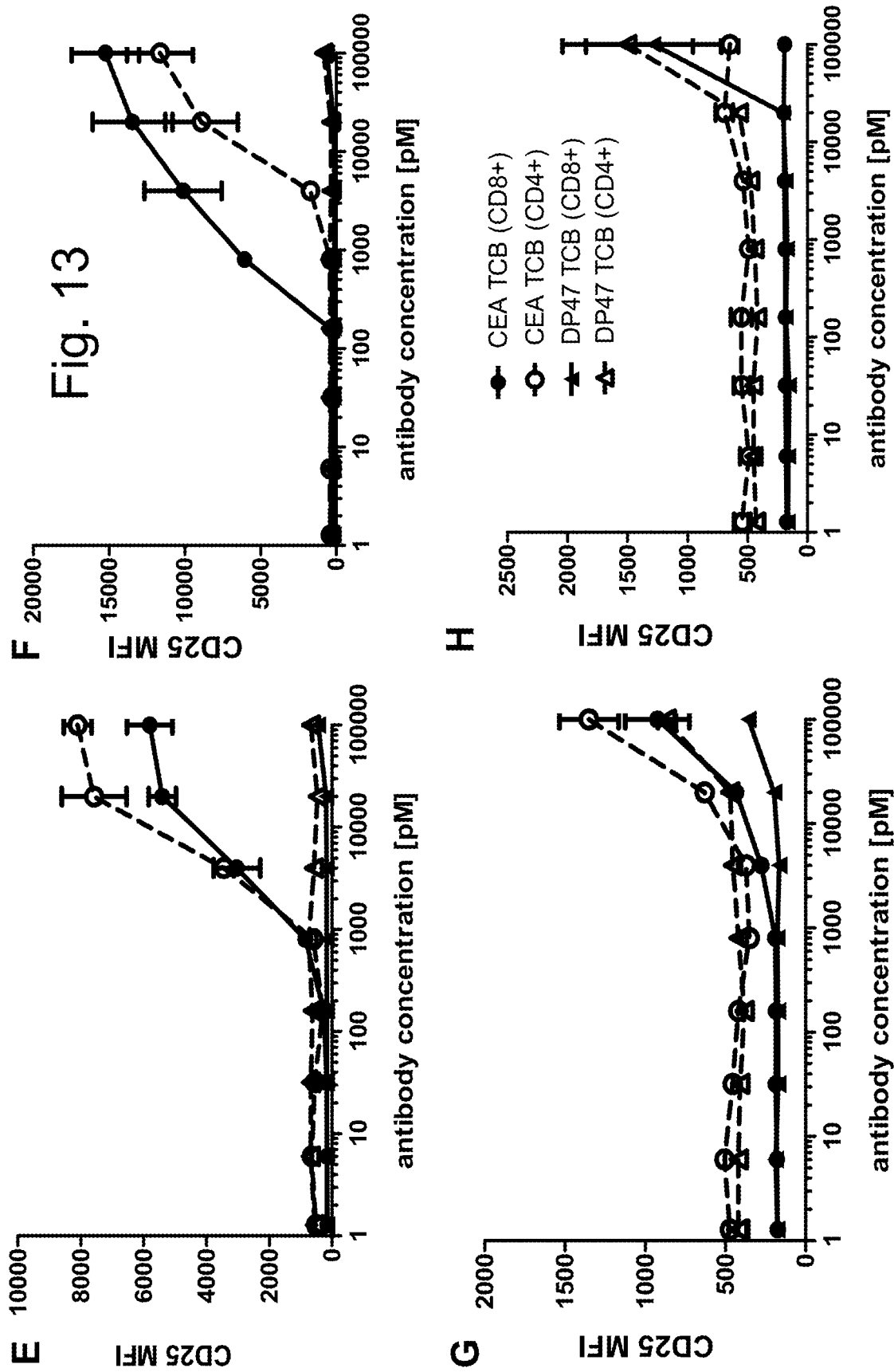
FIG. 13. Human CD8$^+$ and CD4$^+$ T cell proliferation (A-D) and upregulation of CD25 on human CD8$^+$ and CD4 T cells (E-H) 5 days after T cell-mediated killing of HPAFII (high CEA) (A, E), BxPC-3 (medium CEA) (B, F), ASPC-1 (low CEA) (C, G) and HCT-116 cells (CEA negative) (D, H) induced by CEA TCB (SEQ ID NOs: 22, 56, 57 and 58). "DP47 TCB": bispecific antibody engaging CD3 but no second antigen (SEQ ID NOs: 59, 60, 61 and 62).

T Cell Proliferation and Activation 5 Days after CEA TCB-Mediated Killing of CEA-Expressing Tumor Target Cells T cell proliferation and activation was detected 5 days after CEA TCB-mediated killing of CEA-expressing tumor target cells assessed on HPAFII (high CEA), BxPC-3 (medium CEA) and ASPC-1 (low CEA) cells. HCT-116 (CEA negative tumor cell line) and the untargeted TCB were used as negative controls. The experimental conditions for the proliferation assay were similar to the ones described in Example 9, but only 10 000 target cells were plated per well of a 96-flat bottom well plate. To assess T cell proliferation, freshly-isolated PBMCs were labeled using CFSE (Sigma #21888). Briefly, CFSE stock solution was diluted to obtain a working solution of 100 μM. $90 \times 10^6$ PBMC cells were re-suspended in 90 ml pre-warmed PBS and supplemented with 90 μl of the CFSE working solution. Cells were mixed immediately and incubated 15 min at 37° C. 10 ml of pre-warmed FCS were added to cells to stop the reaction. The cells were centrifuged for 10 min at 400 g, re-suspended in 50 ml medium and incubated for 30 min at 37° C. After incubation, cells were washed once with warm medium, counted, re-suspended in medium and added to target cells for the killing assay and subsequent measurement of cell proliferation and activation at an E:T of 10:1. Proliferation was assessed 5 days after killing on CD4 and CD8 positive T cells by quantification of the CFSE dye dilution. CD25 expression was assessed on the same T cell subsets using the anti-human CD25 antibody. Briefly, after centrifugation (400×g for 4 min), cells were resuspended, washed with FACS buffer and incubated with 25 µl of the diluted CD4/CD8/CD25 antibody mix for 30 min at 4° C. (APC/Cy7 anti-human CD4 #317418, APC anti-human CD8 #301014, PE/Cy7 anti-human CD25 #302612). Cells were then washed three times to remove the unbound antibody, and finally resuspended in 200 µl FACS buffer containing propidium iodide (PI) to exclude dead cells for the FACS measurement. Fluorescence was measured using BD FACS CantoII. The results show that the CEA TCB induced a strong and target-specific proliferation of $CD8^+$ and $CD4^+$ T cells (FIG. 13, A-D) as well as their activation as detected by up-regulation of the CD25 activation marker (FIG. 13, E-H).

Example 11

Cytokine Secretion by Human Effector Cells after T Cell-Mediated Killing of CEA-Expressing Tumor Cells Induced by CEA TCB Cytokine secretion by human PBMCs after T cell-mediated killing of CEA-expressing MKN45 tumor cells induced by the CEA TCB was assessed by FACS analysis (CBA kit) of cell supernatants 48 h after killing.

The experimental conditions were identical to the ones described in Example 9. At the end of the incubation time, the plate was centrifuged for 5 min at 350×g, the supernatant transferred into a new 96-well plate and stored at −20° C. until subsequent analysis. (A) IFN-γ, (B) TNFα, (C) Granzyme B, (D) IL-2, (E) IL-6 and (F) IL-10 secreted into cell supernatants were detected using the BD CBA Human Soluble Protein Flex Set, according to the manufacturer's instructions on a FACS CantoII. The following kits were used: BD CBA human IL-2 BD Flex Set #BD 558270; BD CBA human Granzyme B BD Flex Set #BD 560304; BD CBA human TNF Flex Set #BD 558273; BD CBA human IFN-γ Flex Set #BD 558269; BD CBA human IL-4 Flex Set #BD 558272; BD CBA human IL-10 Flex Set #BD 558274.

Figure 14:
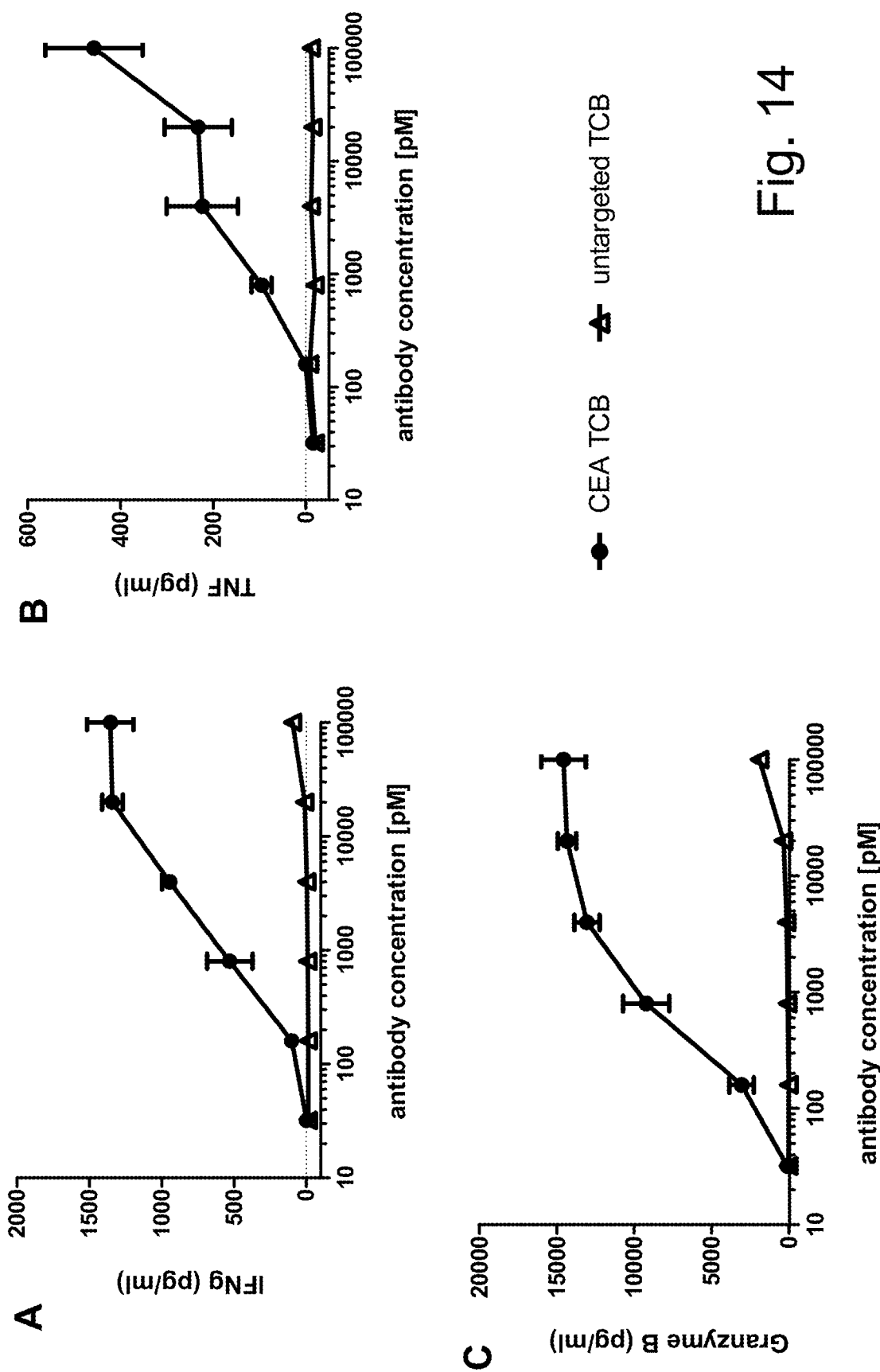
FIG. 14. Secretion of IFN-γ (A), TNFα (B), Granzyme B (C), IL-2 (D), IL-6 (E) and IL-10 (F) after T cell mediated killing of MKN45 tumor cells (E:T=10:1, 48 h incubation) induced by CEA TCB (SEQ ID NOs: 22, 56, 57 and 58).
Figure 14:
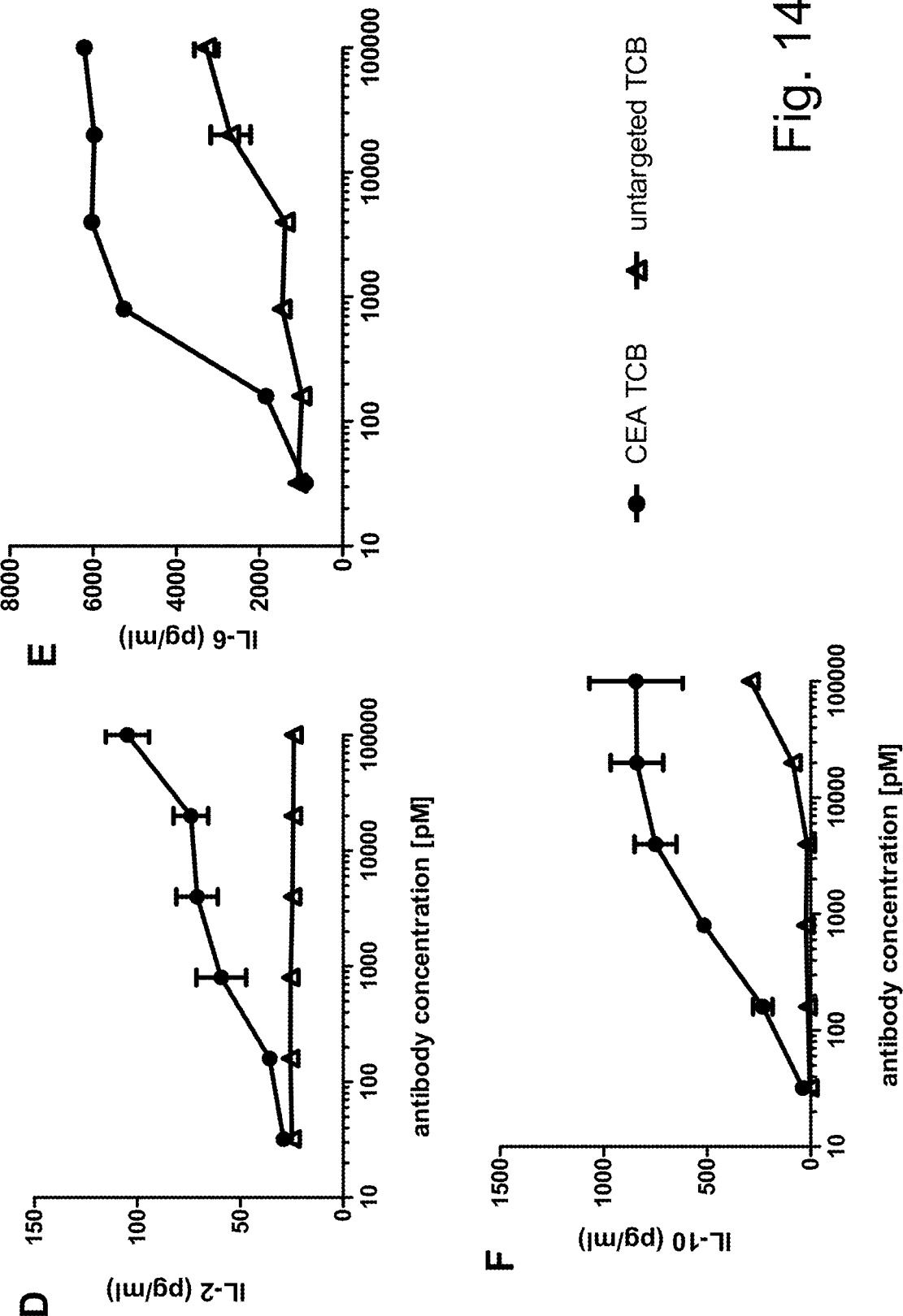

The results show that the CEA TCB mediated killing (but not the killing mediated by untargeted TCB control) induced secretion of IFN-γ, TNFα, Granzyme B, IL-2, IL-6 and IL-10 (FIGS. 14, A-F).

Example 12

T Cell-Mediated Killing of Target Cells in Presence of Increasing Concentrations of Shed CEA (sCEA)

T cell-mediated killing of CEA-expressing tumor target cells (LS180) induced by CEA TCB antibody in presence of increasing concentrations of shed CEA (sCEA 2.5 ng/ml-5 µg/ml) was assessed. Human PBMCs were used as effector cells and killing detected 24 h and 48 h after incubation with the bispecific antibody and sCEA. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new Falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and kept in RPMI1640 medium containing 10% FCS and 1% L-alanyl-L-glutamine (Biochrom, K0302) in cell incubator (37° C., 5% $CO_2$) until further use (no longer than 24 h). For the killing assay, the CEA TCB antibody was used at a fixed concentration of 1 nM and sCEA was spiked into the experiment at a concentration range of 2.5 ng-5 µg/ml. PBMCs were added to target cells at the final E:T ratio of 10:1. Target cell killing was assessed after 24 h and 48 h of incubation by quantification of LDH (lactate dehydrogenase) released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific antibody. The killing mediated by CEA TCB in absence of sCEA was set at 100% and the killing obtained in presence of increasing concentrations of sCEA was normalized to it. Results show that sCEA had only a minor impact on CEA TCB-mediated killing of CEA-expressing target cells (FIG. 15 A, B). No effect on T cell killing was detected up to 0.2 µg/ml of sCEA. The sCEA concentrations above 0.2 µg/ml had only a minor impact on overall killing (10-50% reduction).

Example 13

T Cell-Mediated Killing of Target Cells Using Human and Cynomolgus PBMCs as Effector Cells T cell-mediated killing of A549 (lung adenocarcinoma) cells overexpressing human CEA (A549-hCEA), assessed 21 h and 40 h after incubation with CEA TCB antibody and human PBMCs or cynomolgus PBMCs as effector cells was assessed. Briefly, target cells were harvested with Trypsin/EDTA, washed, and plated at density of 25 000 cells/well using flat-bottom 96-well plates. Cells were left to adhere for several hours. Peripheral blood mononuclear cells (PBMCs) were prepared by Histopaque density centrifugation of enriched lymphocyte preparations (buffy coats) obtained from healthy human donors or healthy cynomolgus monkey. For the later, a 90% Histopaque-PBS density gradient was used. Fresh blood was diluted with sterile PBS and layered over Histopaque gradient (Sigma, #H8889). After centrifugation (450×g, 30 minutes, room temperature for human PBMCs, respective 520×g, 30 min, room temperature for cynomolgus PBMCs), the plasma above the PBMC-containing interphase was discarded and PBMCs transferred in a new Falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). For the preparation of the cynomolgus PBMCs, an additional low-speed centrifugation step was performed at 150×g for 15 min. The resulting PBMC population was counted automatically (ViCell) and kept in RPMI1640 medium containing 10% FCS and 1% L-alanyl-L-glutamine (Biochrom, K0302) in cell incubator (37° C., 5% $CO_2$) until further use (up to 4 h). For the killing assay, the antibodies were added at indicated concentrations (range of 6 pM-100 nM in triplicates). PBMCs were added to target cells at the final E:T ratio of 10:1. Target cell killing was assessed after 21 h and 40 h of incubation by quantification of LDH (lactate dehydrogenase) released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific antibody. Results show that CEA TCB mediates target-specific killing of CEA-positive target cells using both human (FIG. 16, A, C) and cynomolgus (FIG. 16, B, D) effector cells (PBMCs). The $EC_{50}$ values related to 40 h of killing, calculated using GraphPadPrism5 are 306 pM for human PBMCs and 102 pM for cynomolgus PBMCs.

Example 14

T Cell-Mediated Killing of CEA-Expressing Human Colorectal Cancer Cell Lines Induced by CEA TCB Antibody T cell-mediated killing of CEA-expressing human colorectal cancer cell lines 48 h after incubation with human PBMCs and CEA TCB antibody at 0.8 nM, 4 nM and 20 nM was assessed. Briefly, PBMCs were isolated from leukocyte cones obtained from single healthy donors. Cells were diluted with PBS (1:10) and layered on Lymphoprep in 50 mL Falcon tubes. After centrifugation (1800 rpm for 25 min), the PBMC layer was withdrawn from the interface and washed 4× with PBS. PBMCs were counted, frozen in 10% DMSO in FCS under controlled-rate freezing conditions at $40 \times 10^6$ cells/mL and stored in liquid nitrogen until further use. For the T-cell killing assay, tumor cells were plated directly into 96-well plates from frozen stocks. Cells were warmed quickly and transferred immediately into pre-warmed medium, centrifuged, and re-suspended in complete medium (DMEM, Iscoves or RPMI-1640, all supplemented with 10% FCS and 1% penicillin/streptomycin) and plated at a density of $2.5 \times 10^4$ cells/well. Plates were then incubated at 37° C. in a humidified 10% $CO_2$ incubator and medium replaced the next day by 100 μL of RPMI 2% FCS with 1% glutamine and 50 μL CEA TCB (final concentrations ranging from 6.4 to 20000 pM, 1:5 titration steps, in duplicate wells for each condition). Fresh-thawed PBMCs were used for the assay (thawed from frozen vials within 2 hours of the assay start) and 50 μL ($3 \times 10^5$) was added to each well to give an effector: target (E:T) ratio of 10:1. Triton X100 (50 μL of 4%) was added to 150 μL of target cells to obtain maximum release values. Plates were incubated at 37° C. for 48 h and the killing activity determined using the Lactose Dehydrogenase Cytotoxicity Detection Kit (Roche) in accordance with the manufacturer's instructions. Percentage of specific cell lysis was calculated as [sample release−spontaneous release]/[maximum release−spontaneous release]×100. FIG. 17, A-C shows the correlation between CEA expression (receptor copy number quantified using QIFIKIT, see below) and % killing for 31 colorectal cancer cell lines (listed on x axis). FIG. 17, D shows the correlation between CEA expression and % specific lysis at 20 nM of CEA TCB (Spearman correlation=0.7289, p<0.0001, n=31), indicating that tumor cells displaying high CEA receptor copy numbers (>50 000) are efficiently lysed by CEA TCB whereas a cluster of cells displaying low CEA receptor copy numbers (<10 000) are not being lysed by CEA TCB under the same experimental conditions. FIG. 17, E shows the correlation between CEA expression and $EC_{50}$ of CEA TCB. Although the correlation is not statistically significant (Spearman correlation=−0.3994, p=0.1006, $R^2$=0.1358) the graph clearly shows a pattern of better CEA TCB potency (i.e. lower $EC_{50}$ values) on tumor cell lines expressing high CEA receptor copy numbers.

For the analysis of CEA surface expression on cancer cell lines, the Qifikit (DakoCytomation, Glostrup, Denmark) was used to calibrate the fluorescent signals and determine the number of binding sites per cell. Cells were incubated on ice for 30 min with a mouse anti-human CEACAM5 monoclonal antibody (0.5 μg for $5 \times 10^5$ cells, clone: CI-P83-1, sc-23928, Santa Cruz), washed twice with PBS1X-BSA 0.1% followed by a 45 min incubation with polyclonal fluorescein isothiocyanate-conjugated goat anti-mouse antibody provided with the Qifikit. Dead cells were excluded from the analysis using 4',6-diamidino-2-phenylindole (DAPI) staining. Samples were analysed on a CyAn™ ADP Analyzer (Beckman Coulter). All mean fluorescence intensities (MFIs) were obtained after data analyses using Summit 4.3 software. These MFIs were used to determine the relative number of antibody binding sites on the cell lines (named as CEA copy number on the results) using the equation obtained from the calibration curve (Qifikit calibration beads).

The colorectal cancer cell lines used for the T-cell killing assays and CEA surface expression quantification were seeded from cryovials. The method used to maintain the frozen stock was as described in Bracht et al. (Bracht et al. (2010), Br J Cancer 103, 340-346).

Example 15

In Vivo Anti-Tumor Efficacy of CEA TCB in a LS174T-Fluc2 Human Colon Carcinoma Co-Grafted with Human PBMC (E:T Ratio 5:1)

NOG (NOD/Shi-scid/IL-2Rγnull) mice (n=12) were injected subcutaneously with $1 \times 10^6$ LS174T-fluc2 cells pre-mixed with human PBMC in a total volume of 100 μl in PBS, E:T ratio 5:1. LS174T-fluc2 cells have been engineered to express luciferase, which allows monitoring tumor progression by bioluminescence (BLI) in a non-invasive and highly sensitive manner. To assess early and delayed treatment effects, mice received bi-weekly i.v. injections of either 0.5 or 2.5 mg/kg of the CEA TCB starting at day 1 (early treatment) or day 7 (delayed treatment) after tumor cell/PBMCs co-grafting s.c. As a control, one group of mice received bi-weekly i.v. injections of 2.5 mg/kg of a control TCB that had the same format as CEA TCB (in this case the MCSP TCB served as untargeted control since LS174T-fluc2 cells do not express MCSP), and an extra control group received only PBS (vehicle) starting at day 1. Tumor volume was measured once a week by digital caliper. Furthermore, mice were injected i.p. once weekly with D-Luciferin and the bioluminescent light emission of living tumor cells was measured with IVIS Spectrum (Perkin Elmer). Treatment was administered until 19 days after tumor cell inoculation, which corresponds to the day of study termination. The results of the experiment are shown in FIG. 18 A-D. Results show average and SEM from 12 mice of tumor volume measured by caliper (A and C) and by bioluminescence (Total Flux, B and D) in the different study groups ((A, B) early treatment, (C, D) delayed treatment).

Example 16

In Vivo Anti-Tumor Efficacy of CEA TCB in a LS174T-Fluc2 Human Colon Carcinoma Co-Grafted with Human PBMC (E:T Ratio 1:1)

NOG (NOD/Shi-scid/IL-2Rγnull) mice (n=10) were injected subcutaneously with 1×10⁶ LS174T-fluc2 cells (see Example 15) pre-mixed with human PBMC in a total volume of 100 µl in PBS, E:T ratio 1:1. To assess early and delayed treatment effects, mice received bi-weekly i.v. injections of 2.5 mg/kg of the CEA TCB starting at day 1 (early treatment) or day 7 (delayed treatment) after tumor cell inoculation. As control, one group of mice received bi-weekly i.v. injections of 2.5 mg/kg of the MCSP TCB (see also Example 15), and an extra control group received only PBS (vehicle) starting at day 1. Tumor volume was measured once weekly by digital caliper. Furthermore, mice were injected i.p. once weekly with D-Luciferin and the bioluminescent light emission of living tumor cells was measured with IVIS Spectrum (Perkin Elmer). Treatment was administered until 23 days after tumor cell inoculation, which corresponds to the day of study termination. The results of the experiment are shown in FIG. 19. Results show average and SEM of tumor volume measured by caliper (A) as well as by bioluminescence (B) in the different study groups (n=10).

Example 17

In Vivo Efficacy of Murinized CEA TCB in a Panco2-huCEA Orthotopic Tumor Model in Immunocompetent huCD3ε/huCEA Transgenic Mice huCD3ε/huCEA transgenic mice (n=10) received an intra-pancreatic injection of 2×10⁵ Panco2-huCEA cells in a total volume of 10 µl in PBS. As murine cells do not express CEA, the murine pancreatic carcinoma cell line Panco2 was engineered to overexpress human CEA as the target antigen for the CEA TCB. Mice were injected twice weekly i.v. with 0.5 mg/kg of the murinized CEA TCB or PBS as a control group (vehicle) and survival was monitored. Animals were controlled daily for clinical symptoms and detection of adverse effects. Termination criteria for animals were visible sickness: scruffy fur, arched back, breathing problems, impaired locomotion. The result as overall survival is shown in FIG. 20. Result shows percent of surviving animals per time point. The significance of the treatment group to the PBS control group was compared using a paired Student t test (p=0.078).

Example 18

Affinity of the CEA TCB to CEA and CD3 by Surface Plasmon Resonance (SPR)

Surface plasmon resonance (SPR) experiments were performed on a Biacore T100 at 25° C. with HBS-EP as running buffer (0.01 M HEPES pH 7.4, 0.15 M NaCl, 3 mM EDTA, 0.005% Surfactant P20, Biacore, Freiburg/Germany).

For affinity measurements CEA TCB was captured on a CM5 sensorchip surface with immobilized anti human Fab (GE Healthcare #28-9583-25). Capture IgG was coupled to the sensorchip surface by direct immobilization of around 10,000 resonance units (RU) at pH 5.0 using the standard amine coupling kit (Biacore, Freiburg/Germany).

To analyze the interaction to human CD3ε stalk-Fc (knob)-Avi/CD3δ-stalk-Fc(hole) (SEQ ID NOs 120 and 121, respectively), CEA TCB was captured for 30 s at 50 nM with 10 µl/min. CD3ε/CD3δ was passed at a concentration of 0.68-500 nM with a flowrate of 30 µl/min through the flow cells over 360 s. The dissociation was monitored for 360 s.

The $K_D$ value of the interaction between CEA TCB and the recombinant tumor target antigen human NABA-avi-his (containing the B3 domain of human CEA (CEACAM5) surrounded by the N, A1 and A2 domain of human CEACAM1 with a C-terminal avi 6his tag; see SEQ ID NO: 119) was determined by capturing the TCB molecule for 40 s at 10 µl/min. The antigen was flown over the flow cell for 240 s in a concentration range from 0.68 to 500 nM at a flow rate of 30 µl/min. The dissociation was measured over 240 s.

Bulk refractive index differences were corrected for by subtracting the response obtained on a reference flow cell. Here, the antigens were flown over a surface with immobilized anti-human Fab antibody but on which HBS-EP has been injected rather than CEA.

Kinetic constants were derived using the Biacore T200 Evaluation Software (vAA, Biacore AB, Uppsala/Sweden), to fit rate equations for 1:1 Langmuir binding by numerical integration. The half-life ($t_{1/2}$) of the interaction was calculated using following formula: $t_{1/2} = \ln 2/k_{off}$.

The CEA TCB binds to the tumor target and CD3ε/CD3δ in the nM-range with $K_D$ values of 62 nM for the human NABA and 75.3 nM for the human CD3ε/CD3δ. The half-life of the monovalent binding to NABA is 5.3 minutes, the half-life of the binding to CD3ε/CD3δ is 5.7 minutes. The kinetic values are summarized in Table 9.

TABLE 9

Affinity of CEA TCB to human NABA and human CD3ε/CD3δ (T = 25° C.).

| Antigen | TCB | $k_{on}$ [1/Ms] | $k_{off}$ [1/s] | $t_{1/2}$ [min] | $K_D$ [nM] |
|---|---|---|---|---|---|
| Human NABA | CEA TCB | $3.49 \times 10^4$ | $2.18 \times 10^{-3}$ | 5.3 | 62.4 |
| Human CD3ε/CD3δ | CEA TCB | $2.69 \times 10^4$ | $2.03 \times 10^{-3}$ | 5.7 | 75.3 |

Example 19

Affinity of the MSCP TCB to MCSP and CD3 by Surface Plasmon Resonance (SPR)

Surface plasmon resonance (SPR) experiments were performed on a Biacore T100 at 25° C. with HBS-EP as running buffer (0.01 M HEPES pH 7.4, 0.15 M NaCl, 3 mM EDTA, 0.005% Surfactant P20, Biacore, Freiburg/Germany).

For affinity measurements MCSP TCB was captured on a CM5 sensorchip surface with immobilized anti human Fab (GE Healthcare #28-9583-25). Capture IgG was coupled to the sensorchip surface by direct immobilization of around 7,500 resonance units (RU) at pH 5.0 using the standard amine coupling kit (Biacore, Freiburg/Germany). MCSP TCB was captured for 60 s at 30 nM with 10 µl/min. Human and cynomolgus MCSP D3 (see SEQ ID NOs 118 and 117, respectively) were passed at a concentration of 0.024-50 nM with a flowrate of 30 µl/min through the flow cells over 90 s. The concentration range for human and cynomolgus CD3ε stalk-Fc (knob)-Avi/CD3δ-stalk-Fc(hole) was 1.17-600 nM. Since the interaction with murine MCSP D3 (SEQ ID NO: 122) was expected to be weak the concentration range for this antigen was chosen between 3.9 and 500 nM. The dissociation for all interactions was monitored for 120 s. Bulk refractive index differences were corrected for by subtracting the response obtained on a reference flow cell. Here, the antigens were flown over a surface with immobilized anti-human Fab antibody but on which HBS-EP has been injected rather than MCSP TCB.

Kinetic constants were derived using the Biacore T200 Evaluation Software (vAA, Biacore AB, Uppsala/Sweden), to fit rate equations for 1:1 Langmuir binding by numerical integration. The interaction for the MCSP TCB with the murine MCSP D3 was determined in steady state. The half-life ($t_{1/2}$) of the interaction was calculated using following formula: $t_{1/2}=\ln 2/k_{off}$.

The MCSP TCB binds to the tumor target in pM-range with $K_D$ values of 0.15 nM for the human and 0.12 nM for the cynomolgus antigen. Recombinant CD3ε/CD3δ is bound by the MCSP TCB with a $K_D$ value of 78 nM (human) and 104 nM (cynomolgus). The half-life of the monovalent binding is up to 260 minutes for the tumor target and 2.9 minutes for the CD3e/CD3d. Upon affinity maturation the MCSP antibody obtained some binding to recombinant murine MCSP D3. $K_D$ value for this interaction is in mM range (1.6 mM). The kinetic values are summarized in Table 10.

TABLE 10

Affinity of MCSP TCB to the human, cynomolgus and murine MCSP D3 and human and cynomolgus CD3ε/CD3δ (T = 25° C.).

| | $k_{on}$ [1/Ms] | $k_{off}$ [1/s] | $t_{1/2}$ [min] | $K_D$ [nM] |
|---|---|---|---|---|
| Human MCSP D3 | $3.89 \times 10^5$ | $5.63 \times 10^{-5}$ | 205 | 0.15 |
| Cynomolgus MCSP D3 | $3.70 \times 10^5$ | $4.39 \times 10^{-5}$ | 263 | 0.12 |
| Murine MCSP D3 | nd | nd | nd | 1570* |
| Human CD3ε/CD3δ | $4.99 \times 10^4$ | $3.92 \times 10^{-3}$ | 2.9 | 78.7 |
| Cynomolgus CD3ε/CD3δ | $4.61 \times 10^4$ | $4.78 \times 10^{-3}$ | 2.4 | 104 |

*determined by steady state measurement

Example 20

Thermal Stability of CEA TCB

Thermal stability of the CEA TCB was monitored by Dynamic Light Scattering (DLS). 30 μg of filtered protein sample with a protein concentration of 0.5 mg/ml was applied in duplicate to a Dynapro plate reader (Wyatt Technology Corporation; USA). The temperature was ramped from 25 to 75° C. at 0.05° C./min, with the radius and total scattering intensity being collected. The result is shown in FIG. 21. The aggregation temperature of the CEA TCB was measured at 55° C.

Example 21

Thermal Stability of MCSP TCB

Thermal stability of the MCSP TCB was monitored by Dynamic Light Scattering (DLS). 30 μg of filtered protein sample with a protein concentration of 0.5 mg/ml was applied in duplicate to a Dynapro plate reader (Wyatt Technology Corporation; USA). The temperature was ramped from 25 to 75° C. at 0.05° C./min, with the radius and total scattering intensity being collected.

The result is shown in FIG. 22. The aggregation temperature of the MCSP TCB was measured at 55° C.

Example 22

T Cell-Mediated Killing of MCSP-Expressing Tumor Target Cells Induced by MCSP TCB and MCSP 1+1 CrossMab Antibodies T cell-mediated killing of target cells induced by MCSP TCB and MCSP 1+1 CrossMab TCB (a T cell activating bispecific antibody having the same CD3 and MCSP binding sequences as the MCSP TCB, with the molecular format shown in FIG. 1D) antibodies was assessed on A375 (high MCSP), MV-3 (medium MCSP) and HCT-116 (low MCSP) tumor target cells. LS180 (MCSP negative tumor cell line) was used as negative control. Tumor cell killing was assessed 24 h and 48 h post incubation of target cells with the antibodies and effector cells (human PBMCs). Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new Falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and kept in RPMI1640 medium containing 10% FCS and 1% L-alanyl-L-glutamine (Biochrom, K0302) in cell incubator (37° C., 5% $CO_2$) until further use (no longer than 24 h). For the killing assay, the antibodies were added at indicated concentrations (range of 0.01 pM-10 nM in triplicates). PBMCs were added to target cells at the final E:T ratio of 10:1. Target cell killing was assessed after 24 h and 48 h of incubation by quantification of LDH (lactate dehydrogenase) released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific antibody. The results show that MCSP TCB antibody is more potent than the MCSP 1+1 CrossMab TCB as it induced stronger killing of MCSP-positive target cells at both time points and on all tumor target cells (FIG. 23 A-H). The $EC_{50}$ values related to killing assays, calculated using GraphPadPrism5, are given in Table 11.

TABLE 11

MCSP receptor copy number and $EC_{50}$ values (pM) for T-cell mediated killing of MCSP-expressing tumor cells induced by MCSP TCB antibody (n.d. = not determined).

| Cell line | MCSP receptor copy number | EC50 [pM] 24 h | EC50 [pM] 48 h |
|---|---|---|---|
| A375 | 387 058 | 0.1 | n.d. |
| MV-3 | 260 000 | 1.0 | 0.7 |
| HCT-116 | 36770 | ~6.2e−008 | ~0.09 |
| LS180 | negative | ~764 | n.d. |

Example 23

CD25 and CD69 Upregulation on CD8$^+$ and CD4$^+$ Effector Cells after T Cell-Mediated Killing of MCSP-Expressing Tumor Cells Induced by MCSP TCB and MCSP 1+1 CrossMab Antibodies Activation of CD8$^+$ and CD4$^+$ T cells after T-cell killing of MCSP-expressing tumor cells (A375 and MV-3) mediated by the MCSP TCB and MCSP 1+1 CrossMab antibodies was assessed by FACS analysis using antibodies recognizing T cell activation markers CD25 (late activation marker) and CD69 (early activation marker). The antibody and the killing assay conditions were essentially as described above (Example 22), using the same antibody concentration range (0.01 pM-10 nM in triplicates), E:T ratio 10:1 and an incubation time of 48 h.

After the incubation, PBMCs were transferred to a round-bottom 96-well plate, centrifuged at 350×g for 5 min and washed twice with PBS containing 0.1% BSA. Surface staining for CD8 (FITC anti-human CD8, BD #555634), CD4 (PECy7 anti-human CD4, BD #557852), CD69 (PE anti-human CD69, Biolegend #310906) and CD25 (APC anti-human CD25, BD #555434) was performed according to the suppliers' indications. Cells were washed twice with 150 µl/well PBS containing 0.1% BSA and fixed for 15 min at 4° C. using 100 µl/well fixation buffer (BD #554655). After centrifugation, the samples were resuspended in 200 µl/well PBS 0.1% BSA containing DAPI to exclude dead cells for the FACS measurement. Samples were analyzed at BD FACS Fortessa. The results show that MCSP TCB induced a strong and target-specific upregulation of activation markers (CD25, CD69) on CD8$^+$ T cells (FIGS. 24 A, B (for A375 cells) and E, F (for MV-3 cells)) and CD4$^+$ T cells (FIGS. 24 C, D (for A375 cells) and G, H (for MV-3 cells)) after killing. As for the killing results, the activation of T cells was stronger with MCSP TCB than with MCSP 1+1 CrossMab.

Example 24

Preparation of DP47 GS TCB (2+1 Crossfab-IgG P329G LALA Inverted="Untargeted TCB") Containing DP47 GS as Non Binding Antibody and Humanized CH2527 as Anti CD3 Antibody The "untargeted TCB" was used as a control in the above experiments. The bispecific antibody engages CD3ε but does not bind to any other antigen and therefore cannot crosslink T cells to any target cells (and subsequently cannot induce any killing). It was therefore used as negative control in the assays to monitor any unspecific T cell activation.

The variable region of heavy and light chain DNA sequences were subcloned in frame with either the constant heavy chain or the constant light chain pre-inserted into the respective recipient mammalian expression vector. The antibody expression is driven by an MPSV promoter and carries a synthetic polyA signal sequence at the 3' end of the CDS. In addition each vector contains an EBV OriP sequence.

The molecule was produced by co-transfecting HEK293 EBNA cells with the mammalian expression vectors using polyethylenimine (PEI). The cells were transfected with the corresponding expression vectors in a 1:2:1:1 ratio ("vector heavy chain Fc(hole)": "vector light chain": "vector light chain Crossfab": "vector heavy chain Fc(knob)-FabCrossfab").

For transfection HEK293 EBNA cells were cultivated in suspension serum-free in CD CHO culture medium. For the production in 500 ml shake flask 400 million HEK293 EBNA cells were seeded 24 hours before transfection. For transfection cells were centrifuged for 5 min at 210×g, supernatant is replaced by pre-warmed 20 ml CD CHO medium. Expression vectors were mixed in 20 ml CD CHO medium to a final amount of 200 µg DNA. After addition of 540 µl PEI solution the mixture was vortexed for 15 s and subsequently incubated for 10 min at room temperature. Afterwards cells were mixed with the DNA/PEI solution, transferred to a 500 ml shake flask and incubated for 3 hours at 37° C. in an incubator with a 5% $CO_2$ atmosphere. After the incubation time 160 ml F17 medium was added and cell were cultivated for 24 hours. One day after transfection 1 mM valproic acid and 7% Feed 1 (Lonza) was added. After 7 days cultivation supernatant was collected for purification by centrifugation for 15 min at 210×g, the solution was sterile filtered (0.22 µm filter) and sodium azide in a final concentration of 0.01% w/v was added, and kept at 4° C.

The secreted protein was purified from cell culture supernatants by affinity chromatography using Protein A. Supernatant was loaded on a HiTrap Protein A HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volumes 20 mM sodium phosphate, 20 mM sodium citrate, 0.5 M sodium chloride, pH 7.5. Target protein was eluted during a gradient over 20 column volumes from 20 mM sodium citrate, 0.5 M sodium chloride, pH 7.5 to 20 mM sodium citrate, 0.5 M sodium chloride, pH 2.5. Protein solution was neutralized by adding 1/10 of 0.5 M sodium phosphate, pH 8. Target protein was concentrated and filtrated prior loading on a HiLoad Superdex 200 column (GE Healthcare) equilibrated with 20 mM histidine, 140 mM sodium chloride solution of pH 6.0.

The protein concentration of purified protein samples was determined by measuring the optical density (OD) at 280 nm, using the molar extinction coefficient calculated on the basis of the amino acid sequence.

Purity and molecular weight of molecules were analyzed by CE-SDS analyses in the presence and absence of a reducing agent. The Caliper LabChip GXII system (Caliper lifescience) was used according to the manufacturer's instruction. 2 µg sample was used for analyses.

The aggregate content of antibody samples was analyzed using a TSKgel G3000 SW XL analytical size-exclusion column (Tosoh) in 25 mM $K_2HPO_4$, 125 mM NaCl, 200 mM L-arginine monohydrochloride, 0.02% (w/v) $NaN_3$, pH 6.7 running buffer at 25° C.

TABLE 12

Summary production and purification of DP47 GS TCB.

| Construct | Titer [mg/l] | Yield [mg/l] | Aggregate after 1$^{st}$ purification step [%] | HMW [%] | LMW [%] | Monomer [%] |
|---|---|---|---|---|---|---|
| DP47 GS TCB | 103.7 | 8.04 | 8 | 2.3 | 6.9 | 91.8 |

FIG. 25 and Table 13 show CE-SDS analyses of the DP47 GS TCB (2+1 Crossfab-IgG P329G LALA inverted) containing DP47 GS as non-binding antibody and humanized CH2527 as anti-CD3 antibody. (SEQ ID NOs: 59, 60, 61 and 62).

TABLE 13

CE-SDS analyses of DP47 GS TCB.

| | Peak | kDa | Corresponding Chain |
|---|---|---|---|
| DP47 GS TCB non reduced (A) | 1 | 165.22 | Molecule with 2 missing light chains |
| | 2 | 181.35 | Molecule with 1 missing light chain |
| | 3 | 190.58 | Correct molecule without N-linked glycosylation |
| | 4 | 198.98 | Correct molecule |
| DP47 GS TCB reduced (B) | 1 | 27.86 | Light chain DP47 GS |
| | 2 | 35.74 | Light chain huCH2527 |
| | 3 | 63.57 | Fc (hole) |
| | 4 | 93.02 | Fc (knob) |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a CEA-expressing cancer in an individual, the method comprising administering to the individual a therapeutically effective amount of a composition comprising a T cell activating bispecific antigen-binding molecule in a pharmaceutically acceptable form, wherein the T cell activating bispecific antigen-binding molecule comprises:

(i) a first antigen-binding moiety which is a Fab molecule capable of specific binding to CD3, the first antigen-binding moiety comprising a heavy chain variable region comprising the amino acid sequence of SEQ ID NO: 3 and a light chain variable region comprising the amino acid sequence of SEQ ID NO: 7, wherein the first antigen-binding moiety is a crossover Fab molecule, and wherein either the variable or the constant regions of the Fab light chain and the Fab heavy chain are exchanged;

(ii) a second antigen-binding moiety and a third antigen-binding moiety, each of which is a Fab molecule capable of specific binding to CEA, the second and third antigen-binding moieties each comprising the heavy chain complementarity determining region (CDR) 1 of SEQ ID NO: 24, the heavy chain CDR 2 of SEQ ID NO: 25, the heavy chain CDR 3 of SEQ ID NO: 26, the light chain CDR 1 of SEQ ID NO: 28, the light chain CDR 2 of SEQ ID NO: 29, and the light chain CDR 3 of SEQ ID NO: 30; and (iii) an Fc domain comprising a first subunit comprising a first CH3 domain and a second subunit comprising a second CH3 domain, wherein the first subunit and the second subunit are capable of stable association, wherein the second antigen-binding moiety is fused at the C-terminus of the Fab heavy chain to the N-terminus of the Fab heavy chain of the first antigen-binding moiety, and the first antigen-binding moiety is fused at the C-terminus of the Fab heavy chain to the N-terminus of the first subunit of the Fc domain, and wherein the third antigen-binding moiety is fused at the C-terminus of the Fab heavy chain to the N-terminus of the second subunit of the Fc domain.

2. The method of claim 1, wherein the Fc domain is an IgG Fc domain.

3. The method of claim 1, wherein the Fc domain is a human Fc domain.

4. The method of claim 3, wherein the Fc domain is a human IgG1 Fc domain.

5. The method of claim 1, wherein the Fc domain comprises a modification promoting the association of the first subunit and the second subunit of the Fc domain.

6. The method of claim 5, wherein in the first CH3 domain an amino acid residue is replaced with an amino acid residue having a larger side chain volume, thereby generating a protuberance within the first CH3 domain which is positionable in a cavity within the second CH3 domain, and in the second CH3 domain an amino acid residue is replaced with an amino acid residue having a smaller side chain volume, thereby generating a cavity within the second CH3 domain within which the protuberance within the first CH3 domain is positionable.

7. The method of claim 1, wherein the Fc domain exhibits reduced binding affinity to an Fc receptor and/or reduced effector function, as compared to a native IgG1 Fc domain.

8. The method of claim 7, wherein the Fc receptor is an Fcγ receptor.

9. The method of claim 7, wherein the effector function is antibody-dependent cell-mediated cytotoxicity (ADCC).

10. The method of claim 7, wherein the Fc domain is a human IgG1 Fc domain comprising one or more amino acid substitutions at one, two, or all three positions selected from the group of L234, L235, and P329 (EU numbering).

11. The method of claim 4, wherein each subunit of the Fc domain comprises the amino acid substitutions L234A, L235A, and P329G (EU numbering).

12. The method of claim 4, wherein in the first subunit of the Fc domain the threonine residue at position 366 is replaced with a tryptophan residue (T366W), and in the second subunit of the Fc domain the tyrosine residue at position 407 is replaced with a valine residue (Y407V) (EU numbering).

13. The method of claim 12, wherein in the second subunit of the Fc domain the threonine residue at position 366 is replaced with a serine residue (T366S), and the leucine residue at position 368 is replaced with an alanine residue (L368A) (EU numbering).

14. The method of claim 12, wherein in the first subunit of the Fc domain the serine residue at position 354 is replaced with a cysteine residue (S354C), and in the second subunit of the Fc domain the tyrosine residue at position 349 is replaced by a cysteine residue (Y3490) (EU numbering).

15. The method of claim 1, wherein the second antigen-binding moiety and the third antigen-binding moiety each comprises a heavy chain variable region comprising the amino acid sequence of SEQ ID NO: 23 and a light chain variable region comprising the amino acid sequence of SEQ ID NO: 27.

16. The method of claim 15, wherein the T cell activated bispecific antigen-binding molecule comprises a polypeptide sequence comprising the amino acid sequence of SEQ ID NO: 22, a polypeptide sequence comprising the amino acid sequence of SEQ ID NO: 56, a polypeptide sequence comprising the amino acid sequence of SEQ ID NO: 57, and a polypeptide sequence comprising the amino acid sequence of SEQ ID NO: 58.

17. The method of claim 1, wherein the constant regions of the Fab light chain and the Fab heavy chain of the first antigen-binding moiety are exchanged.

18. The method of claim 1, wherein the T cell activating bispecific antigen-binding molecule comprises not more than one antigen-binding moiety capable of specific binding to CD3.

19. The method of claim 1, wherein the CEA-expressing cancer is colorectal cancer, pancreatic cancer, gastric cancer, lung cancer, or breast cancer.

20. A method for inducing lysis of a CEA-expressing tumor target cell, the method comprising contacting the CEA-expressing tumor target cell with a T cell activating bispecific antigen-binding molecule comprising:
(i) a first antigen-binding moiety which is a Fab molecule capable of specific binding to CD3, the first antigen-binding moiety comprising a heavy chain variable region comprising the amino acid sequence of SEQ ID NO: 3 and a light chain variable region comprising the amino acid sequence of SEQ ID NO: 7, wherein the first antigen-binding moiety is a crossover Fab molecule, and wherein either the variable or the constant regions of the Fab light chain and the Fab heavy chain are exchanged;
(ii) a second antigen-binding moiety and a third antigen-binding moiety, each of which is a Fab molecule capable of specific binding to CEA, the second and third antigen-binding moieties each comprising the heavy chain CDR 1 of SEQ ID NO: 24, the heavy chain CDR 2 of SEQ ID NO: 25, the heavy chain CDR 3 of SEQ ID NO: 26, the light chain CDR 1 of SEQ ID NO: 28, the light chain CDR 2 of SEQ ID NO: 29, and the light chain CDR 3 of SEQ ID NO: 30; and
(iii) an Fc domain comprising a first subunit comprising a first CH3 domain and a second subunit comprising a second CH3 domain, wherein the first subunit and the second subunit are capable of stable association, wherein the second antigen-binding moiety is fused at the C-terminus of the Fab heavy chain to the N-terminus of the Fab heavy chain of the first antigen-binding moiety, and the first antigen-binding moiety is fused at the C-terminus of the Fab heavy chain to the N-terminus of the first subunit of the Fc domain, and wherein the third antigen-binding moiety is fused at the C-terminus of the Fab heavy chain to the N-terminus of the second subunit of the Fc domain.

21. The method of claim 20, wherein the Fc domain is an IgG Fc domain.

22. The method of claim 20, wherein the Fc domain is a human Fc domain.

23. The method of claim 22, wherein the Fc domain is a human IgG1 Fc domain.

24. The method of claim 20, wherein the Fc domain comprises a modification promoting the association of the first subunit and the second subunit of the Fc domain.

25. The method of claim 24, wherein in the first CH3 domain an amino acid residue is replaced with an amino acid residue having a larger side chain volume, thereby generating a protuberance within the first CH3 domain which is positionable in a cavity within the second CH3 domain, and in the second CH3 domain an amino acid residue is replaced with an amino acid residue having a smaller side chain volume, thereby generating a cavity within the second CH3 domain within which the protuberance within the first CH3 domain is positionable.

26. The method of claim 20, wherein the Fc domain exhibits reduced binding affinity to an Fc receptor and/or reduced effector function, as compared to a native IgG1 Fc domain.

27. The method of claim 26, wherein the Fc receptor is an Fcγ receptor.

28. The method of claim 26, wherein the effector function is antibody-dependent cell-mediated cytotoxicity (ADCC).

29. The method of claim 26, wherein the Fc domain is a human IgG1 Fc domain comprising one or more amino acid substitutions at one, two, or all three positions selected from the group of L234, L235, and P329 (EU numbering).

30. The method of claim 23, wherein each subunit of the Fc domain comprises the amino acid substitutions L234A, L235A, and P329G (EU numbering).

31. The method of claim 23, wherein in the first subunit of the Fc domain the threonine residue at position 366 is replaced with a tryptophan residue (T366W), and in the second subunit of the Fc domain the tyrosine residue at position 407 is replaced with a valine residue (Y407V) (EU numbering).

32. The method of claim 31, wherein in the second subunit of the Fc domain the threonine residue at position 366 is replaced with a serine residue (T366S), and the leucine residue at position 368 is replaced with an alanine residue (L368A) (EU numbering).

33. The method of claim 31, wherein in the first subunit of the Fc domain the serine residue at position 354 is replaced with a cysteine residue (S354C), and in the second subunit of the Fc domain the tyrosine residue at position 349 is replaced by a cysteine residue (Y3490) (EU numbering).

34. The method of claim 20, wherein the second antigen-binding moiety and the third antigen-binding moiety each comprises a heavy chain variable region comprising the amino acid sequence of SEQ ID NO: 23 and a light chain variable region comprising the amino acid sequence of SEQ ID NO: 27.

35. The method of claim 34, wherein the T cell activated bispecific antigen-binding molecule comprises a polypeptide sequence comprising the amino acid sequence of SEQ ID NO: 22, a polypeptide sequence comprising the amino acid sequence of SEQ ID NO: 56, a polypeptide sequence comprising the amino acid sequence of SEQ ID NO: 57, and a polypeptide sequence comprising the amino acid sequence of SEQ ID NO: 58.

36. The method of claim 20, wherein the constant regions of the Fab light chain and the Fab heavy chain of the first antigen-binding moiety are exchanged.

37. The method of claim 20, wherein the T cell activating bispecific antigen-binding molecule comprises not more than one antigen-binding moiety capable of specific binding to CD3.

38. The method of claim 1, wherein the individual is a human.

39. The method of claim 20, wherein the CEA-expressing tumor target cell is a human CEA-expressing tumor target cell.

* * * * *

UNITED STATES PATENT AND TRADEMARK OFFICE
CERTIFICATE OF CORRECTION

PATENT NO. : 10,781,258 B2  
APPLICATION NO. : 16/134494  
DATED : September 22, 2020  
INVENTOR(S) : Marina Bacac et al.

Page 1 of 1

It is certified that error appears in the above-identified patent and that said Letters Patent is hereby corrected as shown below:

In the Claims

Column 197, Line 56, Claim 14, replace "Y3490" with --Y349C--.

Column 200, Line 3, Claim 33, replace "Y3490" with --Y349C--.

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 122

<210> SEQ ID NO 1
<211> LENGTH: 455
<212> TYPE: PRT
<213> ORGANISM: Artificial Sequence
<220> FEATURE:
<223> OTHER INFORMATION: HC CD3 CH2527 (VH_3-23(12))

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys

```
                    355                 360                 365
Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
450                 455

<210> SEQ ID NO 2
<211> LENGTH: 215
<212> TYPE: PRT
<213> ORGANISM: Artificial Sequence
<220> FEATURE:
<223> OTHER INFORMATION: LC CD3 CH2527 (VL_7-46(13))

<400> SEQUENCE: 2

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 3
<211> LENGTH: 125
<212> TYPE: PRT
<213> ORGANISM: Artificial Sequence
<220> FEATURE:
<223> OTHER INFORMATION: VH CD3 CH2527 (VH_3-23(12))
```

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 4
<211> LENGTH: 5
<212> TYPE: PRT
<213> ORGANISM: Artificial Sequence
<220> FEATURE:
<223> OTHER INFORMATION: HCDR1 CD3 CH2527 (VH_3-23(12))

<400> SEQUENCE: 4

Thr Tyr Ala Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: HCDR2 CD3 CH2527 (VH_3-23(12))

<400> SEQUENCE: 5

Arg Ile Arg Ser Lys Tyr Asn Asn Tyr Ala Thr Tyr Tyr Ala Asp Ser
1               5                   10                  15

Val Lys Gly

<210> SEQ ID NO 6
<211> LENGTH: 14
<212> TYPE: PRT
<213> ORGANISM: Artificial Sequence
<220> FEATURE:
<223> OTHER INFORMATION: HCDR3 CD3 CH2527 (VH_3-23(12))

<400> SEQUENCE: 6

His Gly Asn Phe Gly Asn Ser Tyr Val Ser Trp Phe Ala Tyr
1               5                   10

<210> SEQ ID NO 7
<211> LENGTH: 109
<212> TYPE: PRT
<213> ORGANISM: Artificial Sequence
<220> FEATURE:
<223> OTHER INFORMATION: VL CD3 CH2527 (VL_7-46(13))

<400> SEQUENCE: 7

Gln Ala Val Val Thr Gln Glu Pro Ser Leu Thr Val Ser Pro Gly Gly

```
                1               5                   10                  15
Thr Val Thr Leu Thr Cys Gly Ser Ser Thr Gly Ala Val Thr Thr Ser
                    20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 8
<211> LENGTH: 14
<212> TYPE: PRT
<213> ORGANISM: Artificial Sequence
<220> FEATURE:
<223> OTHER INFORMATION: LCDR1 CD3 CH2527 (VL_7-46(13))

<400> SEQUENCE: 8

```
Gly Ser Ser Thr Gly Ala Val Thr Thr Ser Asn Tyr Ala Asn
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: LCDR2 CD3 CH2527 (VL_7-46(13))

<400> SEQUENCE: 9

```
Gly Thr Asn Lys Arg Ala Pro
1               5
```

<210> SEQ ID NO 10
<211> LENGTH: 9
<212> TYPE: PRT
<213> ORGANISM: Artificial Sequence
<220> FEATURE:
<223> OTHER INFORMATION: LCDR3 CD3 CH2527 (VL_7-46(13))

<400> SEQUENCE: 10

```
Ala Leu Trp Tyr Ser Asn Leu Trp Val
1               5
```

<210> SEQ ID NO 11
<211> LENGTH: 442
<212> TYPE: PRT
<213> ORGANISM: Artificial Sequence
<220> FEATURE:
<223> OTHER INFORMATION: HC MCSP M4-3 (C1)$

<400> SEQUENCE: 11

```
                1               5                   10                  15
Gln Val Gln Leu Gln Glu Ser Gly Pro Gly Leu Val Lys Pro Ser Gln

Thr Leu Ser Leu Thr Cys Thr Val Ser Gly Gly Ser Ile Thr Ser Gly
                    20                  25                  30

Tyr Tyr Trp Asn Trp Ile Arg Gln His Pro Lys Gly Leu Glu Trp
        35                  40                  45

Ile Gly Tyr Ile Thr Phe Asp Gly Ser Asn Asn Tyr Asn Pro Ser Leu
```

```
            50                  55                  60
Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 12
<211> LENGTH: 214
<212> TYPE: PRT
<213> ORGANISM: Artificial Sequence
```

```
<220> FEATURE:
<223> OTHER INFORMATION: LC MCSP ML2 (G3)

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 112
<212> TYPE: PRT
<213> ORGANISM: Artificial Sequence
<220> FEATURE:
<223> OTHER INFORMATION: VH MCSP M4-3 (C1)

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110
```

-continued

```
<210> SEQ ID NO 14
<211> LENGTH: 6
<212> TYPE: PRT
<213> ORGANISM: Artificial Sequence
<220> FEATURE:
<223> OTHER INFORMATION: HCDR1 MCSP M4-3 (C1)

<400> SEQUENCE: 14

Ser Gly Tyr Tyr Trp Asn
1               5

<210> SEQ ID NO 15
<211> LENGTH: 16
<212> TYPE: PRT
<213> ORGANISM: Artificial Sequence
<220> FEATURE:
<223> OTHER INFORMATION: HCDR2 MCSP M4-3 (C1)

<400> SEQUENCE: 15

Tyr Ile Thr Phe Asp Gly Ser Asn Asn Tyr Asn Pro Ser Leu Lys Ser
1               5                   10                  15

<210> SEQ ID NO 16
<211> LENGTH: 3
<212> TYPE: PRT
<213> ORGANISM: Artificial Sequence
<220> FEATURE:
<223> OTHER INFORMATION: HCDR3 MCSP M4-3 (C1)

<400> SEQUENCE: 16

Phe Asp Tyr
1

<210> SEQ ID NO 17
<211> LENGTH: 107
<212> TYPE: PRT
<213> ORGANISM: Artificial Sequence
<220> FEATURE:
<223> OTHER INFORMATION: VL MCSP ML2 (G3)

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys
            100                 105

<210> SEQ ID NO 18
<211> LENGTH: 11
<212> TYPE: PRT
<213> ORGANISM: Artificial Sequence
<220> FEATURE:
<223> OTHER INFORMATION: LCDR1 MCSP ML2 (G3)

<400> SEQUENCE: 18
```

Arg Ala Ser Gln Gly Ile Arg Asn Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: LCDR2 MCSP ML2 (G3)

<400> SEQUENCE: 19

Tyr Thr Ser Ser Leu His Ser
1               5

<210> SEQ ID NO 20
<211> LENGTH: 9
<212> TYPE: PRT
<213> ORGANISM: Artificial Sequence
<220> FEATURE:
<223> OTHER INFORMATION: LCDR3 MCSP ML2 (G3)

<400> SEQUENCE: 20

Gln Gln Tyr Ser Ala Leu Pro Trp Thr
1               5

<210> SEQ ID NO 21
<211> LENGTH: 451
<212> TYPE: PRT
<213> ORGANISM: Artificial Sequence
<220> FEATURE:
<223> OTHER INFORMATION: HC CEA CH1A1A 98-99

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys

-continued

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 22
<211> LENGTH: 215
<212> TYPE: PRT
<213> ORGANISM: Artificial Sequence
<220> FEATURE:
<223> OTHER INFORMATION: LC CEA 2F1

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser

```
                    115                 120                 125
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215

<210> SEQ ID NO 23
<211> LENGTH: 121
<212> TYPE: PRT
<213> ORGANISM: Artificial Sequence
<220> FEATURE:
<223> OTHER INFORMATION: VH CEA CH1A1A 98-99

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
                100                 105                 110

Gln Gly Thr Thr Val Thr Val Ser Ser
        115                 120

<210> SEQ ID NO 24
<211> LENGTH: 5
<212> TYPE: PRT
<213> ORGANISM: Artificial Sequence
<220> FEATURE:
<223> OTHER INFORMATION: HCDR1 CEA CH1A1A 98-99

<400> SEQUENCE: 24

Glu Phe Gly Met Asn
1               5

<210> SEQ ID NO 25
<211> LENGTH: 17
<212> TYPE: PRT
<213> ORGANISM: Artificial Sequence
<220> FEATURE:
<223> OTHER INFORMATION: HCDR2 CEA CH1A1A 98-99

<400> SEQUENCE: 25

Trp Ile Asn Thr Lys Thr Gly Glu Ala Thr Tyr Val Glu Glu Phe Lys
1               5                   10                  15
```

Gly

<210> SEQ ID NO 26
<211> LENGTH: 12
<212> TYPE: PRT
<213> ORGANISM: Artificial Sequence
<220> FEATURE:
<223> OTHER INFORMATION: HCDR3 CEA CH1A1A 98-99

<400> SEQUENCE: 26

Trp Asp Phe Ala Tyr Tyr Val Glu Ala Met Asp Tyr
1               5                   10

<210> SEQ ID NO 27
<211> LENGTH: 108
<212> TYPE: PRT
<213> ORGANISM: Artificial Sequence
<220> FEATURE:
<223> OTHER INFORMATION: VL CEA 2F1

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 28
<211> LENGTH: 11
<212> TYPE: PRT
<213> ORGANISM: Artificial Sequence
<220> FEATURE:
<223> OTHER INFORMATION: LCDR1 CEA 2F1

<400> SEQUENCE: 28

Lys Ala Ser Ala Ala Val Gly Thr Tyr Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: LCDR2 CEA 2F1

<400> SEQUENCE: 29

Ser Ala Ser Tyr Arg Lys Arg
1               5

<210> SEQ ID NO 30
<211> LENGTH: 10
<212> TYPE: PRT
<213> ORGANISM: Artificial Sequence
<220> FEATURE:

<223> OTHER INFORMATION: LCDR3 CEA 2F1

<400> SEQUENCE: 30

His Gln Tyr Tyr Thr Tyr Pro Leu Phe Thr
1               5                   10

<210> SEQ ID NO 31
<211> LENGTH: 111
<212> TYPE: PRT
<213> ORGANISM: Artificial Sequence
<220> FEATURE:
<223> OTHER INFORMATION: VL CD3 CH2527 (VL_7-43(11))

<400> SEQUENCE: 31

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser
            100                 105                 110

<210> SEQ ID NO 32
<211> LENGTH: 125
<212> TYPE: PRT
<213> ORGANISM: Artificial Sequence
<220> FEATURE:
<223> OTHER INFORMATION: VH CD3 CH2527 (VHcomboA49SV93A)

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 33
<211> LENGTH: 125
<212> TYPE: PRT
<213> ORGANISM: Artificial Sequence
<220> FEATURE:
<223> OTHER INFORMATION: VH CD3 CH2527 (VHcomboA49SV93AR94K)

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 34
<211> LENGTH: 112
<212> TYPE: PRT
<213> ORGANISM: Artificial Sequence
<220> FEATURE:
<223> OTHER INFORMATION: VH MCSP M4-3 (D6)

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Lys Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 35
<211> LENGTH: 15
<212> TYPE: PRT
<213> ORGANISM: Artificial Sequence
<220> FEATURE:
<223> OTHER INFORMATION: HCDR2 MCSP M4-3 (D6)

<400> SEQUENCE: 35

Ile Thr Phe Asp Gly Lys Asn Asn Tyr Asn Pro Ser Leu Lys Ser
1               5                   10                  15

<210> SEQ ID NO 36
<211> LENGTH: 112
<212> TYPE: PRT
<213> ORGANISM: Artificial Sequence
<220> FEATURE:
<223> OTHER INFORMATION: VH MCSP M4-3 (A7)

-continued

<400> SEQUENCE: 36

```
Gln Val Gln Leu Gln Glu Ser Gly Pro Gly Leu Val Lys Pro Ser Gln
1               5                  10                  15

Thr Leu Ser Leu Thr Cys Thr Val Ser Gly Gly Ser Ile Thr Asp Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Arg Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110
```

<210> SEQ ID NO 37
<211> LENGTH: 6
<212> TYPE: PRT
<213> ORGANISM: Artificial Sequence
<220> FEATURE:
<223> OTHER INFORMATION: HCDR1 MCSP M4-3 (A7)

<400> SEQUENCE: 37

```
Asp Gly Tyr Tyr Trp Asn
1               5
```

<210> SEQ ID NO 38
<211> LENGTH: 15
<212> TYPE: PRT
<213> ORGANISM: Artificial Sequence
<220> FEATURE:
<223> OTHER INFORMATION: HCDR2 MCSP M4-3 (A7)

<400> SEQUENCE: 38

```
Ile Thr Phe Asp Gly Arg Asn Asn Tyr Asn Pro Ser Leu Lys Ser
1               5                   10                  15
```

<210> SEQ ID NO 39
<211> LENGTH: 112
<212> TYPE: PRT
<213> ORGANISM: Artificial Sequence
<220> FEATURE:
<223> OTHER INFORMATION: VH MCSP M4-3 (B7)

<400> SEQUENCE: 39

```
Gln Val Gln Leu Gln Glu Ser Gly Pro Gly Leu Val Lys Pro Ser Gln
1               5                  10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ile Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110
```

<210> SEQ ID NO 40
<211> LENGTH: 15
<212> TYPE: PRT
<213> ORGANISM: Artificial Sequence
<220> FEATURE:
<223> OTHER INFORMATION: HCDR2 MCSP M4-3 (B7)

<400> SEQUENCE: 40

Ile Thr Phe Asp Gly Ile Asn Asn Tyr Asn Pro Ser Leu Lys Ser
1               5                   10                  15

<210> SEQ ID NO 41
<211> LENGTH: 112
<212> TYPE: PRT
<213> ORGANISM: Artificial Sequence
<220> FEATURE:
<223> OTHER INFORMATION: VH MCSP M4-3 (B8)

<400> SEQUENCE: 41

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Arg Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: VH MCSP M4-3

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 43
<211> LENGTH: 107

```
<212> TYPE: PRT
<213> ORGANISM: Artificial Sequence
<220> FEATURE:
<223> OTHER INFORMATION: VL MCSP ML2 (E10)

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Tyr Gly Ile Arg Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Tyr Ser Lys Leu Pro Trp
                85                  90                  95

Thr Phe Gly Gln Gly Thr Lys Val Glu Ile Lys
            100                 105

<210> SEQ ID NO 44
<211> LENGTH: 11
<212> TYPE: PRT
<213> ORGANISM: Artificial Sequence
<220> FEATURE:
<223> OTHER INFORMATION: LCDR1 MCSP ML2 (E10)

<400> SEQUENCE: 44

Arg Ala Ser Tyr Gly Ile Arg Gly Tyr Leu Asn
1               5                   10

<210> SEQ ID NO 45
<211> LENGTH: 9
<212> TYPE: PRT
<213> ORGANISM: Artificial Sequence
<220> FEATURE:
<223> OTHER INFORMATION: LCDR3 MCSP ML2 (E10)

<400> SEQUENCE: 45

Gln Gln Tyr Ser Lys Leu Pro Trp Thr
1               5

<210> SEQ ID NO 46
<211> LENGTH: 107
<212> TYPE: PRT
<213> ORGANISM: Artificial Sequence
<220> FEATURE:
<223> OTHER INFORMATION: VL MCSP ML2 (E10-G3)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Tyr Gly Ile Arg Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr His Cys Gln Gln Tyr Ser Ala Leu Pro Trp
                85                  90                  95

Thr Phe Gly Gln Gly Thr Lys Val Glu Ile Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: VL MCSP ML2 (C5)

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Arg Glu Tyr
            20                  25                  30

Leu Asn Trp Tyr Gln Gln Lys Pro Gly Lys Ala Pro Lys Leu Leu Ile
        35                  40                  45

Tyr Tyr Thr Gly Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105

<210> SEQ ID NO 48
<211> LENGTH: 11
<212> TYPE: PRT
<213> ORGANISM: Artificial Sequence
<220> FEATURE:
<223> OTHER INFORMATION: LCDR1 MCSP ML2 (C5)

<400> SEQUENCE: 48

Arg Ala Ser Arg Gly Ile Arg Glu Tyr Leu Asn
1               5                   10

<210> SEQ ID NO 49
<211> LENGTH: 7
<212> TYPE: PRT
<213> ORGANISM: Artificial Sequence
<220> FEATURE:
<223> OTHER INFORMATION: LCDR2 MCSP ML2 (C5)

<400> SEQUENCE: 49

Tyr Thr Gly Ser Leu His Ser
1               5

<210> SEQ ID NO 50
<211> LENGTH: 9
<212> TYPE: PRT
<213> ORGANISM: Artificial Sequence
<220> FEATURE:
<223> OTHER INFORMATION: LCDR3 MCSP ML2 (C5)

<400> SEQUENCE: 50

Gln Gln Tyr Ser Glu Leu Pro Trp Thr
1               5

<210> SEQ ID NO 51
<211> LENGTH: 107

```
<212> TYPE: PRT
<213> ORGANISM: Artificial Sequence
<220> FEATURE:
<223> OTHER INFORMATION: VL MCSP ML2 (C5-G3)

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Arg Glu Tyr
            20                  25                  30

Leu Asn Trp Tyr Gln Gln Lys Pro Gly Lys Ala Pro Lys Leu Leu Ile
        35                  40                  45

Tyr Tyr Thr Gly Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys
            100                 105

<210> SEQ ID NO 52
<211> LENGTH: 107
<212> TYPE: PRT
<213> ORGANISM: Artificial Sequence
<220> FEATURE:
<223> OTHER INFORMATION: VL MCSP ML2

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys
            100                 105

<210> SEQ ID NO 53
<211> LENGTH: 214
<212> TYPE: PRT
<213> ORGANISM: Artificial Sequence
<220> FEATURE:
<223> OTHER INFORMATION: LC CD3 CH2527  (Crossfab, VL-CH1)

<400> SEQUENCE: 53

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
```

```
Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 54
<211> LENGTH: 685
<212> TYPE: PRT
<213> ORGANISM: Artificial Sequence
<220> FEATURE:
<223> OTHER INFORMATION: MCSP M4-3 (C1) (VH-CH1) - CD3 CH2527 (Crossfab
      VH-Ck) - Fc(knob) P329GLALA

<400> SEQUENCE: 54

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ser Asn Asn Tyr Asn Pro Ser Leu
    50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190
```

-continued

Tyr Ile Cys Asn Val Asn His Lys Pro Ser Asn Thr Lys Val Asp Lys
        195                 200                 205

Lys Val Glu Pro Lys Ser Cys Asp Gly Gly Gly Ser Gly Gly Gly
210                 215                 220

Gly Ser Glu Val Gln Leu Leu Glu Ser Gly Gly Leu Val Gln Pro
225                 230                 235                 240

Gly Gly Ser Leu Arg Leu Ser Cys Ala Ala Ser Gly Phe Thr Phe Ser
245                 250                 255

Thr Tyr Ala Met Asn Trp Val Arg Gln Ala Pro Gly Lys Gly Leu Glu
            260                 265                 270

Trp Val Ser Arg Ile Arg Ser Lys Tyr Asn Asn Tyr Ala Thr Tyr Tyr
        275                 280                 285

Ala Asp Ser Val Lys Gly Arg Phe Thr Ile Ser Arg Asp Asp Ser Lys
        290                 295                 300

Asn Thr Leu Tyr Leu Gln Met Asn Ser Leu Arg Ala Glu Asp Thr Ala
305                 310                 315                 320

Val Tyr Tyr Cys Val Arg His Gly Asn Phe Gly Asn Ser Tyr Val Ser
                325                 330                 335

Trp Phe Ala Tyr Trp Gly Gln Gly Thr Leu Val Thr Val Ser Ser Ala
            340                 345                 350

Ser Val Ala Ala Pro Ser Val Phe Ile Phe Pro Pro Ser Asp Glu Gln
        355                 360                 365

Leu Lys Ser Gly Thr Ala Ser Val Val Cys Leu Leu Asn Asn Phe Tyr
        370                 375                 380

Pro Arg Glu Ala Lys Val Gln Trp Lys Val Asp Asn Ala Leu Gln Ser
385                 390                 395                 400

Gly Asn Ser Gln Glu Ser Val Thr Glu Gln Asp Ser Lys Asp Ser Thr
                405                 410                 415

Tyr Ser Leu Ser Ser Thr Leu Thr Leu Ser Lys Ala Asp Tyr Glu Lys
            420                 425                 430

His Lys Val Tyr Ala Cys Glu Val Thr His Gln Gly Leu Ser Ser Pro
        435                 440                 445

Val Thr Lys Ser Phe Asn Arg Gly Glu Cys Asp Lys Thr His Thr Cys
450                 455                 460

Pro Pro Cys Pro Ala Pro Glu Ala Ala Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Asn Ser Thr Tyr Arg Val Val Ser Val Leu
        530                 535                 540

Thr Val Leu His Gln Asp Trp Leu Asn Gly Lys Glu Tyr Lys Cys Lys
545                 550                 555                 560

Val Ser Asn Lys Ala Leu Gly Ala Pro Ile Glu Lys Thr Ile Ser Lys
                565                 570                 575

Ala Lys Gly Gln Pro Arg Glu Pro Gln Val Tyr Thr Leu Pro Pro Cys
            580                 585                 590

Arg Asp Glu Leu Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln

```
                610              615              620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
                660                 665                 670

His Tyr Thr Gln Lys Ser Leu Ser Leu Ser Pro Gly Lys
                675                 680                 685

<210> SEQ ID NO 55
<211> LENGTH: 442
<212> TYPE: PRT
<213> ORGANISM: Artificial Sequence
<220> FEATURE:
<223> OTHER INFORMATION: MCSP M4-3 (C1) (VH-CH1) - Fc(hole) P329GLALA

<400> SEQUENCE: 55

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
                20                  25                  30

Tyr Tyr Trp Asn Trp Ile Arg Gln His Pro Gly Lys Gly Leu Glu Trp
            35                  40                  45

Ile Gly Tyr Ile Thr Phe Asp Gly Ser Asn Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
                100                 105                 110

Ala Ser Thr Lys Gly Pro Ser Val Phe Pro Leu Ala Pro Ser Ser Lys
                115                 120                 125

Ser Thr Ser Gly Gly Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp Lys Thr His Thr Cys Pro Pro Cys
            210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
```

```
                290                 295                 300
His Gln Asp Trp Leu Asn Gly Lys Glu Tyr Lys Cys Lys Val Ser Asn
305                 310                 315                 320

Lys Ala Leu Gly Ala Pro Ile Glu Lys Thr Ile Ser Lys Ala Lys Gly
                325                 330                 335

Gln Pro Arg Glu Pro Gln Val Cys Thr Leu Pro Pro Ser Arg Asp Glu
                340                 345                 350

Leu Thr Lys Asn Gln Val Ser Leu Ser Cys Ala Val Lys Gly Phe Tyr
                355                 360                 365

Pro Ser Asp Ile Ala Val Glu Trp Glu Ser Asn Gly Gln Pro Glu Asn
                370                 375                 380

Asn Tyr Lys Thr Thr Pro Pro Val Leu Asp Ser Asp Gly Ser Phe Phe
385                 390                 395                 400

Leu Val Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
                435                 440

<210> SEQ ID NO 56
<211> LENGTH: 214
<212> TYPE: PRT
<213> ORGANISM: Artificial Sequence
<220> FEATURE:
<223> OTHER INFORMATION: LC CD3 CH2527 (Crossfab, VL-CH1)

<400> SEQUENCE: 56

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
                115                 120                 125

Thr Ser Gly Gly Thr Ala Ala Leu Gly Cys Leu Val Lys Asp Tyr Phe
                130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
                180                 185                 190

Ile Cys Asn Val Asn His Lys Pro Ser Asn Thr Lys Val Asp Lys Lys
                195                 200                 205

Val Glu Pro Lys Ser Cys
```

<210> SEQ ID NO 57
<211> LENGTH: 694
<212> TYPE: PRT
<213> ORGANISM: Artificial Sequence
<220> FEATURE:
<223> OTHER INFORMATION: CEA CH1A1A 98/99 - CD3 CH2527 (Crossfab VH-Ck) - Fc(knob) P329GLALA

<400> SEQUENCE: 57

```
Gln Val Gln Leu Val Gln Ser Gly Ala Glu Val Lys Pro Gly Ala
1               5                   10                  15
Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
        35                  40                  45
Gly Trp Ile Asn Thr Lys Thr Gly Glu Ala Thr Tyr Val Glu Glu Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Trp Asp Phe Ala Tyr Tyr Val Glu Ala Met Asp Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Gly Gly Gly Gly Ser Gly Gly Gly Ser Glu Val Gln Leu Leu
225                 230                 235                 240
Glu Ser Gly Gly Gly Leu Val Gln Pro Gly Gly Ser Leu Arg Leu Ser
                245                 250                 255
Cys Ala Ala Ser Gly Phe Thr Phe Ser Thr Tyr Ala Met Asn Trp Val
            260                 265                 270
Arg Gln Ala Pro Gly Lys Gly Leu Glu Trp Val Ser Arg Ile Arg Ser
        275                 280                 285
Lys Tyr Asn Asn Tyr Ala Thr Tyr Tyr Ala Asp Ser Val Lys Gly Arg
    290                 295                 300
Phe Thr Ile Ser Arg Asp Asp Ser Lys Asn Thr Leu Tyr Leu Gln Met
305                 310                 315                 320
Asn Ser Leu Arg Ala Glu Asp Thr Ala Val Tyr Tyr Cys Val Arg His
                325                 330                 335
Gly Asn Phe Gly Asn Ser Tyr Val Ser Trp Phe Ala Tyr Trp Gly Gln
            340                 345                 350
```

```
Gly Thr Leu Val Thr Val Ser Ala Ser Val Ala Ala Pro Ser Val
            355                 360                 365

Phe Ile Phe Pro Pro Ser Asp Glu Gln Leu Lys Ser Gly Thr Ala Ser
370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
                420                 425                 430

Thr Leu Ser Lys Ala Asp Tyr Glu Lys His Lys Val Tyr Ala Cys Glu
            435                 440                 445

Val Thr His Gln Gly Leu Ser Ser Pro Val Thr Lys Ser Phe Asn Arg
450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
                500                 505                 510

Val Ser His Glu Asp Pro Glu Val Lys Phe Asn Trp Tyr Val Asp Gly
515                 520                 525

Val Glu Val His Asn Ala Lys Thr Lys Pro Arg Glu Glu Gln Tyr Asn
530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
                580                 585                 590

Pro Gln Val Tyr Thr Leu Pro Pro Cys Arg Asp Glu Leu Thr Lys Asn
            595                 600                 605

Gln Val Ser Leu Trp Cys Leu Val Lys Gly Phe Tyr Pro Ser Asp Ile
610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
            690

<210> SEQ ID NO 58
<211> LENGTH: 451
<212> TYPE: PRT
<213> ORGANISM: Artificial Sequence
<220> FEATURE:
<223> OTHER INFORMATION: CEA CH1A1A 98/99 (VH-CH1) - Fc(hole) P329GLALA

<400> SEQUENCE: 58

Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Glu Phe
             20                  25                  30
Gly Met Asn Trp Val Arg Gln Ala Pro Gly Gln Gly Leu Glu Trp Met
             35                  40                  45
Gly Trp Ile Asn Thr Lys Thr Gly Glu Ala Thr Tyr Val Glu Glu Phe
 50                  55                  60
Lys Gly Arg Val Thr Phe Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Trp Asp Phe Ala Tyr Tyr Val Glu Ala Met Asp Tyr Trp Gly
            100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
                340                 345                 350
Cys Thr Leu Pro Pro Ser Arg Asp Glu Leu Thr Lys Asn Gln Val Ser
                355                 360                 365
Leu Ser Cys Ala Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
```

-continued

Pro Gly Lys
    450

<210> SEQ ID NO 59
<211> LENGTH: 215
<212> TYPE: PRT
<213> ORGANISM: Artificial Sequence
<220> FEATURE:
<223> OTHER INFORMATION: LC DP47 GS

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 60
<211> LENGTH: 214
<212> TYPE: PRT
<213> ORGANISM: Artificial Sequence
<220> FEATURE:
<223> OTHER INFORMATION: LC CD3 CH2527 (Crossfab, VL-CH1)

<400> SEQUENCE: 60

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

```
Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 61
<211> LENGTH: 688
<212> TYPE: PRT
<213> ORGANISM: Artificial Sequence
<220> FEATURE:
<223> OTHER INFORMATION: DP47 GS (VH-CH1) - CD3 CH2527 (Crossfab
      VH-Ck) - Fc(knob) P329GLALA

<400> SEQUENCE: 61

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

Val Asp Lys Lys Val Glu Pro Lys Ser Cys Asp Gly Gly Gly Ser
    210                 215                 220

Gly Gly Gly Gly Ser Glu Val Gln Leu Leu Glu Ser Gly Gly Gly Leu
225                 230                 235                 240

Val Gln Pro Gly Gly Ser Leu Arg Leu Ser Cys Ala Ala Ser Gly Phe
                245                 250                 255

Thr Phe Ser Thr Tyr Ala Met Asn Trp Val Arg Gln Ala Pro Gly Lys
            260                 265                 270

Gly Leu Glu Trp Val Ser Arg Ile Arg Ser Lys Tyr Asn Asn Tyr Ala
        275                 280                 285

Thr Tyr Tyr Ala Asp Ser Val Lys Gly Arg Phe Thr Ile Ser Arg Asp
    290                 295                 300

Asp Ser Lys Asn Thr Leu Tyr Leu Gln Met Asn Ser Leu Arg Ala Glu
305                 310                 315                 320

Asp Thr Ala Val Tyr Tyr Cys Val Arg His Gly Asn Phe Gly Asn Ser
                325                 330                 335

Tyr Val Ser Trp Phe Ala Tyr Trp Gly Gln Gly Thr Leu Val Thr Val
            340                 345                 350

Ser Ser Ala Ser Val Ala Ala Pro Ser Val Phe Ile Phe Pro Pro Ser
        355                 360                 365

Asp Glu Gln Leu Lys Ser Gly Thr Ala Ser Val Val Cys Leu Leu Asn
    370                 375                 380

Asn Phe Tyr Pro Arg Glu Ala Lys Val Gln Trp Lys Val Asp Asn Ala
385                 390                 395                 400

Leu Gln Ser Gly Asn Ser Gln Glu Ser Val Thr Glu Gln Asp Ser Lys
                405                 410                 415

Asp Ser Thr Tyr Ser Leu Ser Ser Thr Leu Thr Leu Ser Lys Ala Asp
            420                 425                 430

Tyr Glu Lys His Lys Val Tyr Ala Cys Glu Val Thr His Gln Gly Leu
        435                 440                 445

Ser Ser Pro Val Thr Lys Ser Phe Asn Arg Gly Glu Cys Asp Lys Thr
    450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Cys Arg Asp Glu Leu Thr Lys Asn Gln Val Ser Leu Trp Cys
        595                 600                 605

Leu Val Lys Gly Phe Tyr Pro Ser Asp Ile Ala Val Glu Trp Glu Ser
    610                 615                 620

```
Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
            645                 650                 655

Arg Trp Gln Gln Gly Asn Val Phe Ser Cys Ser Val Met His Glu Ala
        660                 665                 670

Leu His Asn His Tyr Thr Gln Lys Ser Leu Ser Leu Ser Pro Gly Lys
    675                 680                 685

<210> SEQ ID NO 62
<211> LENGTH: 445
<212> TYPE: PRT
<213> ORGANISM: Artificial Sequence
<220> FEATURE:
<223> OTHER INFORMATION: DP47 GS (VH-CH1) - Fc(hole) P329GLALA

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
            325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 63
<211> LENGTH: 1365
<212> TYPE: DNA
<213> ORGANISM: Artificial Sequence
<220> FEATURE:
<223> OTHER INFORMATION: HC CD3 CH2527 (VH_3-23(12))

<400> SEQUENCE: 63
gaggtgcagc tgctggaatc tggcggcgga ctggtgcagc ctggcggatc tctgagactg     60
agctgtgccg ccagcggctt caccttcagc acctacgcca tgaactgggt gcgccaggcc    120
cctggcaaag gcctggaatg ggtgtcccgg atcagaagca agtacaacaa ctacgccacc    180
tactacgccg acagcgtgaa gggccggttc accatcagcc gggacgacag caagaacacc    240
ctgtacctgc agatgaacag cctgcgggcc gaggacaccg ccgtgtacta ttgtgtgcgg    300
cacggcaact tcggcaacag ctatgtgtct tggtttgcct actggggcca gggcacccto    360 gtgaccgtgt catctgctag caccaagggc ccatcggtct tccccctggc accctcctcc    420
aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaactcctgg ggggaccgtc agtcttcctc ttccccccaa acccaaggac accctcatg     780 atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caaagggcag ccccgagaac acaggtgta cccctgccc    1080 ccatcccggg atgagctgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
```

```
gacaagagca ggtggcagca ggggaacgtc ttctcatgct ccgtgatgca tgaggctctg   1320
cacaaccact acacgcagaa gagcctctcc ctgtctccgg gtaaa                  1365
```

<210> SEQ ID NO 64
<211> LENGTH: 645
<212> TYPE: DNA
<213> ORGANISM: Artificial Sequence
<220> FEATURE:
<223> OTHER INFORMATION: LC CD3 CH2527 (VL_7-46(13))

<400> SEQUENCE: 64

```
caggccgtcg tgacccagga acccagcctg acagtgtctc ctggcggcac cgtgaccctg    60
acatgtggca gttctacagg cgccgtgacc accagcaact acgccaactg ggtgcaggaa   120
aagcccggcc aggccttcag aggactgatc ggcggcacca acaagagagc ccctggcacc   180
cctgccagat tcagcggatc tctgctggga ggaaaggccg ccctgacact gtctggcgcc   240
cagccagaag atgaggccga gtactactgc gccctgtggt acagcaacct gtgggtgttc   300
ggcggaggca ccaagctgac agtcctaggt caacccaagg ctgccccag cgtgaccctg    360 ttccccccca gcagcgagga actgcaggcc aacaaggcca cctggtctg cctgatcagc    420 gacttctacc caggcgccgt gaccgtggcc tggaaggccg acagcagccc cgtgaaggcc    480
ggcgtggaga ccaccacccc cagcaagcag agcaacaaca gtacgccgc cagcagctac    540 ctgagcctga cccccgagca gtggaagagc acaggtcct acagctgcca ggtgaccgac    600
gagggcagca ccgtggagaa aaccgtggcc ccaccgagt gcagc                   645
```

<210> SEQ ID NO 65
<211> LENGTH: 375
<212> TYPE: DNA
<213> ORGANISM: Artificial Sequence
<220> FEATURE:
<223> OTHER INFORMATION: VH CD3 CH2527 (VH_3-23(12))

<400> SEQUENCE: 65

```
gaggtgcagc tgctggaatc tggcggcgga ctggtgcagc ctggcggatc tctgagactg    60
agctgtgccg ccagcggctt caccttcagc acctacgcca tgaactgggt gcgccaggcc   120
cctggcaaag gcctggaatg ggtgtcccgg atcagaagca agtacaacaa ctacgccacc   180
tactacgccg acagcgtgaa gggccggttc accatcagcc gggacgacag caagaacacc   240
ctgtacctgc agatgaacag cctgcgggcc gaggacaccg ccgtgtacta ttgtgtgcgg   300
cacggcaact cggcaacag ctatgtgtct tggtttgcct actggggcca gggcaccctc    360
gtgaccgtgt catct                                                   375
```

<210> SEQ ID NO 66
<211> LENGTH: 15
<212> TYPE: DNA
<213> ORGANISM: Artificial Sequence
<220> FEATURE:
<223> OTHER INFORMATION: HCDR1 CD3 CH2527 (VH_3-23(12))

<400> SEQUENCE: 66

```
acctacgcca tgaac                                                    15
```

<210> SEQ ID NO 67
<211> LENGTH: 57
<212> TYPE: DNA
<213> ORGANISM: Artificial Sequence
<220> FEATURE:
<223> OTHER INFORMATION: HCDR2 CD3 CH2527 (VH_3-23(12))

```
<400> SEQUENCE: 67
cggatcagaa gcaagtacaa caactacgcc acctactacg ccgacagcgt gaagggc        57

<210> SEQ ID NO 68
<211> LENGTH: 42
<212> TYPE: DNA
<213> ORGANISM: Artificial Sequence
<220> FEATURE:
<223> OTHER INFORMATION: HCDR3 CD3 CH2527 (VH_3-23(12))

<400> SEQUENCE: 68
cacggcaact tcggcaacag ctatgtgtct tggtttgcct ac                        42

<210> SEQ ID NO 69
<211> LENGTH: 327
<212> TYPE: DNA
<213> ORGANISM: Artificial Sequence
<220> FEATURE:
<223> OTHER INFORMATION: VL CD3 CH2527 (VL_7-46(13))

<400> SEQUENCE: 69
caggccgtcg tgacccagga acccagcctg acagtgtctc ctggcggcac cgtgaccctg     60
acatgtggca gttctacagg cgccgtgacc accagcaact acgccaactg ggtgcaggaa    120
aagcccggcc aggccttcag aggactgatc ggcggcacca caagagagc cctggcacc     180 cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtccta                                        327

<210> SEQ ID NO 70
<211> LENGTH: 42
<212> TYPE: DNA
<213> ORGANISM: Artificial Sequence
<220> FEATURE:
<223> OTHER INFORMATION: LCDR1 CD3 CH2527 (VL_7-46(13))

<400> SEQUENCE: 70
ggcagttcta caggcgccgt gaccaccagc aactacgcca ac                        42

<210> SEQ ID NO 71
<211> LENGTH: 21
<212> TYPE: DNA
<213> ORGANISM: Artificial Sequence
<220> FEATURE:
<223> OTHER INFORMATION: LCDR2 CD3 CH2527 (VL_7-46(13))

<400> SEQUENCE: 71
ggcaccaaca agagagcccc t                                               21

<210> SEQ ID NO 72
<211> LENGTH: 27
<212> TYPE: DNA
<213> ORGANISM: Artificial Sequence
<220> FEATURE:
<223> OTHER INFORMATION: LCDR3 CD3 CH2527 (VL_7-46(13))

<400> SEQUENCE: 72
gccctgtggt acagcaacct gtgggtg                                         27

<210> SEQ ID NO 73
<211> LENGTH: 1326
<212> TYPE: DNA
```

<213> ORGANISM: Artificial Sequence
<220> FEATURE:
<223> OTHER INFORMATION: HC MCSP M4-3 (C1)

<400> SEQUENCE: 73

| | |
|---|---|
| caggtgcaat tgcaggaaag cggccctggc ctggtcaagc ccagccagac cctgagcctg | 60 |
| acctgcaccg tgtccggcgg cagcatcacc agcggctatt attggaactg gattcggcag | 120 |
| caccccggca agggcctgga atggatcggc tacatcactt tcgacggctc taacaactac | 180 |
| aaccccagcc tgaagtccag agtgaccatc agccgggaca ccagcaagaa ccagttcagc | 240 |
| ctgaagctgt ccagcgtgac agccgccgac accgccgtgt actactgcgc cgacttcgac | 300 |
| tactggggcc agggcaccct ggtcaccgtg tccagcgcta gcaccaaggg cccatcggtc | 360 |
| ttccccctgg cacctcctc caagagcacc tctgggggca gcggccct gggctgcctg | 420 |
| gtcaaggact acttccccga accggtgacg gtgtcgtgga actcaggcgc cctgaccagc | 480 |
| ggcgtgcaca ccttcccggc tgtcctacag tcctcaggac tctactccct cagcagcgtg | 540 |
| gtgaccgtgc cctccagcag cttgggcacc cagacctaca tctgcaacgt gaatcacaag | 600 |
| cccagcaaca ccaaggtgga caagaaagtt gagcccaaat cttgtgacaa aactcacaca | 660 |
| tgcccaccgt gcccagcacc tgaactcctg ggggaccgt cagtcttcct cttccccca | 720 |
| aaacccaagg acaccctcat gatctcccgg acccctgagg tcacatgcgt ggtggtggac | 780 |
| gtgagccacg aagaccctga ggtcaagttc aactggtacg tggacggcgt ggaggtgcat | 840 |
| aatgccaaga caaagccgcg ggaggagcag tacaacagca cgtaccgtgt ggtcagcgtc | 900 |
| ctcaccgtcc tgcaccagga ctggctgaat ggcaaggagt acaagtgcaa ggtctccaac | 960 |
| aaagccctcc cagcccccat cgagaaaacc atctccaaag ccaaagggca gccccgagaa | 1020 |
| ccacaggtgt acaccctgcc cccatcccgg gatgagctga ccaagaacca ggtcagcctg | 1080 |
| acctgcctgg tcaaaggctt ctatcccagc gacatcgccg tggagtggga gagcaatggg | 1140 |
| cagccggaga caactacaa gaccacgcct cccgtgctgg actccgacgg ctccttcttc | 1200 |
| ctctacagca agctcaccgt ggacaagagc aggtggcagc aggggaacgt cttctcatgc | 1260 |
| tccgtgatgc atgaggctct gcacaaccac tacacgcaga agagcctctc cctgtctccg | 1320 |
| ggtaaa | 1326 |

<210> SEQ ID NO 74
<211> LENGTH: 642
<212> TYPE: DNA
<213> ORGANISM: Artificial Sequence
<220> FEATURE:
<223> OTHER INFORMATION: LC MCSP ML2 (G3)

<400> SEQUENCE: 74

| | |
|---|---|
| gacatccaga tgacccagag ccccagcagc ctgagcgcca gcgtgggcga cagagtgacc | 60 |
| atcacctgcc gggccagcca gggcatccgg aactacctga actggtatca gcagaagccc | 120 |
| ggcaaggccc ccaagctgct gatctactac accagcagcc tgcacagcgg cgtgcctagc | 180 |
| cggtttagcg gcagcggctc cggcaccgac tacaccctga ccattagctc cctgcagccc | 240 |
| gaggacttcg ccacctacta ctgccagcag tactctgctc tgccgtggac cttcggccag | 300 |
| ggaacaaagg tggagatcaa gcgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |

```
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 75
<211> LENGTH: 336
<212> TYPE: DNA
<213> ORGANISM: Artificial Sequence
<220> FEATURE:
<223> OTHER INFORMATION: VH MCSP M4-3 (C1)

<400> SEQUENCE: 75

```
caggtgcaat tgcaggaaag cggccctggc ctggtcaagc ccagccagac cctgagcctg    60
acctgcaccg tgtccggcgg cagcatcacc agcggctatt attggaactg gattcggcag    120 cacccoggca agggcctgga atggatcggc tacatcactt tcgacggctc taacaactac    180
aaccccagcc tgaagtccag agtgaccatc agccgggaca ccagcaagaa ccagttcagc    240
ctgaagctgt ccagcgtgac agccgccgac accgccgtgt actactgcgc cgacttcgac    300
tactggggcc agggcaccct ggtcaccgtg tccagc                              336
```

<210> SEQ ID NO 76
<211> LENGTH: 18
<212> TYPE: DNA
<213> ORGANISM: Artificial Sequence
<220> FEATURE:
<223> OTHER INFORMATION: HCDR1 MCSP M4-3 (C1)

<400> SEQUENCE: 76

```
agcggctatt attggaac                                                  18
```

<210> SEQ ID NO 77
<211> LENGTH: 48
<212> TYPE: DNA
<213> ORGANISM: Artificial Sequence
<220> FEATURE:
<223> OTHER INFORMATION: HCDR2 MCSP M4-3 (C1)

<400> SEQUENCE: 77

```
tacatcactt tcgacggctc taacaactac aaccccagcc tgaagtcc                 48
```

<210> SEQ ID NO 78
<211> LENGTH: 9
<212> TYPE: DNA
<213> ORGANISM: Artificial Sequence
<220> FEATURE:
<223> OTHER INFORMATION: HCDR3 MCSP M4-3 (C1)

<400> SEQUENCE: 78

```
ttcgactac                                                            9
```

<210> SEQ ID NO 79
<211> LENGTH: 321
<212> TYPE: DNA
<213> ORGANISM: Artificial Sequence
<220> FEATURE:
<223> OTHER INFORMATION: VL MCSP ML2 (G3)

<400> SEQUENCE: 79

```
gacatccaga tgacccagag ccccagcagc ctgagcgcca gcgtgggcga cagagtgacc    60
atcacctgcc gggccagcca gggcatccgg aactacctga actggtatca gcagaagccc    120
ggcaaggccc ccaagctgct gatctactac accagcagcc tgcacagcgg cgtgcctagc    180
```

| | |
|---|---|
| cggtttagcg gcagcggctc cggcaccgac tacaccctga ccattagctc cctgcagccc | 240 |
| gaggacttcg ccacctacta ctgccagcag tactctgctc tgccgtggac cttcggccag | 300 |
| ggaacaaagg tggagatcaa g | 321 |

<210> SEQ ID NO 80
<211> LENGTH: 33
<212> TYPE: DNA
<213> ORGANISM: Artificial Sequence
<220> FEATURE:
<223> OTHER INFORMATION: LCDR1 MCSP ML2 (G3)

<400> SEQUENCE: 80

| | |
|---|---|
| cgggccagcc agggcatccg gaactacctg aac | 33 |

<210> SEQ ID NO 81
<211> LENGTH: 21
<212> TYPE: DNA
<213> ORGANISM: Artificial Sequence
<220> FEATURE:
<223> OTHER INFORMATION: LCDR2 MCSP ML2 (G3)

<400> SEQUENCE: 81

| | |
|---|---|
| tacaccagca gcctgcacag c | 21 |

<210> SEQ ID NO 82
<211> LENGTH: 27
<212> TYPE: DNA
<213> ORGANISM: Artificial Sequence
<220> FEATURE:
<223> OTHER INFORMATION: LCDR3 MCSP ML2 (G3)

<400> SEQUENCE: 82

| | |
|---|---|
| cagcagtact ctgctctgcc gtggacc | 27 |

<210> SEQ ID NO 83
<211> LENGTH: 1353
<212> TYPE: DNA
<213> ORGANISM: Artificial Sequence
<220> FEATURE:
<223> OTHER INFORMATION: HC CEA CH1A1A 98-99

<400> SEQUENCE: 83

| | |
|---|---|
| caggtgcagc tggtgcagtc tggcgccgaa gtgaagaaac tggagctagt gtgaaggtg | 60 |
| tcctgcaagg ccagcggcta caccttcacc gagttcggca tgaactgggt ccgacaggct | 120 |
| ccaggccagg gcctcgaatg gatgggctgg atcaacacca gaccggcga ggccacctac | 180 |
| gtggaagagt tcaagggcag agtgaccttc accacggaca ccagcaccag caccgcctac | 240 |
| atggaactgc ggagcctgag aagcgacgac accgccgtgt actactgcgc cagatgggac | 300 |
| ttcgcctatt acgtggaagc catggactac tggggccagg gcaccaccgt gaccgtgtct | 360 |
| agcgctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca cctcatgat ctcccggacc | 780 |
| cctgaggtca catgcgtggt ggtggacgtg agccacgaag accctgaggt caagttcaac | 840 |

```
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca gaaccaggt cagcctgacc tgcctggtca aaggcttcta tcccagcgac    1140
atcgccgtgg agtgggagag caatgggcag ccggagaaca actacaagac cacgcctccc   1200
gtgctggact ccgacggctc cttcttcctc tacagcaagc tcaccgtgga agagcagg    1260 tggcagcagg ggaacgtctt ctcatgctcc gtgatgcatg aggctctgca caaccactac   1320
acgcagaaga gcctctccct gtctccgggt aaa                              1353
```

<210> SEQ ID NO 84
<211> LENGTH: 645
<212> TYPE: DNA
<213> ORGANISM: Artificial Sequence
<220> FEATURE:
<223> OTHER INFORMATION: LC CEA 2F1

<400> SEQUENCE: 84

```
gatatccaga tgacccagtc tccatcctcc ctgtctgcat ctgtgggaga cagagtcacc     60
atcacttgca aggccagtgc ggctgtgggt acgtatgttg cgtggtatca gcagaaacca    120
gggaaagcac ctaagctcct gatctattcg gcatcctacc gcaaaagggg agtcccatca    180
aggttcagtg gcagtggatc tgggacagat ttcactctca ccatcagcag tctgcaacct    240
gaagatttcg caacttacta ctgtcaccaa tattacacct atcctctatt cacgtttggc    300
cagggcacca agctcgagat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                   645
```

<210> SEQ ID NO 85
<211> LENGTH: 363
<212> TYPE: DNA
<213> ORGANISM: Artificial Sequence
<220> FEATURE:
<223> OTHER INFORMATION: VH CEA CH1A1A 98-99

<400> SEQUENCE: 85

```
caggtgcagc tggtgcagtc tggcgccgaa gtgaagaaac tggagctag tgtgaaggtg      60 tcctgcaagg ccagcggcta caccttcacc gagttcggca tgaactgggt ccgacaggct    120
ccaggccagg gctcgaatg gatgggctgg atcaacacca gaccggcga ggccacctac     180 gtggaagagt tcaagggcag agtgaccttc accacggaca ccagcaccag caccgcctac    240
atggaactgc ggagcctgag aagcgacgac accgccgtgt actactgcgc cagatgggac    300
ttcgcctatt acgtggaagc catggactac tggggccagg gcaccaccgt gaccgtgtct    360
agc                                                                  363
```

<210> SEQ ID NO 86
<211> LENGTH: 15
<212> TYPE: DNA

```
<213> ORGANISM: Artificial Sequence
<220> FEATURE:
<223> OTHER INFORMATION: HCDR1 CEA CH1A1A 98-99

<400> SEQUENCE: 86
gagttcggca tgaac                                                         15

<210> SEQ ID NO 87
<211> LENGTH: 51
<212> TYPE: DNA
<213> ORGANISM: Artificial Sequence
<220> FEATURE:
<223> OTHER INFORMATION: HCDR2 CEA CH1A1A 98-99

<400> SEQUENCE: 87
tggatcaaca ccaagaccgg cgaggccacc tacgtggaag agttcaaggg c                 51

<210> SEQ ID NO 88
<211> LENGTH: 36
<212> TYPE: DNA
<213> ORGANISM: Artificial Sequence
<220> FEATURE:
<223> OTHER INFORMATION: HCDR3 CEA CH1A1A 98-99

<400> SEQUENCE: 88
tgggacttcg cctattacgt ggaagccatg gactac                                  36

<210> SEQ ID NO 89
<211> LENGTH: 324
<212> TYPE: DNA
<213> ORGANISM: Artificial Sequence
<220> FEATURE:
<223> OTHER INFORMATION: VL CEA 2F1

<400> SEQUENCE: 89
gatatccaga tgacccagtc tccatcctcc ctgtctgcat ctgtgggaga cagagtcacc        60
atcacttgca aggccagtgc ggctgtgggt acgtatgttg cgtggtatca gcagaaacca      120
gggaaagcac ctaagctcct gatctattcg catcctacc gcaaaggggg agtcccatca       180
aggttcagtg gcagtggatc tgggacagat ttcactctca ccatcagcag tctgcaacct     240
gaagatttcg caacttacta ctgtcaccaa tattacacct atcctctatt cacgtttggc     300
cagggcacca agctcgagat caag                                             324

<210> SEQ ID NO 90
<211> LENGTH: 33
<212> TYPE: DNA
<213> ORGANISM: Artificial Sequence
<220> FEATURE:
<223> OTHER INFORMATION: LCDR1 CEA 2F1

<400> SEQUENCE: 90
aaggccagtg cggctgtggg tacgtatgtt gcg                                     33

<210> SEQ ID NO 91
<211> LENGTH: 21
<212> TYPE: DNA
<213> ORGANISM: Artificial Sequence
<220> FEATURE:
<223> OTHER INFORMATION: LCDR2 CEA 2F1

<400> SEQUENCE: 91
tcggcatcct accgcaaaag g                                                  21
```

```
<210> SEQ ID NO 92
<211> LENGTH: 30
<212> TYPE: DNA
<213> ORGANISM: Artificial Sequence
<220> FEATURE:
<223> OTHER INFORMATION: LCDR3 CEA 2F1

<400> SEQUENCE: 92
caccaatatt acacctatcc tctattcacg                                  30

<210> SEQ ID NO 93
<211> LENGTH: 642
<212> TYPE: DNA
<213> ORGANISM: Artificial Sequence
<220> FEATURE:
<223> OTHER INFORMATION: LC CD3 CH2527 (Crossfab, VL-CH1)

<400> SEQUENCE: 93
caggccgtcg tgacccagga acccagcctg acagtgtctc ctggcggcac cgtgaccctg   60
acatgtggca gttctacagg cgccgtgacc accagcaact acgccaactg ggtgcaggaa  120
aagcccggcc aggccttcag aggactgatc ggcggcacca caagagagc cctggcacc    180 cctgccagat tcagcggatc tctgctggga ggaaaggccg ccctgacact gtctggcgcc  240
cagccagaag atgaggccga gtactactgc gccctgtggt acagcaacct gtgggtgttc  300
ggcggaggca ccaagctgac agtgctgagc agcgcttcca ccaaaggccc ttccgtgttt  360
cctctggctc ctagctccaa gtccacctct ggaggcaccg ctgctctcgg atgcctcgtg  420
aaggattatt ttcctgagcc tgtgacagtg tcctggaata gcggagcact gacctctgga  480
gtgcatactt tccccgctgt gctgcagtcc tctggactgt acagcctgag cagcgtggtg  540
acagtgccca gcagcagcct gggcacccag acctacatct gcaacgtgaa ccacaagccc  600
agcaacacca aggtggacaa gaaggtggaa cccaagtctt gt                     642

<210> SEQ ID NO 94
<211> LENGTH: 2055
<212> TYPE: DNA
<213> ORGANISM: Artificial Sequence
<220> FEATURE:
<223> OTHER INFORMATION: MCSP M4-3 (C1) (VH-CH1) - CD3 CH2527 (Crossfab
      VH-Ck) - Fc(knob) P329GLALA

<400> SEQUENCE: 94
caggtgcaat tgcaggaaag cggccctggc ctggtcaagc ccagccagac cctgagcctg   60
acctgcaccg tgtccggcgg cagcatcacc agcggctatt attggaactg gattcggcag  120
caccccggca agggcctgga atggatcggc tacatcactt tcgacggctc taacaactac  180
aaccccagcc tgaagtccag agtgaccatc agcgggaca ccagcaagaa ccagttcagc   240
ctgaagctgt ccagcgtgac agccgccgac accgccgtgt actactgcgc cgacttcgac  300 tactgggggcc agggcaccct ggtcaccgtg tccagcgcta gcacaaaggg cccagcgtg   360 ttccctctgg cccctagcag caagagcaca tctgcggaa cagccgccct gggctgcctc   420
gtgaaggact actttcccga gcctgtgacc gtgtcctgga actctggcgc cctgacaagc   480
ggcgtgcaca ccttttccagc cgtgctgcag agcagcggcc tgtactctct gagcagcgtg  540
gtcaccgtgc ctagcagcag cctgggcacc cagacctaca tctgcaacgt gaaccacaag  600
cccagcaaca ccaaagtgga caagaaggtg gagcccaaga gctgtgatgg cggaggaggg  660
tccggaggcg gaggatccga ggtgcagctg ctggaatctg gcggcggact ggtgcagcct  720
ggcggatctc tgagactgag ctgtgccgcc agcggcttca ccttcagcac ctacgccatg  780
```

```
aactgggtgc gccaggcccc tggcaaaggc ctggaatggg tgtcccggat cagaagcaag      840
tacaacaact acgccaccta ctacgccgac agcgtgaagg gccggttcac catcagccgg      900
gacgacagca agaacaccct gtacctgcag atgaacagcc tgcgggccga ggacaccgcc      960
gtgtactatt gtgtgcggca cggcaacttc ggcaacagct atgtgtcttg gtttgcctac     1020
tggggccagg gcaccctcgt gaccgtgtca agcgctagcg tggccgctcc ctccgtgttt     1080
atctttcccc catccgatga acagctgaaa agcggcaccg cctccgtcgt gtgtctgctg     1140
aacaattttt accctaggga agctaaagtg cagtggaaag tggataacgc actgcagtcc     1200
ggcaactccc aggaatctgt gacagaacag gactccaagg acagcaccta ctccctgtcc     1260
tccaccctga cactgtctaa ggctgattat gagaaacaca agtctacgc ctgcgaagtc      1320 acccatcagg gcctgagctc gcccgtcaca aagagcttca caggggaga gtgtgacaag      1380 acccacacct gtcccccttg tcctgcccct gaagctgctg gcggcccttc tgtgttcctg     1440 ttcccccaa agcccaagga caccctgatg atcagccgga ccccgaagt gacctgcgtg       1500 gtggtggatg tgtcccacga ggaccctgaa gtgaagttca attggtacgt ggacggcgtg     1560
gaagtgcaca cgccaagac aaagccgcgg gaggagcagt acaacagcac gtaccgtgtg      1620
gtcagcgtcc tcaccgtcct gcaccaggac tggctgaatg gcaaggagta caagtgcaag    1680
gtctccaaca agcccctcgg cgcccccatc gagaaaacca tctccaaagc caagggcag     1740 ccccgagaac acaggtgta caccctgccc ccatgccggg atgagctgac caagaaccag     1800
gtcagcctgt ggtgcctggt caaaggcttc tatcccagcg acatcgccgt ggagtgggag    1860
agcaatgggc agccggagaa caactacaag accacgcctc ccgtgctgga ctccgacggc    1920
tccttcttcc tctacagcaa gctcaccgtg gacaagagca ggtggcagca ggggaacgtc    1980
ttctcatgct ccgtgatgca tgaggctctg cacaaccact acacgcagaa gagcctctcc    2040
ctgtctccgg gtaaa                                                     2055
```

<210> SEQ ID NO 95
<211> LENGTH: 1326
<212> TYPE: DNA
<213> ORGANISM: Artificial Sequence
<220> FEATURE:
<223> OTHER INFORMATION: MCSP M4-3 (C1) (VH-CH1) - Fc(hole) P329GLALA

<400> SEQUENCE: 95

```
caggtgcaat tgcaggaaag cggccctggc ctggtcaagc ccagccagac cctgagcctg       60
acctgcaccg tgtccggcgg cagcatcacc agcggctatt attggaactg gattcggcag      120
caccccggca agggcctgga atggatcggc tacatcactt tcgacggctc taacaactac      180
aaccccagcc tgaagtccag agtgaccatc agccgggaca ccagcaagaa ccagttcagc      240
ctgaagctgt ccagcgtgac agccgccgac accgccgtgt actactgcgc cgacttcgac      300
tactggggcc agggcaccct ggtcaccgtg tccagcgcta gcaccaaggg cccctccgtg      360
ttccccctgg cccccagcag caagagcacc agcggcggca gccgctctct ggctgcctg      420 gtcaaggact acttccccga gcccgtgacc gtgtcctgga acagcggagc cctgacctcc     480
ggcgtgcaca ccttccccgc cgtgctgcag agttctggcc tgtatagcct gagcagcgtg     540
gtcaccgtgc cttctagcag cctgggcacc cagacctaca tctgcaacgt gaaccacaag     600
cccagcaaca ccaaggtgga caagaaggtg gagcccaaga gctgcgacaa aactcacaca     660
tgcccaccgt gcccagcacc tgaagctgca ggggaccgt cagtcttcct cttccccca      720
```

```
aaacccaagg acaccctcat gatctcccgg accccctgagg tcacatgcgt ggtggtggac     780
gtgagccacg aagaccctga ggtcaagttc aactggtacg tggacggcgt ggaggtgcat     840
aatgccaaga caaagccgcg ggaggagcag tacaacagca cgtaccgtgt ggtcagcgtc     900
ctcaccgtcc tgcaccagga ctggctgaat ggcaaggagt acaagtgcaa ggtctccaac     960
aaagccctcg cgcccccat cgagaaaacc atctccaaag ccaaagggca gccccgagaa      1020
ccacaggtgt gcaccctgcc cccatcccgg gatgagctga ccaagaacca ggtcagcctc     1080
tcgtgcgcag tcaaaggctt ctatcccagc gacatcgccg tggagtggga gagcaatggg    1140
cagccggaga caactacaa gaccacgcct cccgtgctgg actccgacgg ctccttcttc      1200
ctcgtgagca agctcaccgt ggacaagagc aggtggcagc aggggaacgt cttctcatgc    1260
tccgtgatgc atgaggctct gcacaaccac tacacgcaga gagcctctc cctgtctccg     1320 ggtaaa                                                                1326
```

<210> SEQ ID NO 96
<211> LENGTH: 642
<212> TYPE: DNA
<213> ORGANISM: Artificial Sequence
<220> FEATURE:
<223> OTHER INFORMATION: LC CD3 CH2527 (Crossfab, VL-CH1)

<400> SEQUENCE: 96

```
caggccgtcg tgacccagga acccagcctg acagtgtctc ctggcggcac cgtgaccctg       60
acatgtggca gttctacagg cgccgtgacc accagcaact acgccaactg ggtgcaggaa     120
aagcccggcc aggccttcag aggactgatc ggcggcacca caagagagc ccctggcacc      180 cctgccagat tcagcggatc tctgctggga ggaaaggccg ccctgacact gtctggcgcc    240
cagccagaag atgaggccga gtactactgc gccctgtggt acagcaacct gtgggtgttc     300
ggcggaggca ccaagctgac agtgctgagc agcgcttcca ccaaaggccc ttccgtgttt     360
cctctggctc ctagctccaa gtccacctct ggaggcaccg ctgctctcgg atgcctcgtg    420
aaggattatt ttcctgagcc tgtgacagtg tcctggaata cggagcact gacctctgga      480 gtgcatactt tccccgctgt gctgcagtcc tctggactgt acagcctgag cagcgtggtg    540
acagtgccca gcagcagcct gggcacccag acctacatct gcaacgtgaa ccacaagccc    600
agcaacacca aggtggacaa gaaggtggaa cccaagtctt gt                         642
```

<210> SEQ ID NO 97
<211> LENGTH: 2082
<212> TYPE: DNA
<213> ORGANISM: Artificial Sequence
<220> FEATURE:
<223> OTHER INFORMATION: CEA CH1A1A 98/99 - CD3 CH2527 (Crossfab VH-Ck) - Fc(knob) P329GLALA

<400> SEQUENCE: 97

```
caggtgcagc tggtgcagtc tggcgccgaa gtgaagaaac tggcgccag cgtgaaggtg       60 tcctgcaagg ccagcggcta caccttcacc gagttcggca tgaactgggt ccgacaggcc    120
cctggacagg gcctggaatg gatgggctgg atcaacacca gaccggcga ggccacctac     180 gtggaagagt tcaagggcag agtgaccttc accaccgaca ccagcaccag caccgcctac    240
atggaactgc ggagcctgag aagcgacgac accgccgtgt actactgcgc cagatgggac    300
ttcgcctact atgtggaagc catggactac tggggccagg gcaccaccgt gaccgtgtct    360
agtgctagca caaagggccc cagcgtgttc cctctggccc ctagcagcaa gagcacatct    420
```

```
ggcggaacag ccgccctggg ctgcctggtc aaggactact ttcccgagcc cgtgacagtg    480
tcctggaact ctggcgccct gacaagcggc gtgcacacct tccagccgt gctgcagagc     540 agcggcctgt actctctgag cagcgtggtc accgtgccta gctctagcct gggcacccag    600
acctacatct gcaacgtgaa ccacaagccc agcaacacca aggtggacaa gaaggtggaa    660
cccaagagct gcgatggcgg aggcggctcc ggaggcggag atccgaggt gcagctgctg     720 gaatctggcg gcggactggt gcagcctggc ggatctctga gactgagctg tgccgccagc    780
ggcttcacct tcagcaccta cgccatgaac tgggtgcgcc aggcccctgg caaaggcctg    840
gaatgggtgt cccggatcag aagcaagtac aacaactacg ccacctacta cgccgacagc    900
gtgaagggcc ggttcaccat cagccgggac gacagcaaga cacccctgta cctgcagatg    960
aacagcctgc gggccgagga caccgccgtg tactattgtg tgcggcacgg caacttcggc   1020
aacagctatg tgtcttggtt tgcctactgg ggccagggca ccctcgtgac cgtgtcaagc   1080
gctagcgtgg ccgctccctc cgtgtttatc tttcccccat ccgatgaaca gctgaaaagc   1140
ggcaccgcct ccgtcgtgtg tctgctgaac aattttttacc ctaggaagc taaagtgcag   1200 tggaaagtgg ataacgcact gcagtccggc aactcccagg aatctgtgac agaacaggac   1260
tccaaggaca gcacctactc cctgtcctcc accctgacac tgtctaaggc tgattatgag   1320
aaacacaaag tctacgcctg cgaagtcacc catcagggcc tgagctcgcc cgtcacaaag   1380
agcttcaaca ggggagagtg tgacaagacc cacacctgtc cccttgtcc tgcccctgaa     1440 gctgctggcg gccttctgt gttcctgttc cccccaaagc caaggacac cctgatgatc      1500 agccggaccc ccgaagtgac ctgcgtggtg gtggatgtgt cccacgagga ccctgaagtg   1560
aagttcaatt ggtacgtgga cggcgtggaa gtgcacaacg ccaagacaaa gccgcgggag   1620
gagcagtaca acagcacgta ccgtgtggtc agcgtcctca ccgtcctgca ccaggactgg   1680
ctgaatggca aggagtacaa gtgcaaggtc tccaacaaag ccctcggcgc ccccatcgag   1740
aaaaccatct ccaaagccaa agggcagccc cgagaaccac aggtgtacac cctgccccca   1800
tgccgggatg agctgaccaa gaaccaggtc agcctgtggt gcctggtcaa aggcttctat   1860
cccagcgaca tcgccgtgga gtgggagagc aatgggcagc cggagaacaa ctacaagacc   1920
acgcctcccg tgctggactc cgacggctcc ttcttcctct acagcaagct caccgtggac   1980
aagagcaggt ggcagcaggg gaacgtcttc tcatgctccg tgatgcatga ggctctgcac   2040
aaccactaca cgcagaagag cctctccctg tctccgggta aa                       2082
```

<210> SEQ ID NO 98
<211> LENGTH: 1353
<212> TYPE: DNA
<213> ORGANISM: Artificial Sequence
<220> FEATURE:
<223> OTHER INFORMATION: CEA CH1A1A 98/99 (VH-CH1) - Fc(hole) P329GLALA

<400> SEQUENCE: 98

```
caggtgcagc tggtgcagtc tggcgccgaa gtgaagaaac tggagctag tgtgaaggtg      60 tcctgcaagg ccagcggcta caccttcacc gagttcggca tgaactgggt ccgacaggct   120
ccaggccagg gctcgaatg gatgggctgg atcaacacca gaccggcga ggccacctac    180 gtggaagagt tcaagggcag agtgaccttc accacggaca ccagcaccag cacggcctac   240
atggaactgc ggagcctgag aagcgacgac accgccgtgt actactgcgc cagatgggac   300
ttcgcctatt acgtggaagc catggactac tggggccagg gcaccaccgt gaccgtgtct   360
agcgctagca ccaagggccc ctccgtgttc cccctggccc ccagcagcaa gagcaccagc   420
```

```
ggcggcacag ccgctctggg ctgcctggtc aaggactact tccccgagcc cgtgaccgtg      480
tcctggaaca gcggagccct gacctccggc gtgcacacct ccccgccgt gctgcagagt      540 tctggcctgt atagcctgag cagcgtggtc accgtgcctt ctagcagcct gggcacccag      600
acctacatct gcaacgtgaa ccacaagccc agcaacacca aggtggacaa gaaggtggag      660
cccaagagct gcgacaaaac tcacacatgc ccaccgtgcc cagcacctga gctgcaggg      720 ggaccgtcag tcttcctctt cccccaaaa cccaaggaca ccctcatgat ctcccggacc      780
cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcggcg cccccatcga gaaaaccatc     1020
tccaaagcca agggcagcc ccgagaacca caggtgtgca ccctgccccc atcccgggat     1080
gagctgacca gaaccaggt cagcctctcg tgcgcagtca aaggcttcta tcccagcgac     1140
atcgccgtgg agtgggagag caatgggcag ccggagaaca actacaagac cacgcctccc     1200
gtgctggact ccgacggctc cttcttcctc gtgagcaagc tcaccgtgga caagagcagg     1260
tggcagcagg ggaacgtctt ctcatgctcc gtgatgcatg aggctctgca caaccactac     1320
acgcagaaga gcctctccct gtctccgggt aaa                                 1353

<210> SEQ ID NO 99
<211> LENGTH: 645
<212> TYPE: DNA
<213> ORGANISM: Artificial Sequence
<220> FEATURE:
<223> OTHER INFORMATION: LC DP47 GS

<400> SEQUENCE: 99
gaaatcgtgt taacgcagtc tccaggcacc ctgtctttgt ctccagggga aagagccacc       60
ctctcttgca gggccagtca gagtgttagc agcagctact tagcctggta ccagcagaaa      120
cctggccagg ctcccaggct cctcatctat ggagcatcca gcagggccac tggcatccca      180
gacaggttca gtggcagtgg atccgggaca gacttcactc tcaccatcag cagactggag      240
cctgaagatt ttgcagtgta ttactgtcag cagtatggta gctcaccgct gacgttcggc      300
caggggacca aagtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagacta cgagaaacac aaagtctacg cctgcgaagt cacccatcag      600
ggcctgagct cgcccgtcac aaagagcttc aacaggggag agtgt                     645

<210> SEQ ID NO 100
<211> LENGTH: 642
<212> TYPE: DNA
<213> ORGANISM: Artificial Sequence
<220> FEATURE:
<223> OTHER INFORMATION: LC CD3 CH2527 (Crossfab, VL-CH1)

<400> SEQUENCE: 100
caggccgtcg tgacccagga acccagcctg acagtgtctc ctggcggcac cgtgaccctg       60
acatgtggca gttctacagg cgccgtgacc accagcaact acgccaactg ggtgcaggaa      120
```

| | |
|---|---|
| aagcccggcc aggccttcag aggactgatc ggcggcacca acaagagagc ccctggcacc | 180 |
| cctgccagat tcagcggatc tctgctggga ggaaaggccg ccctgacact gtctggcgcc | 240 |
| cagccagaag atgaggccga gtactactgc gccctgtggt acagcaacct gtgggtgttc | 300 |
| ggcggaggca ccaagctgac agtgctgagc agcgcttcca ccaaaggccc ttccgtgttt | 360 |
| cctctggctc ctagctccaa gtccacctct ggaggcaccg ctgctctcgg atgcctcgtg | 420 |
| aaggattatt ttcctgagcc tgtgacagtg tcctggaata gcggagcact gacctctgga | 480 |
| gtgcatactt tccccgctgt gctgcagtcc tctggactgt acagcctgag cagcgtggtg | 540 |
| acagtgccca gcagcagcct gggcacccag acctacatct gcaacgtgaa ccacaagccc | 600 |
| agcaacacca aggtggacaa gaaggtggaa cccaagtctt gt | 642 |

<210> SEQ ID NO 101
<211> LENGTH: 2064
<212> TYPE: DNA
<213> ORGANISM: Artificial Sequence
<220> FEATURE:
<223> OTHER INFORMATION: DP47 GS (VH-CH1) - CD3 CH2527 (Crossfab VH-Ck) - Fc(knob) P329GLALA

<400> SEQUENCE: 101

| | |
|---|---|
| gaggtgcaat tgttggagtc tgggggaggc ttggtacagc ctggggggtc cctgagactc | 60 |
| tcctgtgcag cctccggatt caccttagc agttatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gaaaggcagc | 300 |
| ggatttgact actggggcca aggaaccctg gtcaccgtct cgagtgctag cacaaagggc | 360 |
| cccagcgtgt tccctctggc ccctagcagc aagagcacat ctggcggaac agccgccctg | 420 |
| ggctgcctcg tgaaggacta cttccccgag cctgtgaccg tgtcctggaa ctctggcgcc | 480 |
| ctgacaagcg gcgtgcacac ctttccagcc gtgctgcaga gcagcggcct gtactctctg | 540 |
| agcagcgtgg tcaccgtgcc tagcagcagc ctgggcaccc agacctacat ctgcaacgtg | 600 |
| aaccacaagc ccagcaacac caaagtggac aagaaggtgg agcccaagag ctgtgatggc | 660 |
| ggaggagggt ccggaggcgg aggatccgag gtgcagctgc tggaatctgg cggcggactg | 720 |
| gtgcagcctg gcggatctct gagactgagc tgtgccgcca gcggcttcac cttcagcacc | 780 |
| tacgccatga actgggtgcg ccaggcccct ggcaaaggcc tggaatgggt gtcccggatc | 840 |
| agaagcaagt acaacaacta cgccacctac tacgccgaca gcgtgaaggg ccggttcacc | 900 |
| atcagccggg acgacagcaa gaacaccctg tacctgcaga tgaacagcct gcgggccgag | 960 |
| gacaccgccg tgtactattg tgtgcggcac ggcaacttcg gcaacagcta tgtgtcttgg | 1020 |
| tttgcctact ggggccaggg caccctcgtg accgtgtcaa gcgctagcgt ggccgctccc | 1080 |
| tccgtgttta tctttccccc atccgatgaa cagctgaaaa gcggcaccgc ctccgtcgtg | 1140 |
| tgtctgctga caatttttta ccctagggaa gctaaagtgc agtggaaagt ggataacgca | 1200 |
| ctgcagtccg gcaactccca ggaatctgtg acagaacagg actccaagga cagcacctac | 1260 |
| tccctgtcct ccaccctgac actgtctaag gctgattatg agaaacacaa agtctacgcc | 1320 |
| tgcgaagtca cccatcaggg cctgagctcg cccgtcacaa agagcttcaa caggggagag | 1380 |
| tgtgacaaga cccacacctg tcccccttgt cctgccctg aagctgctgg cggcccttct | 1440 |
| gtgttcctgt tccccccaaa gcccaaggac accctgatga tcagcggac ccccgaagtg | 1500 |

```
acctgcgtgg tggtggatgt gtcccacgag gaccctgaag tgaagttcaa ttggtacgtg    1560
gacggcgtgg aagtgcacaa cgccaagaca aagccgcggg aggagcagta caacagcacg    1620
taccgtgtgg tcagcgtcct caccgtcctg caccaggact ggctgaatgg caaggagtac    1680
aagtgcaagg tctccaacaa agccctcggc gcccccatcg agaaaaccat ctccaaagcc    1740
aaagggcagc ccgagaacc acaggtgtac accctgcccc catgccggga tgagctgacc     1800
aagaaccagg tcagcctgtg gtgcctggtc aaaggcttct atcccagcga catcgccgtg    1860
gagtgggaga gcaatgggca gccggagaac aactacaaga ccacgcctcc cgtgctggac    1920
tccgacggct ccttcttcct ctacagcaag ctcaccgtgg acaagagcag gtggcagcag    1980
gggaacgtct tctcatgctc cgtgatgcat gaggctctgc acaaccacta cacgcagaag    2040
agcctctccc tgtctccggg taaa                                            2064

<210> SEQ ID NO 102
<211> LENGTH: 1335
<212> TYPE: DNA
<213> ORGANISM: Artificial Sequence
<220> FEATURE:
<223> OTHER INFORMATION: DP47 GS (VH-CH1) - Fc(hole) P329GLALA

<400> SEQUENCE: 102
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
ctgcagatga acagcctgag agccgaggac acggccgtat attactgtgc gaaaggcagc    300
ggatttgact actggggcca aggaaccctg gtcaccgtct cgagtgctag caccaagggc    360
ccctccgtgt tcccctggc cccagcagc aagagcacca gcggcggcac agccgctctg     420
ggctgcctgg tcaaggacta cttccccgag cccgtgaccg tgtcctggaa cagcggagcc    480
ctgacctccg gcgtgcacac cttccccgcc gtgctgcaga gttctggcct gtatagcctg    540
agcagcgtgt tcaccgtgcc ttctagcagc ctgggcaccc agacctacat ctgcaacgtg    600
aaccacaagc ccagcaacac caaggtggac aagaaggtgg agcccaagag ctgcgacaaa    660
actcacacat gcccaccgtg cccagcacct gaagctgcag ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctcgg cgcccccatc gagaaaacca tctccaaagc caaagggcag    1020
ccccgagaac acaggtgtg cacctgcccc ccatcccggg atgagctgac caagaaccag    1080
gtcagcctct cgtgcgcagt caaaggcttc tatcccagcg acatcgccgt ggagtgggag    1140
agcaatgggc agccggagaa caactacaag accacgcctc ccgtgctgga ctccgacggc    1200
tccttcttcc tctgtagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                      1335

<210> SEQ ID NO 103
<211> LENGTH: 207
```

<212> TYPE: PRT
<213> ORGANISM: Homo sapiens

<400> SEQUENCE: 103

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 104
<211> LENGTH: 198
<212> TYPE: PRT
<213> ORGANISM: Macaca fascicularis

<400> SEQUENCE: 104

```
Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Leu Val Tyr Tyr Trp Ser Lys
    130                 135                 140
```

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
            165                 170                 175

Pro Asp Tyr Glu Pro Ile Arg Lys Gly Gln Gln Asp Leu Tyr Ser Gly
            180                 185                 190

Leu Asn Gln Arg Arg Ile
            195

<210> SEQ ID NO 105
<211> LENGTH: 15
<212> TYPE: PRT
<213> ORGANISM: Artificial Sequence
<220> FEATURE:
<223> OTHER INFORMATION: linker

<400> SEQUENCE: 105

Glu Pro Lys Ser Cys Gly Gly Gly Ser Gly Gly Gly Gly Ser
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: linker

<400> SEQUENCE: 106

Glu Pro Lys Ser Cys Gly Gly Gly Ser Gly Gly Gly Gly Ser
1               5                   10                  15

<210> SEQ ID NO 107
<211> LENGTH: 227
<212> TYPE: PRT
<213> ORGANISM: Homo sapiens

<400> SEQUENCE: 107

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

-continued

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 108
<211> LENGTH: 19
<212> TYPE: PRT
<213> ORGANISM: Artificial Sequence
<220> FEATURE:
<223> OTHER INFORMATION: leader peptide

<400> SEQUENCE: 108

Met Asp Trp Thr Trp Arg Ile Leu Phe Leu Val Ala Ala Ala Thr Gly
1               5                   10                  15

Ala His Ser

<210> SEQ ID NO 109
<211> LENGTH: 57
<212> TYPE: DNA
<213> ORGANISM: Artificial Sequence
<220> FEATURE:
<223> OTHER INFORMATION: leader peptide

<400> SEQUENCE: 109
atggactgga cctggagaat cctcttcttg gtggcagcag ccacaggagc ccactcc        57

<210> SEQ ID NO 110
<211> LENGTH: 57
<212> TYPE: DNA
<213> ORGANISM: Artificial Sequence
<220> FEATURE:
<223> OTHER INFORMATION: leader peptide

<400> SEQUENCE: 110
atggactgga cctggaggat cctcttcttg gtggcagcag ccacaggagc ccactcc        57

<210> SEQ ID NO 111
<211> LENGTH: 22
<212> TYPE: PRT
<213> ORGANISM: Artificial Sequence
<220> FEATURE:
<223> OTHER INFORMATION: leader peptide

<400> SEQUENCE: 111

Met Asp Met Arg Val Pro Ala Gln Leu Leu Gly Leu Leu Leu Leu Trp
1               5                   10                  15

Phe Pro Gly Ala Arg Cys
            20

<210> SEQ ID NO 112
<211> LENGTH: 66
<212> TYPE: DNA
<213> ORGANISM: Artificial Sequence
<220> FEATURE:
<223> OTHER INFORMATION: leader peptide

<400> SEQUENCE: 112
atggacatga gggtccccgc tcagctcctg ggcctcctgc tgctctggtt cccaggtgcc        60
```

```
aggtgt                                                             66

<210> SEQ ID NO 113
<211> LENGTH: 19
<212> TYPE: PRT
<213> ORGANISM: Artificial Sequence
<220> FEATURE:
<223> OTHER INFORMATION: leader peptide

<400> SEQUENCE: 113

Met Gly Trp Ser Cys Ile Ile Leu Phe Leu Val Ala Thr Ala Thr Gly
1               5                   10                  15

Val His Ser

<210> SEQ ID NO 114
<211> LENGTH: 57
<212> TYPE: DNA
<213> ORGANISM: Artificial Sequence
<220> FEATURE:
<223> OTHER INFORMATION: leader peptide

<400> SEQUENCE: 114
atgggatgga gctgtatcat cctcttcttg gtagcaacag ctaccggtgt gcattcc       57

<210> SEQ ID NO 115
<211> LENGTH: 57
<212> TYPE: DNA
<213> ORGANISM: Artificial Sequence
<220> FEATURE:
<223> OTHER INFORMATION: leader peptide

<400> SEQUENCE: 115
atgggctggt cctgcatcat cctgtttctg gtggctaccg ccactggagt gcattcc       57

<210> SEQ ID NO 116
<211> LENGTH: 57
<212> TYPE: DNA
<213> ORGANISM: Artificial Sequence
<220> FEATURE:
<223> OTHER INFORMATION: leader peptide

<400> SEQUENCE: 116
atgggctggt cctgcatcat cctgtttctg gtcgccacag ccaccggcgt gcactct       57

<210> SEQ ID NO 117
<211> LENGTH: 643
<212> TYPE: PRT
<213> ORGANISM: Macaca fascicularis

<400> SEQUENCE: 117

Leu Ser Leu Glu Gly Ser Arg Thr Leu Thr Val Cys Pro Gly Ser Val
1               5                   10                  15

Gln Pro Leu Ser Ser Gln Thr Leu Arg Ala Ser Ser Ser Ala Gly Thr
            20                  25                  30

Asp Pro Gln Leu Leu Leu Tyr Arg Val Val Arg Gly Pro Gln Leu Gly
        35                  40                  45

Arg Leu Phe His Ala Gln Gln Asp Ser Thr Gly Glu Ala Leu Val Asn
    50                  55                  60

Phe Thr Gln Ala Glu Val Tyr Ala Gly Asn Ile Leu Tyr Glu His Glu
65                  70                  75                  80

Met Pro Thr Glu Pro Phe Trp Glu Ala His Asp Thr Leu Glu Leu Gln
                85                  90                  95
```

-continued

```
Leu Ser Ser Pro Pro Ala Arg Asp Val Ala Ala Thr Leu Ala Val Ala
            100                 105                 110
Val Ser Phe Glu Ala Ala Cys Pro Gln Arg Pro Ser His Leu Trp Lys
        115                 120                 125
Asn Lys Gly Leu Trp Val Pro Glu Gly Gln Arg Ala Lys Ile Thr Met
    130                 135                 140
Ala Ala Leu Asp Ala Ser Asn Leu Leu Ala Ser Val Pro Ser Pro Gln
145                 150                 155                 160
Arg Leu Glu His Asp Val Leu Phe Gln Val Thr Gln Phe Pro Ser Arg
                165                 170                 175
Gly Gln Leu Leu Val Ser Glu Glu Pro Leu His Ala Gly Gln Pro His
            180                 185                 190
Phe Leu Gln Ser Gln Leu Ala Ala Gly Gln Leu Val Tyr Ala His Gly
        195                 200                 205
Gly Gly Gly Thr Gln Gln Asp Gly Phe His Phe Arg Ala His Leu Gln
    210                 215                 220
Gly Pro Ala Gly Ala Thr Val Ala Gly Pro Gln Thr Ser Glu Ala Phe
225                 230                 235                 240
Ala Ile Thr Val Arg Asp Val Asn Glu Arg Pro Pro Gln Pro Gln Ala
                245                 250                 255
Ser Val Pro Leu Arg Ile Thr Arg Gly Ser Arg Ala Pro Ile Ser Arg
            260                 265                 270
Ala Gln Leu Ser Val Val Asp Pro Asp Ser Ala Pro Gly Glu Ile Glu
        275                 280                 285
Tyr Glu Val Gln Arg Ala Pro His Asn Gly Phe Leu Ser Leu Val Gly
    290                 295                 300
Gly Gly Pro Gly Pro Val Thr His Phe Thr Gln Ala Asp Val Asp Ser
305                 310                 315                 320
Gly Arg Leu Ala Phe Val Ala Asn Gly Ser Ser Val Ala Gly Val Phe
                325                 330                 335
Gln Leu Ser Met Ser Asp Gly Ala Ser Pro Pro Leu Pro Met Ser Leu
            340                 345                 350
Ala Val Asp Ile Leu Pro Ser Ala Ile Glu Val Gln Leu Gln Ala Pro
        355                 360                 365
Leu Glu Val Pro Gln Ala Leu Gly Arg Ser Ser Leu Ser Gln Gln Gln
    370                 375                 380
Leu Arg Val Val Ser Asp Arg Glu Glu Pro Glu Ala Ala Tyr Arg Leu
385                 390                 395                 400
Ile Gln Gly Pro Lys Tyr Gly His Leu Leu Val Gly Gly Arg Pro Ala
                405                 410                 415
Ser Ala Phe Ser Gln Leu Gln Ile Asp Gln Gly Glu Val Val Phe Ala
            420                 425                 430
Phe Thr Asn Phe Ser Ser His Asp His Phe Arg Val Leu Ala Leu
        435                 440                 445
Ala Arg Gly Val Asn Ala Ser Ala Val Val Asn Ile Thr Val Arg Ala
    450                 455                 460
Leu Leu His Val Trp Ala Gly Pro Trp Pro Gln Gly Ala Thr Leu
465                 470                 475                 480
Arg Leu Asp Pro Thr Ile Leu Asp Ala Gly Glu Leu Ala Asn Arg Thr
                485                 490                 495
Gly Ser Val Pro His Phe Arg Leu Leu Glu Gly Pro Arg His Gly Arg
            500                 505                 510
Val Val Arg Val Pro Arg Ala Arg Thr Glu Pro Gly Gly Ser Gln Leu
```

```
                515                 520                 525
Val Glu Gln Phe Thr Gln Gln Asp Leu Glu Asp Gly Arg Leu Gly Leu
    530                 535                 540

Glu Val Gly Arg Pro Glu Gly Arg Ala Pro Ser Pro Thr Gly Asp Ser
545                 550                 555                 560

Leu Thr Leu Glu Leu Trp Ala Gln Gly Val Pro Pro Ala Val Ala Ser
                565                 570                 575

Leu Asp Phe Ala Thr Glu Pro Tyr Asn Ala Ala Arg Pro Tyr Ser Val
            580                 585                 590

Ala Leu Leu Ser Val Pro Glu Ala Thr Arg Met Glu Ala Gly Lys Pro
        595                 600                 605

Glu Ser Ser Thr Pro Thr Gly Glu Pro Gly Pro Met Ala Ser Ser Pro
    610                 615                 620

Val Pro Ala Val Ala Lys Gly Gly Phe Leu Gly Phe Leu Glu Ala Asn
625                 630                 635                 640

Met Phe Ser

<210> SEQ ID NO 118
<211> LENGTH: 643
<212> TYPE: PRT
<213> ORGANISM: Homo sapiens

<400> SEQUENCE: 118

Leu Ser Leu Lys Gly Ser Gln Thr Leu Thr Val Cys Pro Gly Ser Val
1               5                   10                  15

Gln Pro Leu Ser Ser Gln Thr Leu Arg Ala Ser Ser Ala Gly Thr
            20                  25                  30

Asp Pro Gln Leu Leu Leu Tyr Arg Val Val Arg Gly Pro Gln Leu Gly
            35                  40                  45

Arg Leu Phe His Ala Gln Gln Asp Ser Thr Gly Glu Ala Leu Val Asn
    50                  55                  60

Phe Thr Gln Ala Glu Val Tyr Ala Gly Asn Ile Leu Tyr Glu His Glu
65                  70                  75                  80

Met Pro Pro Glu Pro Phe Trp Glu Ala His Asp Thr Leu Glu Leu Gln
                85                  90                  95

Leu Ser Ser Pro Pro Ala Arg Asp Val Ala Ala Thr Leu Ala Val Ala
            100                 105                 110

Val Ser Phe Glu Ala Ala Cys Pro Gln His Pro Ser His Leu Trp Lys
        115                 120                 125

Asn Lys Gly Leu Trp Val Pro Glu Gly Gln Arg Ala Arg Ile Thr Val
    130                 135                 140

Ala Ala Leu Asp Ala Ser Asn Leu Leu Ala Ser Val Pro Ser Pro Gln
145                 150                 155                 160

Arg Ser Glu His Asp Val Leu Phe Gln Val Thr Gln Phe Pro Ser Arg
                165                 170                 175

Gly Gln Leu Leu Val Ser Glu Glu Pro Leu His Ala Gly Gln Pro His
            180                 185                 190

Phe Leu Gln Ser Gln Leu Ala Ala Gly Gln Leu Val Tyr Ala His Gly
        195                 200                 205

Gly Gly Gly Thr Gln Gln Asp Gly Phe His Phe Arg Ala His Leu Gln
    210                 215                 220

Gly Pro Ala Gly Ala Ser Val Ala Gly Pro Gln Thr Ser Glu Ala Phe
225                 230                 235                 240

Ala Ile Thr Val Arg Asp Val Asn Glu Arg Pro Pro Gln Pro Gln Ala
```

```
            245                 250                 255
Ser Val Pro Leu Arg Leu Thr Arg Gly Ser Arg Ala Pro Ile Ser Arg
            260                 265                 270

Ala Gln Leu Ser Val Val Asp Pro Asp Ser Ala Pro Gly Glu Ile Glu
        275                 280                 285

Tyr Glu Val Gln Arg Ala Pro His Asn Gly Phe Leu Ser Leu Val Gly
    290                 295                 300

Gly Gly Leu Gly Pro Val Thr Arg Phe Thr Gln Ala Asp Val Asp Ser
305                 310                 315                 320

Gly Arg Leu Ala Phe Val Ala Asn Gly Ser Ser Val Ala Gly Ile Phe
                325                 330                 335

Gln Leu Ser Met Ser Asp Gly Ala Ser Pro Pro Leu Pro Met Ser Leu
            340                 345                 350

Ala Val Asp Ile Leu Pro Ser Ala Ile Glu Val Gln Leu Arg Ala Pro
        355                 360                 365

Leu Glu Val Pro Gln Ala Leu Gly Arg Ser Ser Leu Ser Gln Gln Gln
    370                 375                 380

Leu Arg Val Val Ser Asp Arg Glu Pro Glu Ala Ala Tyr Arg Leu
385                 390                 395                 400

Ile Gln Gly Pro Gln Tyr Gly His Leu Leu Val Gly Arg Pro Thr
                405                 410                 415

Ser Ala Phe Ser Gln Phe Gln Ile Asp Gln Gly Glu Val Val Phe Ala
            420                 425                 430

Phe Thr Asn Phe Ser Ser Ser His Asp His Phe Arg Val Leu Ala Leu
        435                 440                 445

Ala Arg Gly Val Asn Ala Ser Ala Val Val Asn Val Thr Val Arg Ala
    450                 455                 460

Leu Leu His Val Trp Ala Gly Gly Pro Trp Pro Gln Gly Ala Thr Leu
465                 470                 475                 480

Arg Leu Asp Pro Thr Val Leu Asp Ala Gly Glu Leu Ala Asn Arg Thr
                485                 490                 495

Gly Ser Val Pro Arg Phe Arg Leu Leu Glu Gly Pro Arg His Gly Arg
            500                 505                 510

Val Val Arg Val Pro Arg Ala Arg Thr Glu Pro Gly Gly Ser Gln Leu
        515                 520                 525

Val Glu Gln Phe Thr Gln Gln Asp Leu Glu Asp Gly Arg Leu Gly Leu
    530                 535                 540

Glu Val Gly Arg Pro Glu Gly Arg Ala Pro Gly Pro Ala Gly Asp Ser
545                 550                 555                 560

Leu Thr Leu Glu Leu Trp Ala Gln Gly Val Pro Pro Ala Val Ala Ser
                565                 570                 575

Leu Asp Phe Ala Thr Glu Pro Tyr Asn Ala Ala Arg Pro Tyr Ser Val
            580                 585                 590

Ala Leu Leu Ser Val Pro Glu Ala Ala Arg Thr Glu Ala Gly Lys Pro
        595                 600                 605

Glu Ser Ser Thr Pro Thr Gly Glu Pro Gly Pro Met Ala Ser Ser Pro
    610                 615                 620

Glu Pro Ala Val Ala Lys Gly Gly Phe Leu Ser Phe Leu Glu Ala Asn
625                 630                 635                 640

Met Phe Ser

<210> SEQ ID NO 119
<211> LENGTH: 428
```

```
<212> TYPE: PRT
<213> ORGANISM: Artificial Sequence
<220> FEATURE:
<223> OTHER INFORMATION: NABA-avi-his

<400> SEQUENCE: 119
```

| | | | | | | | | | | | | | | |
|---|---|---|---|---|---|---|---|---|---|---|---|---|---|---|
| Gln | Leu | Thr | Thr | Glu | Ser | Met | Pro | Phe | Asn | Val | Ala | Glu | Gly | Lys | Glu |
| 1 | | | | 5 | | | | | 10 | | | | | 15 |
| Val | Leu | Leu | Leu | Val | His | Asn | Leu | Pro | Gln | Gln | Leu | Phe | Gly | Tyr | Ser |
| | | | 20 | | | | | 25 | | | | | 30 | |
| Trp | Tyr | Lys | Gly | Glu | Arg | Val | Asp | Gly | Asn | Arg | Gln | Ile | Val | Gly | Tyr |
| | | 35 | | | | | 40 | | | | | 45 | | |
| Ala | Ile | Gly | Thr | Gln | Gln | Ala | Thr | Pro | Gly | Pro | Ala | Asn | Ser | Gly | Arg |
| | 50 | | | | | 55 | | | | | 60 | | | | |
| Glu | Thr | Ile | Tyr | Pro | Asn | Ala | Ser | Leu | Leu | Ile | Gln | Asn | Val | Thr | Gln |
| 65 | | | | | 70 | | | | | 75 | | | | | 80 |
| Asn | Asp | Thr | Gly | Phe | Tyr | Thr | Leu | Gln | Val | Ile | Lys | Ser | Asp | Leu | Val |
| | | | | 85 | | | | | 90 | | | | | 95 | |
| Asn | Glu | Glu | Ala | Thr | Gly | Gln | Phe | His | Val | Tyr | Pro | Glu | Leu | Pro | Lys |
| | | | | 100 | | | | | 105 | | | | | 110 | |
| Pro | Ser | Ile | Ser | Ser | Asn | Asn | Ser | Asn | Pro | Val | Glu | Asp | Lys | Asp | Ala |
| | | | 115 | | | | | 120 | | | | | 125 | | |
| Met | Ala | Phe | Thr | Cys | Glu | Pro | Glu | Thr | Gln | Asp | Thr | Thr | Tyr | Leu | Trp |
| | 130 | | | | | 135 | | | | | 140 | | | | |
| Trp | Ile | Asn | Asn | Gln | Ser | Leu | Pro | Val | Ser | Pro | Arg | Leu | Gln | Leu | Ser |
| 145 | | | | | 150 | | | | | 155 | | | | | 160 |
| Asn | Gly | Asn | Arg | Thr | Leu | Thr | Leu | Leu | Ser | Val | Thr | Arg | Asn | Asp | Thr |
| | | | | 165 | | | | | 170 | | | | | 175 | |
| Gly | Pro | Tyr | Glu | Cys | Glu | Ile | Gln | Asn | Pro | Val | Ser | Ala | Asn | Arg | Ser |
| | | | 180 | | | | | 185 | | | | | 190 | | |
| Asp | Pro | Val | Thr | Leu | Asn | Val | Thr | Tyr | Gly | Pro | Asp | Thr | Pro | Thr | Ile |
| | | | 195 | | | | | 200 | | | | | 205 | | |
| Ser | Pro | Pro | Asp | Ser | Ser | Tyr | Leu | Ser | Gly | Ala | Asn | Leu | Asn | Leu | Ser |
| | 210 | | | | | 215 | | | | | 220 | | | | |
| Cys | His | Ser | Ala | Ser | Asn | Pro | Ser | Pro | Gln | Tyr | Ser | Trp | Arg | Ile | Asn |
| 225 | | | | | 230 | | | | | 235 | | | | | 240 |
| Gly | Ile | Pro | Gln | Gln | His | Thr | Gln | Val | Leu | Phe | Ile | Ala | Lys | Ile | Thr |
| | | | | 245 | | | | | 250 | | | | | 255 | |
| Pro | Asn | Asn | Asn | Gly | Thr | Tyr | Ala | Cys | Phe | Val | Ser | Asn | Leu | Ala | Thr |
| | | | 260 | | | | | 265 | | | | | 270 | | |
| Gly | Arg | Asn | Asn | Ser | Ile | Val | Lys | Ser | Ile | Thr | Val | Ser | Ala | Leu | Ser |
| | | 275 | | | | | 280 | | | | | 285 | | | |
| Pro | Val | Val | Ala | Lys | Pro | Gln | Ile | Lys | Ala | Ser | Lys | Thr | Thr | Val | Thr |
| | 290 | | | | | 295 | | | | | 300 | | | | |
| Gly | Asp | Lys | Asp | Ser | Val | Asn | Leu | Thr | Cys | Ser | Thr | Asn | Asp | Thr | Gly |
| 305 | | | | | 310 | | | | | 315 | | | | | 320 |
| Ile | Ser | Ile | Arg | Trp | Phe | Phe | Lys | Asn | Gln | Ser | Leu | Pro | Ser | Ser | Glu |
| | | | | 325 | | | | | 330 | | | | | 335 | |
| Arg | Met | Lys | Leu | Ser | Gln | Gly | Asn | Ile | Thr | Leu | Ser | Ile | Asn | Pro | Val |
| | | | 340 | | | | | 345 | | | | | 350 | | |
| Lys | Arg | Glu | Asp | Ala | Gly | Thr | Tyr | Trp | Cys | Glu | Val | Phe | Asn | Pro | Ile |
| | | 355 | | | | | 360 | | | | | 365 | | | |
| Ser | Lys | Asn | Gln | Ser | Asp | Pro | Ile | Met | Leu | Asn | Val | Asn | Tyr | Asn | Ala |
| | 370 | | | | | 375 | | | | | 380 | | | | |

```
Leu Pro Gln Glu Asn Leu Ile Asn Val Asp Leu Glu Val Leu Phe Gln
385                 390                 395                 400

Gly Pro Gly Ser Gly Leu Asn Asp Ile Phe Glu Ala Gln Lys Ile Glu
                405                 410                 415

Trp His Glu Ala Arg Ala His His His His His His
            420                 425

<210> SEQ ID NO 120
<211> LENGTH: 360
<212> TYPE: PRT
<213> ORGANISM: Artificial Sequence
<220> FEATURE:
<223> OTHER INFORMATION: CD3e stalk-Fc(knob)-Avi

<400> SEQUENCE: 120

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Ser Glu Asn Cys Val Asp Glu Gln Leu Tyr Phe Gln Gly Gly Ser
            100                 105                 110

Pro Lys Ser Ala Asp Lys Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Asp Glu Leu Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320
```

```
Cys Ser Val Met His Glu Ala Leu His Asn His Tyr Thr Gln Lys Ser
                325                 330                 335

Leu Ser Leu Ser Pro Gly Lys Ser Gly Gly Leu Asn Asp Ile Phe Glu
            340                 345                 350

Ala Gln Lys Ile Glu Trp His Glu
        355                 360

<210> SEQ ID NO 121
<211> LENGTH: 325
<212> TYPE: PRT
<213> ORGANISM: Artificial Sequence
<220> FEATURE:
<223> OTHER INFORMATION: CD3d stalk-Fc(hole)

<400> SEQUENCE: 121

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Arg Ser Glu Gln Leu Tyr Phe Gln
65                  70                  75                  80

Gly Asp Lys Thr His Thr Cys Pro Pro Cys Pro Ala Pro Glu Leu Leu
                85                  90                  95

Gly Gly Pro Ser Val Phe Leu Phe Pro Pro Lys Pro Lys Asp Thr Leu
            100                 105                 110

Met Ile Ser Arg Thr Pro Glu Val Thr Cys Val Val Val Asp Val Ser
        115                 120                 125

His Glu Asp Pro Glu Val Lys Phe Asn Trp Tyr Val Asp Gly Val Glu
    130                 135                 140

Val His Asn Ala Lys Thr Lys Pro Arg Glu Glu Gln Tyr Asn Ser Thr
145                 150                 155                 160

Tyr Arg Val Val Ser Val Leu Thr Val Leu His Gln Asp Trp Leu Asn
                165                 170                 175

Gly Lys Glu Tyr Lys Cys Lys Val Ser Asn Lys Ala Leu Pro Ala Pro
            180                 185                 190

Ile Glu Lys Thr Ile Ser Lys Ala Lys Gly Gln Pro Arg Glu Pro Gln
        195                 200                 205

Val Cys Thr Leu Pro Pro Ser Arg Asp Glu Leu Thr Lys Asn Gln Val
    210                 215                 220

Ser Leu Ser Cys Ala Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                245                 250                 255

Pro Val Leu Asp Ser Asp Gly Ser Phe Phe Leu Val Ser Lys Leu Thr
            260                 265                 270

Val Asp Lys Ser Arg Trp Gln Gln Gly Asn Val Phe Ser Cys Ser Val
        275                 280                 285

Met His Glu Ala Leu His Asn His Tyr Thr Gln Lys Ser Leu Ser Leu
    290                 295                 300

Ser Pro Gly Lys Ser Gly Gly Leu Asn Asp Ile Phe Glu Ala Gln Lys
305                 310                 315                 320
```

Ile Glu Trp His Glu
             325

<210> SEQ ID NO 122
<211> LENGTH: 658
<212> TYPE: PRT
<213> ORGANISM: Mus musculus

<400> SEQUENCE: 122

Leu Ser Leu Glu Gly Thr Arg Lys Leu Thr Val Cys Pro Ser Val
1               5                   10                  15

Gln Pro Leu Ser Ser Gln Ser Leu Ser Ala Ser Ser Ser Thr Gly Ala
            20                  25                  30

Asp Pro Arg His Leu Leu Tyr Arg Val Val Arg Gly Pro Gln Leu Gly
            35                  40                  45

Arg Leu Leu His Ala Gln Gln Gly Ser Ala Glu Val Leu Val Asn
50                  55                  60

Phe Thr Gln Ala Glu Val Asn Ala Gly Asn Ile Leu Tyr Glu His Glu
65                  70                  75                  80

Met Ser Ser Glu Pro Phe Trp Glu Ala His Asp Thr Ile Gly Leu Leu
            85                  90                  95

Leu Ser Ser Pro Pro Ala Arg Asp Leu Ala Ala Thr Leu Ala Val Met
            100                 105                 110

Val Ser Phe Asp Ala Ala Cys Pro Gln Arg Pro Ser Arg Leu Trp Lys
        115                 120                 125

Asn Lys Gly Leu Trp Val Pro Glu Gly Gln Arg Ala Lys Ile Thr Val
130                 135                 140

Ala Ala Leu Asp Ala Ala Asn Leu Leu Ala Ser Val Pro Ala Ser Gln
145                 150                 155                 160

Arg Ser Arg His Asp Val Leu Phe Gln Val Thr Gln Phe Pro Thr Arg
            165                 170                 175

Gly Gln Leu Leu Val Ser Glu Glu Pro Leu His Ala Arg Arg Pro Tyr
            180                 185                 190

Phe Leu Gln Ser Glu Leu Ala Ala Gly Gln Leu Val Tyr Ala His Gly
        195                 200                 205

Gly Gly Gly Thr Gln Gln Asp Gly Phe Arg Phe Arg Ala His Leu Gln
210                 215                 220

Gly Pro Thr Gly Thr Ser Val Ala Gly Pro Gln Thr Ser Glu Ala Phe
225                 230                 235                 240

Val Ile Thr Val Arg Asp Val Asn Glu Arg Pro Pro Gln Pro Gln Ala
            245                 250                 255

Ser Ile Pro Leu Arg Val Thr Arg Gly Ser Arg Ala Pro Val Ser Arg
            260                 265                 270

Ala Gln Leu Ser Val Val Asp Pro Asp Ser Ala Pro Gly Glu Ile Glu
        275                 280                 285

Tyr Glu Val Gln Arg Ala Pro His Asn Gly Phe Leu Ser Leu Ala Gly
            290                 295                 300

Asp Asn Thr Gly Pro Val Thr His Phe Thr Gln Ala Asp Val Asp Ala
305                 310                 315                 320

Gly Arg Leu Ala Phe Val Ala Asn Gly Ser Ser Val Ala Gly Val Phe
            325                 330                 335

Gln Leu Ser Met Ser Asp Gly Ala Ser Pro Pro Ile Pro Met Ser Leu
        340                 345                 350

Ala Val Asp Val Leu Pro Ser Thr Ile Glu Val Gln Leu Arg Ala Pro
            355                 360                 365

```
Leu Glu Val Pro Gln Ala Leu Gly Arg Thr Ser Leu Ser Arg Gln Gln
        370             375             380

Leu Gln Val Ile Ser Asp Arg Glu Pro Asp Val Ala Tyr Arg Leu
385             390             395             400

Thr Gln Gly Pro Leu Tyr Gly Gln Leu Leu Val Gly Gln Pro Ala
            405             410             415

Ser Ala Phe Ser Gln Leu Gln Val Asp Gln Gly Asp Val Val Phe Val
            420             425             430

Phe Thr Asn Phe Ser Ser Ser Gln Asp His Phe Lys Val Val Ala Leu
        435             440             445

Ala Arg Gly Val Asn Ala Ser Ala Thr Val Asn Val Thr Val Gln Ala
        450             455             460

Leu Leu His Val Trp Ala Gly Gly Pro Trp Pro Gln Gly Thr Thr Leu
465             470             475             480

Arg Leu Asp Pro Thr Val Leu Asp Ala Ser Glu Leu Ala Asn Arg Thr
                485             490             495

Gly Ser Met Pro His Phe Arg Leu Leu Ala Gly Pro Arg Tyr Gly Arg
            500             505             510

Val Val Arg Val Ser Gln Gly Arg Thr Glu Ser Arg Ser Asn Gln Leu
        515             520             525

Val Glu His Phe Thr Gln Arg Asp Leu Glu Glu Gly Gln Leu Gly Leu
        530             535             540

Glu Val Gly Lys Pro Glu Gly Arg Ser Thr Gly Pro Ala Gly Asp Arg
545             550             555             560

Leu Thr Leu Glu Leu Trp Ala Lys Gly Val Pro Pro Ala Val Ala Leu
                565             570             575

Leu Asp Phe Ala Thr Glu Pro Tyr His Ala Ala Lys Ser Tyr Ser Val
            580             585             590

Ala Leu Leu Ser Val Pro Glu Ala Val Arg Thr Glu Thr Glu Lys Pro
        595             600             605

Gly Arg Ser Val Pro Thr Gly Gln Pro Gly Gln Ala Ala Ser Ser Pro
        610             615             620

Val Pro Thr Ala Ala Lys Gly Gly Val Asp Gly Leu Asn Asp Ile Phe
625             630             635             640

Glu Ala Gln Lys Ile Glu Trp His Glu Ala Arg Ala His His His His
                645             650             655

His His
```